United States Patent
Ferrara et al.

(10) Patent No.: US 11,286,263 B2
(45) Date of Patent: Mar. 29, 2022

(54) MACROCYCLIC FLUORINE SUBSTITUTED INDOLE DERIVATIVES

(71) Applicants: The Broad Institute, Inc., Cambridge, MA (US); Bayer Aktiengesellschaft, Leverkusen (DE); Bayer Pharma Aktiengesellschaft, Berlin (DE)

(72) Inventors: Steven James Ferrara, Cambridge, MA (US); Michael H. Serrano-Wu, Cambridge, MA (US); Chris Lemke, Cambridge, MA (US); David McKinney, Cambridge, MA (US); Mark Fitzgerald, Cambridge, MA (US); Christopher Nasveschuk, Cambridge, MA (US); Kiel Lazarski, Cambridge, MA (US); Laura Furst, Cambridge, MA (US); Guo Wei, Cambridge, MA (US); Patrick Ryan McCarren, Cambridge, MA (US); Kai Thede, Leverkusen (DE); Anne Mengel, Leverkusen (DE); Clara Christ, Leverkusen (DE); Joachim Kuhnke, Leverkusen (DE); Sarah Anna Liesa Johannes, Leverkusen (DE); Philipp Buchgraber, Leverkusen (DE); Ulrich Klar, Leverkusen (DE); Ulrike Sack, Leverkusen (DE); Stefan Kaulfuss, Leverkusen (DE); Amaury Ernesto Fernandez-Montalvan, Leverkusen (DE); Nicolas Werbeck, Leverkusen (DE); Ursula Mönning, Leverkusen (DE)

(73) Assignees: The Broad Institute, Inc., Cambridge, MA (US); Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/764,563

(22) PCT Filed: Nov. 15, 2018

(86) PCT No.: PCT/EP2018/081378
§ 371 (c)(1),
(2) Date: May 15, 2020

(87) PCT Pub. No.: WO2019/096909
PCT Pub. Date: May 23, 2019

(65) Prior Publication Data
US 2021/0079018 A1 Mar. 18, 2021

Related U.S. Application Data

(60) Provisional application No. 62/587,928, filed on Nov. 17, 2017.

(51) Int. Cl.
*C07D 487/14* (2006.01)
*C07D 403/14* (2006.01)
(Continued)

(52) U.S. Cl.
CPC ............ *C07D 498/14* (2013.01); *A61P 35/00* (2018.01); *C07D 487/14* (2013.01)

(58) Field of Classification Search
CPC .. C07D 487/14; C07D 403/14; C07D 498/14; A61K 31/4162; A61P 35/00
See application file for complete search history.

(56) References Cited

U.S. PATENT DOCUMENTS 10,981,932 B2    4/2021  Johannes et al.
2015/0336925 A1  11/2015 Lee et al.
(Continued)

FOREIGN PATENT DOCUMENTS

WO   WO-2008/130970 A1   10/2008
WO   WO-2008/131000 A2   10/2008
(Continued)

OTHER PUBLICATIONS

Adams et al., "The Bcl-2 apoptotic switch in cancer development and therapy," Oncogene, 26:1324-1337 (2007).
(Continued)

*Primary Examiner* — Bruck Kifle
(74) *Attorney, Agent, or Firm* — Foley Hoag LLP; David P. Halstead

(57) ABSTRACT

The present invention relates to macrocyclic indole derivatives of general formula (I):

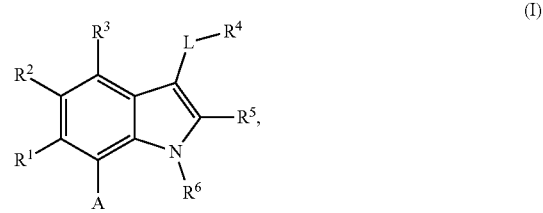

in which $R^1$, $R^2$, $R^3$, $R^4$, $R^5$, $R^6$, A and L are as defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, as a sole agent or in combination with other active ingredients.

9 Claims, No Drawings
Specification includes a Sequence Listing.

(51) Int. Cl.
  *C07D 498/14*   (2006.01)
  *A61K 31/4162*  (2006.01)
  *A61P 35/00*    (2006.01)

(56) References Cited

U.S. PATENT DOCUMENTS

| | | |
|---|---|---|
| 2016/0106731 A1 | 4/2016 | Lee et al. |
| 2017/0305926 A1 | 10/2017 | Hird et al. |
| 2020/0087322 A1 | 3/2020 | Johannes et al. |
| 2021/0079018 A1 | 3/2021 | Ferrara et al. |
| 2021/0253598 A1 | 8/2021 | Thede et al. |
| 2021/0269456 A1 | 9/2021 | Thede et al. |
| 2021/0277022 A1 | 9/2021 | Thede et al. |
| 2021/0292341 A1 | 9/2021 | Furst et al. |

FOREIGN PATENT DOCUMENTS

| | | |
|---|---|---|
| WO | WO-2014/047427 A2 | 3/2014 |
| WO | WO-2015/031608 A1 | 3/2015 |
| WO | WO-2015/148854 A1 | 10/2015 |
| WO | WO-2017/152076 A1 | 9/2017 |
| WO | WO-2017/182625 A1 | 10/2017 |
| WO | WO-2017/198341 A1 | 11/2017 |
| WO | WO-2018/098534 A1 | 6/2018 |
| WO | WO-2019/096905 A1 | 5/2019 |
| WO | WO-2019/096907 A1 | 5/2019 |
| WO | WO-2019/096909 A1 | 5/2019 |
| WO | WO-2019/096911 A1 | 5/2019 |
| WO | WO-2019/096914 A1 | 5/2019 |
| WO | WO-2019/096922 A1 | 5/2019 |
| WO | WO-2020/151738 A1 | 7/2020 |
| WO | WO-2020/236556 A1 | 11/2020 |

OTHER PUBLICATIONS

Beroukhim et al., "The Landscape of Somatic Copy-Number Alteration Across Human Cancers," Nature, 463(7283):899-905 (2010).
Glaser et al., "Anti-apoptotic Mcl-1 is essential for the development and sustained growth of acute myeloid leukemia," Genes Dev, 26:120-125 (2012).
Hanahan et al., "Hallmarks of Cancer: The Next Generation," Cell 144(5):646-674 (2011).
International Preliminary Report on Patentability for International Application No. PCT/EP2017/000629 dated Nov. 20, 2018.
International Preliminary Report on Patentability for International Application No. PCT/EP2018/081370 dated May 19, 2020.
International Preliminary Report on Patentability for International Application No. PCT/EP2018/081374 dated May 19, 2020.
International Preliminary Report on Patentability for International Application No. PCT/EP2018/081378 dated May 19, 2020.
International Preliminary Report on Patentability for International Application No. PCT/EP2018/081381 dated May 19, 2020.
International Preliminary Report on Patentability for International Application No. PCT/EP2018/081388 dated May 19, 2020.
International Preliminary Report on Patentability for International Application No. PCT/EP2018/081406 dated May 19, 2020.
International Search Report and Written Opinion for International Application No. PCT/EP2017/000629 dated Sep. 6, 2017.
International Search Report and Written Opinion for International Application No. PCT/EP2018/081370 dated Feb. 13, 2019.
International Search Report and Written Opinion for International Application No. PCT/EP2018/081374 dated Feb. 13, 2019.
International Search Report and Written Opinion for International Application No. PCT/EP2018/081378 dated Jan. 9, 2019.
International Search Report and Written Opinion for International Application No. PCT/EP2018/081381 dated Jan. 15, 2019.
International Search Report and Written Opinion for International Application No. PCT/EP2018/081388 dated Feb. 14, 2019.
International Search Report and Written Opinion for International Application No. PCT/EP2018/081406 dated Feb. 11, 2019.
International Search Report and Written Opinion for International Application No. PCT/US2020/033067 dated Jul. 19, 2020.
Korsmeyer, "BCL-2 Gene Family and the Regulation of Programmed Cell Death," Cancer Res Suppl, 59(7):1693s-1700s (1999).
Pelz et al., "Discovery of 2-Indole-acylsulfonamide Myeloid Cell Leukemia 1 (Mcl-1) Inhibitors Using Fragment-Based Methods," Journal of Medicinal Chemistry, 59(5): 2054-2066 (2016).
Wertz et al., "Sensitivity to antitubulin chemotherapeutics is regulated by MCL1 and FBW7," Nature, 471:110-114 (2011).
Zhou et al., "MCL1 transgenic mice exhibit a high incidence of B-cell lymphoma manifested as a spectrum of histologic subtypes," Blood, 97(12):3902-3909 (2001).
Zhang et al., "Research progress of GSK-3 inhibitors," Progress in Chemistry, 19(4): 614-623 (2007).

```
SEQUENCE LISTING

<160> NUMBER OF SEQ ID NOS: 5

<210> SEQ ID NO 1
<211> LENGTH: 519
<212> TYPE: PRT
<213> ORGANISM: Artificial Sequence
<220> FEATURE:
<223> OTHER INFORMATION: Modified Sequence

<400> SEQUENCE: 1

Gly Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220
```

```
Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
        260                 265                 270

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Ser Ser Glu Leu Tyr Arg Gln Ser Leu Glu Ile Ile Ser Arg Tyr Leu
    370                 375                 380

Arg Glu Gln Ala Thr Gly Ala Ala Asp Thr Ala Pro Met Gly Ala Ser
385                 390                 395                 400

Gly Ala Thr Ser Arg Lys Ala Leu Glu Thr Leu Arg Arg Val Gly Asp
                405                 410                 415

Gly Val Gln Arg Asn His Glu Thr Ala Phe Gln Gly Met Leu Arg Lys
            420                 425                 430

Leu Asp Ile Lys Asn Glu Asp Val Lys Ser Leu Ser Arg Val Met
        435                 440                 445

Ile His Val Phe Ser Asp Gly Val Thr Asn Trp Gly Arg Ile Val Thr
    450                 455                 460

Leu Ile Ser Phe Gly Ala Phe Val Ala Lys His Leu Lys Thr Ile Asn
465                 470                 475                 480

Gln Glu Ser Cys Ile Glu Pro Leu Ala Glu Ser Ile Thr Asp Val Leu
                485                 490                 495

Val Arg Thr Lys Arg Asp Trp Leu Val Lys Gln Arg Gly Trp Asp Gly
            500                 505                 510

Phe Val Glu Phe Phe His Val
        515

<210> SEQ ID NO 2
<211> LENGTH: 26
<212> TYPE: PRT
<213> ORGANISM: Artificial Sequence
<220> FEATURE:
<221> NAME/KEY: MOD_RES
<222> LOCATION: 1
<223> OTHER INFORMATION: Biotin-PEG-PEG-PEG-PEG
<220> FEATURE:
<223> OTHER INFORMATION: Modfied Sequence
<220> FEATURE:
<221> NAME/KEY: MOD_RES
<222> LOCATION: 8
<223> OTHER INFORMATION: Norvalin
<220> FEATURE:
<221> NAME/KEY: MOD_RES
<222> LOCATION: 26
<223> OTHER INFORMATION: AMIDATION

<400> SEQUENCE: 2
```

```
Pro Ala Glu Leu Glu Val Glu Val Ala Thr Gln Leu Arg Arg Phe Gly
1               5                   10                  15

Asp Lys Leu Asn Phe Arg Gln Lys Leu Leu
            20                  25
```

<210> SEQ ID NO 3
<211> LENGTH: 212
<212> TYPE: PRT
<213> ORGANISM: Artificial Sequence
<220> FEATURE:
<223> OTHER INFORMATION: Modifed Sequence
<220> FEATURE:
<221> NAME/KEY: MOD_RES
<222> LOCATION: 212
<223> OTHER INFORMATION: HHHHHH

<400> SEQUENCE: 3

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg
    210
```

<210> SEQ ID NO 4
<211> LENGTH: 25
<212> TYPE: PRT
<213> ORGANISM: Artificial Sequence
<220> FEATURE:
<221> NAME/KEY: MOD_RES
<222> LOCATION: 1
<223> OTHER INFORMATION: Biotin-PEG-PEG-PEG-PEG
<220> FEATURE:
<223> OTHER INFORMATION: Modified Sequence
<220> FEATURE:
<221> NAME/KEY: MOD_RES
<222> LOCATION: 15
<223> OTHER INFORMATION: Norleucin
<220> FEATURE:

```
<221> NAME/KEY: MOD_RES
<222> LOCATION: 25
<223> OTHER INFORMATION: AMIDATION

<400> SEQUENCE: 4

Asn Leu Trp Ala Ala Gln Arg Tyr Gly Arg Glu Leu Arg Arg Leu Ser
1               5                   10                  15

Asp Glu Phe Val Asp Ser Phe Lys Lys
            20                  25

<210> SEQ ID NO 5
<211> LENGTH: 211
<212> TYPE: PRT
<213> ORGANISM: Artificial Sequence
<220> FEATURE:
<223> OTHER INFORMATION: Modified Sequence
<220> FEATURE:
<221> NAME/KEY: MOD_RES
<222> LOCATION: 211
<223> OTHER INFORMATION: HHHHHH

<400> SEQUENCE: 5

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp
    210
```

MACROCYCLIC FLUORINE SUBSTITUTED INDOLE DERIVATIVES

RELATED APPLICATIONS

This application is the U.S. national phase of International Patent Application No. PCT/EP2018/081378, filed Nov. 15, 2018, which claims the benefit of U.S. Provisional Application No. 62/587,928 filed on Nov. 17, 2017. The International Patent Application No. PCT/EP2018/081378 is hereby incorporated by reference in its entirety.

BACKGROUND

The present invention covers macrocyclic indole derivatives of general formula (I) which inhibit the antiapoptotic activity of MCL-1 by inhibiting its interaction with proapototic proteins.

Apoptosis, also called programmed cell death, is a natural process which allows a damaged or unwanted cell to die in a controlled manner. Deregulation of this process leads to unrestrained cell proliferation and is thus a hallmark of cancer (Hanahan and Weinberg, 2011).

Apoptosis is highly controlled by proteins of the B-cell lymphoma 2 (BCL-2) family. These proteins are characterized by their conserved regions known as BCL-2 homology (BH) domains (BH1-BH4) (Korsmeyer, 1999) through which they interact with each other. The BCL-2 family can be divided into pro-apoptotic members including BAX, BAK, BAD, BID, BIM, BMF, NOXA, and PUMA, which induce cell death, and anti-apoptotic members such as BCL-2, BCL-XL, BCL-w, Bfl1-AI, and myeloid cell leukemia-1 (MCL-1) which block apoptosis (Adams and Cory, 2007). The relative expression level of these two opponent groups of the BCL-2 family will decide if a cell will go into apoptosis or not.

MCL-1 has been identified as an important therapeutic target in cancer. MCL-1 is highly expressed in a variety of human cancers, and amplification of the MCL-1 locus is one of the most frequent somatic genetic events in human cancer, further pointing to its centrality in the pathogenesis of malignancy (Beroukhim et al., 2010). Its expression has been linked to deregulated anti-apoptotic pathways in cancer, thus leading to increased cancer cell survival, tumor development (Zhou et al., 2001) and resistance to anticancer therapies (Wertz et al., 2011). MCL-1 protein has been shown to mediate survival in models of acute myeloid leukemia (Glaser et al., 2012), lymphomas (Kelly et al., 2014) and multiple myeloma (Zhang et al., 2002). Many chemotherapeutics as well as radiation aim at inducing apoptosis in cancer cells. However, in malignant cells, apoptotic signaling is often deregulated, leading to uncontrolled growth and therapeutic resistance. One key resistance mechanism to apoptosis is to upregulate or genetically amplify MCL-1.

MCl-1 is a major inhibitor of apoptosis in cancer. MCL-1 is the largest member of the anti-apoptotic BCl-2 proteins. Its expression is tightly controlled with a half-life of only 1-4 h. With its BH-3 domain, MCL-1 tightly binds to BH-3 only containing pro-apoptotic proteins such as BAK or BAX and hinders them from inducing pores in the mitochondrial membrane, thereby blocking the intrinsic apoptotic pathway.

Thus, the specific inhibition of the interaction of MCL-1 with BH-3 only containing pro-apoptotic proteins like BAK or BAX represents a very attractive therapeutic principle to induce apoptosis in cancer cells and to address resistance against chemotherapeutics, radiation and new targeted agents. However, from WO 2015/148854, US 2016/0106731, WO 2008/130970, some indole derivatives are known as MCL-1 inhibitors. As no inhibitors have shown efficacy in the clinic yet, there is still a need for further MCL-1 inhibitors to be provided.

SUMMARY

It has now been found that the compounds of the present invention effectively inhibit the activity of the anti-apoptotic BCL-2 family member Myeloid cell leukemia-1 (MCL-1) protein for which data are given in the biological experimental section, especially the efficacy is unexpectedly enhanced. The compounds of the present invention may therefore be used for the treatment or prophylaxis of hyperproliferative disorders, such as cancer disorders.

In accordance with a first aspect, the present invention provides compounds of general formula (I):

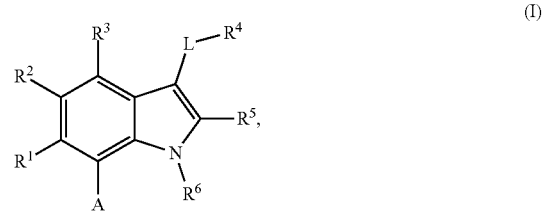

wherein
A is

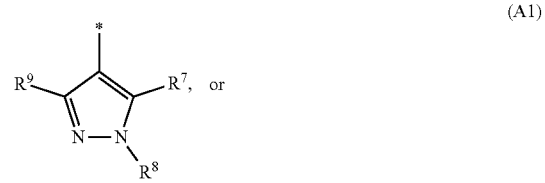

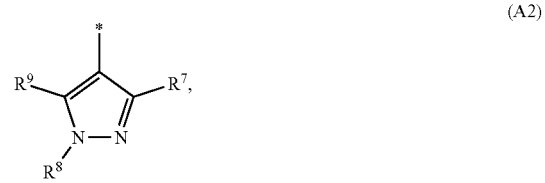

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent; or A is

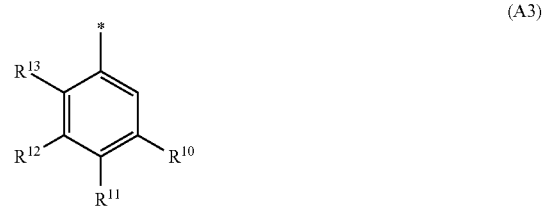

wherein optionally one or two of the groups selected from $CR^{11}$, $CR^{12}$ and $CR^{13}$ are replaced by a nitrogen atom,
  wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ is a fluorine atom, $R^2$ and $R^3$ are each a hydrogen atom;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group, and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —$NR^{14}$— group;

E is a bond, an oxygen atom, a sulfur atom, a —S(O)— group, a —S(O)$_2$— group or a —$NR^{14}$— group and constitutes the connecting element to $R^4$, m is 2, 3, or 4;

$R^5$ is selected from a COOH group, a

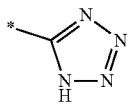

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$($CH_2$)$_s$NHCO($C_1$-$C_6$-alkyl) group, a —C(O)—NHS(O)$_2$($CH_2$)$_s$NHCO($C_3$-$C_6$-cycloalkyl) group, and a —C(O)—NHS(O)$_2$($CH_2$)$_s$NHCO(aryl) group;

—$R^6$-$R^7$— is selected from #—$(CH_2)_n$—(B)$_t$—$(CH_2)_p$—X—##, #—$(C_2$-$C_6$-alkenylene)-(B)$_t$—$(CH_2)_p$—X—##, #—$(CH_2)_n$—(B)$_t$—$(C_2$-$C_5$-alkenylene)-X—##, and #—$(CH_2)_q$—(B)—$(CH_2)_r$—(B)—$(CH_2)_v$—X—##,
  wherein # is the point of attachment with the indole nitrogen atom and ## is the point of attachment with the pyrazole carbon atom bearing the $R^7$ substituent; and
  wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and
  where a —H=CH— group in any alkenylene can be replaced by a 1,2-($C_3$-$C_5$)cycloalkylene group which is unsubstituted or substituted one or two times with a halogen atom or a $C_1$-$C_2$-alkyl group; and
  where X is an unsubstituted —$CH_2$— group;

—$R^6$-$R^{10}$— is selected from #—$(CH_2)_n$—(B)$_t$—$(CH_2)_p$—X—##, #—$(C_2$-$C_6$-alkenylene)-(B)$_t$—$(CH_2)_p$—X—##, #—$(CH_2)_n$—(B)$_t$—$(C_2$-$C_5$-alkenylene)-X—##, and #—$(CH_2)_q$—(B)—$(CH_2)_r$—(B)—$(CH_2)_v$—X—##,
  wherein # is the point of attachment with the indole nitrogen atom and ## is the point of attachment with the carbon atom of the phenyl moiety bearing the $R^{10}$ substituent, and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group,
  where a —CH=CH— group in any alkenylene can be replaced by a 1,2-($C_1$-$C_6$)cycloalkylene group which is unsubstituted or substituted one or two times with a halogen atom or a $C_1$-$C_2$-alkyl group, and
  where X is an unsubstituted —$CH_2$— group;

n is 2, 3, 4, 5, 6, 7, 8, or 9;

t is 0 or 1;

p is 0, 1, 2, 3, 4, or 5;

q is 2, 3, 4, 5, or 6;

r is 2, 3, 4, 5, or 6;

v is 0 or 1;

s is 0, 1, 2, or 3;

where the integers selected for variables n, t, p, q, r, and v result in forming a 9- to 16-membered ring independently from the selection of variable A1, A2 or A3;

B is independently selected from a —C(O)$NR^{15}$— group, a —$NR^{15}$C(O)— group, a —$N(R^{15})$— group, a —[N(CH_3)_2]^+— group, a —$N(R^{15})$—C(=O)—$N(R^{15})$— group, a —O—C(=O)—$N(R^{15})$— group, a —$N(R^{15})$—C(=O)—O— group, —O—, —S—, —S(O)—, and —S(O)$_2$—;

$R^8$ is selected from a hydrogen atom,
  a $C_1$-$C_6$-alkyl group, which is unsubstituted or substituted with one or more substituents independently selected from
    a halogen atom, a hydroxyl group, a $C_1$-$C_3$-alkoxy group, a $C_1$-$C_3$-haloalkoxy group,
    a $C_3$-$C_6$-cycloalkyl group, a heterocycloalkyl group, and a $NR^{20}R^{21}$ group; and
  a $C_3$-$C_6$-cycloalkyl group, $R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)- group,
  a $C_2$-$C_6$-haloalkenyl group,
  a $C_1$-$C_6$-alkyl-O— group,
  a $C_1$-$C_4$-haloalkoxy group,
  a $C_1$-$C_6$-alkyl-O—($C_1$-$C_3$-alkylene)- group,
  a ($C_3$-$C_7$)-cycloalkyl group,
  a ($C_3$-$C_7$)-cycloalkyl-O—($C_1$-$C_3$-alkylene)- group,
  a phenyl-O—($C_1$-$C_3$-alkylene)- group,
  a phenyl-($C_1$-$C_3$-alkylene)-O—($C_1$-$C_3$-alkylene)- group,
  a $R^{18}$-(phenylene)-($C_1$-$C_3$-alkylene)-O—($C_1$-$C_3$-alkylene)- group,
  a $R^{18}$-(phenylene)-O—($C_1$-$C_3$-alkylene)- group,
  a $R^{18}$-(phenylene)-(heteroarylene)-O—($C_1$-$C_3$-alkylene) group, a $(R^{18})$-(heterocycloalkylene)-$(C_1$-$C_3$-alkylene)- group,
a $(R^{18})$-(heterocycloalkylene)-(phenylene)-O—$(C_1$-$C_3$-alkylene)- group,
a (heterocycloalkenyl)-(phenylene)-O—$(C_1$-$C_3$-alkylene)- group,
a $(R^{18})$-(heteroarylene)-$(C_1$-$C_3$-alkylene)-O—$(C_1$-$C_3$-alkylene)- group,
a $(R^{18})$-(heteroarylene)-(phenylene)-O—$(C_1$-$C_3$-alkylene)- group,
a $(R^{19})$—S(O)$_2$-(phenylene)-O—$(C_1$-$C_3$-alkylene)- group,
a $(R^{19})$—S(O)$_2$—NH-(phenylene)-O—$(C_1$-$C_3$-alkylene)- group,
a $(R^{19})$—S(O)$_2$—NH-(phenylene)-O—$(C_1$-$C_3$-alkylene)- group,
a $(R^{19})$—S(O)$_2$—N($C_1$-$C_6$-alkyl)-(phenylene)-O—$(C_1$-$C_3$-alkylene)- group,
a $(R^{19})$—S(O)$_2$-(heterocycloalkylene)-(phenylene)-O—$(C_1$-$C_3$-alkylene)- group,
a $(R^{18})$-(heterocycloalkylene)-(heteroarylene)-O—$(C_1$-$C_3$-alkylene)- group,
a $(R^{19})$-(heteroarylene)-O—$(C_1$-$C_3$-alkylene)- group,
a $(R^{18})$-(heteroarylene)-O—$(C_1$-$C_3$-alkylene)- group,
a $(R^{19})$—S(O)$_2$-(heteroarylene)-O—$(C_1$-$C_3$-alkylene)- group,
a $(R^{19})$—S(O)$_2$-(heterocycloalkylene)-(heteroarylene)-O—$(C_1$-$C_3$-alkylene)- group,
a $NR^{20}R^{21}$—$(C_1$-$C_3$-alkylene)- group,
a ($C_1$-$C_3$-alkyl)-NH—$(C_1$-$C_3$-alkylene)- group,
a ($C_1$-$C_3$-haloalkyl)-$(C_1$-$C_3$-alkylene)-NH—$(C_1$-$C_3$-alkylene)- group,
a ($C_1$-$C_3$-haloalkyl)-NH—$(C_1$-$C_3$-alkylene)- group,
a ($C_1$-$C_3$-alkyl)-NH—C(O)—$(C_1$-$C_3$-alkylene)- group,
a ($C_1$-$C_3$-alkyl)-$NR^{15}$—C(O)—$(C_1$-$C_3$-alkylene)- group,
a ($C_1$-$C_3$-alkyl)-C(O)—NHZ—$(C_1$-$C_3$-alkylene)- group,
a ($C_1$-$C_3$-alkyl)-C(O)—$NR^{15}$—$(C_1$-$C_3$-alkylene)- group,
a

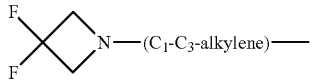

group, and a

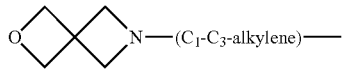

group, where the phenyl ring is unsubstituted or substituted with a halogen atom, a hydroxyl group, or a $C_1$-$C_3$-alkoxy group and
    the heterocycloalkyl group is unsubstituted or substituted with an oxo (=O) group or is unsubstituted or substituted with one or more substituents independently selected from a halogen atom, a hydroxyl group, a $C_1$-$C_3$-alkyl group, and a $C_1$-$C_3$-alkoxy group,
or $R^8$ and $R^9$ together form a 5- or 6-membered ring optionally comprising one or two heteroatoms selected from —O— and —$NR^{14}$—;
$R^{11}$ and $R^{13}$ are each independently selected from a hydrogen atom, a halogen atom, a $C_1$-$C_3$-alkyl group, and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;

$R^{14}$ is a hydrogen atom or a $C_1$-$C_3$-alkyl group;
$R^{15}$ is independently selected from a hydrogen atom,
    a $C_1$-$C_6$-alkyl group which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a $(R^{18})$-(heterocycloalkylene)-(arylene)-O— group, a (heterocycloalkyl)-(arylene)-O— group, an aryl-O— group, an aryl-($C_1$-$C_3$-alkylene)-O— group, a $(R^{19})$—S(O)$_2$-arylene-O— group, a $(R^{19})$S(O)$_2$-(heterocycloalkylene)-(arylene)-O— group, an (aryl)-(heteroarylene)-O— group, and an (aryl)-(heteroarylene)-O—$(C_1$-$C_3$-alkylene)- group;
a phenyl group,
a group

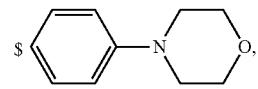

a group

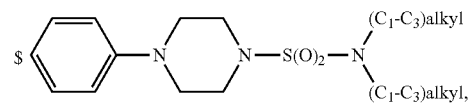

and
a group

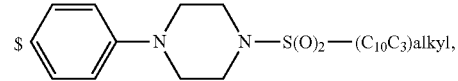

where $ is the point of attachment to the nitrogen atom, to which $R^{15}$ is attached,
$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;
$R^{18}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $R^{21}OC(O)$—$(C_1$-$C_3$-alkylene)- group, a —C(O)$OR^{21}$ group, a —C(O)$NR^{20}R^{21}$ group, a ($C_1$-$C_3$-alkyl)-O—$(C_1$-$C_3$-alkylene)-C(O)— group, a ($C_1$-$C_6$-alkyl)-C(O)— group, and a $C_3$-$C_6$-cycloalkyl-C(O)— group;
$R^{19}$ is selected from a $C_1$-$C_3$-alkyl group, a $C_3$-$C_6$-cycloalkyl group, and a $NR^{20}R^{21}$ group; and
$R^{20}$ and $R^{21}$ are each independently selected from a hydrogen atom and a $C_1$-$C_6$-alkyl group;
or a tautomer, an N-oxide, or a salt thereof, or a salt of a tautomer, or a salt of an N-oxide, or a mixture of same.

DETAILED DESCRIPTION

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "unsubstituted or substituted" means that the number of substituents can be equal to or different from zero. Unless otherwise indicated, it is possible that substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two, three, four or five identical or different substituents, particularly with one, two or three substituents.

Oxo, an oxo group or an oxo substituent means a doubly attached oxygen atom =o. Oxo may be attached to atoms of suitable valency, for example to a saturated carbon atom or to a sulfur atom. For example, but without limitation, one oxo group is can be attached to a carbon atom, resulting in the formation of a carbonyl group C(=O), or two oxo groups are can be attached to one sulfur atom, resulting in the formation of a sulfonyl group —(=O)$_2$. The term "ring substituent" means a substituent attached to an aromatic or nonaromatic ring which replaces an available hydrogen atom on the ring.

Should a composite substituent be composed of more than one parts, e.g., ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of" but does not have to be the scope indicated by "consisting of.

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The terms as mentioned in the present text have the following meanings:

The term "halogen atom" means a fluorine, chlorine, bromine or iodine atom, particularly a fluorine, chlorine or bromine atom.

The term "$C_1$-$C_8$-alkyl-" means a linear or branched, saturated hydrocarbon group having 1, 2, 3, 4, 5, 6, 7 or 8 carbon atoms, e.g., a methyl-, ethyl-, propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-, n-heptyl-, 5-methylhexyl-, 4-methylhexyl-, 2-methylhexyl-, 1-methylhexyl-, 2-ethylpentyl-, 1-ethylpentyl-, 3,3-dimethylpentyl-, 2,2-dimethylpentyl-, 1,1-dimethylpentyl-, 2,3-dimethylpentyl-, 1,3-dimethylpentyl-, 1,2-dimethylpentyl-, n-octyl-, 6-methylheptyl-, 4-methylheptyl-, 2-methylheptyl-, 1-methylheptyl-, 2-ethylhexyl-, 1-ethylhexyl-, 3,3-dimethylhexyl-, 2,2-dimethylhexyl-, 1,1-dimethylhexyl-, 2,3-dimethylhexyl-, 1,3-dimethylhexyl-, 1,2-dimethylhexyl-group, or an isomer thereof. Preferably, said group has 1, 2, 3, 4, 5 or 6 carbon atoms ("$C_1$-$C_6$-alkyl-"), e.g., a methyl-, ethyl-, n-propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl- or 1,2-dimethylbutyl group, or an isomer thereof. More preferably, said group has 1, 2, 3 or 4 carbon atoms ("$C_1$-$C_4$-alkyl-"), e.g., a methyl-, ethyl-, n-propyl-, iso-propyl-, n-butyl-, iso-butyl-, sec-butyl- or tert-butyl- group, 1, 2 or 3 carbon atoms ("$C_1$-$C_3$-alkyl-"), e.g., a methyl-, ethyl-, n-propyl- or iso-propyl group, or 1 or 2 carbon atoms ("$C_1$-$C_2$-alkyl-"), e.g., a methyl group or an ethyl group.

The same definitions can be applied should the alkyl group be placed within a chain as a bivalent "$C_1$-$C_6$-alkylene" moiety. All names as mentioned above then will bear an "ene" added to the end, thus e.g., a "pentyl" becomes a bivalent "pentylene" group. In addition, the term "$C_1$-$C_6$-heteroalkyl" refers to a $C_1$-$C_6$-alkyl group in which one or more of the carbon atoms have been replaced with an atom selected from N, O, S, or P, which are substituted as mentioned herein to satisfy atom valency requirements.

The term "$C_2$-$C_6$-alkylene" means a linear or branched, saturated, divalent hydrocarbon chain (or "tether") having 2, 3, 4, 5 or 6 carbon atoms, e.g., —CH$_2$—CH$_2$— ("ethylene" or "$C_2$-alkylene"), —CH$_2$—CH$_2$—CH$_2$—, —C(H)(CH$_3$)—CH$_2$— or —C(CH$_3$)$_2$— ("propylene" or "$C_3$-alkylene"), or, for example —CH$_2$—C(H)(CH$_3$)—CH$_2$—, CH$_2$—C(CH$_3$)$_2$—, —CH$_2$—CH$_2$—CH$_2$—CH$_2$— ("butylene" or "$C_4$-alkylene"), "$C_5$-alkylene", e.g., —CH$_2$—CH$_2$—CH$_2$—CH$_2$—CH$_2$— ("n-pentylene"), or "—$C_6$-alkylene-", e.g., —CH$_2$—CH$_2$—CH$_2$—CH$_2$—CH$_2$—CH$_2$— ("n-hexylene") or a —C(CH$_3$)$_2$—C(CH$_3$)$_2$ group.

The term "hydroxy-($C_1$-$C_6$-alkyl)-" means a linear or branched, saturated, hydrocarbon group in which one or more hydrogen atoms of a "$C_1$-$C_6$-alkyl-" as defined supra are each replaced by a hydroxy group, e.g., a hydroxymethyl-, 1-hydroxyethyl-, 2-hydroxyethyl-, 1,2-dihydroxyethyl-, 3-hydroxypropyl-, 2-hydroxypropyl-, 2,3-dihydroxypropyl-, 1,3-dihydroxypropan-2-yl-, 3-hydroxy-2-methylpropyl-, 2-hydroxy-2-methyl-propyl-, or a 1-hydroxy-2-methyl-propyl- group. Particularly the hydroxyalkyl group means a linear or branched, saturated, monovalent hydrocarbon group has 1, 2 or 3 carbon atoms in which 1 hydrogen atom is replaced with a hydroxy group e.g. a hydroxymethyl-, 1-hydroxyethyl-, 2-hydroxyethyl-, 3-hydroxypropyl-, 2-hydroxypropyl-, 1-hydroxypropyl-, 2-hydroxy-2-methyl-ethyl group.

The term "$C_1$-$C_6$-haloalkyl" means a linear or branched, saturated, monovalent hydrocarbon group in which the term "$C_1$-$C_6$-alkyl" is as defined supra and in which one or more of the hydrogen atoms are replaced, identically or differently, with a halogen atom. Preferably, said halogen atom is a fluorine atom. Said $C_1$-$C_6$-haloalkyl, particularly a $C_1$-$C_3$-haloalkyl group is, for example, fluoromethyl-, difluoromethyl-, trifluoromethyl-, 2-fluoroethyl-, 2,2-difluoroethyl-, 2,2,2-trifluoroethyl-, pentafluoroethyl-, 3,3,3-trifluoropropyl- or a 1,3-difluoropropan-2-yl group.

The term "$C_1$-$C_6$-alkoxy" means a linear or branched, saturated, monovalent group of formula ($C_1$-$C_6$-alkyl)-O—, in which the term "$C_1$-$C_6$-alkyl" group is as defined supra, e.g. methoxy-, ethoxy-, n-propoxy-, isopropoxy-, n-butoxy-, sec-butoxy-, isobutoxy-, tert-butoxy-, pentyloxy-, isopentyloxy- or a n-hexyloxy group, or an isomer thereof.

The term "$C_1$-$C_6$-alkylthio" or "$C_1$-$C_6$-thioalkyl" means a linear or branched, saturated, monovalent group of formula ($C_1$-$C_6$-alkyl)-S—, in which the term "$C_1$-$C_6$-alkyl" is as defined supra, e.g. methylthio-, ethylthio-, n-propylthio-, isopropylthio-, n-butylthio-, sec-butylthio-, isobutylthio-, tert-butylthio-, pentylthio-, isopentylthio- or a n-hexylthio group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Preferably, said halogen atom in "$C_1$-$C_6$-haloalkoxy-" is fluorine, resulting in a group referred herein as "$C_1$-$C_6$-fluoroalkoxy-". Representative $C_1$-$C_6$-fluoroalkoxy- groups include, for example, —$OCF_3$, —$OCHF_2$, —$OCH_2F$, —$OCF_2CF_3$ and —$OCH_2CF_3$.

The term "$C_1$-$C_6$-haloalkylthio" or "$C_1$-$C_6$-halothioalkyl" or "$C_1$-$C_6$-haloalkyl-S—" means a linear or branched, saturated, monovalent $C_1$-$C_6$-alkylthio group, as defined supra, in which one or more of the hydrogen atoms is replaced, identically or differently, with a halogen atom. Preferably, said halogen atom in "$C_1$-$C_6$-haloalkylthio-" is fluorine.

The term "$C_2$-$C_6$-alkenyl-" means a linear or branched, monovalent hydrocarbon group, which contains one or more double bonds and which has 2, 3, 4, 5 or 6 carbon atoms, preferably 2, 3 or 4 carbon atoms ("$C_2$-$C_4$-alkenyl-") or 2 or 3 carbon atoms ("$C_2$-$C_3$-alkenyl-"), it being understood that in the case in which said alkenyl- group contains more than one double bond, then said double bonds may be isolated from, or conjugated with, each other. Representative alkenyl groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl, 2-methylprop-2-enyl-, 1-methylprop-2-enyl-, 2-methylprop-1-enyl-, (E)-1-methylprop-1-enyl-, (Z)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propyl prop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and a 1-(1,1-dimethylethyl-)ethenyl group. Particularly, said group is an ethenyl- or a prop-2-enyl group.

The same definitions can be applied should the alkenyl group be placed within a chain as a bivalent "$C_2$-$C_6$-alkenylene" moiety. All names as mentioned above then will bear a "ene" added to their end, thus e.g., a "pentenyl" becomes a bivalent "pentenylene" group.

The term "$C_2$-$C_6$-haloalkenyl-" means a linear or branched hydrocarbon group in which one or more of the hydrogen atoms of a "$C_2$-$C_6$-alkenyl-" as defined supra are each replaced, identically or differently, by a halogen atom. Preferably, said halogen atom is fluorine, resulting in a group referred herein as "$C_2$-$C_6$-fluoroalkenyl-". Representative $C_2$-$C_6$-fluoroalkenyl- groups include, for example, —$CH=CF_2$, —$CF=CH_2$, —$CF=CF_2$, —$C(CH_3)=CF_2$, —$CH=C(F)$—$CH_3$, —$CH_2$—$CF=CF2$ and —$CF_2$—$CH=CH_2$.

The term "$C_2$-$C_6$-alkynyl-" means a linear or branched, monovalent hydrocarbon group which contains one or more triple bonds, and which contains 2, 3, 4, 5 or 6 carbon atoms, preferably 2, 3 or 4 carbon atoms ("$C_2$-$C_4$-alkynyl-") or 2 or 3 carbon atoms ("$C_2$-$C_3$-alkynyl-"). Representative $C_2$-$C_6$-alkynyl- groups include, for example, an ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methyl-pent-4-ynyl-, 2-methylpent-3-ynyl-, 1-methylpent-3-ynyl-, 4-methylpent-2-ynyl-, 1-methyl-pent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and a 3,3-dimethylbut-1-ynyl- group. Particularly, said alkynyl- group is an ethynyl-, a prop-1-ynyl- or a prop-2-ynyl- group.

The term "$C_3$-$C_{10}$-cycloalkyl-" means a saturated mono- or bicyclic hydrocarbon ring which contains 3, 4, 5, 6, 7, 8, 9 or 10 carbon atoms ("$C_3$-$C_{10}$-cycloalkyl-"). Said $C_3$-$C_{10}$-cycloalkyl- group may be, for example, a monocyclic hydrocarbon ring, e.g., a cyclopropyl-, cyclobutyl-, cyclopentyl-, cyclohexyl- or cycloheptyl- group, or a bicyclic hydrocarbon ring, such as a decalinyl group. Preferably, said hydrocarbon ring is monocyclic and contains 3, 4, 5, 6 or 7 carbon atoms ("$C_3$-$C_7$-cycloalkyl-"), e.g., a cyclopropyl-, cyclobutyl-, cyclopentyl-, cyclohexyl- or cycloheptyl- group, or 3, 4, 5 or 6 carbon atoms ("$C_3$-$C_6$-cycloalkyl-"), e.g., a cyclopropyl-, cyclobutyl-, cyclopentyl- or a cyclohexyl- group. A cycloalkyl group may be unsubstituted or substituted as defined at the respective part wherein such term is used.

The term "1,2($C_3$-$C_5$)cycloakylene is used in the definition of —$R^6$-$R^7$— and means particularly

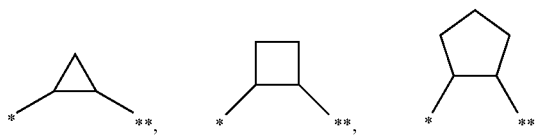

where * is the point of attachment of the ring to the adjacent —$CH_2$— group or to the indole nitrogen atom and ** is the point of attachment to the adjacent —$CH_2$— group or to —B)$_t$—.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g., a cyclobutenyl-, cyclopentenyl-, cyclohexenyl-, cycloheptenyl- or a cyclooctenyl group, or a bicyclic hydrocarbon ring, e.g., a bicyclo[2.2.1]hept-2-enyl or a bicyclo[2.2.2]oct-2-enyl group.

The term "4- to 10-membered heterocycloalkyl-" means a saturated mono- or bicyclic hydrocarbon ring which contains 3, 4, 5, 6, 7, 8 or 9 carbon atoms, and which contains 1, 2, 3 or 4 heteroatoms which may be identical or different, said heteroatoms are preferably selected from oxygen, nitrogen or sulfur, and wherein carbon atoms and heteroatoms add up to 4, 5, 6, 7, 8, 9 or 10 ring atoms in total, it being possible for said heterocycloalkyl- group to be attached to the rest of the molecule via any one of the carbon atoms or, if present, a nitrogen atom. "Heterospirocycloalkyl-", "heterobicycloalkyl-" and "bridged heterocycloalkyl-", as defined infra, are also included within the scope of this definition.

Preferably, said "4- to 10-membered heterocycloalkyl-" group is monocyclic and contains 3, 4, 5 or 6 carbon atoms, and one or two of the above-mentioned heteroatoms, adding up to 4, 5, 6 or 7 ring atoms in total (a "4- to 7-membered monocyclic heterocycloalkyl-"), or contains 3, 4 or 5 carbon atoms, and one or two of the above-mentioned heteroatoms, adding up to 4, 5 or 6 ring atoms in total (a "4- to 6-membered monocyclic heterocycloalkyl-"), or contains 3, 4 or 5 carbon atoms, and one or two of the above-mentioned heteroatoms, adding up to 5 or 6 ring atoms in total (a "5- to 6-membered monocyclic heterocycloalkyl-"); it being possible for said heterocycloalkyl- group to be attached to the rest of the molecule via any one of the carbon atoms or the nitrogen atoms, if present.

Exemplarily, without being limited thereto, said "4-membered to 7-membered monocyclic heterocycloalkyl-", can be a 4-membered ring, a "4-membered heterocycloalkyl-" group, such as an azetidinyl- or an oxetanyl group; or a 5-membered ring, a "5-membered heterocycloalkyl-" group, such as a tetrahydrofuranyl-, dioxolinyl-, pyrrolidinyl-, imidazolidinyl-, pyrazolidinyl- or a pyrrolinyl group; or a 6-membered ring, a "6-membered heterocycloalkyl-" group, such as a tetrahydropyranyl-, piperidinyl-, morpholinyl-, 3-oxomorpholin-4-yl, dithianyl-, thiomorpholinyl- or a piperazinyl group; or a 7-membered ring, a "7-membered heterocycloalkyl-" group, such as an azepanyl-, diazepanyl- or an oxazepanyl group, for example. The heterocycloalkyl groups may be one or more times substituted with $C_1$-$C_3$-alkyl, $C_1$-$C_3$-alkoxy, hydroxy, halogen or a carbonyl group.

The term "5- to 7-membered heterocycloalkenyl" means a monocyclic, unsaturated, non-aromatic heterocycle with 5, 6, or 7 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, a 4H-pyranyl-, 3,6-dihydro-2H-pyran-4-yl-, 2H-pyranyl-, dihydropyridinyl-, tetrahydropyridinyl-, 2-oxopyridin-1(2H)-yl-, 2,5-dihydro-1H-pyrrolyl-, [1,3]dioxolyl-, 4H-[1,3,4]thiadiazinyl-, 2,5-dihydrofuranyl-, 2,3-dihydrofuranyl-, 2,5-dihydrothiophenyl-, 2,3-dihydrothiophenyl-, 4,5-dihydrooxazolyl- or a 4H-[1,4]thiazinyl group. Those heterocycloalkenyl groups may be substituted with a hydroxy group or a methoxy group.

The term "fused heterocycloalkyl" or "heterobicycloalkyl-" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl or "heterobicycloalkyl-" group is, for example, an azabicyclo[3.3.0]octyl-, azabicyclo[4.3.0]nonyl-, diazabicyclo[4.3.0]nonyl-, oxazabicyclo[4.3.0]nonyl-, an thiazabicyclo[4.3.0]nonyl- or an azabicyclo[4.4.0]decyl group.

The term "aryl" means a phenyl-, naphthyl-, 5,6-dihydronaphthyl-, 7,8-dihydronaphthyl-, 5,6,7,8-tetrahydronaphthyl- indanyl-, or an indenyl group, which is unsubstituted or substituted with one, two, three, four or five substituents, each substituent independently selected from halogen, cyano, $C_1$-$C_3$-alkyl, $C_1$-$C_3$-haloalkyl, $C_1$-$C_3$-alkoxy, $C_1$-$C_3$-thioalkyl, $C_1$-$C_3$-haloalkoxy, $C_1$-$C_3$-halothioalkyl, $C_3$-$C_5$-cycloalkyl, particularly halogen, $C_1$-$C_3$-alkyl, $C_1$-$C_3$-haloalkyl, $C_1$-$C_3$-alkoxy, $C_1$-$C_3$-haloalkoxy.

The term "heteroaryl-" means a monocyclic, bicyclic or tricyclic aromatic ring system having 5, 6, 7, 8, 9, 10, 11, 12, 13 or 14 ring atoms (a "5- to 14-membered heteroaryl-" group), preferably 5, 6, 9 or 10 ring atoms, and which contains 1, 2, 3 or 4 heteroatoms which may be identical or different, said heteroatoms selected from oxygen, nitrogen and sulfur. Said heteroaryl- group can be a 5-membered heteroaryl- group, such as, for example, thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or tetrazolyl-; or a 6-membered heteroaryl- group, such as, for example, pyridyl-, pyridazinyl-, pyrimidyl-, pyrazinyl- or triazinyl-; or a benzo-fused 5-membered heteroaryl- group, such as, for example, benzofuranyl-, benzothienyl-, benzoxazolyl-, benzisoxazolyl-, benzimidazolyl-, benzothiazolyl-, benzotriazolyl-, indazolyl-, indolyl- or isoindolyl-; or a benzo-fused 6-membered heteroaryl- group, such as, for example, quinolinyl-, quinazolinyl-, isoquinolinyl-, cinnolinyl-, phthalazinyl- or quinoxalinyl-; or another bicyclic group, such as, for example, indolizinyl-, purinyl- or pteridinyl-; or a tricyclic heteroaryl- group, such as, for example, carbazolyl-, acridinyl- or phenazinyl-.

Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur ("5- to 6-membered monocyclic heteroaryl-"), such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-, pyridyl-, pyridazinyl-, pyrimidyl-, pyrazinyl- or a triazinyl- group.

In general, and unless otherwise mentioned, said heteroaryl- groups include all the possible isomeric forms thereof, e.g., the positional isomers thereof. Thus, for some illustrative non-restricting example, the term pyridyl- includes a pyridin-2-yl-, pyridin-3-yl- and a pyridin-4-yl- group; the term thienyl- includes a thien-2-yl- and a thien-3-yl- group. Furthermore, said heteroaryl- groups can be attached to the rest of the molecule via any one of the carbon atoms, or, if applicable, a nitrogen atom, e.g., pyrrol-1-yl-, pyrazol-1-yl- or imidazol-1-yl-.

In general, and unless otherwise mentioned, the heteroaryl or heteroarylene groups include all possible isomeric forms thereof, e.g., tautomers and positional isomers with respect to the point of linkage to the rest of the molecule. Thus, for some illustrative non-restricting examples, the term pyridinyl includes a pyridin-2-yl, pyridin-3-yl and a pyridin-4-yl group; or the term thienyl includes thien-2-yl and thien-3-yl.

Particularly, the heteroaryl group is a pyridyl- or pyrimidyl group or a imidazolyl group. including a hydroxy substitution of the pyridyl group leading e.g. to a 2-hydroxypyridine which is the tautomeric form to a 2-oxo-2(1H)-pyridine.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_2$, $C_1$-$C_3$, $C_1$-$C_4$, $C_1$-$C_5$, $C_1$-$C_6$; more preferably $C_1$-$C_4$; in the case of "$C_1$-$C_6$-haloalkyl-" or "$C_1$-$C_6$-haloalkoxy-" even more preferably $C_1$-$C_2$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl- group or an alkynyl group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_5$, $C_3$-$C_4$, $C_2$-$C_3$, $C_2$-$C_4$, $C_2$-$C_5$; preferably $C_2$-$C_3$.

Further, as used herein, the term "$C_3$-$C_7$", as used throughout this text, e.g., in the context of the definition of "$C_3$-$C_7$-cycloalkyl-", is to be understood as meaning a cycloalkyl- group having a whole number of carbon atoms of 3 to 7, i.e., 3, 4, 5, 6 or 7 carbon atoms. It is to be understood further that said term "$C_3$-$C_7$" is to be interpreted as disclosing any sub-range comprised therein, e.g., $C_3$-$C_6$, $C_4$-$C_5$, $C_3$-$C_5$, $C_3$-$C_4$, $C_4$-$C_6$, $C_5$-$C_7$; preferably $C_3$-$C_6$.

As used herein, the term "leaving group" refers to an atom or a group of atoms that is displaced in a chemical reaction as stable species taking with it the bonding electrons, e.g., typically forming an anion. Preferably, a leaving group is selected from the group comprising: halo, in particular a chloro, bromo or iodo, (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitrophenyl) sulfonyl]oxy-, [(4-isopropylphenyl)sulfonyl]oxy-, [(2,4,6-triisopropylphenyl)sulfonyl]oxy-, [(2,4,6-trimethylphenyl) sulfonyl]oxy-, [(4-tert-butylphenyl)sulfonyl]oxy-, (phenylsulfonyl)oxy-, and a [(4-methoxyphenyl)sulfonyl] oxy group.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are described for example in T. W. Greene and P. G. M. Wuts in *Protective Groups in Organic Synthesis,* 4th edition, Wiley 2006; more specifically, protective groups for amino groups can be selected from substituted sulfonyl groups, such as a mesyl-, tosyl- or a phenylsulfonyl group, acyl groups such as a benzoyl-, acetyl- or a tetrahydropyranoyl group, or carbamate based groups, such as a tert-butoxycarbonyl group (Boc). Protective groups for hydroxy groups can be selected from acyl groups such as a benzoyl-, acetyl, pivaloyl- or a tetrahydropyranoyl group, or can include silicon, as in e.g., a tert-butyldimethylsilyl-, tert-butyldiphenylsilyl-, triethylsilyl- or a triisopropylsilyl group.

The term "substituent" refers to a group "substituted" on, e.g., an alkyl, haloalkyl, cycloalkyl, heterocyclyl, heterocycloalkenyl, cycloaikenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline.

It is possible for the compounds of general formula (I) to exist as isotopic variants. The invention therefore includes one or more isotopic variant(s) of the compounds of general formula (I), particularly deuterium-containing compounds of general formula (I).

The invention also includes all suitable isotopic variations of a compound of the invention.

The term "isotopic variant" of a compound or a reagent is defined as a compound exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70(1), 217-235, 1998.

An isotopic variation of a compound of the invention is defined as one in which at least one atom is replaced by an atom having the same atomic number but an atomic mass different from the atomic mass usually or predominantly found in nature.

Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Accordingly, recitation of "hydrogen" or "H" should be understood to encompass $^1$H (protium), $^2$H (deuterium), and $^3$H (tritium) unless otherwise specified. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

With respect to the treatment and/or prophylaxis of the disorders specified herein, the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful, e.g., in drug and/or substrate tissue distribution studies. These isotopes are particularly preferred for the ease of their incorporation and detectability. Positron-emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of vulnerability to metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g., cytochrome $P_{450}$.

For example, in some embodiments, the present invention concerns a deuterium-containing compound of general formula (I), e.g.:

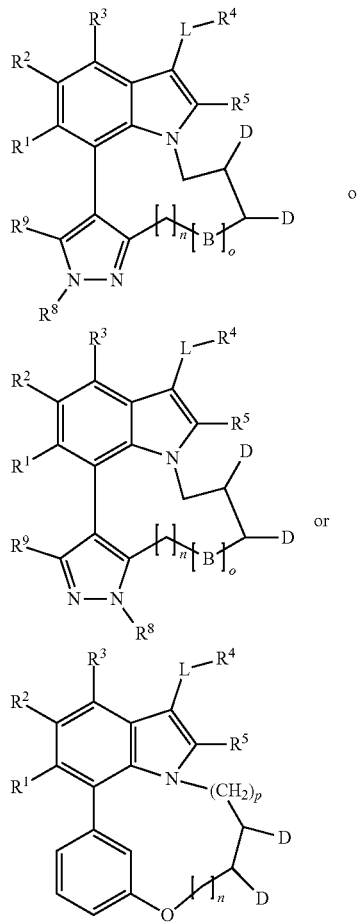

Such deuterium-containing compounds can be prepared by methods well-known to the person skilled in the art. Particularly, such deuterium-containing compounds can be prepared from the corresponding olefins, which are available by methods known to the person skilled in the art, such as ring closing metathesis reactions, as discussed e.g., in the general description of the synthesis of compounds of general formula (I), infra, in the context of Schemes 2c and 2j, respectively.

Where the plural form of the word compounds, salts, polymorphs, hydrates, solvates and the like, is used herein, this is taken to mean also a single compound, salt, polymorph, isomer, hydrate, solvate or the like. The terms "a" or "an," as used in herein means one or more.

By "stable compound" or "stable structure" is meant a compound that is sufficiently robust to survive isolation to a useful degree of purity from a reaction mixture, and formulation into an efficacious therapeutic agent.

Compounds of the present invention, as well as the corresponding macrocyclic intermediates of formula (II), are typically chiral merely as a result of restricted rotation around at least one single bond, which is due to limited comformational flexibility of their macrocyclic core as a whole or even of open chain precursors. Hence, compounds of the present invention as well as the corresponding macrocyclic intermediates of formula (II), can exist as atropisomers. Atropisomers represent a subclass of conformers which arise from restricted rotation around a single bond. The conformers (called atropisomers) can be isolated as separated species (IUPAC Gold book, http://goldbook.iupac.org/A00511.html; Pure and Appl. Chem., 2009, 68, 2193-2222). This induced chirality belongs to the axial type of chirality. The compounds of the present invention as well as the corresponding macrocyclic intermediates of formula (II), furthermore optionally contain one or more asymmetric centrers, depending upon the location and nature of the various substituents desired. It is possible that one or more asymmetric carbon atoms are present in the (R) or (S) configuration, which can result in racemic mixtures in the case of a single asymmetric center, and in diastereomeric mixtures in the case of multiple asymmetric centers. Hence, compounds of the present invention, as well as the corresponding macrocyclic intermediates of formula (II), featuring the abovementioned atropisomerism and an additional asymmetric centre can also exist as diasteromeric mixtures as described supra.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

If only one isomer (enantiomer) displays the desired biological activity, and the second isomer (enantiomer) is inactive, the preferred isomer is the one which produces the more desirable biological activity. Should one isomer (enantiomer/diastereomer) display better activity than the other isomer (enantiomer/diastreromer) the preferred isomer is the one which produces the better biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions, and other suitable methods.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

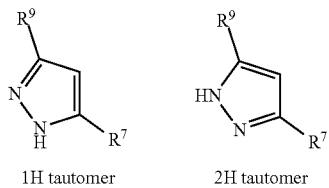

1H tautomer    2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19. It includes any physiologically acceptable salt as referred to below.

Physiologically acceptable salts of the compounds according to the invention encompass acid addition salts of mineral acids, carboxylic acids and sulfonic acids, for example salts of hydrochloric acid, hydrobromic acid, hydroiodic acid, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalenedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol.

Additionally, the compounds according to the invention may form salts with a quaternary ammonium ion obtainable, e.g., by quaternisation of a basic nitrogen-containing group with agents such as lower alkylhalides such as methyl-, ethyl-, propyl-, and butylchlorides, -bromides and -iodides; dialkylsulfates such as dimethyl-, diethyl-, dibutyl- and diamylsulfates, long chain halides such as decyl-, lauryl-, myristyl- and stearylchlorides, -bromides and -iodides, aralkylhalides such as benzyl- and phenethylbromides and others. Examples of suitable quaternary ammonium ions are tetramethylammonium, tetraethylammonium, tetra(n-propyl)ammonium, tetra (n-butyl)ammonium, or N-benzyl-N,N,N-trimethylammonium.

The present invention includes all possible salts of the compounds of the present invention as single salts, or as any mixture of said salts, in any ratio.

Unless specified otherwise, suffixes to chemical names or structural formulae relating to salts, such as "hydrochloride", "trifluoroacetate", "sodium salt", or "x HCl", "x CF$_3$COOH", "x Na+", for example, mean a salt form, the stoichiometry of which salt form not being specified.

Solvates and hydrates of disclosed intermediates or example compounds, or salts thereof, which have been obtained, by the preparation and/or purification processes described herein, may be formed in any ratio.

Furthermore, the present invention includes all possible crystalline forms, or polymorphs, of the compounds of the present invention, either as a single polymorph, or as a mixture of more than one polymorph, in any ratio.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. For example, a prodrug may be in the form of an in vivo hydrolysable ester of the specified compound. Derivatives of the compounds of formula (I) and the salts thereof which are converted into a compound of formula (I) or a salt thereof in a biological system (bioprecursors or pro-drugs) are covered by the invention. Said biological system may be, for example, a mammalian organism, particularly a human subject. The bioprecursor is, for example, converted into the compound of formula (I) or a salt thereof by metabolic processes.

Description

In accordance with a first aspect, the present invention provides compounds of formula (I)

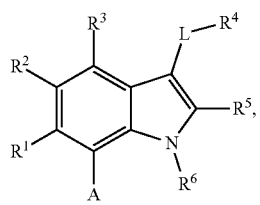

(I)

wherein
A is

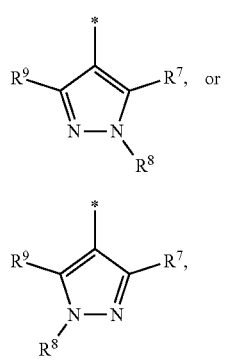

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;

or
A is

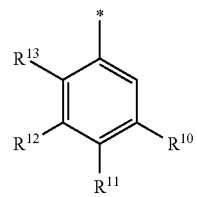

(A3)

wherein optionally one or two of the groups selected from $CR^{11}$, $CR^{12}$ and $CR^{13}$ are replaced by a nitrogen atom,
wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ is a fluorine atom,
$R^2$ and $R^3$ are each a hydrogen atom;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group, and a $C_3$-$C_5$-cycloalkyl group;
L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —(O)— group, a —S(O)$_2$— group, and a —$NR^{14}$— group;
E is a bond, an oxygen atom, a sulfur atom, a —S(O)— group, a —S(O)$_2$— group or a —$NR^{14}$— group and constitutes the connecting element to $R^4$,
m is 2, 3, or 4;
$R^5$ is selected from a COOH group, a

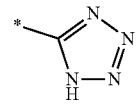

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group, and a —C(O)—NHS(O)$_2$(CH$_2$)$_s$NHCO(aryl) group;
—$R^6$-$R^7$— is selected from $^\#$—(CH$_2$)$_n$—(B)$_t$—(CH$_2$)$_p$—X—$^{\#\#}$, $^\#$—(C$_2$-$C_6$-alkenylene)-(B)$_t$—(CH$_2$)$_p$—X—$^{\#\#}$, $^\#$—(CH$_2$)$_n$—(B)$_t$—(C$_2$-$C_5$-alkenylene)-X—$^{\#\#}$, $^\#$—(CH$_2$)$_q$—(B)—(CH$_2$)$_r$—(B)—(CH$_2$)$_v$—X—$^{\#\#}$,
wherein $^\#$ is the point of attachment with the indole nitrogen atom and $^{\#\#}$ is the point of attachment with the pyrazole carbon atom bearing the $R^7$ substituent; and wherein one or more —CH$_2$— groups may be unsubstituted or substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, and where a —H═CH— group in any alkenylene can be replaced by a 1,2-(C$_3$-C$_5$)cycloalkylene group which is unsubstituted or substituted one or two times with a halogen atom or a C$_1$-C$_2$-alkyl group; and where X is an unsubstituted —H$_2$— group;

—R$^6$-R$^{10}$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$, wherein $^{\#}$ is the point of attachment with the indole nitrogen atom and $^{\#\#}$ is the point of attachment with the carbon atom of the phenyl moiety bearing the R$^{10}$ substituent, one or more —CH$_2$— groups may be unsubstituted or substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, where a —CH═CH— group in any alkenylene can be replaced by a 1,2-(C$_1$-C$_6$)cycloalkylene group which is unsubstituted or substituted one or two times with a halogen atom or a C$_1$-C$_2$-alkyl group, and where X is an unsubstituted —H$_2$— group;

n is 2, 3, 4, 5, 6, 7, 8, or 9;

t is 0 or 1;

p is 0, 1, 2, 3, 4, or 5;

q is 2, 3, 4, 5, or 6;

r is 2, 3, 4, 5, or 6;

v is 0 or 1;

s is 0, 1, 2, or 3;

where the integers selected for variables n, r, and v result in forming a 9- to 16-membered ring independently from the selection of variable A1, A2 or A3;

B is independently selected from a —C(O)NR$^{15}$— group, a —NR$^{15}$C(O)— group, a —N(R$^{15}$)— group, a —[N(CH$_3$)$_2$]$^+$— group, a —N(R$^{15}$)—C(═O)—N(R$^{15}$)— group, a —O—C(═O)—N(R$^{15}$)— group, a —N(R$^{15}$)—C(═O)—O— group, —O—, —S—, —S(O)—, and —S(O)$_2$—:

R$^9$ is selected from a hydrogen atom, a C$_1$-C$_6$-alkyl group, which is unsubstituted or substituted with one or more substituents independently selected from a halogen atom, a hydroxyl group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group; and a C$_3$-C$_6$-cycloalkyl group, R$^9$ is selected from a hydrogen atom, a C$_1$-C$_4$-alkyl group, a C$_1$-C$_3$-hydroxyalkyl group, a C$_1$-C$_4$-haloalkyl group, a C$_1$-C$_4$-haloalkyl-NH—C(O)—O—(C$_1$-C$_3$-alkylene)- group, a C$_2$-C$_6$-haloalkenyl group, a C$_1$-C$_6$-alkyl-O— group, a C$_1$-C$_4$-haloalkoxy group, a C$_1$-C$_6$-alkyl-O—(C$_1$-C$_3$-alkylene)- group, a (C$_3$-C$_7$)-cycloalkyl group, a (C$_3$-C$_7$)-cycloalkyl-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a R$^{18}$-(phenylene)-(C$_1$-C$_3$-alkylene)-O—(C$_1$-C$_3$-alkylene)- group, a R$^{18}$-(phenylene)-O—(C$_1$-C$_3$-alkylene)- group, a R$^{18}$-(phenylene)-(heteroarylene)-O—(C$_1$-C$_3$-alkylene) group, a (R$^{18}$)-(heterocycloalkylene)-(C$_1$-C$_3$-alkylene)- group, a (R$^{18}$)-(heterocycloalkylene)-(phenylene)-O—(C$_1$-C$_3$-alkylene)- group, a (heterocycloalkenyl)-(phenylene)-O—(C$_1$-C$_3$-alkylene)- group, a (R$^{18}$)-(heteroarylene)-(C$_1$-C$_3$-alkylene)-O—(C$_1$-C$_3$-alkylene)- group, a (R$^{18}$)-(heteroarylene)-(phenylene)-O—(C$_1$-C$_3$-alkylene)- group, a (R$^{19}$)—S(O)$_2$-(phenylene)-O—(C$_1$-C$_3$-alkylene)- group, a (R$^{19}$)—S(O)$_2$—NH-(phenylene)-O—(C$_1$-C$_3$-alkylene)- group, a (R$^{19}$)—S(O)$_2$—NH-(phenylene)-O—(C$_1$-C$_3$-alkylene)- group, a (R$^{19}$)—S(O)$_2$—N(C$_1$-C$_6$-alkyl)-(phenylene)-O—(C$_1$-C$_3$-alkylene)- group, a (R$^{19}$)—S(O)$_2$-(heterocycloalkylene)-(phenylene)-O—(C$_1$-C$_3$-alkylene)- group, a (R$^{18}$)-(heterocycloalkylene)-(heteroarylene)-O—(C$_1$-C$_3$-alkylene)- group, a (R$^{19}$)-(heteroarylene)-O—(C$_1$-C$_3$-alkylene)- group, a (R$^{18}$)-(heteroarylene)-O—(C$_1$-C$_3$-alkylene)- group, a (R$^{19}$)—S(O)$_2$-(heteroarylene)-O—(C$_1$-C$_3$-alkylene)- group, a (R$^{19}$)—S(O)$_2$-(heterocycloalkylene)-(heteroarylene)-O—(C$_1$-C$_3$-alkylene)- group, a NR$^{20}$R$^{21}$—(C$_1$-C$_3$-alkylene)- group, a (C$_1$-C$_3$-alkyl)-NH—(C$_1$-C$_3$-alkylene)- group, a (C$_1$-C$_3$-haloalkyl)-(C$_1$-C$_3$-alkylene)-NH—(C$_1$-C$_3$-alkylene)- group, a (C$_1$-C$_3$-haloalkyl)-NH—(C$_1$-C$_3$-alkylene)- group, a (C$_1$-C$_3$-alkyl)-NH—C(O)—(C$_1$-C$_3$-alkylene)- group, a (C$_1$-C$_3$-alkyl)-NR$^{15}$—C(O)—(C$_1$-C$_3$-alkylene)- group, a (C$_1$-C$_3$-alkyl)-C(O)—NH—(C$_1$-C$_3$-alkylene)- group, a (C$_1$-C$_3$-alkyl)-C(O)—NR$^{15}$—(C$_1$-C$_3$-alkylene)- group, a

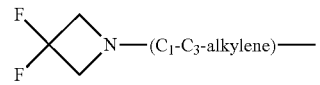

group, and a

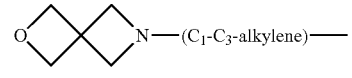

group, where the phenyl ring is unsubstituted or substituted with a halogen atom, a hydroxyl group, or a C$_1$-C$_3$-alkoxy group and the heterocycloalkyl group is unsubstituted or substituted with an oxo (═O) group or is unsubstituted or substituted with one or more substituents independently selected from a halogen atom, a hydroxyl group, a $C_1$-$C_3$-alkyl group, and a $C_1$-$C_3$-alkoxy group, or $R^8$ and $R^9$ together form a 5- or 6-membered ring optionally comprising one or two heteroatoms selected from —O— and —$NR^{14}$—;

$R^{11}$ and $R^{13}$ are each independently selected from a hydrogen atom, a halogen atom, a $C_1$-$C_3$-alkyl group, and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;

$R^{14}$ is a hydrogen atom or a $C_1$-$C_3$-alkyl group;

$R^{15}$ is independently selected from a hydrogen atom,
a $C_1$-$C_6$-alkyl group
which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;
a phenyl group,
a group

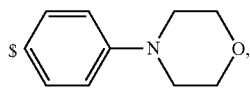

a group

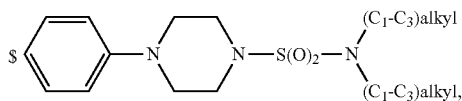

and
a group

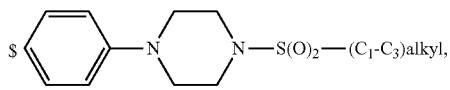

where $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;

$R^{18}$ is selected from a hydrogen atom, hydroxyl group, a cyano group, a $C_1$-$C_3$-alkyl group, a $C_1$-$C_6$-hydroxyalkyl group, a $C_1$-$C_3$-alkoxy group, a $R^{21}OC(O)$—($C_1$-$C_3$-alkylene)- group, a —$C(O)OR^{21}$ group, a —$C(O)NR^{20}R^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a $NR^{20}R^{21}$ group; and $R^{20}$ and $R^{21}$ are each independently selected from a hydrogen atom and a $C_1$-$C_6$-alkyl group;

or a tautomer, an N-oxide, or a salt thereof, or a salt of a tautomer, or a salt of an N-oxide, or a mixture of same.

Further Embodiments of the First Aspect of the Present Invention

In accordance with a further aspect, the present invention provides compounds of general formula (I), wherein A is

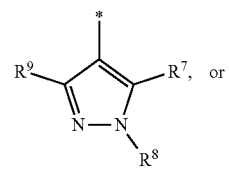

(A1)

or

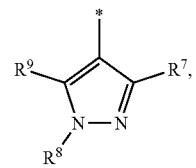

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ is a fluorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group and a —$NR^{14}$— group;

E is a bond, an oxygen atom, a sulfur atom, a —S(O)— group, a —S(O)$_2$— group or a —$NR^{14}$— group and constitutes the connecting element to $R^4$, $R^5$ is selected from a COOH group, a

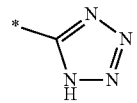

group, a —C(O)—NHS(O)$_2$(C$_1$-C$_6$-alkyl) group, a —C(O)—NHS(O)$_2$(C$_3$-C$_6$-cycloalkyl) group, a —C(O)—NHS(O)$_2$(aryl) group, a —C(O)—NHS(O)$_2$(CH$_2$)$_s$NHCO (C$_1$-C$_6$-alkyl) group, a —C(O)—NHS(O)$_2$(CH$_2$)$_s$NHCO (C$_3$-C$_6$-cycloalkyl) group and a —C(O)—NHS(O)$_2$(CH$_2$)$_s$NHCO(aryl) group;

—R$^6$-R$^7$— is selected from $^\#$—(CH$_2$)$_n$—(B)$_t$—(CH$_2$)$_p$—X—$^{\#\#}$, $^\#$—(C$_2$-C$_6$-alkenylene)-(B)$_t$—(CH$_2$)$_p$—X—$^{\#\#}$, $^\#$—(CH$_2$)$_n$—(B)$_t$(C$_2$-C$_5$-alkenylene)-X—$^{\#\#}$, and $^\#$—(CH$_2$)$_q$—(B)—(CH$_2$)$_r$—(B)—(CH$_2$)$_v$—X—$^{\#\#}$, wherein $^\#$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, a C$_1$-C$_3$-alkoxy group, and a C$_1$-C$_3$-haloalkoxy group, and where a —CH=CH— group in any alkenylene can be replaced by a 1,2-(C$_3$-C$_5$)cycloalkylene group which is unsubstituted or substituted one or two times with a halogen atom or a C$_1$-C$_2$-alkyl group, and where X is an unsubstituted CH$_2$— group;

n is 2, 3, 4, 5, 6, 7, 8, or 9;
p is 0, 1, 2, 3, 4, or 5;
t is 0 or 1;
s is 0, 1, 2, or 3;
where the integers selected for variables n, t, and p result in forming a 9- to 16-membered ring independently from the selection of variable A1 or A2;

B is independently selected from a —C(O)NR$^{15}$— group, a —NR$^{15}$C(O)— group, a —N(R$^{15}$)— group, a —[N(CH$_3$)$_2$]$^+$— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—:

R$^8$ is a hydrogen atom,
a C$_1$-C$_6$-alkyl group, which is unsubstituted or substituted with one or more substituents independently selected from a halogen atom, a hydroxyl group, a C$_1$-C$_3$-alkoxy group, a C$_1$-C$_3$-haloalkoxy group, a C$_3$-C$_6$-cycloalkyl group, a heterocycloalkyl group and a NR$^{20}$R$^{21}$ group;
a C$_1$-C$_3$-haloalkyl group,
a C$_3$-C$_6$-cycloalkyl group, and
a C$_1$-C$_6$-alkyl group in which one or two not directly adjacent carbon atoms are independently replaced by a heteroatom selected from —O— and —NH—;

R$^9$ is selected from a hydrogen atom,
a C$_1$-C$_4$-alkyl group,
a C$_1$-C$_3$-hydroxyalkyl group,
a C$_1$-C$_4$-haloalkyl group,
a C$_1$-C$_4$-haloalkyl-NH—C(O)—O—(C$_1$-C$_3$-alkylene)- group,
a C$_2$-C$_6$-haloalkenyl group,
a C$_1$-C$_6$-alkyl-O— group,
a C$_1$-C$_4$-haloalkoxy group,
a C$_1$-C$_6$-alkyl-O—(C$_1$-C$_3$-alkylene)- group,
a (C$_3$-C$_7$)-cycloalkyl group,
a (C$_3$-C$_7$-cycloalkyl)-O—(C$_1$-C$_3$-alkylene)- group,
a phenyl-O—(C$_1$-C$_3$-alkylene)- group,
a phenyl-(C$_1$-C$_3$-alkylene)-O—(C$_1$-C$_3$-alkylene)- group,
a (R$^{18}$)-(phenylene)-O—(C$_1$-C$_3$-alkylene)- group,
a (R$^{18}$)-(phenylene)-(C$_1$-C$_3$-alkylene)-O—(C$_1$-C$_3$-alkylene)- group,
a (R$^{18}$)-(phenylene)-(heteroarylene)-O—(C$_1$-C$_3$-alkylene)- group,
a (R$^{18}$)-(heterocycloalkylene)-(C$_1$-C$_6$-alkylene)- group,
a (R$^{18}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{18}$)-(heteroarylene)-(C$_1$-C$_3$-alkylene)-O—(C$_1$-C$_3$-alkylene)- group,
a (R$^{18}$)-(heteroarylene)-(phenylene)-O—(C$_1$-C$_3$-alkylene)- group,
a (R$^{18}$)-(phenylene)-(C$_1$-C$_3$-alkylene)-O—(C$_1$-C$_3$-alkylene)- group,
a (R$^{19}$)—S(O)$_2$-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—N(C$_1$-C$_6$-alkyl)-(phenylene)-O—(C$_1$-C$_3$-alkylene)- group,
a (R$^{19}$)—S(O)$_2$-(heterocycloalkylene)-(phenylene)-O—(C$_1$-C$_3$-alkylene)- group,
a (R$^{18}$)-(heterocycloalkylene)-(heteroarylene)-O—(C$_1$-C$_3$-alkylene)- group,
a (R$^{19}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a (R$^{19}$)—S(O)$_2$-(heterocycloalkylene)-(heteroarylene)-O—(C$_1$-C$_3$-alkylene)- group,
a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group
a (C$_1$-C$_3$-alkyl)-NR$^{15}$—C(O)—(C$_1$-C$_3$-alkylene)- group
a (C$_1$-C$_3$-alkyl)-C(O)—NH—(C$_1$-C$_3$-alkylene)- group
a (C$_1$-C$_3$-alkyl)-C(O)—NR$^{15}$—(C$_1$-C$_3$-alkylene)- group,
a

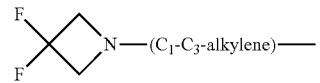

group, and a

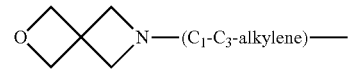

group,
where the phenyl ring is optionally substituted with a halogen atom, a hydroxyl group, or a C$_1$-C$_3$-alkoxy group and
the heterocycloalkyl group is optionally substituted with an oxo (=O) group or is optionally substituted with one or more substituents independently selected from a halogen atom and a C$_1$-C$_3$-alkyl group;
or R$^8$ and R$^9$ together form a 5- or 6-membered ring optionally comprising one or two heteroatoms selected from of —O—, and —NR$^{14}$—;

R$^{14}$ is a hydrogen atom or a C$_1$-C$_3$-alkyl group;
R$^{15}$ is independently selected from a hydrogen atom,
a C$_1$-C$_6$-alkyl group
which is optionally substituted with one or more substituents selected from a halogen atom, a C$_1$-C$_3$-alkyl group, a C$_1$-C$_3$-haloalkyl group, a C$_1$-C$_3$-hydroxyalkyl group, a $C_1$-$C_3$-alkoxy group, a $C_1$-$C_3$-haloalkoxy group, a heterocycloalkyl group, an aryl group, a $(R^{18})$-(heterocycloalkylene)-(arylene)-O— group, an aryl-O— group, an aryl-($C_1$-$C_3$-alkylene)-O— group, a $(R^{19})$—$S(O)_2$-arylene-O— group, a $(R^{19})S(O)_2$-heterocycloalkylene-arylene-O— group and an aryl-heteroarylene-O— group;

a phenyl group, a group

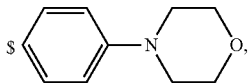

a group

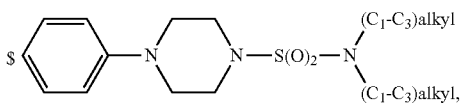

and a group

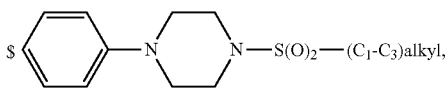

where $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)_2$— group and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}OC(O)$—($C_1$-$C_3$-alkylene)- group, a —$C(O)OR^{21}$ group, a —$C(O)NR^{20}R^{21}$ group, a ($C_1$-$C_3$-alkyl)-O—($C_1$-$C_3$-alkylene)-C(O)— group, ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group, and a $NR^{20}R^{21}$ group; and $R^{20}$ and $R^{21}$ are each independently selected from a hydrogen atom and a $C_1$-$C_6$-alkyl group;

or a tautomer, an N-oxide, or a salt thereof, or a salt of a tautomer, or a salt of an N-oxide, or a mixture of same.

In accordance with a further aspect, the present invention provides compounds of general formula (I): wherein
A is

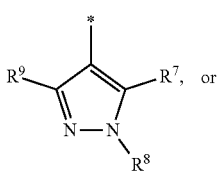

(A1)

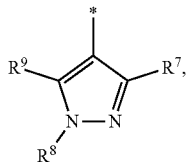

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ is a fluorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —$S(O)_2$— group and a —$NR^{14}$— group;

E is a bond, an oxygen atom, a sulfur atom, a —S(O)— group, a —$S(O)_2$— group or a —$NR^{14}$— group and constitutes the connecting element to $R^4$, $R^5$ is selected from a COOH group, a

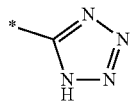

group, a —C(O)—$NHS(O)_2$($C_1$-$C_6$-alkyl) group, a —C(O)—$NHS(O)_2$($C_3$-$C_6$-cycloalkyl) group, a —C(O)—$NHS(O)_2$(aryl) group, a —C(O)—$NHS(O)_2(CH_2)_s$NHCO($C_1$-$C_6$-alkyl) group, a —C(O)—$NHS(O)_2(CH_2)_s$NHCO($C_3$-$C_6$-cycloalkyl) group and a —C(O)—$NHS(O)_2(CH_2)_s$NHCO(aryl) group;

—$R^6$-$R^7$— is selected from #—$(CH_2)_n$—(B)$_t$—$(CH_2)_p$—X—##, #—($C_2$-$C_6$-alkenylene)-(B)$_t$—$(CH_2)_p$—X—##, #—$(CH_2)_n$—(B)$_t$—($C_2$-$C_5$-alkenylene)-X—##, and #—$(CH_2)_q$—(B)—$(CH_2)_r$—(B)—$(CH_2)_v$—X—##, wherein # is the point of attachment with the indole nitrogen atom and ## is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group, and
 where a —CH═CH— group in any alkenylene can be replaced by a 1,2-cyclopropylene group or a 1,2-cyclobutylene group which are unsubstituted or substituted one or two times with a halogen atom or a $C_1$-$C_2$-alkyl group, and
 where X is an unsubstituted —CH$_2$— group;
n is 2, 3, 4, 5, 6, 7, 8, or 9;
p is 0, 1, 2, 3, 4, or 5;
t is 0 or 1;
s is 0, 1, 2, or 3;
where the integers selected for variables n, t, and p result in forming a 9- to 16-membered ring independently from the selection of variable A1 or A2;
B is independently selected from a —C(O)NR$^{15}$— group, a —NR$^{15}$C(O)— group, a —N(R$^{15}$)— group, a —[N(CH$_3$)$_2$]$^+$ group, a —N(R$^{15}$)—C(═O)—N(R$^{15}$)— group, a —O—C(═O)—N(R$^{15}$)— group, a —N(R$^{15}$)—C(═O)—O— group, —O—, —S—, —S(O)—, and —S(O)$_2$—:
R$^8$ is a hydrogen atom,
 a $C_1$-$C_6$-alkyl group, which is unsubstituted or substituted with one or more substituents independently selected from a halogen atom, a hydroxyl group, a $C_1$-$C_3$-alkoxy group,
 a $C_1$-$C_3$-haloalkoxy group, a $C_3$-$C_6$-cycloalkyl group, a heterocycloalkyl group and a NR$^{20}$R$^{21}$ group;
 a $C_1$-$C_3$-haloalkyl group,
 a $C_3$-$C_6$-cycloalkyl group, or
 a $C_1$-$C_6$-alkyl group in which one or two not directly adjacent carbon atoms are independently replaced by a heteroatom selected from —O— and —NH—;
R$^9$ is selected from a hydrogen atom,
 a $C_1$-$C_4$-alkyl group,
 a $C_1$-$C_3$-hydroxyalkyl group,
 a $C_1$-$C_4$-haloalkyl group,
 a $C_1$-$C_4$-haloalkyl-NH—C(O)—O—($C_1$-$C_3$-alkylene)- group,
 a $C_2$-$C_6$-haloalkenyl group,
 a $C_1$-$C_6$-alkyl-O— group,
 a $C_1$-$C_4$-haloalkoxy group,
 a $C_1$-$C_6$-alkyl-O—($C_1$-$C_3$-alkylene)- group,
 a ($C_3$-$C_7$)-cycloalkyl group,
 a ($C_3$-$C_7$-cycloalkyl)-O—($C_1$-$C_3$-alkylene)- group,
 a phenyl-O—($C_1$-$C_3$-alkylene)- group,
 a phenyl-($C_1$-$C_3$-alkylene)-O—($C_1$-$C_3$-alkylene)- group,
 a (R$^{18}$)-(phenylene)-O—($C_1$-$C_3$-alkylene)- group,
 a (R$^{18}$)-(phenylene)-($C_1$-$C_3$-alkylene)-O—($C_1$-$C_3$-alkylene)- group,
 a (R$^{18}$)-(phenylene)-(heteroarylene)-O—($C_1$-$C_3$-alkylene)- group,
 a (R$^{18}$)-(heterocycloalkylene)-($C_1$-$C_6$-alkylene)- group,
 a (R$^{18}$)-(heterocycloalkylene)-(phenylene)-O—($C_1$-$C_3$-alkylene)- group,
 a (heterocycloalkenyl)-(phenylene)-O—($C_1$-$C_3$-alkylene)- group,
 a (R$^{18}$)-(heteroarylene)-($C_1$-$C_3$-alkylene)-O—($C_1$-$C_3$-alkylene)- group,
 a (R$^{18}$)-(heteroarylene)-(phenylene)-O—($C_1$-$C_3$-alkylene)- group,
 a (R$^{18}$)-(phenylene)-($C_1$-$C_3$-alkylene)-O—($C_1$-$C_3$-alkylene)- group,
 a (R$^{19}$)—S(O)$_2$-(phenylene)-O—($C_1$-$C_3$-alkylene)- group,
 a (R$^{19}$)—S(O)$_2$—NH-(phenylene)-O—($C_1$-$C_3$-alkylene)- group,
 a (R$^{19}$)—S(O)$_2$—N($C_1$-$C_6$-alkyl)-(phenylene)-O—($C_1$-$C_3$-alkylene)- group,
 a (R$^{19}$)—S(O)$_2$-(heterocycloalkylene)-(phenylene)-O—($C_1$-$C_3$-alkylene)- group,
 a (R$^{18}$)-(heterocycloalkylene)-(heteroarylene)-O—($C_1$-$C_3$-alkylene)- group,
 a (R$^{19}$)-(heteroarylene)-O—($C_1$-$C_3$-alkylene)- group,
 a (R$^{19}$)—S(O)$_2$-(heteroarylene)-O—($C_1$-$C_3$-alkylene)- group,
 a (R$^{19}$)—S(O)$_2$-(heterocycloalkylene)-(heteroarylene)-O—($C_1$-$C_3$-alkylene)- group,
 a NR$^{20}$R$^{21}$—($C_1$-$C_3$-alkylene)- group,
 a ($C_1$-$C_3$-alkyl)-NH—($C_1$-$C_3$-alkylene)- group,
 a ($C_1$-$C_3$-haloalkyl)-($C_1$-$C_3$-alkylene)-NH—($C_1$-$C_3$-alkylene)- group,
 a ($C_1$-$C_3$-haloalkyl)-NH—($C_1$-$C_3$-alkylene)- group,
 a ($C_1$-$C_3$-alkyl)-NH—C(O)—($C_1$-$C_3$-alkylene)- group,
 a ($C_1$-$C_3$-alkyl)-NR$^{15}$—C(O)—($C_1$-$C_3$-alkylene)- group,
 a ($C_1$-$C_3$-alkyl)-(O)—NH—($C_1$-$C_3$-alkylene)- group,
 a ($C_1$-$C_3$-alkyl)-C(O)—NR$^{15}$—($C_1$-$C_3$-alkylene)- group,
a group, and a group,
 where the phenyl ring is optionally substituted with a halogen atom, a hydroxyl group, or a $C_1$-$C_3$-alkoxy group and
 the heterocycloalkyl group is optionally substituted with an oxo (═O) group or is optionally substituted with one or more substituents independently selected from a halogen atom and a $C_1$-$C_3$-alkyl group;
or R$^8$ and R$^9$ together form a 5- or 6-membered ring optionally containing one or two heteroatoms selected from —O—, and —NR$^{14}$—;
R$^{14}$ is a hydrogen atom or a $C_1$-$C_3$-alkyl group;
R$^{15}$ is independently selected from a hydrogen atom,
 a $C_1$-$C_6$-alkyl group
 which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a (R$^{18}$)-(heterocycloalkylene)-(arylene)-O— group, an aryl-O— group, an aryl-($C_1$-$C_3$-alkylene)-O— group, a (R$^{19}$)—S(O)$_2$— arylene-O— group, a (R$^{19}$)S(O)$_2$-heterocycloalkylene-arylene-O— group and an aryl-heteroarylene-O— group;
 a phenyl group, a group a group

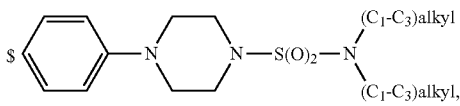

and
a group

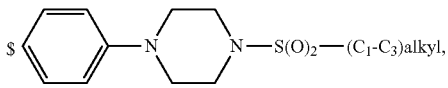

where $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}$R$^{21}$ group; and $R^{20}$ and $R^{21}$ are each independently selected from a hydrogen atom and a $C_1$-$C_6$-alkyl group;

or a tautomer, an N-oxide, or a salt thereof, or a salt of a tautomer, or a salt of an N-oxide, or a mixture of same.

In accordance with a further aspect, the present invention provides compounds of general formula (I): wherein
A is

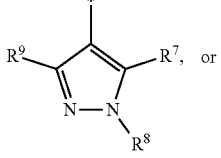 (A1)

or

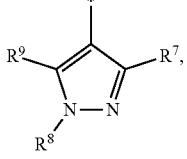 (A2)

wherein $R^6$ and $R^7$, together with two carbon atoms of the pyrazole ring, two carbon atoms of the indole moiety and the nitrogen atom to which $R^6$ is attached, form a 10- to 12-membered ring and * is the point of attachment of these moieties to the indole carbon atom bearing the A substituent;

$R^1$ is a fluorine atom;
$R^2$ and $R^3$ are each a hydrogen atom;
$R^4$ is selected from an aryl group and a heteroaryl group, each of which is unsubstituted or substituted with one, two, or three, substituents and each substituent is independently selected from a halogen atom, a $C_1$-$C_3$-alkyl group and a $C_1$-$C_3$-haloalkyl group;

L is a group —(CH$_2$)$_m$-E-;
E is a bond or an oxygen atom and constitutes the connecting element to $R^4$,
m is 2, 3, or 4;
$R^5$ is a COOH group;
—$R^6$-$R^7$— is selected from $^\#$—(CH$_2$)$_n$—(B)$_t$—(CH$_2$)$_p$—X—$^{\#\#}$, $^\#$—(C$_2$-$C_6$-alkenylene)-(B)$_t$—(CH$_2$)$_p$—X—$^{\#\#}$,
wherein $^\#$ is the point of attachment with the indole nitrogen atom and $^{\#\#}$ is the point of attachment with the pyrazole carbon atom bearing the $R^7$ substituent; and
wherein one or more —CH$_2$— groups may be unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, and a $C_1$-$C_3$-alkoxy group, and where a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group, and
where X is an unsubstituted —CH$_2$— group;
n is 3, 4, 5, or 6;
t is 0 or 1;
p is 0;
where the integers selected for variables n, t, and p result in forming a 10- to 12-membered ring independently from the selection of variable A1 or A2;
B is independently selected from a —N($R^{15}$)— group, a —[N(CH$_3$)$_2$]$^+$ group and —O— group;
$R^8$ is selected from a hydrogen atom and
a $C_1$-$C_4$-alkyl group, which is unsubstituted or substituted with one or more substituents independently selected from a halogen atom, a hydroxy group, a $C_1$-$C_3$-alkoxy group,
a $C_1$-$C_3$-haloalkoxy group, a $C_3$-$C_6$-cycloalkyl group, a heterocycloalkyl group and a NR$^{20}$R$^{21}$ group;
$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_2$-$C_6$-haloalkenyl group,
a $C_1$-$C_6$-alkyl-O—($C_1$-$C_3$-alkylene)- group,
a ($C_3$-$C_7$-cycloalkyl)- group,
a phenyl-O—($C_1$-$C_3$-alkylene)- group,
a ($R^{18}$)-(phenylene)-O—($C_1$-$C_3$-alkylene)- group,
a ($R^{18}$)-(heterocycloalkylene)-($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a NR$^{20}$R$^{21}$—($C_1$-$C_3$-alkylene)- group, and
a ($C_1$-$C_3$-alkyl)-NH—($C_1$-$C_3$-alkylene)- group,
where the phenyl group is unsubstituted or substituted with a halogen atom, a hydroxyl group, or a $C_1$-$C_3$-alkoxy group and
the heterocycloalkylene group is unsubstituted or substituted with a substituent independently selected from an oxo (=O) group and a $C_1$-$C_3$-alkyl group;
or
$R^8$ and $R^9$ together form 6-membered ring optionally comprising one or two oxygen atoms;
$R^{15}$ is selected from a hydrogen atom, a $C_1$-$C_3$-alkyl group, a $C_1$-$C_3$-haloalkyl group, a phenyl group, a benzyl group,

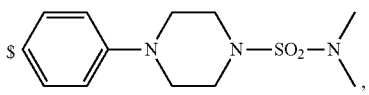

a group

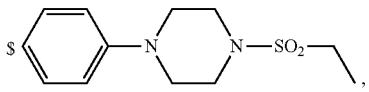

and a group

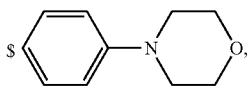 [SMILES: c1ccc(N2CCOCC2)cc1]

$R^{16}$ and $R^{17}$ are each independently selected from a hydrogen atom, a $C_1$-$C_6$-alkyl group, and a $C_1$-$C_6$-haloalkyl group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}OC(O)$—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_3$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a N$R^{20}R^{21}$ group; and $R^{20}$ and $R^{21}$ are each independently selected from a hydrogen atom and a $C_1$-$C_3$-alkyl group;

or a tautomer, an N-oxide, or a salt thereof, or a salt of a tautomer, or a salt of an N-oxide, or a mixture of same.

In accordance with a further aspect, the present invention provides compounds of general formula (I): wherein A is

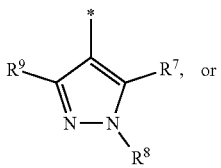

(A1)

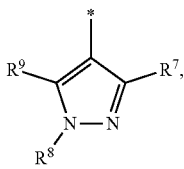

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a fluorine atom;

$R^2$ and $R^3$ are each a hydrogen atom;

$R^4$ is an aryl group, which is unsubstituted or substituted with a halogen atom;

L is a group —$(CH_2)_m$-E-;

E is an oxygen atom and constitutes the connecting element to $R^4$, m is 3;

$R^5$ is a COOH group;

—$R^6$-$R^7$— is selected from $^{\#}$—$(CH_2)_n$—(B)$_t$—$(CH_2)_p$—X—$^{\#\#}$ and $^{\#}$—($C_2$-$C_6$-alkenylene)-(B)$_t$—$(CH_2)_p$—X—$^{\#\#}$, wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more substituents independently selected from a halogen atom, a hydroxyl group, a N$R^{16}R^{17}$ group, a $C_1$-$C_3$-alkyl group, a $C_1$-$C_3$-haloalkyl group, and a $C_1$-$C_3$-alkoxy group, and where a —CH=CH— group in any alkenylene can be replaced by a 1,2-($C_3$-$C_5$)cycloalkylene group and where X is an unsubstituted —$CH_2$— group;

n is 3 or 4;

t is 1;

p is 0 where the integers selected for variables n, t, and p result in forming a 10- to 11-membered ring independently from the selection of variable A1 or A2;

B is independently selected from —O— and —($R^{15}$)—;

$R^8$ is selected from a hydrogen atom and, a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group, a $C_1$-$C_3$-hydroxyalkyl group, a $C_1$-$C_3$-haloalkyl group, a $C_1$-$C_3$-alkyl-O— group, a $C_1$-$C_3$-haloalkoxy group, a $C_1$-$C_3$-alkyl-O—($C_1$-$C_3$-alkylene)- group, a ($C_3$-$C_6$)-cycloalkyl group, a $R^{18}$-(phenylene)-O—($C_1$-$C_3$-alkylene)- group, a N$R^{20}R^{21}$—($C_1$-$C_3$-alkylene)- group, and a ($C_1$-$C_3$-alkyl)-NH—($C_1$-$C_3$-alkylene)- group;

$R^{15}$ is selected from a hydrogen atom, a $C_1$-$C_3$-alkyl group and a $C_1$-$C_3$-haloalkyl group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)O$R^{21}$ group, a —C(O)N$R^{20}R^{21}$ group and ($C_1$-$C_6$-alkyl)-C(O)— group;

$R^{20}$ and $R^{21}$ are each independently selected from a hydrogen atom and a $C_1$-$C_3$-alkyl group;

or a tautomer, or a salt thereof, or a salt of a tautomer, or a mixture of same.

In accordance with a further aspect, the present invention provides compounds of general formula (I): wherein A is

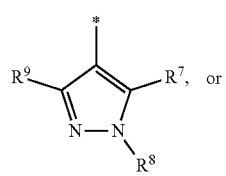

(A1)

-continued (A2)

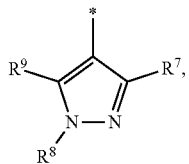

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent R¹ is a fluorine atom;
R² and R³ are each a hydrogen atom;
R⁴ is a naphthyl group, which is unsubstituted or substituted with a halogen atom;
L is a group —(CH₂)₃—O—;
R⁵ is a COOH group;
—R⁶-R⁷— is selected from #—(CH₂)ₙ—(B)ₜ—(CH₂)ₚ—X—## and #—(C₂-C₆-alkenylene)-(B)ₜ—(CH₂)ₚ—X—##, and wherein # is the point of attachment with the indole nitrogen atom and ## is the point of attachment with the pyrazole carbon atom bearing the R⁷ substituent and wherein one or more —CH₂— groups may be unsubstituted or substituted with one or more halogen atoms,
and where a —CH=CH— group in any alkenylene can be replaced by a

group or a

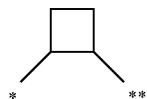

group where * is the point of attachment of the ring to the adjacent —CH₂— group or to the indole nitrogen atom and ** is the point of attachment to the adjacent CH₂— group or to —(B)ₜ— and
where X is an unsubstituted —CH₂— group;
n is 4;
t is 1;
p is 0;
where the integers selected for variables n, t, and p result in forming a 11-membered ring independently from the selection of variable A1 or A2;
B is independently selected from —O— and —N(R¹⁵)—;
R⁸ is a C₁-C₃-alkyl group;
R⁹ is a C₁-C₃-alkyl group;
R¹⁵ is selected from a hydrogen atom, a C₁-C₃-alkyl group, and a C₁-C₃-haloalkyl group; or a tautomer, or a salt thereof, or a salt of a tautomer, or a mixture of same.

In accordance with a further aspect, the present invention provides compounds of general formula (I): wherein A is (A1)

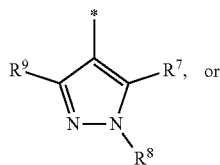

, or (A2)

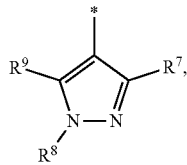

wherein R⁶ and R⁷, together with two carbon atoms of the pyrazole ring, two carbon atoms of the indole moiety and the nitrogen atom to which R⁶ is attached, form a 10- or 11-membered ring and * is the point of attachment of these moieties to the indole carbon atom bearing the A substituent;

R¹ is a fluorine atom;
R² and R³ are each a hydrogen atom;
R⁴ is selected from an aryl group and a heteroaryl group, each of which is unsubstituted or substituted with one or two substituents and each substituent is independently selected from a halogen atom and a C₁-C₃-alkyl group;
L is a group —(CH₂)ₘ-E-;
E is an oxygen atom and constitutes the connecting element to R⁴,
m is 3;
R⁵ is a COOH group;
—R⁶-R⁷— is selected from #—(CH₂)ₙ—(B)ₜ—(CH₂)ₚ—X—## and #—(C₂-C₆-alkenylene)-(B)ₜ—(CH₂)ₚ—X—##, and wherein # is the point of attachment with the indole nitrogen atom and ## is the point of attachment with the pyrazole carbon atom bearing the R⁷ substituent and
wherein one or more —CH₂— groups may be unsubstituted or substituted with one or more substituents independently selected from a halogen atom, a hydroxyl group, a NR¹⁶R¹⁷ group, a C₁-C₃-alkyl group, a C₁-C₃-haloalkyl group, and a C₁-C₃-alkoxy group, and
where a double bond in any alkenylene can be replaced by a 1,2-cyclopropylene group or a 1,2-cyclobutylene group and
where X is an unsubstituted —CH₂— group;
n is 3 or 4;
t is 1;
p is 0;
where the integers selected for variables n, t, and p result in forming a 10- to 11-membered ring independently from the selection of variable A1 or A2;
B is independently selected from —O— and —N(R¹⁵)—;
R⁸ is selected from a hydrogen atom and
a C₁-C₄-alkyl group, which is unsubstituted or substituted with one or more substituents independently selected from a halogen atom, a hydroxy group, a C₃-C₆-cycloalkyl group and a heterocycloalkyl group;
R⁹ is a C₁-C₄-alkyl group,
R¹⁵ is selected from a hydrogen atom, a C₁-C₃-alkyl group and a C₁-C₃-haloalkyl group;
or a tautomer, or a salt thereof, or a salt of a tautomer, or a mixture of same.

In accordance with a further aspect, the present invention provides compounds of general formula (I): wherein
A is

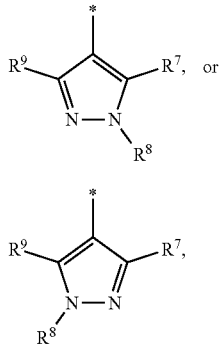

(A1)

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;
$R^1$ is a fluorine atom;
$R^2$ and $R^3$ are each a hydrogen atom;
$R^4$ is an aryl group, which is unsubstituted or substituted with a halogen atom;
L is a group —$(CH_2)_m$-E-;
E is an oxygen atom and constitutes the connecting element to $R^4$,
m is 3;
$R^5$ is a COOH group;
—$R^6$-$R^7$— is selected from $^{\#}$—$(CH_2)_n$—$(B)_t$—$(CH_2)_p$—X—$^{\#\#}$ and $^{\#}$—$(C_2$-$C_6$-alkenylene)-$(B)_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, and a $C_1$-$C_3$-alkoxy group, and where a double bond in any alkenylene can be replaced by a 1,2-cyclopropylene group or a 1,2-cyclobutylene group and
where X is an unsubstituted —$CH_2$— group;
n is 3 or 4;
t is 1;
p is 0;
where the integers selected for variables n, t, and p result in forming a 10- to 11-membered ring independently from the selection of variable A1 or A2;
B is independently selected from —O— and —$N(R^{15})$—;
$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;
$R^9$ is a $C_1$-$C_4$-alkyl group,
$R^{15}$ is selected from a hydrogen atom, a $C_1$-$C_3$-alkyl group and a $C_1$-$C_3$-haloalkyl group;
or a tautomer, or a salt thereof, or a salt of a tautomer, or a mixture of same.

In accordance with a further aspect, the present invention provides compounds of general formula (I): wherein
A is

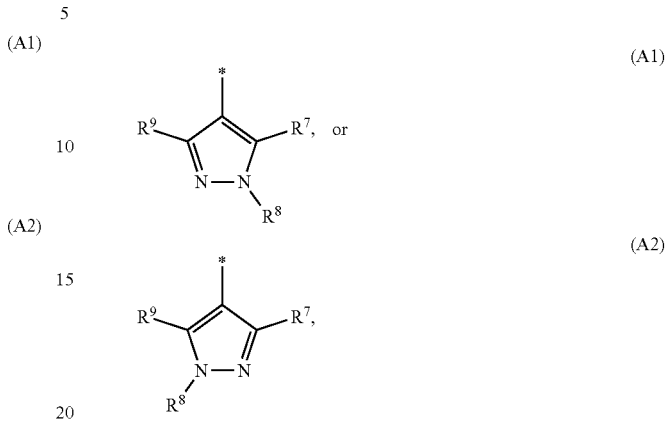

(A1)

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;
$R^1$ is a fluorine atom;
$R^2$ and $R^3$ are a hydrogen atom;
$R^4$ is a naphthyl group, which is unsubstituted or substituted with a fluorine atom;
L is a group —$(CH_2)_3$—O—;
$R^5$ is a COOH group;
—$R^6$-$R^7$— is selected from $^{\#}$—$(CH_2)_n$—$(B)_t$—$(CH_2)_p$—X—$^{\#\#}$ and $^{\#}$—$(C_2$-$C_6$-alkenylene)-$(B)_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or two substituents independently selected from a halogen atom, a hydroxyl group and a $C_1$-$C_3$-alkyl group, and
where X is an unsubstituted —$CH_2$— group;
n is 3 or 4;
t is 1;
p is 1 or 2;
where the integers selected for variables n, t, and p result in forming a 10- or 11-membered ring independently from the selection of variable A1 or A2;
B is independently selected from —O— and —$N(R^{15})$—;
$R^8$ is selected from a methyl group and a 2-morpholinoethyl group;
$R^9$ is selected from a methyl group and an ethyl group;
$R^{15}$ is selected from a hydrogen atom, a methyl group, a 2,2-difluoroethyl group and a 2,2,2-trifluoroethyl group;
or a tautomer, or a salt thereof, or a salt of a tautomer, or a mixture of same.

In accordance with a further aspect, the present invention provides compounds of general formula (I):

wherein
A is

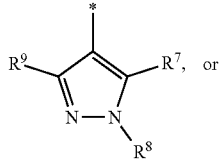 (A1)

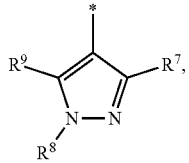 (A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a fluorine atom;
$R^2$ and $R^3$ are each a hydrogen atom;
$R^4$ is a naphthyl group, which is unsubstituted or substituted with a halogen atom;
L is a group —$CH_2$)$_3$—O—;
$R^5$ is a COOH group;
—$R^6$-$R^7$— is selected from $^\#$—$(CH_2)_n$—$(B)_t$—$(CH_2)_p$—X—$^{\#\#\#}$ and $^\#$—$(C_2$-$C_6$-alkenylene)-$(B)_t$—$(CH_2)_p$—X—$^{\#\#\#}$, and wherein $^\#$ is the point of attachment with the indole nitrogen atom and $^{\#\#\#}$ is the point of attachment with the pyrazole carbon atom bearing the $R^7$ substituent and
wherein one or more —$CH_2$— groups may be unsubstituted or substituted with one or more halogen atoms,
and
where X is an unsubstituted —$CH_2$— group;
n is 4;
t is 1;
p is 0;
where the integers selected for variables n, t, and p result in forming a 11-membered ring independently from the selection of variable A1 or A2;
B is independently selected from —O— and N($R^{15}$)—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, and a $C_1$-$C_3$-haloalkyl group;
or a tautomer, or a salt thereof, or a salt of a tautomer, or a mixture of same.

In accordance with a further aspect, the present invention provides compounds of general formula (I) wherein:
A is

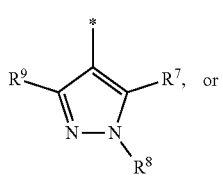 (A1)

-continued

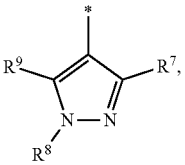 (A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a fluorine atom;
$R^2$ and $R^3$ are each a hydrogen atom;
$R^4$ is a naphthyl group, which is unsubstituted or substituted with a halogen atom;
L is a group —$CH_2$)$_3$—O—;
$R^5$ is a COOH group;
—$R^6$-$R^7$— is selected from $^\#$—$(CH_2)_n$—$(B)_t$—$(CH_2)_p$—X—$^{\#\#\#}$ and $^\#$—$(C_2$-$C_6$-alkenylene)-$(B)_t$—$(CH_2)_p$—X—$^{\#\#\#}$, wherein $^\#$ is the point of attachment with the indole nitrogen atom and $^{\#\#\#}$ is the point of attachment with the pyrazole carbon atom bearing the $R^7$ substituent and
wherein one or more —$CH_2$— groups may be unsubstituted or substituted with one or more halogen atoms,
where a —CH=CH— group in any alkenylene can be replaced by a 1,2-($C_3$-$C_5$-cycloalkylene) group and said 1,2-($C_3$-$C_5$-cycloalkylene) is unsubstituted;
where X is an unsubstituted —$CH_2$— group;
n is 3 or 4;
t is 1;
p is 1 or 2;
where the integers selected for variables n, t, and p result in forming a 11-membered ring independently from the selection of variable A1 or A2;
B is independently selected from —O— and —N($R^{15}$)—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, and a $C_1$-$C_3$-haloalkyl group;
or a tautomer, or a salt thereof; or a salt of a tautomer; or a mixture of same.

In accordance with a further aspect, the present invention provides compounds of general formula (I) wherein
A is

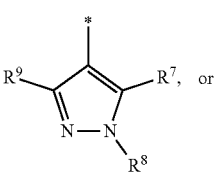 (A1)

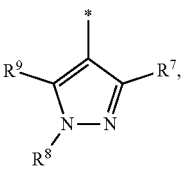 (A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a fluorine atom;

$R^2$ and $R^3$ are each a hydrogen atom;

$R^4$ is a naphthyl group, which is unsubstituted or substituted with a halogen atom;

L is a group —$(CH_2)_3$—O—;

$R^5$ is a COOH group;

—$R^6$-$R^7$— is #—$(CH_2)_n$—$(B)_t$—$(CH_2)_p$—X—##, and wherein # is the point of attachment with the indole nitrogen atom and ## is the point of attachment with the pyrazole carbon atom bearing the $R^7$ substituent, and wherein one or more —$CH_2$— groups may be unsubstituted or substituted with one or more halogen atoms, and where X is an unsubstituted —$CH_2$— group;

n is 3 or 4;

t is 1;

p is 1 or 2;

where the integers selected for variables n, t, and p result in forming a 11-membered ring independently from the selection of variable A1 or A2;

B is independently selected from —O— and $N(R^{15})$—;

$R^8$ is a $C_1$-$C_3$-alkyl group, which is unsubstituted or substituted with a heterocycloalkyl group;

$R^9$ is a $C_1$-$C_3$-alkyl group;

$R^{15}$ is selected from a hydrogen atom, a $C_1$-$C_3$-alkyl group, a $C_1$-$C_3$-haloalkyl group;

or a tautomer, or a salt thereof, or a salt of a tautomer, or a mixture of same.

In accordance with a further aspect, the present invention provides compounds of general formula (I):
wherein
A is

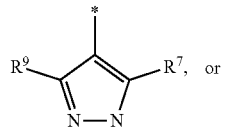

(A1)

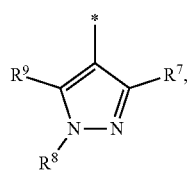

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a fluorine atom;

$R^2$ and $R^3$ are each a hydrogen atom;

$R^4$ is a naphthyl group, which is unsubstituted or substituted with a halogen atom;

L is a group —$(CH_2)_3$—O—;

$R^5$ is a COOH group; —$R^6$-$R^7$— is #—$(C_2$-$C_6$-alkenylene)-$(B)_t$—$(CH_2)_p$—X—##, and wherein # is the point of attachment with the indole nitrogen atom and ## is the point of attachment with the pyrazole carbon atom bearing the $R^7$ substituent, and wherein one or more —$CH_2$— groups may be unsubstituted or substituted with one or more halogen atoms, and where a —CH=CH— group in any alkenylene can be replaced by a 1,2-($C_3$-$C_5$-cycloalkylene) group and said 1,2-($C_3$-$C_5$-cycloalkylene) is unsubstituted; and wherein X is an unsubstituted —$CH_2$— group;

n is 3 or 4;

t is 1;

p is 1 or 2;

where the integers selected for variables n, t, and p result in forming a 11-membered ring independently from the selection of variable A1 or A2;

B is independently selected from —O— and $N(R^{15})$—;

$R^8$ is a $C_1$-$C_3$-alkyl group, which is unsubstituted or substituted with a heterocycloalkyl group;

$R^9$ is a $C_1$-$C_3$-alkyl group;

$R^{15}$ is selected from a hydrogen atom, a $C_1$-$C_3$-alkyl group, and a $C_1$-$C_3$-haloalkyl group;

or a tautomer, or a salt thereof, or a salt of a tautomer, or a mixture of same.

In accordance with a further aspect, the present invention provides compounds of general formula (I) wherein
A is

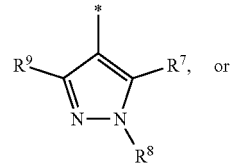

(A1)

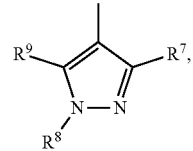

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a fluorine atom;

$R^2$ and $R^3$ are each a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group —$(CH_2)_m$-E-;

E is an oxygen atom and constitutes the connecting element to $R^4$, m is 3;

$R^5$ is a COOH group;

—$R^6$-$R^7$— is selected from #—$(CH_2)_n$—$(B)_t$—$(CH_2)_p$—X—## and #—$(C_2$-$C_6$-alkenylene)-$(B)_t$—$(CH_2)_p$—X—##, and wherein # is the point of attachment with the indole nitrogen atom and ## is the point of attachment with the pyrazole carbon atom bearing the $R^7$ substituent and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, and a $C_1$-$C_3$-alkoxy group, and where X is an unsubstituted —$CH_2$— group;

n is 3 or 4;
t is 1;
p is 0;
where the integers selected for variables n, t, and p result in forming a 10- to 11-membered ring independently from the selection of variable A1 or A2;
B is independently selected from —O— and —($R^{15}$)—;
$R^8$ is selected from a hydrogen atom and
a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;
$R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{18}$-(phenylene)-O—($C_1$-$C_3$-alkylene)- group,
a $NR^{20}R^{21}$—($C_1$-$C_3$-alkylene)- group, or
a ($C_1$-$C_3$-alkyl)-NH—($C_1$-$C_3$-alkylene)- group;
$R^{15}$ is selected from a hydrogen atom, a $C_1$-$C_3$-alkyl group and a $C_1$-$C_3$-haloalkyl group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)O$R^{21}$ group, a —C(O)N$R^{20}R^{21}$ group and ($C_1$-$C_6$-alkyl)-C(O)— group;
$R^{20}$ and $R^{21}$ are each independently selected from a hydrogen atom and a $C_1$-$C_3$-alkyl group;
or a tautomer, or a salt thereof, or a salt of a tautomer, or a mixture of same.

In accordance with a further aspect, the present invention provides compounds of general formula (I) wherein A is

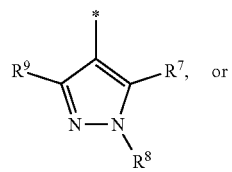

(A1)

or

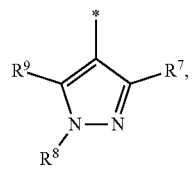

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a fluorine atom;
$R^2$ and $R^3$ are each a hydrogen atom;
$R^4$ is an aryl group, which is unsubstituted or substituted with a halogen atom;
L is a group —$(CH_2)_m$-E-;
E is an oxygen atom and constitutes the connecting element to $R^4$,
m is 3;
$R^5$ is a COOH group;
—$R^6$-$R^7$— is selected from #—$(CH_2)_n$—$(B)_t$—$(CH_2)_p$—X—## and #—($C_2$-$C_6$-alkenylene)-$(B)_t$—$(CH_2)_p$—X—##
and wherein # is the point of attachment with the indole nitrogen atom and ## is the point of attachment with the pyrazole carbon atom bearing the $R^7$ substituent and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, and a $C_1$-$C_3$-alkoxy group, and where X is an unsubstituted $CH_2$— group;

n is 3 or 4;
t is 1;
p is 0;
where the integers selected for variables n, t, and p result in forming a 10- to 11-membered ring independently from the selection of variable A1 or A2;
B is independently selected from —O— and —N($R^{15}$)—;
$R^8$ is selected from a hydrogen atom and
a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;
$R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{18}$-(phenylene)-O—($C_1$-$C_3$-alkylene)- group,
a $NR^{20}R^{21}$—($C_1$-$C_3$-alkylene)- group, or
a ($C_1$-$C_3$-alkyl)-NH—($C_1$-$C_3$-alkylene)- group;
$R^{15}$ is selected from a hydrogen atom, a $C_1$-$C_3$-alkyl group and a $C_1$-$C_3$-haloalkyl group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)O$R^{21}$ group, a —C(O)N$R^{20}R^{21}$ group and ($C_1$-$C_6$-alkyl)-C(O)— group;
$R^{20}$ and $R^{21}$ are each independently selected from a hydrogen atom and a $C_1$-$C_3$-alkyl group;
or a tautomer, or a salt thereof, or a salt of a tautomer, or a mixture of same.

In accordance with a further aspect, the present invention provides compounds of general formula (I) wherein A is

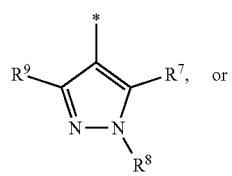

(A1)

or

-continued

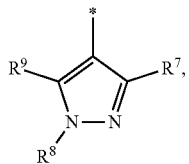
(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a fluorine atom;
$R^2$ and $R^3$ are each a hydrogen atom;
$R^4$ is a naphthyl group, which is unsubstituted or substituted with a halogen atom;
L is a group —$(CH_2)_3$—O—;
$R^5$ is a COOH group;
—$R^6$-$R^7$— is selected from $^{\#}$—$(CH_2)_n$—(B)$_t$—$(CH_2)_p$—X—$^{\#\#}$ and $^{\#}$—($C_2$-$C_6$-alkenylene)-(B)$_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more halogen atoms, where X is an unsubstituted —$CH_2$— group;
n is 4;
t is 1;
p is 0;
where the integers selected for variables n, t, and p result in forming a 11-membered ring independently from the selection of variable A1 or A2;
B is independently selected from —O— and —($R^{15}$)—;
$R^5$ is a $C_1$-$C_3$-alkyl group;
$R^9$ is a $C_1$-$C_3$-alkyl group;
$R^{15}$ is selected from a hydrogen atom, a $C_1$-$C_3$-alkyl group, and a $C_1$-$C_3$-haloalkyl group;
or a tautomer, or a salt thereof, or a salt of a tautomer, or a mixture of same.

In accordance with a further aspect, the present invention provides compounds of general formula (I):
wherein
A is

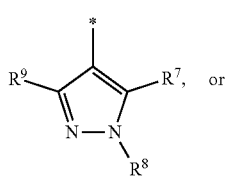
(A1)

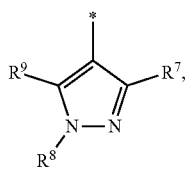
(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a fluorine atom;
$R^2$ and $R^3$ are each a hydrogen atom;
$R^4$ is a naphthyl group, which is unsubstituted or substituted with a halogen atom;
L is a group —$(CH_2)_3$—O—;
$R^5$ is a COOH group;
—$R^6$-$R^7$— is selected from $^{\#}$—$(CH_2)_n$—(B)$_t$—$(CH_2)_p$—X—$^{\#\#}$ and $^{\#}$—($C_2$-$C_6$-alkenylene)-(B)$_t$—$(CH_2)_p$—X—$^{\#\#}$,
wherein $^{\#}$ is the point of attachment with the indole nitrogen atom and $^{\#\#}$ is the point of attachment with the pyrazole carbon atom bearing the $R^7$ substituent, and wherein one or more —$CH_2$— groups may be unsubstituted or substituted with one or two fluorine atoms, and
wherein X is an unsubstituted —$CH_2$— group;
n is 3 or 4;
t is 1;
p is 1 or 2;
where the integers selected for variables n, t, and p result in forming a 11-membered ring independently from the selection of variable A1 or A2;
B is independently selected from —O— and —N($R^{15}$)—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, and a $C_1$-$C_3$-haloalkyl group;
or a tautomer, or a salt thereof, or a salt of a tautomer, or a mixture of same.

In accordance with a further aspect, the present invention provides compounds of general formula (I) wherein
A is

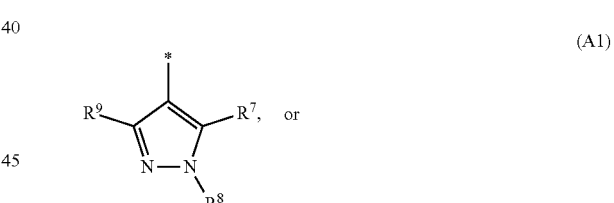
(A1)

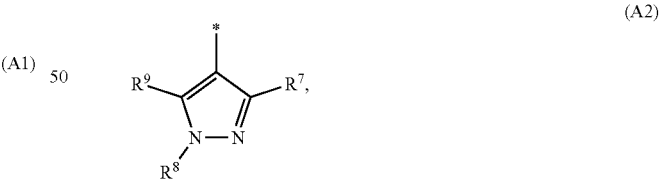
(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a fluorine atom;
$R^2$ and $R^3$ are each a hydrogen atom;
$R^4$ is a naphthyl group, which is unsubstituted or substituted with a fluorine atom;
L is a group —$(CH_2)_3$—O—;
$R^5$ is a COOH group;

—R⁶-R⁷— is selected from #—(CH₂)ₙ—(B)ₜ—(CH₂)ₚ—X—## and #—(C₂-C₆-alkenylene)-(B)ₜ—(CH₂)ₚ—X—##, and wherein # is the point of attachment with the indole nitrogen atom and ## is the point of attachment with the pyrazole carbon atom bearing the R⁷ substituent and wherein one or more —CH₂— groups may be unsubstituted or substituted with one or more fluorine atoms, where X is an unsubstituted —CH₂— group;

n is 4;
t is 1;
p is 0;
  where the integers selected for variables n, t, and p result in forming a 11-membered ring independently from the selection of variable A1 or A2;
B is independently selected from —O— and —N(R¹⁵)—;
R⁸ is a C₁-C₃-alkyl group, which is unsubstituted or substituted with a morpholino or 4-methyl-piperazino group;
R⁹ is a C₁-C₂-alkyl group;
R¹⁵ is selected from a hydrogen atom, a C₁-C₃-alkyl group, and a C₁-C₃-haloalkyl group;
  or a tautomer, or a salt thereof, or a salt of a tautomer, or a mixture of same.

In accordance with a further aspect, the present invention provides compounds of general formula (I) wherein:
A is

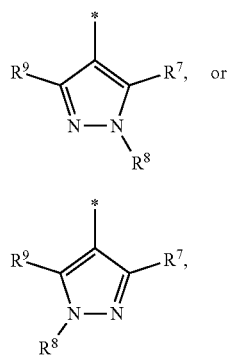

(A1)

(A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a fluorine atom;
R² and R³ are each a hydrogen atom;
R⁴ is a naphthyl group, which is unsubstituted or substituted with a fluorine atom;
L is a group —(CH₂)₃—O—;
R⁵ is a COOH group;
—R⁶-R⁷— is #—(CH₂)ₙ—(B)ₜ—(CH₂)ₚ—X—##, and wherein # is the point of attachment with the indole nitrogen atom and ## is the point of attachment with the pyrazole carbon atom bearing the R⁷ substituent and wherein one or more —CH₂— groups may be unsubstituted or substituted with one or more fluorine atoms, where X is an unsubstituted —CH₂— group;
n is 4;
t is 1;
p is 0;
  where the integers selected for variables n, t, and p result in forming a 11-membered ring independently from the selection of variable A1 or A2;
B is independently selected from —O— and —(R¹⁵)—;
R⁸ is a methyl group;
R⁹ is a C₁-C₂-alkyl group;
R¹⁵ is selected from a hydrogen atom, a methyl group, a CH₂CF₃ and a CH₂CHF₂ group;
or a tautomer, or a salt thereof, or a salt of a tautomer, or a mixture of same.

In accordance with a further aspect, the present invention provides compounds of general formula (I) wherein:
A is

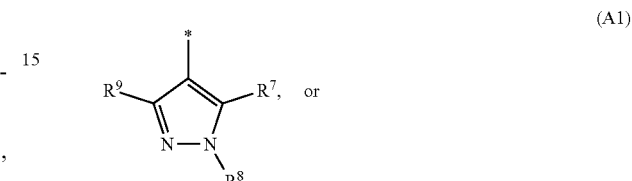

(A1)

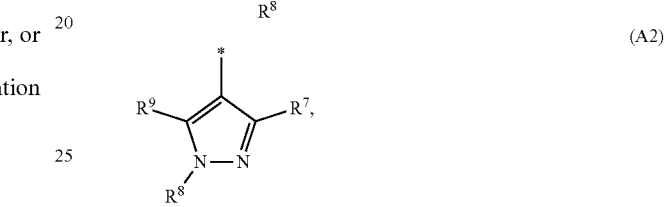

(A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a fluorine atom;
R² and R³ are each a hydrogen atom;
R⁴ is an aryl group, which is unsubstituted or substituted with one, two, three, four or five substituents and each substituent is independently selected from a halogen atom, a cyano group, a C₁-C₃-alkyl group, a C₁-C₃-haloalkyl group, a C₁-C₃-alkoxy group, a C₁-C₃-thioalkyl group, a C₁-C₃-haloalkoxy group, a (C₁-C₃)-haloalkyl-S— group, and a C₃-C₅-cycloalkyl group;
L is a group —(CH₂)₃—O—;
R⁵ is a COOH group;
—R⁶-R⁷— is #—(CH₂)ₙ—(B)ₜ—(CH₂)ₚ—X—##, and wherein # is the point of attachment with the indole nitrogen atom and ## is the point of attachment with the pyrazole carbon atom bearing the R⁷ substituent and wherein one or more —CH₂— groups may be unsubstituted or substituted with one or more fluorine atoms, where X is an unsubstituted —CH₂— group;
n is 4;
t is 1;
p is 0;
  where the integers selected for variables n, t, and p result in forming a 11-membered ring independently from the selection of variable A1 or A2;
B is independently selected from —O—, a —[N(CH₃)₂]⁺ group and —N(R¹⁵)—;
R⁸ is a methyl group;
R⁹ is a C₁-C₂-alkyl group;
R¹⁵ is selected from a hydrogen atom, a methyl group, a CH₂CF₃ and a CH₂CHF₂ group;
or a tautomer, or a salt thereof, or a salt of a tautomer, or a mixture of same.

In accordance with a further aspect, the present invention provides compounds of general formula (I) wherein A is

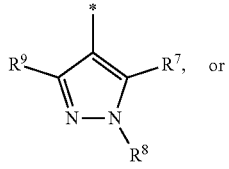
(A1)

or

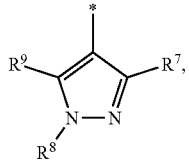
(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a fluorine atom;
$R^2$ and $R^3$ are each a hydrogen atom;
$R^4$ is a 6-fluoro-naphthyl group;
L is a group —$(CH_2)_3$—O—;
$R^5$ is a COOH group;
—$R^6$-$R^7$— is $^{\#}$—$(CH_2)_n$—(B)$_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more fluorine atoms, where X is an unsubstituted —$CH_2$— group;
n is 4;
t is 1;
p is 0;
where the integers selected for variables n, t, and p result in forming a 11-membered ring independently from the selection of variable A1 or A2;
B is —O—;
$R^8$ is a methyl group;
$R^9$ is a $C_1$-$C_2$-alkyl group;
or a tautomer, or a salt thereof, or a salt of a tautomer, or a mixture of same.

In accordance with a further aspect, the present invention provides compounds of general formula (I) wherein A is

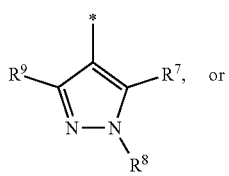
(A1)

or

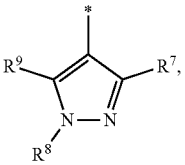
(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a fluorine atom;
$R^2$ and $R^3$ are each a hydrogen atom;
$R^4$ is a 6-fluoro-naphthyl group;
L is a group —$(CH_2)_3$—O—;
$R^5$ is a COOH group;
—$R^6$-$R^7$— is $^{\#}$—$(CH_2)_n$—(B)$_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more fluorine atoms, where X is an unsubstituted —$CH_2$— group;
n is 4;
t is 1;
p is 0;
where the integers selected for variables n, t, and p result in forming a 11-membered ring independently from the selection of variable A1 or A2;
B is —$NR^{15}$—;
$R^8$ is a methyl group;
$R^9$ is a $C_1$-$C_2$-alkyl group;
$R^{15}$ is selected from a hydrogen atom, a methyl group, a $CH_2CF_3$ and a $CH_2CHF_2$ group;
or a tautomer, or a salt thereof, or a salt of a tautomer, or a mixture of same.

In accordance with a further aspect, the present invention provides compounds of general formula (I) wherein: is

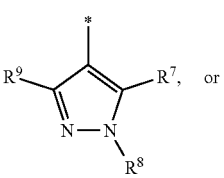
(A1)

or

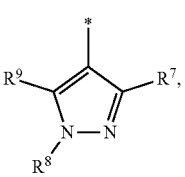
(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

R¹ is a fluorine atom;
R² and R³ are each a hydrogen atom;
R⁴ is a naphthyl group, which is unsubstituted or substituted with a fluorine atom;
L is a group —(CH$_2$)$_3$—O—;
R⁵ is a COOH group;
—R⁶-R⁷— is $^\#$—(CH$_2$)$_n$—(B)$_t$—(CH$_2$)$_p$—X—$^{\#\#}$, and wherein $^\#$ is the point of attachment with the indole nitrogen atom and $^{\#\#}$ is the point of attachment with the pyrazole carbon atom bearing the R⁷ substituent;
B is —NR¹⁵— or —O—;
n is 4;
t is 1;
p is 0;
  where the integers selected for variables n, t, and p result in forming a 11-membered ring independently from the selection of variable A1 or A2;
R⁸ is methyl or —(CH$_2$)$_2$-morpholino;
R⁹ is methyl or ethyl;
R¹⁵ is methyl or —CH$_2$—CF$_3$;
or a tautomer, or a salt thereof, or a salt of a tautomer, or a mixture of same.

In accordance with a further aspect, the present invention provides compounds of general formula (I):
wherein
A is

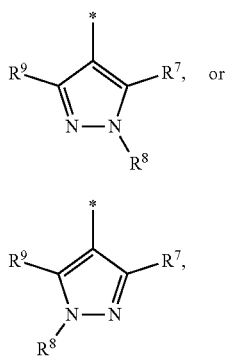

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a fluorine atom;
R² and R³ are each a hydrogen atom;
R⁴ is a naphthyl group, which is unsubstituted or substituted with a fluorine atom;
L is a group —(CH$_2$)$_3$—O—;
R⁵ is a COOH group;
—R⁶-R⁷— is selected from $^\#$—(CH$_2$)$_4$—NH—CH$_2$—$^{\#\#}$, $^\#$—(CH$_2$)$_4$—[N(CH$_3$)$_2$]$^+$—CH$_2$—$^{\#\#}$, $^\#$—CH$_2$—CH=CH—CH$_2$—O—CH$_2$—$^{\#\#}$, and $^\#$—(CH$_2$)$_4$—O—CH$_2$—$^{\#\#}$, hand wherein $^\#$ is the point of attachment with the indole nitrogen atom and $^{\#\#}$ is the point of attachment with the pyrazole carbon atom bearing the R⁷ substituent;
n is 4;
t is 1;
p is 1;
  where the integers selected for variables n, t, and p result in forming a 11-membered ring independently from the selection of variable A1 or A2;
R⁸ is methyl;
R⁹ is a methyl group or an ethyl group;
or a tautomer, or a salt thereof, or a salt of a tautomer, or a mixture of same.

In accordance with a further aspect, the present invention provides compounds of general formula (I):
wherein
A is

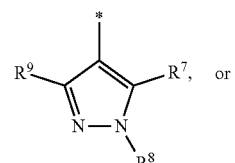

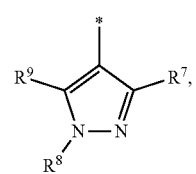

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a fluorine atom;
R² and R³ are each a hydrogen atom;
R⁴ is a naphthyl group, which is unsubstituted or substituted with a fluorine atom;
L is a group —(CH$_2$)$_3$—O—;
R⁵ is a COOH group;
—R⁶-R⁷— is selected from $^\#$—(CH$_2$)$_4$—NH—CH$_2$—$^{\#\#}$, $^\#$—(CH$_2$)$_4$—[N(CH$_3$)$_2$]$^+$—CH$_2$—$^{\#\#}$, and $^\#$—(CH$_2$)$_4$—O—CH$_2$—$^{\#\#}$, and wherein $^\#$ is the point of attachment with the indole nitrogen atom and $^{\#\#}$ is the point of attachment with the pyrazole carbon atom bearing the R⁷ substituent;
R⁸ is methyl;
R⁹ is a methyl group or an ethyl group;
or a tautomer, or a salt thereof, or a salt of a tautomer, or a mixture of same.

In some embodiments, the present invention includes compounds of general formula (I) selected from:
(rac)-(11Z)-4-fluoro-2,3-dimethyl-7-[3-(naphthalen-1-yloxy)propyl]-2,10,13,15-tetrahydro-pyrazolo[4',3':9,10][1,6]oxazacycloundecino[8,7,6-hi]indole-8-carboxylic acid,
(rac)-4-fluoro-2,3-dimethyl-7-[3-(naphthalen-1-yloxy)propyl]-2,10,11,12,13,15-hexahydro-pyrazolo[4',3':9,10][1,6]oxazacycloundecino[8,7,6-hi]indole-8-carboxylic acid,
4-fluoro-2,3-dimethyl-7-[3-(naphthalen-1-yloxy)propyl]-2,10,11,12,13,15-hexahydropyrazolo-[4',3':9,10][1,6]oxazacycloundecino[8,7,6-hi]indole-8-carboxylic acid-N-ethylethanamine salt (enantiomer 1),
4-fluoro-2,3-dimethyl-7-[3-(naphthalen-1-yloxy)propyl]-2,10,11,12,13,15-hexahydropyrazolo-[4',3':9,10][1,6]oxazacycloundecino[8,7,6-hi]indole-8-carboxylic acid-N-ethylethanamine salt (enantiomer 2)

(rac)-(11Z)-3-ethyl-4-fluoro-2-methyl-7-[3-(naphthalen-1-yloxy)propyl]-2,10,13,15-tetrahydro-pyrazolo[4',3':9,10][1,6]oxazacycloundecino[8,7,6-hi]indole-8-carboxylic acid, (rac)-3-ethyl-4-fluoro-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 3-ethyl-4-fluoro-2-methyl-7-{3-[(naphthalen-1-yl)oxy]propyl}-2,10,11,12,13,15-hexahydro-pyrazolo[4',3':9,10][1,6]oxazacycloundecino[8,7,6-hi]indole-8-carboxylic acid-N-ethylethanamine salt (enantiomer 1), 3-ethyl-4-fluoro-2-methyl-7-{3-[(naphthalen-1-yl)oxy]propyl}-2,10,11,12,13,15-hexahydro-pyrazolo[4',3':9,10][1,6]oxazacycloundecino[8,7,6-hi]indole-8-carboxylic acid-N-ethylethanamine salt (enantiomer 2), (rac)-(Z)-13-fluoro-10,12-dimethyl-1-(3-(naphthalen-1-yloxy)propyl)-4,7,9,10-tetrahydro-pyrazolo[4',3':9,10][1]oxa[6]azacycloundecino[8,7,6-hi]indole-2-carboxylic acid, (rac)-13-fluoro-10,12-dimethyl-1-(3-(naphthalen-1-yloxy)propyl)-4,5,6,7,9,10-hexahydro-pyrazolo[4',3':9,10][1]oxa[6]azacycloundecino[8,7,6-hi]indole-2-carboxylic acid, (rac)-(Z)-12-ethyl-13-fluoro-10-methyl-1-(3-(naphthalen-1-yloxy)propyl)-4,7,9,10-tetrahydro-pyrazolo[4',3':9,10][1]oxa[6]azacycloundecino[8,7,6-hi]indole-2-carboxylic acid, (rac)-13-fluoro-1-(3-((6-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylic acid, 4-fluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 4-fluoro-7-{3-[(6-fluoronaphthalen-1-yl)oxy]propyl}-2,3-dimethyl-2,10,11,12,13,15-hexahydropyrazolo[4',3'9,10][1,6]oxazacycloundecino[8,7,6-hi]indole-8-carboxylic acid-N-ethylethanamine salt (enantiomer 2), (rac)-13-fluoro-1-(3-((4-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylic acid, 4-fluoro-7-{3-[(4-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 1), 4-fluoro-7-{3-[(4-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 2), (rac)-13-fluoro-11,12-dimethyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylic acid, (rac)-1-(3-((2,3-dihydro-1H-inden-4-yl)oxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylic acid, (rac)-12-ethyl-13-fluoro-1-(3-((6-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylic acid, 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 2)

(rac)-12-ethyl-13-fluoro-1-(3-((4-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylic acid, 3-ethyl-4-fluoro-7-{3-[(4-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 3-ethyl-4-fluoro-7-{3-[(4-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-12-ethyl-13-fluoro-11-methyl-1-(3-((5,6,7,8-tetrahydronaphthalen-1-yl)oxy) propyl)-4,5,6,7,9,11-hexahydropyrazolo[4',3':9,10][1]oxa[6]azacycloundecino[8,7,6-hi]indole-2-carboxylic acid, (rac)-1-(3-((2,3-dihydro-1H-inden-4-yl)oxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylic acid, (rac)-13-fluoro-1-(3-((6-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylic acid, (rac)-13-fluoro-1-(3-((4-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylic acid, (rac)-13-fluoro-10,12-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid (rac)-1-(3-((2,3-dihydro-1H-inden-4-yl)oxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylic acid, (rac)-12-ethyl-13-fluoro-10-methyl-1-(3-(naphthalen-1-yloxy)propyl)-4,5,6,7,9,10-hexahydro-pyrazolo[4',3':9,10][1]oxa[6]azacycloundecino[8,7,6-hi]indole-2-carboxylic acid, (rac)-12-ethyl-13-fluoro-1-(3-((6-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylic acid, 3-ethyl-4-fluoro-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), 3-ethyl-4-fluoro-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-12-ethyl-13-fluoro-1-(3-((4-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylic acid, 3-ethyl-4-fluoro-7-{3-[(4-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 1), 3-ethyl-4-fluoro-7-{3-[(4-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 2), (rac)-12-ethyl-13-fluoro-10-methyl-1-(3-((5,6,7,8-tetrahydronaphthalen-1-yl)oxy) propyl)-4,5,6,7,9,10-hexahydropyrazolo[4',3': 9,10][1]oxa[6]azacycloundecino[8,7,6-hi]indole-2-carboxylic acid, (rac)-1-(3-((2,3-dihydro-1H-inden-4-yl)oxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylic acid, (rac)-4-fluoro-2,3-dimethyl-7-[3-(1-naphthyloxy)propyl]-10,11,12,13,14,15-hexahydro-2H-pyrazolo[3',4':8,9][1,6]diazacycloundecino[10,11,1-hi]indole-8-carboxylic acid trifluoroacetic acid salt, 4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid (enantiomer 1), 4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid (enantiomer 2) and 8-carboxy-4-fluoro-2,3,14,14-tetramethyl-7-[3-(1-naphthyloxy)propyl]-10,11,12,13,14,15-hexahydro-2H-pyrazolo[3',4':8,9][1,6]diazacycloundecino[10,11,1-hi]indol-14-ium trifluroacetate or a tautomer, an N-oxide, or a salt thereof, or a salt of a tautomer, or a salt of an N-oxide, or a mixture of same.

In some embodiments, the present invention includes compounds of general formula (I) selected from:

(rac)-7-[3-(2,3-dihydro-1H-inden-4-yloxy)propyl]-3-ethyl-4-fluoro-2,14-dimethyl-10,11,12,13,14,15-hexahydro-2H-pyrazolo[3',4':8,9][1,6]diazacycloundecino[10,11,1-hi]indole-8-carboxylic acid, (rac)-3-ethyl-4-fluoro-2,14-dimethyl-7-[3-(5,6,7,8-tetrahydronaphthalen-1-yloxy)propyl]-10,11,12,13,14,15-hexahydro-2H-pyrazolo[3',4':8,9][1,6]diazacycloundecino[10,11,1-hi]indole-8-carboxylic acid, (rac)-3-ethyl-4-fluoro-7-{3-[(6-fluoro-1-naphthyhoxy]propyl}-2,14-dimethyl-10,11,12,13,14,15-hexahydro-2H-pyrazolo[3',4':8,9][1,6]diazacycloundecino[10,11,1-hi]indole-8-carboxylic acid and (rac)-3-ethyl-4-fluoro-2,14-dimethyl-7-[3-(1-naphthyloxy)propyl]-10,11,12,13,14,15-hexahydro-2H-pyrazolo[3',4': 8,9][1,6]diazacycloundecino[10,11,1-hi]indole-8-carboxylic acid or a tautomer, an N-oxide, or a salt thereof, or a salt of a tautomer, or a salt of an N-oxide, or a mixture of same.

In some embodiments, the present invention includes compounds of general formula (I) selected from:

(rac)-12-ethyl-13-fluoro-1-(3-((6-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylic acid, 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1) and 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 2)

or a tautomer, an N-oxide, or a salt thereof, or a salt of a tautomer, or a salt of an N-oxide, or a mixture of same.

In some embodiments, the present invention includes compounds of general formula (I) selected from example 01-example 50, or a tautomer, an N-oxide, or a salt thereof, or a salt of a tautomer, or a salt of an N-oxide, or a mixture of same.

In some embodiments, the present invention includes compounds of general formula (I) selected from example 51-example 54, or a tautomer, an N-oxide, or a salt thereof, or a salt of a tautomer, or a salt of an N-oxide, or a mixture of same.

In some embodiments, the present invention includes compounds of general formula (I) selected from example 01-example 54, or a tautomer, an N-oxide, or a salt thereof, or a salt of a tautomer, or a salt of an N-oxide, or a mixture of same.

In some embodiments, the present invention includes compounds of general formula (I) selected from example 21-example 25, or a tautomer, an N-oxide, or a salt thereof, or a salt of a tautomer, or a salt of an N-oxide, or a mixture of same.

In some embodiments, the present invention includes compounds of general formula (I) selected from example 14, example 51, example 52, example 53 and example 54, or a tautomer, an N-oxide, or a salt thereof, or a salt of a tautomer, or a salt of an N-oxide, or a mixture of same.

In some embodiments, the present invention includes all intermediate compounds leading to a compound of general formula (I) as disclosed in the example section and their use for the synthesis of the compound of formula (I), starting from Intermediate 1 and ending up with intermediate 138, or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalky-S— group, and a $C_3$-$C_5$-cycloalkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, and a ($C_1$-$C_3$)-haloalky-S— group and a $C_3$-$C_5$-cycloalkyl group; or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group and a heteroaryl group, each of which is unsubstituted or substituted with one, two, or three, substituents and each substituent is independently selected from a halogen atom, a $C_1$-$C_3$-alkyl group and a $C_1$-$C_3$-haloalkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group and a heteroaryl group, each of which is unsubstituted or substituted with one or two substituents and each substituent is independently selected from a halogen atom and a $C_1$-$C_3$-alkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group, each of which is unsubstituted or substituted with one, two or three substituents and each substituent is independently selected from a halogen atom and a $C_1$-$C_3$-alkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is an aryl group, which is unsubstituted or substituted with one or two substituents and each substituent is independently selected from a halogen atom and a $C_1$-$C_3$-alkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is an aryl group, which is unsubstituted or substituted with one substituent which is a halogen atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a aryl group, which is unsubstituted or substituted with a fluorine or a chlorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a aryl group, which is unsubstituted or substituted with a fluorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphthyl group, which is unsubstituted or substituted with a halogen atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphthyl group, which is unsubstituted or substituted with a fluorine atom or a chlorine atom or tautomer, an N-oxide, or a salt thereof or a salt of a tautomer or a salt of an N-oxide or a mixture of same.

In some embodiments, the present invention includes compounds of formula (I), supra, in which $R^4$ is a naphthyl group, which is unsubstituted or substituted with a fluorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphthyl group, which is unsubstituted or substituted with a chlorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphthyl group, which is unsubstituted or substituted with a fluorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a napht-1-yl group or a 6-fluoro-naphth-1-yl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is a napht-1-yl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is a 6-fluoro-naphth-1-yl group or a tautomer, an N-oxide, or a salt thereof, or a salt of a tautomer, or a salt of an N-oxide, or a mixture of same.

In further embodiments the present invention includes compounds of formula (I), supra, in which $R^4$ is selected from 1-naphthyl group, a 4-chloro-3,5-dimethyl-phenyl-1-yl group, and a 5,6,7,8-tetrahydronaphthalene-1-yl group, a 6-fluoro-naphthyl group, a 6-chloro-naphthyl group In further embodiments the present invention includes compounds of formula (I), supra, in which $R^4$ is selected from a naphth-1-yl group, a 6-fluoro-naphthyl group and a 6-chloro-naphth-1-yl group In further embodiments the present invention includes compounds of formula (I), supra, in which $R^4$ is selected from a 1-naphthyl group, a 4-chloro-3,5-dimethyl-phenyl-1-yl group, and a 5,6,7,8-tetrahydronaphthalene-1-yl group, or a tautomer, an N-oxide, or a salt thereof, or a salt of a tautomer, or a salt of an N-oxide, or a mixture of same.

In further embodiments the present invention includes compounds of formula (I), supra, in which $R^4$ is selected from a 1-naphthyl group, a 4-chloro-3,5-dimethyl-phenyl-1-yl group, indane and a 5,6,7,8-tetrahydronaphthalene-1-yl group, or a tautomer, an N-oxide, or a salt thereof, or a salt of a tautomer, or a salt of an N-oxide, or a mixture of same.

In further embodiments the present invention includes compounds of formula (I), supra, in which $R^4$ is selected from indane and a 5,6,7,8-tetrahydronaphthalene-1-yl group, or a tautomer, an N-oxide, or a salt thereof, or a salt of a tautomer, or a salt of an N-oxide, or a mixture of same.

In further embodiments, the present invention includes compounds of formula (I), supra, in which $R^4$ is a halogen substituted naphthyl group, particularly 6-halo-naphthyl group, more particularly a 6-chloro-naphthyl group or a 6-fluoro-naphthyl group or a tautomer, an N-oxide, or a salt thereof, or a salt of a tautomer, or a salt of an N-oxide, or a mixture of same.

In further embodiments, the present invention includes compounds of formula (I), supra, in which $R^4$ is a halogen substituted naphthyl group, particularly 6-halo-naphthyl group, more particularly a 6-fluoro-naphthyl group or a tautomer, an N-oxide, or a salt thereof, or a salt of a tautomer, or a salt of an N-oxide, or a mixture of same.

In other embodiments, the present invention includes compounds of formula (I), supra, in which $R^4$ has one, two or three optional substituents.

In other embodiments, the present invention includes compounds of formula (I), supra, in which L is a group —$(CH_2)_m$-E- which is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group, or a tautomer, an N-oxide, or a salt thereof, or a salt of a tautomer, or a salt of an N-oxide, or a mixture of same.

In other embodiments, the present invention includes compounds of formula (I), supra, in which L is a —$(CH_2)_m$-E- group which is unsubstituted or substituted with a $C_1$-$C_3$-alkyl group or a tautomer, an N-oxide, or a salt thereof, or a salt of a tautomer, or a salt of an N-oxide, or a mixture of same.

In other embodiments, the present invention includes compounds of formula (I), in which L is an unsubstituted group —$(CH_2)_m$-E- or a tautomer, an N-oxide, or a salt thereof, or a salt of a tautomer, or a salt of an N-oxide, or a mixture of same.

In further embodiments the present invention includes compounds of formula (I), supra, in which E is an oxygen atom and constitutes the connecting element to $R^4$, or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group —$(CH_2)_m$-E- and E is an oxygen atom or a tautomer, an N-oxide, or a salt thereof, or a salt of a tautomer, or a salt of an N-oxide, or a mixture of same.

In other embodiments, the present invention includes compounds of formula (I), supra, in which L-$R^4$ is an unsubstituted group —$(CH_2)_m$-E-$R^4$ in which m is 3, E is an oxygen atom and $R^4$ is a fluorine substituted naphthyl group or a tautomer, an N-oxide, or a salt thereof, or a salt of a tautomer, or a salt of an N-oxide, or a mixture of same.

In other embodiments, the present invention includes compounds of formula (I), supra, in which L-$R^4$ is an unsubstituted group —$(CH_2)_m$-E-$R^4$ in which m is 3, E is an oxygen atom and $R^4$ is 6-fluoro-naphthyl group or a tautomer, an N-oxide, or a salt thereof, or a salt of a tautomer, or a salt of an N-oxide, or a mixture of same.

In yet further embodiments, the present invention includes compounds of formula (I), supra, in which $R^5$ is a COOH group, a

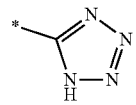

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group, and a —C(O)—NHS(O)$_2$(CH$_2$)$_s$NHCO(aryl) group; and s is 0, 1, 2, or 3; or a tautomer, an N-oxide, or a salt thereof or a salt of a tautomer or a salt of an N-oxide or a mixture of same In yet further embodiments, the present invention includes compounds of formula (I), supra, in which $R^5$ is a COOH group, a

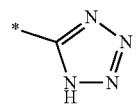

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group and s is 0, 1, 2, or 3, or a tautomer, an N-oxide, or a salt thereof or a salt of a tautomer or a salt of an N-oxide or a mixture of same In further embodiments, the present invention includes compounds of formula (I), supra, in $R^5$ is a COOH group, or a

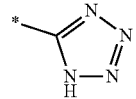

group, or a tautomer, an N-oxide, or a salt thereof, or a salt of a tautomer, or a salt of an N-oxide, or a mixture of same.

In further embodiments, the present invention includes compounds of formula (I), supra, in $R^5$ is a COOH group, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^{\#}$—$(CH_2)_n$—(B)$_t$—$(CH_2)_p$—X—$^{\#\#}$, $^{\#}$—($C_2$-$C_6$-alkenylene)-(B)$_t$—$(CH_2)_p$—X—$^{\#\#}$, $^{\#}$—$(CH_2)_n$—(B)$_t$—($C_2$-$C_5$-alkenylene)-X—$^{\#\#}$, and $^{\#}$—$(CH_2)_q$—(B)—$(CH_2)_r$—(B)—$(CH_2)_v$—X—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and where a —CH=CH— group in any alkenylene can be replaced by a 1,2-($C_3$-$C_6$)cycloalkylene group which is unsubstituted or substituted one or two times with a halogen atom or a $C_1$-$C_2$-alkyl group; and where X is an unsubstituted $CH_2$— group;
or a tautomer, an N-oxide, or a salt thereof, or a salt of a tautomer, or a salt of an N-oxide, or a mixture of same.

In further embodiments, the present invention includes compounds of formula (I), supra, in which —$R^6$-$R^7$— is selected from $^{\#}$—$(CH_2)_n$—$(B)_t$—$(CH_2)_p$—$X$—$^{\#\#}$, $^{\#}$—$(C_2$-$C_6$-alkenylene)-$(B)_t$—$(CH_2)_p$—$X$—$^{\#\#}$, $^{\#}$—$(CH_2)_n$—$(B)_t$—$(C_2$-$C_5$-alkenylene)-$X$—$^{\#\#}$, and $^{\#}$—$(CH_2)_q$—$(B)$—$(CH_2)_r$—$(B)$—$(CH_2)_v$—$X$—$^{\#\#}$,
wherein $^{\#}$ is the point of attachment with the indole nitrogen atom and $^{\#\#}$ is the point of attachment with the pyrazole carbon atom bearing the $R^7$ substituent; and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, and where a —CH=CH— group in any alkenylene can be replaced by a 1,2-($C_3$-$C_6$)cycloalkylene group which is unsubstituted or substituted one or two times with a halogen atom or a $C_1$-$C_2$-alkyl group, and where X is an unsubstituted —$CH_2$— group; or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^{\#}$—$(CH_2)_n$—$(B)_t$—$(CH_2)_p$—$X$—$^{190}$ $^{\#}$, $^{\#}$—$(C_2$-$C_6$-alkenylene)-$(B)_t$—$(CH_2)_p$—$X$—$^{\#\#}$, and where a double bond in any alkenylene can be replaced by an unsubstituted a 1,2-($C_3$-$C_5$-cycloalkyl) group, and wherein $^{\#}$ is the point of attachment with the indole nitrogen atom and $^{\#\#}$ is the point of attachment with the pyrazole carbon atom bearing the $R^7$ substituent; and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, and a $C_1$-$C_3$-alkoxy group, and where a CH=CH— group in any alkenylene can be replaced by a 1,2-($C_3$-$C_6$)cycloalkylene group which is unsubstituted or substituted one or two times with a halogen atom or a $C_1$-$C_2$-alkyl group, and where X is an unsubstituted —$CH_2$— group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^{\#}$—$(CH_2)_n$—$(B)_t$—$(CH_2)_p$—$X$—$^{\#\#}$, $^{\#}$—$(C_2$-$C_6$-alkenylene)-$(B)_t$—$(CH_2)_p$—$X$—$^{\#\#}$, and wherein $^{\#}$ is the point of attachment with the indole nitrogen atom and $^{\#\#}$ is the point of attachment with the pyrazole carbon atom bearing the $R^7$ substituent and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, and a $C_1$-$C_3$-alkoxy group, and where a —CH=CH— group in any alkenylene can be replaced by a 1,2-cyclopropylene group or a 1,2-cyclobutylene group and
where X is an unsubstituted —$H_2$— group;
or a tautomer or a salt thereof or a salt of a tautomer or a mixture of same.

In other embodiments, the present invention includes compounds of formula (I), supra, in which —$R^6$-$R^7$— is selected from $^{\#}$—$(CH_2)_n$—$(B)_t$—$(CH_2)_p$—$X$—$^{\#\#}$ and $^{\#}$—$(C_2$-$C_6$-alkenylene)-$(B)_t$—$(CH_2)_p$—$X$—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more a halogen atoms,
and where a —CH=CH— group in any alkenylene can be replaced by a 1,2-cyclopropylene group or a 1,2-cyclobutylene group and where X is an unsubstituted —$CH_2$— group; or a tautomer or a salt thereof or a salt of a tautomer or a mixture of same.

In other embodiments, the present invention includes compounds of formula (I), supra, in which —$R^6$-$R^7$— is selected from $^{\#}$—$(CH_2)_n$—$(B)_t$—$(CH_2)_p$—$X$—$^{\#\#}$ and $^{\#}$—$(C_2$-$C_6$-alkenylene)-$(B)_t$—$(CH_2)_p$—$X$—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more a halogen atoms,
and where a —CH=CH— group in any alkenylene can be replaced by the groups

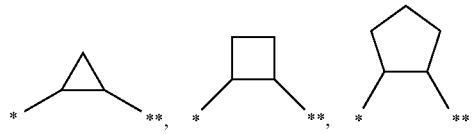

and where X is an unsubstituted —$CH_2$— group; or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^{\#}$—$(CH_2)_n$—$(B)_t$—$(CH_2)_p$—$X$—$^{\#\#}$ and $^{\#}$—$(C_2$-$C_6$-alkenylene)-$(B)_t$—$(CH_2)_p$—$X$—$^{\#\#}$, wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_n$—$(B)_t$—$(CH_2)_p$—$X$—$^{\#\#}$, wherein $^{\#}$ is the point of attachment with the indole nitrogen atom and $^{\#\#}$ is the point of attachment with the pyrazole carbon atom bearing the $R^7$ substituent, and A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(C_2$-$C_6$-alkenylene)-$(B)_t$—$(CH_2)_p$—$X$—$^{\#\#}$, wherein $^{\#}$ is the point of attachment with the indole nitrogen atom and $^{\#\#}$ is the point of attachment with the pyrazole carbon atom bearing the $R^7$ substituent, and A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which $R^6$-$R^7$— is selected from $^{\#}$—(CH$_2$)$_n$—(B)$_t$—(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent and wherein one or more —CH$_2$— groups may be unsubstituted or substituted with one or more fluorine atoms, where X is an unsubstituted —CH$_2$— group or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—(CH$_2$)$_3$—N(CH$_3$)—CH$_2$—$^{\#\#}$, $^{\#}$—(CH$_2$)$_3$—NH—CH$_2$—$^{\#\#}$, $^{\#}$—(CH$_2$)$_4$—N(CH$_3$)—CH$_2$—$^{\#\#}$, $^{\#}$—(CH$_2$)$_4$—N(CH$_2$CF$_3$)—CH$_2$—$^{\#\#}$, $^{\#}$—(CH$_2$)$_4$—N(CH$_2$CHF$_2$)—CH$_2$—$^{\#\#}$, $^{\#}$—CH$_2$—CH=CH—CH$_2$—O—CH$_2$—$^{\#\#}$, $^{\#}$—CH$_2$—CH=CH—CH$_2$—N(CH$_3$)—CH$_2$—$^{\#\#}$, $^{\#}$—(CH$_2$)$_4$—O—CH$_2$—$^{\#\#}$, $^{\#}$—(CH$_2$—)$_6$$^{\#\#}$, $^{\#}$—(CH$_2$)$_2$—CF$_2$—CH$_2$—O—CH$_2$—$^{\#\#}$, $^{\#}$—CH$_2$—CF$_2$—(CH$_2$)$_2$—O—CH$_2$—$^{\#\#}$, $^{\#}$—CH$_2$—CF$_2$—CF$_2$—CH$_2$—O—CH$_2$—$^{\#\#}$,

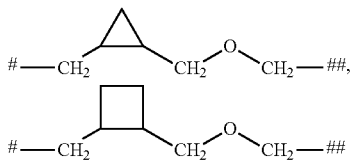

and wherein $^{\#}$ is the point of attachment with the indole nitrogen atom and $^{\#\#}$ is the point of attachment with the pyrazole carbon atom bearing the R$^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—(CH$_2$)$_3$—N(CH$_3$)—CH$_2$—$^{\#\#}$, $^{\#}$—(CH$_2$)$_3$—NH—CH$_2$—$^{\#\#}$, $^{\#}$—(CH$_2$)$_4$—N(CH$_3$)—CH$_2$—$^{\#\#}$, $^{\#}$—(CH$_2$)$_4$—N(CH$_2$CF$_3$)—CH$_2$—$^{\#\#}$, $^{\#}$—(CH$_2$)$_4$—N(CH$_2$CHF$_2$)—CH$_2$—$^{\#\#}$, $^{\#}$—CH$_2$—CH=CH—CH$_2$—O—CH$_2$—$^{\#\#}$, $^{\#}$—CH$_2$—CH=CH—CH$_2$—N(CH$_3$)—CH$_2$—$^{\#\#}$, $^{\#}$—(CH$_2$)$_4$—O—CH$_2$—$^{\#\#}$, $^{\#}$—(CH$_2$—)$_6$$^{\#\#}$, $^{\#}$—(CH$_2$)$_2$—CF$_2$—CH$_2$—O—CH$_2$$^{\#\#}$,

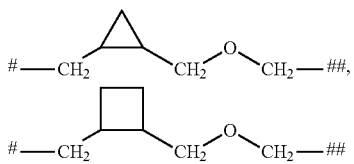

and wherein $^{\#}$ is the point of attachment with the indole nitrogen atom and $^{\#\#}$ is the point of attachment with the pyrazole carbon atom bearing the R$^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—(CH$_2$)$_3$—N(CH$_3$)—CH$_2$—$^{\#\#}$, $^{\#}$—(CH$_2$)$_3$—NH—CH$_2$—$^{\#\#}$, $^{\#}$—(CH$_2$)$_4$—N(CH$_3$)—CH$_2$—$^{\#\#}$, $^{\#}$—(CH$_2$)$_4$—N(CH$_2$CF$_3$)—CH$_2$—$^{\#\#}$, $^{\#}$—(CH$_2$)$_4$—N(CH$_2$CHF$_2$)—CH$_2$—$^{\#\#}$, $^{\#}$—(CH$_2$)$_4$—O—CH$_2$—$^{\#\#}$, $^{\#}$—(CH$_2$—)$_6$$^{\#\#}$, $^{\#}$—(CH$_2$)$_2$—CF$_2$—CH$_2$—O—CH$_2$—$^{\#\#}$,

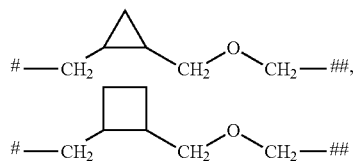

and wherein $^{\#}$ is the point of attachment with the indole nitrogen atom and $^{\#\#}$ is the point of attachment with the pyrazole carbon atom bearing the R$^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—(CH$_2$)$_3$—N(CH$_3$)—CH$_2$—$^{\#\#}$, $^{\#}$—(CH$_2$)$_3$—NH—CH$_2$—$^{\#\#}$, $^{\#}$—(CH$_2$)$_4$—N(CH$_3$)—CH$_2$—$^{\#\#}$, $^{\#}$—(CH$_2$)$_4$—N(CH$_2$CF$_3$)—CH$_2$—$^{\#\#}$, $^{\#}$—(CH$_2$)$_4$—N(CH$_2$CHF$_2$)—CH$_2$—$^{\#\#}$, $^{\#}$—(CH$_2$)$_4$—O—CH$_2$—$^{\#\#}$, $^{\#}$—(CH$_2$—)$_6$$^{\#\#}$, $^{\#}$—(CH$_2$)$_2$—CF$_2$—CH$_2$—O—CH$_2$—$^{\#\#}$, and wherein $^{\#}$ is the point of attachment with the indole nitrogen atom and $^{\#\#}$ is the point of attachment with the pyrazole carbon atom bearing the R$^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—CH$_2$—CH=CH—CH$_2$—O—CH$_2$$^{\#\#}$—, $^{\#}$—CH$_2$—CH=CH—CH$_2$—N(CH$_3$)—CH$_2$—$^{\#\#}$,

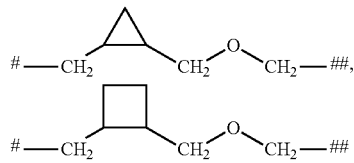

and wherein $^{\#}$ is the point of attachment with the indole nitrogen atom and $^{\#\#}$ is the point of attachment with the pyrazole carbon atom bearing the R$^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$(CH$_2$)$_3$—N(CH$_3$)—CH$_2$$^{\#\#}$—, $^{\#}$(CH$_2$)$_3$—NH—CH$_2$—$^{\#\#}$, $^{\#}$—CH$_2$)$_4$—N(CH$_3$)—CH$_2$—$^{\#\#}$, $^{\#}$(CH$_2$)$_4$—N(CH$_2$CF$_3$)—CH$_2$—$^{\#\#}$, $^{\#}$—(CH$_2$)$_4$—N(CH$_2$CHF$_2$)—CH$_2$—$^{\#\#}$, $^{\#}$—CH$_2$—CH=CH—CH$_2$—N(CH$_3$)—CH$_2$—$^{\#\#}$, and wherein $^{\#}$ is the point of attachment with the indole nitrogen atom and $^{\#\#}$ is the point of attachment with the pyrazole carbon atom bearing the R$^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—CH$_2$—CH=CH—CH$_2$—O—CH$_2$—$^{\#\#}$, $^{\#}$—(CH$_2$)$_4$—O—CH$_2$—$^{\#\#}$, $^{\#}$—(CH$_2$)$_2$—CF$_2$—CH$_2$—O—CH$_2$—$^{\#\#}$,

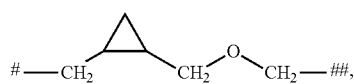

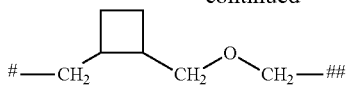

and wherein # is the point of attachment with the indole nitrogen atom and ## is the point of attachment with the pyrazole carbon atom bearing the $R^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is —($CH_2$—)$_6$ and wherein # is the point of attachment with the indole nitrogen atom and ## is the point of attachment with the pyrazole carbon atom bearing the $R^7$ substituent; or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^{10}$— is selected from #—($CH_2$)$_n$—(B)$_t$—($CH_2$)$_p$—X—##, #—($C_2$-$C_6$-alkenylene)-(B)$_t$—($CH_2$)$_p$—X—##, #—($CH_2$)$_n$—(B)$_t$—($C_2$-$C_6$-alkenylene)-X—## and #—($CH_2$)$_q$—(B)—($CH_2$)$_r$—(B)—($CH_2$)$_v$—X—##, wherein # is the point of attachment with the indole nitrogen atom and ## is the point of attachment with the carbon atom of the phenyl moiety bearing the $R^{10}$ substituent, or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, where a —H=CH— group in any alkenylene can be replaced by a 1,2-($C_1$-$C_6$)cycloalkylene group which is unsubstituted or substituted one or two times with a halogen atom or a $C_1$-$C_2$-alkyl group, and where X is an unsubstituted —$H_2$— group;

or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)$NR^{15}$— group, a —$NR^{15}$C(O)— group, a —N($R^{15}$)— group, a —N($R^{15}$)—C(=O)—N($R^{15}$)— group, a —O—C(=O)—N($R^{15}$)— group, a —N($R^{15}$)—C(=O)—O— group, —O—, —S—, —S(O)—, —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)$NR^{15}$— group, a —$NR^{15}$C(O)— group, a —N($R^{15}$)— group, a —[N($CH_3$)$_2$]$^+$ group, a —N($R^{15}$)—C(=O)—N($R^{15}$)— group, a —O—C(=O)—N($R^{15}$)— group, a —N($R^{15}$)—C(=O)—O— group, —O—, —S—, —S(O)—, —S(O)$_2$—, or a tautomer, an N-oxide, or a salt thereof, or a salt of a tautomer, or a salt of an N-oxide, or a mixture of same. In further embodiments, the present invention includes compounds of formula (I), supra, in which B is independently selected from a —C(O)$NR^{15}$— group, a —$NR^{15}$C(O)— group, a —N($R^{15}$)— group, —O—, —S—, —S(O)— and —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)$NR^{15}$— group, a —$NR^{15}$C(O)— group, a —N($R^{15}$)— group, a [N($CH_3$)$_2$]$^+$ group, —O—, —S—, —S(O)— and —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —N($R^{15}$)— group, —O—, —S—, —S(O)— and —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —N($R^{15}$)— group, a [N($CH_3$)$_2$]$^+$ group, —O—, —S—, —S(O)— and —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)$NR^{15}$— group, a —$NR^{15}$C(O)— group, a —N($R^{15}$)— group, —O— and —S— or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)$NR^{15}$— group, a —$NR^{15}$C(O)— group, a —N($R^{15}$)— group, a [N($CH_3$)$_2$]$^+$ group, —O— and —S— or a tautomer, an N-oxide, or a salt thereof, or a salt of a tautomer, or a salt of an N-oxide, or a mixture of same.

In further embodiments, the present invention includes compounds of formula (I), supra, in which B is independently selected from In further embodiments, the present invention includes compounds of formula (I), supra, in which B is independently selected from —O—, —S— and a —N($R^{15}$)— group or a tautomer, an N-oxide, or a salt thereof, or a salt of a tautomer, or a salt of an N-oxide, or a mixture of same.

In further embodiments, the present invention includes compounds of formula (I), supra, in which B is independently selected from In further embodiments, the present invention includes compounds of formula (I), supra, in which B is independently selected from —O—, —S— and a —N($R^{15}$)— group, a [N($CH_3$)$_2$]$^+$ group, or a tautomer, an N-oxide, or a salt thereof, or a salt of a tautomer, or a salt of an N-oxide, or a mixture of same.

In further embodiments, the present invention includes compounds of formula (I), supra, in which B is independently selected from In further embodiments, the present invention includes compounds of formula (I), supra, in which B is independently selected from —O— and a —N($R^{15}$)— group or a tautomer, an N-oxide, or a salt thereof, or a salt of a tautomer, or a salt of an N-oxide, or a mixture of same. In further embodiments, the present invention includes compounds of formula (I), supra, in which B is independently selected from In further embodiments, the present invention includes compounds of formula (I), supra, in which B is independently selected from —O—, a [N($CH_3$)$_2$]$^+$ group and a —N($R^{15}$)— group or a tautomer, an N-oxide, or a salt thereof, or a salt of a tautomer, or a salt of an N-oxide, or a mixture of same.

In further embodiments, the present invention includes compounds of formula (I), supra, in which B is a —$NR^{15}$— group or a tautomer, an N-oxide, or a salt thereof, or a salt of a tautomer, or a salt of an N-oxide, or a mixture of same.

In further embodiments, the present invention includes compounds of formula (I), supra, in which B is a —$NR^{15}$— group, a [N(CH$_3$)$_2$]$^+$ group, or a tautomer, an N-oxide, or a salt thereof, or a salt of a tautomer, or a salt of an N-oxide, or a mixture of same.

In further embodiments, the present invention includes compounds of formula (I), supra, in which B is a —[N(CH$_3$)$_2$]$^+$ group, or a tautomer, an N-oxide, or a salt thereof, or a salt of a tautomer, or a salt of an N-oxide, or a mixture of same.

In further embodiments, the present invention includes compounds of formula (I), supra, in which B is an oxygen atom or a tautomer, an N-oxide, or a salt thereof, or a salt of a tautomer, or a salt of an N-oxide, or a mixture of same.

In further embodiments, the present invention includes compounds of formula (I), supra, in which B is —NR$^{15}$—, particularly —NH—, —N(C$_1$-C$_3$-alkyl)-, or —(C$_1$-C$_3$-haloalkyl), more particularly —NH—, —(CH$_3$)—, N(CH$_2$—CF$_3$)—, or —N(CH$_2$CHF$_2$) or a tautomer, an N-oxide, or a salt thereof, or a salt of a tautomer, or a salt of an N-oxide, or a mixture of same.

In further embodiments, the present invention includes compounds of formula (I), supra, in which B is —NR$^{15}$—, particularly —NH—, —N(C$_1$-C$_3$-alkyl)-, or —N(C$_1$-C$_3$-haloalkyl), more particularly —N(CH$_3$)— or a tautomer, an N-oxide, or a salt thereof, or a salt of a tautomer, or a salt of an N-oxide, or a mixture of same.

In other embodiments, the present invention includes compounds of formula (I), supra, in which A is A1, or a tautomer, an N-oxide, or a salt thereof, or a salt of a tautomer, or a salt of an N-oxide, or a mixture of same.

In further embodiments, the present invention includes compounds of formula (I), supra, in which A is A2, or a tautomer, an N-oxide, or a salt thereof, or a salt of a tautomer, or a salt of an N-oxide, or a mixture of same.

In yet other embodiments, the present invention includes compounds of formula (I), supra, in which A is A3, or a tautomer, an N-oxide, or a salt thereof, or a salt of a tautomer, or a salt of an N-oxide, or a mixture of same.

In yet other embodiments, the present invention includes compounds of formula (I), supra, in which A is A3 and the macrocyclic ring is a 9-membered-, a 10-membered-, a 11-membered-, a 12-membered-, a 13-membered-, a 14-membered-, a 15-membered- or a 16-membered ring, particularly a 9-membered-, a 10-membered-, a 11-membered-, or a 12-membered ring, more particularly a 12-membered ring or a tautomer, an N-oxide, or a salt thereof, or a salt of a tautomer, or a salt of an N-oxide, or a mixture of same.

In further embodiments, the present invention includes compounds of formula (I), supra, in which A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which A is A1 or A2 and the macrocyclic ring is a 9-membered-, a 10-membered-, a 11-membered-, a 12-membered-, a 13-membered-, a 14-membered-, a 15-membered- or a 16-membered ring, particularly a 9- to 12-membered ring or a 12- or a 13-membered ring, more particularly a 10- to 11-membered ring, even more particularly a 11-membered ring or a tautomer, an N-oxide, or a salt thereof, or a salt of a tautomer, or a salt of an N-oxide, or a mixture of same.

In other embodiments, the present invention includes compounds of formula (I), supra, in which A is A1 or A2, which together with the indole moiety and the R$^6$-R$^7$ form a 9-membered-, a 10-membered-, a 11-membered- or a 12-membered macrocyclic ring or a tautomer, an N-oxide, or a salt thereof, or a salt of a tautomer, or a salt of an N-oxide, or a mixture of same.

In other embodiments, the present invention includes compounds of formula (I), supra, in which A is A1 or A2, which together with the indole moiety and the R$^6$-R$^7$ form a 9-membered-, a 10-membered- or a 11-membered-macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1, which together with the indole moiety and the R$^6$-R$^7$ form a 9-membered-, a 10-membered-, a 11-membered- or a 12-membered macrocyclic ring or a tautomer, an N-oxide, or a salt thereof, or a salt of a tautomer, or a salt of an N-oxide, or a mixture of same.

In other embodiments, the present invention includes compounds of formula (I), supra, in which A is A1, which together with the indole moiety and the R$^6$-R$^7$ form a 9-membered-, a 10-membered- or a 11-membered-macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A2, which together with the indole moiety and the R$^6$-R$^7$ form a 9-membered-, a 10-membered-, a 11-membered- or a 12-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A2, which together with the indole moiety and the R$^6$-R$^7$ form a 9-membered-, a 10-membered- or a 11-membered-macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2, which together with the indole moiety and the R$^6$-R$^7$ form a 10-membered- or a 11-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2, which together with the indole moiety and the R$^6$-R$^7$ form a 11-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 and R$^8$ and R$^9$ are C$_1$-C$_3$-alkyl, R$^8$ is particularly methyl and R$^9$ is methyl or ethyl or a tautomer, an N-oxide, or a salt thereof, or a salt of a tautomer, or a salt of an N-oxide, or a mixture of same.

In yet other embodiments, the present invention includes compounds of formula (I), supra, in which A is A2 and R$^8$ and R$^9$ are C$_1$-C$_3$-alkyl, R$^8$ is particularly methyl and R$^9$ is methyl or ethyl or a tautomer, an N-oxide, or a salt thereof, or a salt of a tautomer, or a salt of an N-oxide, or a mixture of same.

In other embodiments, the present invention includes compounds of formula (I), supra, in which A is A1 or A2 and R$^8$ and R$^9$ are C$_1$-C$_3$-alkyl, R$^8$ is particularly methyl, morpholinoethyl or morpholinopropyl and R$^9$ is methyl or ethyl or a tautomer, an N-oxide, or a salt thereof, or a salt of a tautomer, or a salt of an N-oxide, or a mixture of same.

In further embodiments, the present invention includes compounds of formula (I), supra, in which A is A1 or A2 and $R^8$ and $R^9$ are independently selected from $C_1$-$C_3$-alkyl or a ($C_1$-$C_3$-alkyl)-heterocyclyl or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2 and $R^8$ and $R^9$ are $C_1$-$C_3$-alkyl, $R^8$ is particularly methyl and $R^9$ is methyl or ethyl or a tautomer, an N-oxide, or a salt thereof, or a salt of a tautomer, or a salt of an N-oxide, or a mixture of same.

The integers selected for variables n, t, p, q, r, and v may result in different ring sizes but still the rings obtained have to fulfill the rule that only rings of a ring size of 9 members up to a ring size of 16 members including 9 and 16 members are encompassed.

In some embodiments, the present invention includes compounds of formula (I), supra, in which
n is 2, 3, 4, 5, 6, 7, 8, or 9;
t is 0 or 1;
p is 0, 1, 2, 3, 4, 5, or 6;
q is 2, 3, 4, 5, or 6;
r is 2, 3, 4, 5, or 6;
v is 0, 1, or 2;

In further embodiments, the present invention includes compounds of formula (I), supra, in which
n is 2, 3, 4, 5, 6;
t is 0 or 1;
p is 0, 1, or 2;
q is 2;
r is 2;
v is 0 or 1.

In further embodiments, the present invention includes compounds of formula (I), supra, in which n is 2, 3, 4, 5, 6;
t is 1;
is 1;
q is 2;
  r is 2;
v is 0 or 1.

In further embodiments, the present invention includes compounds of formula (I), supra, in which n is 3, 4, 5, or 6;
t is 0 or 1;
p is 0 or 1.

In further embodiments, the present invention includes compounds of formula (I), supra, in which n is 3 or 4;
t is 1;
p is 1 or 2

The limitations relating to A1 and A2 are independent from the limitations relating to A3.

In further embodiments, the present invention includes compounds of formula (I), supra, in which $R^8$ is selected from a hydrogen atom
  a $C_1$-$C_6$-alkyl group which is unsubstituted or substituted with one or more substituents independently selected from
    a halogen atom, a hydroxyl group, a $C_1$-$C_3$-alkoxy group, a $C_1$-$C_3$-haloalkoxy group,
    a $C_3$-$C_6$-cycloalkyl group, a heterocycloalkyl group and a $NR^{20}R^{21}$ group; and
  a $C_3$-$C_6$-cycloalkyl group, or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from a hydrogen atom and, a $C_1$-$C_4$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group; or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from a hydrogen atom and, a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_6$-alkyl group which is unsubstituted or substituted with one or more heterocycloalkyl groups or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_6$-alkyl group which is unsubstituted or substituted with a heterocycloalkyl group or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_6$-alkyl group which is unsubstituted or substituted with a morpholino group or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_3$-alkyl group which is unsubstituted or substituted with a morpholino group or a tautomer, an N-oxide, or a salt thereof, or a salt of a tautomer, or a salt of an N-oxide, or a mixture of same.

In further embodiments, the present invention includes compounds of formula (I), supra, in which
$R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)- group,
  a $C_2$-$C_6$-haloalkenyl group,
  a $C_1$-$C_6$-alkyl-O— group,
  a $C_1$-$C_4$-haloalkoxy group,
  a $C_1$-$C_6$-alkyl-O—($C_1$-$C_3$-alkylene)- group,
  a ($C_3$-$C_7$)-cycloalkyl group,
  a ($C_3$-$C_7$)-cycloalkyl-O—($C_1$-$C_3$-alkylene)- group,
  a phenyl-O—($C_1$-$C_3$-alkylene)- group,
  a phenyl-($C_1$-$C_3$-alkylene)-O—($C_1$-$C_3$-alkylene)- group,
  a $R^{18}$-(phenylene)-($C_1$-$C_3$-alkylene)-O—($C_1$-$C_3$-alkylene)- group,
  a $R^{18}$-(phenylene)-O—($C_1$-$C_3$-alkylene)- group,
  a $R^{18}$-(phenylene)-(heteroarylene)-O—($C_1$-$C_3$-alkylene) group,
  a ($R^{18}$)-(heterocycloalkylene)-($C_1$-$C_3$-alkylene)- group,
  a ($R^{18}$)-(heterocycloalkylene)-(phenylene)-O—($C_1$-$C_3$-alkylene)- group,
  a (heterocycloalkenyl)-(phenylene)-O—($C_1$-$C_3$-alkylene)- group, a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a NR$^{20}$R$^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group
a ($C_1$-$C_3$-alkyl)-NR$^{15}$—C(O)—($C_1$-$C_3$-alkylene)- group
a ($C_1$-$C_3$-alkyl)-C(O)—NH—($C_1$-$C_3$-alkylene)- group
a ($C_1$-$C_3$-alkyl)-C(O)—NR$^{15}$—($C_1$-$C_3$-alkylene)- group,
a

[structure: F,F-substituted azetidine N—(C$_1$C$_3$)-alkylene—]

group, and a

[structure: spiro oxetane-azetidine N—(C$_1$-C$_3$)-alkylene—]

group, where the phenyl ring is unsubstituted or substituted with a halogen atom, a hydroxyl group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxyl group, a $C_1$-$C_3$-alkyl group, and a $C_1$-$C_3$-alkoxy group,
or R$^8$ and R$^9$ together form a 5- or 6-membered ring optionally containing one or two heteroatoms selected from —O—, and —NR$^{14}$—;
and where
R$^{19}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a R$^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group and where R$^{18}$ is located at any position chemically possible;

where R$^{19}$ is selected from a $C_1$-$C_3$-alkyl group, a $C_3$-$C_6$-cycloalkyl group, and a NR$^{20}$R$^{21}$ group and where R$^{19}$ is located at any position chemically possible; and
where R$^{20}$, R$^{21}$ are independently selected from a hydrogen atom or a $C_1$-$C_6$-alkyl group;
or a tautomer, an N-oxide, or a salt thereof, or a salt of a tautomer, or a salt of an N-oxide, or a mixture of same.
In further embodiments, the present invention includes compounds of formula (I), supra, in which
R$^9$ is selected from
a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a R$^{18}$-(phenylene)-($C_1$-$C_3$-alkylene)-O—($C_1$-$C_3$-alkylene)- group,
a R$^{18}$-(phenylene)-O—($C_1$-$C_3$-alkylene)- group,
a R$^{18}$-(phenylene)-(heteroarylene)-O—($C_1$-$C_3$-alkylene) group,
a (R$^{18}$)-(heterocycloalkylene)-($C_1$-$C_3$-alkylene)- group,
a (R$^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a (R$^{18}$)-(heteroarylene)-($C_1$-$C_3$-alkylene)-O—($C_1$-$C_3$-alkylene)- group,
a (R$^{18}$)-(heteroarylene)-(phenylene)-O—($C_1$-$C_3$-alkylene)- group,
a (R$^{19}$)—S(O)$_2$-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—N($C_1$-$C_6$-alkyl)-(phenylene)-O—($C_1$-$C_3$-alkylene)- group,
a (R$^{19}$)—S(O)$_2$-(heterocycloalkylene)-(phenylene)-O—($C_1$-$C_3$-alkylene)- group,
a (R$^{18}$)-(heterocycloalkylene)-(heteroarylene)-O—($C_1$-$C_3$-alkylene)- group,
a (R$^{19}$)-(heteroarylene)-O—($C_1$-$C_3$-alkylene)- group,
a (R$^{18}$)-(heteroarylene)-O—($C_1$-$C_3$-alkylene)- group,
a (R$^{19}$)—S(O)$_2$-(heteroarylene)-O—($C_1$-$C_3$-alkylene)- group,
a (R$^{18}$)—S(O)$_2$-(heterocycloalkylene)-(heteroarylene)-O—($C_1$-$C_3$-alkylene)- group,
a NR$^{20}$R$^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group
a ($C_1$-$C_3$-alkyl)-NR$^{15}$—C(O)—($C_1$-$C_3$-alkylene)- group a (C$_1$-C$_3$-alkyl)-C(O)—NH—(C$_1$-C$_3$-alkylene)- group
a (C$_1$-C$_3$-alkyl)-C(O)—NR$^{15}$—(C$_1$-C$_3$-alkylene)- group,
a

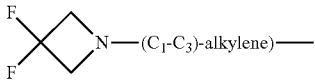

a group, and a

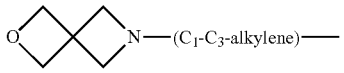

group,
where the phenyl ring is unsubstituted or substituted with
   a halogen atom, a hydroxyl group, or a C$_1$-C$_3$-alkoxy group and
the heterocycloalkyl group is unsubstituted or substituted with an oxo (═O) group or is unsubstituted or substituted with one or more substituents independently selected from a halogen atom, a hydroxyl group, a C$_1$-C$_3$-alkyl group, and a C$_1$-C$_3$-alkoxy group,
or R$^8$ and R$^9$ together form a 5- or 6-membered ring optionally containing one or two heteroatoms selected from —O—, and —NR$^{14}$—;
or a tautomer, an N-oxide, or a salt thereof, or a salt of a tautomer, or a salt of an N-oxide, or a mixture of same.

In further embodiments, the present invention includes compounds of formula (I), supra, in which R$^9$ is selected from
a hydrogen atom,
   a C$_1$-C$_4$-alkyl group,
   a C$_1$-C$_3$-hydroxyalkyl group,
   a C$_1$-C$_4$-haloalkyl group,
   a C$_1$-C$_4$-haloalkyl-NH—C(O)—O—(C$_1$-C$_3$-alkylene)- group,
   a C$_2$-C$_6$-haloalkenyl group,
   a C$_1$-C$_6$-alkyl-O— group,
   a C$_1$-C$_4$-haloalkoxy group,
   a C$_1$-C$_6$-alkyl-O—(C$_1$-C$_3$-alkylene)- group,
   a (C$_3$-C$_7$)-cycloalkyl group,
   a (C$_3$-C$_7$-cycloalkyl)-O—(C$_1$-C$_3$-alkylene)- group,
   a phenyl-O—(C$_1$-C$_3$-alkylene)- group,
   a phenyl-(C$_1$-C$_3$-alkylene)-O—(C$_1$-C$_3$-alkylene)- group,
   a (R$^{18}$)-(phenylene)-O—(C$_1$-C$_3$-alkylene)- group,
   a (R$^{18}$)-(phenylene)-(C$_1$-C$_3$-alkylene)-O—(C$_1$-C$_3$-alkylene)- group,
   a (R$^{18}$)-(phenylene)-(heteroarylene)-O—(C$_1$-C$_3$-alkylene) group,
   a (R$^{18}$)-(heterocycloalkylene)-(C$_1$-C$_6$-alkylene)- group,
   a (R$^{18}$)-(heterocycloalkylene)-(phenylene)-O—(C$_1$-C$_3$-alkylene)- group,
   a (heterocycloalkenyl)-(phenylene)-O—(C$_1$-C$_3$-alkylene)- group,
   a (R$^{18}$)-(heteroarylene)-(C$_1$-C$_3$-alkylene)-O—(C$_1$-C$_3$-alkylene)- group,
   a (R$^{18}$)-(heteroarylene)-(phenylene)-O—(C$_1$-C$_3$-alkylene)- group,
   a (R$^{18}$)-(phenylene)-(C$_1$-C$_3$-alkylene)-O—(C$_1$-C$_3$-alkylene)- group,
   a (R$^{19}$)—S(O)$_2$-(phenylene)-O—(C$_1$-C$_3$-alkylene)- group,
   a (R$^{19}$)—S(O)$_2$—NH-(phenylene)-O—(C$_1$-C$_3$-alkylene)- group,
   a (R$^{19}$)—S(O)$_2$—N(C$_1$-C$_6$-alkyl)-(phenylene)-O—(C$_1$-C$_3$-alkylene)- group,
   a (R$^{19}$)—S(O)$_2$-(heterocycloalkylene)-(phenylene)-O—(C$_1$-C$_3$-alkylene)- group,
   a (R$^{18}$)-(heterocycloalkylene)-(heteroarylene)-O—(C$_1$-C$_3$-alkylene)- group,
   a (R$^{19}$)-(heteroarylene)-O—(C$_1$-C$_3$-alkylene)- group,
   a (R$^{19}$)—S(O)$_2$-(heteroarylene)-O—(C$_1$-C$_3$-alkylene)- group,
   a (R$^{19}$)—S(O)$_2$-(heterocycloalkylene)-(heteroarylene)-O—(C$_1$-C$_3$-alkylene)- group,
   a NR$^{20}$R$^{21}$—(C$_1$-C$_3$-alkylene)- group,
   a (C$_1$-C$_3$-alkyl)-NH—(C$_1$-C$_3$-alkylene)- group,
   a (C$_1$-C$_3$-haloalkyl)-(C$_1$-C$_3$-alkylene)-NH—(C$_1$-C$_3$-alkylene)- group,
   a (C$_1$-C$_3$-haloalkyl)-NH—(C$_1$-C$_3$-alkylene)- group,
   a (C$_1$-C$_3$-alkyl)-NH—C(O)—(C$_1$-C$_3$-alkylene)- group
   a (C$_1$-C$_3$-alkyl)-NR$^{19}$—C(O)—(C$_1$-C$_3$-alkylene)- group
   a (C$_1$-C$_3$-alkyl)-C(O)—NH—(C$_1$-C$_3$-alkylene)- group
   a (C$_1$-C$_3$-alkyl)-C(O)—NR$^{15}$—(C$_1$-C$_3$-alkylene)- group,
a

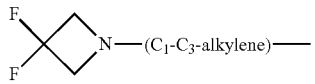

group, and a

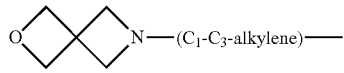

group,
where the phenyl ring is optionally substituted with a halogen atom, a hydroxyl group, or a C$_1$-C$_3$-alkoxy group and
the heterocycloalkyl group is optionally substituted with an oxo (═O) group or is optionally substituted with one or more substituents independently selected from a halogen atom, and a C$_1$-C$_3$-alkyl group;
or R$^8$ and R$^9$ together form a 5- or 6-membered ring optionally containing one or two heteroatoms selected from of —O—, and —NR$^{14}$—;
or a tautomer, an N-oxide, or a salt thereof, or a salt of a tautomer, or a salt of an N-oxide, or a mixture of same.

In further embodiments, the present invention includes compounds of formula (I), supra, in which
R$^9$ is selected from
a hydrogen atom,
   a C$_1$-C$_4$-alkyl group,
   a C$_1$-C$_3$-hydroxyalkyl group,
   a C$_1$-C$_4$-haloalkyl group,
   a C$_2$-C$_6$-haloalkenyl group,
   a C$_1$-C$_6$-alkyl-O— group,
   a C$_1$-C$_4$-haloalkoxy group,
   a C$_1$-C$_6$-alkyl-O—(C$_1$-C$_3$-alkylene)- group,
   a (C$_3$-C$_7$)-cycloalkyl group,
   a (C$_3$-C$_7$-cycloalkyl)-O—(C$_1$-C$_3$-alkylene)- group,
   a phenyl-O—(C$_1$-C$_3$-alkylene)- group,
   a (R$^{19}$)-(phenylene)-O—(C$_1$-C$_3$-alkylene)- group,
   a (R$^{18}$)-(heterocycloalkylene)-(C$_1$-C$_6$-alkylene)- group, a (R$^{19}$)—S(O)$_2$-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group
a (C$_1$-C$_3$-alkyl)-NR$^{15}$—C(O)—(C$_1$-C$_3$-alkylene)- group
a (C$_1$-C$_3$-alkyl)-C(O)—NH—(C$_1$-C$_3$-alkylene)- group
a (C$_1$-C$_3$-alkyl)-C(O)—NR$^{15}$—(C$_1$-C$_3$-alkylene)- group,
where the phenyl ring is optionally substituted with a halogen atom, a hydroxyl group, or a C$_1$-C$_3$-alkoxy group and
the heterocycloalkyl group is optionally substituted with an oxo (═O) group or is optionally substituted with one or more substituents independently selected from a halogen atom, and a C$_1$-C$_3$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which R$^9$ is selected from
a C$_1$-C$_4$-haloalkyl-NH—C(O)—O—(C$_1$-C$_3$-alkylene)- group,
a phenyl-(C$_1$-C$_3$-alkylene)-O—(C$_1$-C$_3$-alkylene)- group,
a (R$^{18}$)-(phenylene)-(C$_1$-C$_3$-alkylene)-O—(C$_1$-C$_3$-alkylene)- group,
a (R$^{18}$)-(phenylene)-(heteroarylene)-O—(C$_1$-C$_3$-alkylene) group,
a (R$^{18}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{18}$)-(heteroarylene)-(C$_1$-C$_3$-alkylene)-O—(C$_1$-C$_3$-alkylene)- group,
a (R$^{18}$)-(heteroarylene)-(phenylene)-O—(C$_1$-C$_3$-alkylene)- group,
a (R$^{18}$)-(phenylene)-(C$_1$-C$_3$-alkylene)-O—(C$_1$-C$_3$-alkylene)- group,
a (R$^{19}$)—S(O)$_2$—N(C$_1$-C$_6$-alkyl)-(phenylene)-O—(C$_1$-C$_3$-alkylene)- group,
a (R$^{19}$)—S(O)$_2$-(heterocycloalkylene)-(phenylene)-O—(C$_1$-C$_3$-alkylene)- group,
a (R$^{18}$)-(heterocycloalkylene)-(heteroarylene)-O—(C$_1$-C$_3$-alkylene)- group,
a (R$^{19}$)—S(O)$_2$-(heterocycloalkylene)-(heteroarylene)-O—(C$_1$-C$_3$-alkylene)- group,
a

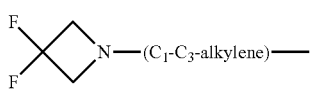

group, and a group,

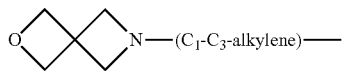

group
where the phenyl ring is optionally substituted with a halogen atom, a hydroxyl group, or a C$_1$-C$_3$-alkoxy group and the heterocycloalkyl group is optionally substituted with an oxo (═O) group or is optionally substituted with one or more substituents independently selected from a halogen atom, and a C$_1$-C$_3$-alkyl group;
or R$^8$ and R$^9$ together form a 5- or 6-membered ring optionally containing one or two heteroatoms selected from of —O—, and —NR$^{14}$—;
or a tautomer, an N-oxide, or a salt thereof, or a salt of a tautomer, or a salt of an N-oxide, or a mixture of same.

In further embodiments, the present invention includes compounds of formula (I), supra, in which
R$^9$ is selected from
a hydrogen atom,
a C$_1$-C$_4$-alkyl group,
a C$_1$-C$_3$-hydroxyalkyl group,
a C$_1$-C$_4$-haloalkyl group,
a C$_2$-C$_6$-haloalkenyl group,
a C$_1$-C$_6$-alkyl-O—(C$_1$-C$_3$-alkylene)- group,
a (C$_3$-C$_7$-cycloalkyl) group,
a phenyl-O—(C$_1$-C$_3$-alkylene)- group,
a (R$^{18}$)-(phenylene)-O—(C$_1$-C$_3$-alkylene)- group,
a (R$^{18}$)-(heterocycloalkylene)-(C$_1$-C$_3$-alkylene)- group,
a (R$^{18}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a NR$^{29}$R$^{21}$—(C$_1$-C$_3$-alkylene)- group,
a (C$_1$-C$_3$-alkyl)-NH—(C$_1$-C$_3$-alkylene)- group,
where the phenyl group is unsubstituted or substituted with a halogen atom, a hydroxyl group, or a C$_1$-C$_3$-alkoxy group and
the heterocycloalkylene group is unsubstituted or substituted with a substituent independently selected from an oxo (═O) group and a C$_1$-C$_3$-alkyl group;
or R$^8$ and R$^9$ together form 6-membered ring optionally containing one or two oxygen atoms; or a tautomer, an N-oxide, or a salt thereof, or a salt of a tautomer, or a salt of an N-oxide, or a mixture of same.

In further embodiments, the present invention includes compounds of formula (I), supra, in which
R$^9$ is a C$_1$-C$_4$-alkyl group,
a C$_1$-C$_3$-hydroxyalkyl group,
a C$_1$-C$_3$-haloalkyl group,
a C$_1$-C$_3$-alkyl-O— group,
a C$_1$-C$_3$-haloalkoxy group,
a C$_1$-C$_3$-alkyl-O—(C$_1$-C$_3$-alkylene)- group,
a (C$_3$-C$_6$)-cycloalkyl group,
a R$^{18}$-(phenylene)-O—(C$_1$-C$_3$-alkylene)- group,
a NR$^{29}$R$^{21}$—(C$_1$-C$_3$-alkylene)- group, and
a (C$_1$-C$_3$-alkyl)-NH—(C$_1$-C$_3$-alkylene)- group;
or a tautomer, an N-oxide, or a salt thereof, or a salt of a tautomer, or a salt of an N-oxide, or a mixture of same.

In further embodiments, the present invention includes compounds of formula (I), supra, in which
R$^9$ is a C$_1$-C$_4$-alkyl group,
a C$_1$-C$_3$-hydroxyalkyl group,
a C$_1$-C$_3$-haloalkyl group,
a C$_1$-C$_3$-alkyl-O—(C$_1$-C$_3$-alkylene)- group,
a R$^{18}$-(phenylene)-O—(C$_1$-C$_3$-alkylene)- group,
a NR$^{29}$R$^{21}$—(C$_1$-C$_3$-alkylene)- group, and
a (C$_1$-C$_3$-alkyl)-NH—(C$_1$-C$_3$-alkylene)- group;

or a tautomer, an N-oxide, or a salt thereof, or a salt of a tautomer, or a salt of an N-oxide, or a mixture of same. (no claim, more limited than claim 4, no cycloalkyl, no alkoxy, haloalkoxy)

In further embodiments, the present invention includes compounds of formula (I), supra, in which $R^9$ is a $C_1$-$C_4$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_3$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 5- or 6-membered ring optionally containing one or two heteroatoms selected from —O—, and —$NR^{14}$—, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 5- or 6-membered ring optionally containing one or two oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 6-membered ring optionally containing one or two oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 6-membered ring optionally containing one oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together are *—(CH$_2$—)$_3$—O—**, *—(CH$_2$)$_2$—O—CH$_2$—**, —(CH$_2$)$_4$—, where * means the point of attachment to the pyrazol nitrogen atom ($R^8$ site) whereas ** means the point of attachment to the carbon atom ($R^9$ site) of the pyrazol. or a tautomer, an N-oxide, or a salt thereof, or a salt of a tautomer, or a salt of an N-oxide, or a mixture of same.

In further embodiments, the present invention includes compounds of formula (I), supra, in which $R^{12}$ is a methoxy group, or a tautomer, an N-oxide, or a salt thereof, or a salt of a tautomer, or a salt of an N-oxide, or a mixture of same.

In further embodiments, the present invention includes compounds of formula (I), supra, in which $R^{12}$ is hydrogen or a methoxy group, or a tautomer, an N-oxide, or a salt thereof, or a salt of a tautomer, or a salt of an N-oxide, or a mixture of same.

In further embodiments, the present invention includes compounds of formula (I), supra, in which $R^{13}$ is hydrogen or a methyl group, or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from a hydrogen atom, a $C_1$-$C_6$-alkyl group
which is unsubstituted or substituted with one or more substituents selected from a halogen atom, a $C_1$-$C_3$-alkyl group, a $C_1$-$C_3$-haloalkyl group a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;

a phenyl group, a group

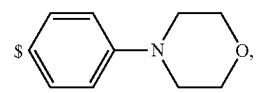

a group and

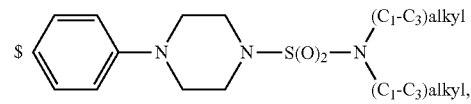

a group

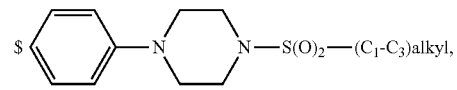

where $ is the point of attachment to the nitrogen atom, to which $R^{15}$ is attached, or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from a hydrogen atom, a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group and an aryl-heteroarylene-O— group;

a phenyl group, a group

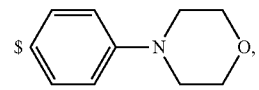

a group and

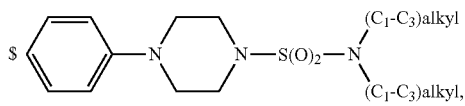

a group

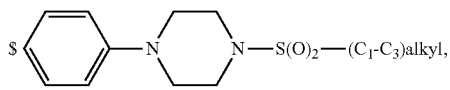

where $ is the point of attachment to the nitrogen atom, to which $R^{15}$ is attached, or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom, a $C_1$-$C_3$-alkyl group, a $C_1$-$C_3$-haloalkyl group, a phenyl group, a benzyl group, a group

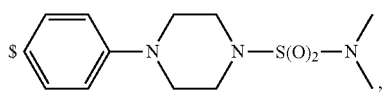

a group

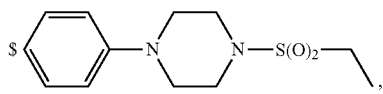

and a group

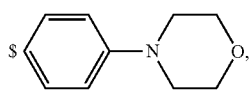 [SMILES: c1ccc(N2CCOCC2)cc1]

or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom, a $C_1$-$C_3$-alkyl group and a $C_1$-$C_3$-haloalkyl group;

or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom, a methyl group, a 2,2-difluoroethyl group and a 2,2,2-trifluoroethyl group;

or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom and a methyl group; or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is a methyl group or a tautomer, an N-oxide, or a salt thereof, or a salt of a tautomer, or a salt of an N-oxide, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group; or a tautomer, an N-oxide, or a salt thereof, or a salt of a tautomer, or a salt of an N-oxide, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group or a tautomer, an N-oxide, or a salt thereof, or a salt of a tautomer, or a salt of an N-oxide, or a mixture of same.

In further embodiments, the present invention includes compounds of formula (I), supra, in which $R^{18}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and $C_3$-$C_6$-cycloalkyl-C(O)— group; or a tautomer, an N-oxide, or a salt thereof, or a salt of a tautomer, or a salt of an N-oxide, or a mixture of same.

In yet further embodiments, the present invention includes compounds of formula (I), supra, in which $R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)OR$^{21}$ group, a —C(O)NR$^{20}$R$^{21}$ group and ($C_1$-$C_6$-alkyl)-C(O)— group;

or a tautomer, an N-oxide, or a salt thereof, or a salt of a tautomer, or a salt of an N-oxide, or a mixture of same.

In further embodiments, the present invention includes compounds of formula (I), supra, wherein $R^{19}$ is selected from a $C_1$-$C_3$-alkyl group, a $C_3$-$C_6$-cycloalkyl group, and a NR$^{20}$R$^{21}$ group; and or a tautomer, an N-oxide, or a salt thereof, or a salt of a tautomer, or a salt of an N-oxide, or a mixture of same.

In further embodiments, the present invention includes compounds of formula (I), supra, wherein $R^{19}$ is a $C_1$-$C_3$-alkyl group, or a tautomer, an N-oxide, or a salt thereof, or a salt of a tautomer, or a salt of an N-oxide, or a mixture of same.

In further embodiments, the present invention includes compounds of formula (I), supra, in which $R^{20}$ and $R^{21}$ are each independently selected from a hydrogen atom or a $C_1$-$C_6$-alkyl group; or a tautomer, an N-oxide, or a salt thereof, or a salt of a tautomer, or a salt of an N-oxide, or a mixture of same.

In further embodiments, the present invention includes compounds of formula (I), supra, in which $R^{20}$ and $R^{21}$ are each independently selected from a hydrogen atom and a $C_1$-$C_3$-alkyl group; or a tautomer, an N-oxide, or a salt thereof, or a salt of a tautomer, or a salt of an N-oxide, or a mixture of same.

In further embodiments, the present invention includes compounds of formula (I), or a tautomer, an N-oxide, or a salt thereof or a salt of a tautomer or a N-oxide or a mixture of same.

In further embodiments, the present invention includes compounds of formula (I), or a salt thereof.

In further embodiments, the present invention includes compounds of formula (I), or a tautomer or a salt thereof or a salt of a tautomer or a mixture of same.

In further embodiments, the present invention includes compounds of formula (I), which are salts.

In further embodiments, the present invention includes compounds of formula (I), which are a tautomer, or a salt of a tautomer or a mixture of same In further embodiments, the present invention includes compounds of formula (I), which are a an N-oxide, or a salt of an N-oxide or a mixture of same In further embodiments of the first aspect, the present invention provides combinations of two or more of the above mentioned embodiments under the heading "further embodiments of the first aspect of the present invention".

Furthermore it is understood that the invention includes any subcombination of the disclosed single embodiments herein for certain residues or subcombination of residues of formula (I).

The present invention includes any sub-combination within any embodiments or aspects of the present invention of compounds of general formula (I), supra.

The present invention includes any sub-combination within any embodiments or aspects of the present invention of compounds or intermediate compounds of general formula (I or II). The present invention includes the compounds of general formula (I) which are disclosed in the Example Section of this text, infra.

General Synthesis of Compounds of General Formula (I) of the Present Invention
A. General Synthesis Route Dependent inter alia on the nature of $R^{p1}$ and $R^{p2}$, which together give rise to a group $^{\#}$—$(CH_2)_n$—$(B)_t$—$(CH_2)_p$—$X$—$^{\#\#}$, $^{\#}$—$(CH_2)_n$—$(B)_t$—$(CH_2)_p$—$X$—$^{\#\#}$, $^{\#}$—$(C_2$-$C_6$-alkenylene)-$(B)_t$—$(CH_2)_p$—$X$—$^{\#\#}$, $^{\#}$—$(CH_2)_n$—$(B)_t$—$(C_2$-$C_5$-alkenylene)-$X$—$^{\#\#}$ or $^{\#}$—$(CH_2)_q$—$(B)$—$CH_2)_r$—$(B)$—$(CH_2)_v$—$X$—$^{\#\#}$, which groups are as defined for the compounds of general formula (I) after elaboration into the compounds of the present invention, the conversion of compounds of formula (V) into said macrocyclic intermediates of formula (II) may proceed with or without the intermediacy of intermediates of formula (III) e.g. directly from the compounds of formula (V) to the macrocyclic intermediates of formula (II) without requiring the use of compounds of formula (IV); for details see e.g. the Schemes 2a-2j, infra. Finally, conversion of $R^{5E}$ into $R^5$, e.g. by ester saponification, optionally followed by conversion of the resulting carboxylic acid into an acylsulfonamide according to methods known to the person skilled in the art (see for example: *Bioorg. Med Chem. Lett.* 2006, 16, 3639-3641; *Bioorg. Med Chem. Lett.* 2012, 22, 713-717; *Org. Lett.* 2012, 14(2), 556-559), yields the compounds of formula (I).

Said general synthesis route commences with a well-known Suzuki coupling of compounds of formula (VII), in which $R^1$, $R^2$, $R^3$, $R^4$ and L are as defined for the compounds of general formula (I), and in which $R^{5E}$ represents a group suitable to act as a precursor of a —C(=O)OH or a tetrazol-5-yl group, preferably a group —C(=O)O—$C_{1-4}$-alkyl, with compounds of formula (VI), in which A', together Scheme 1

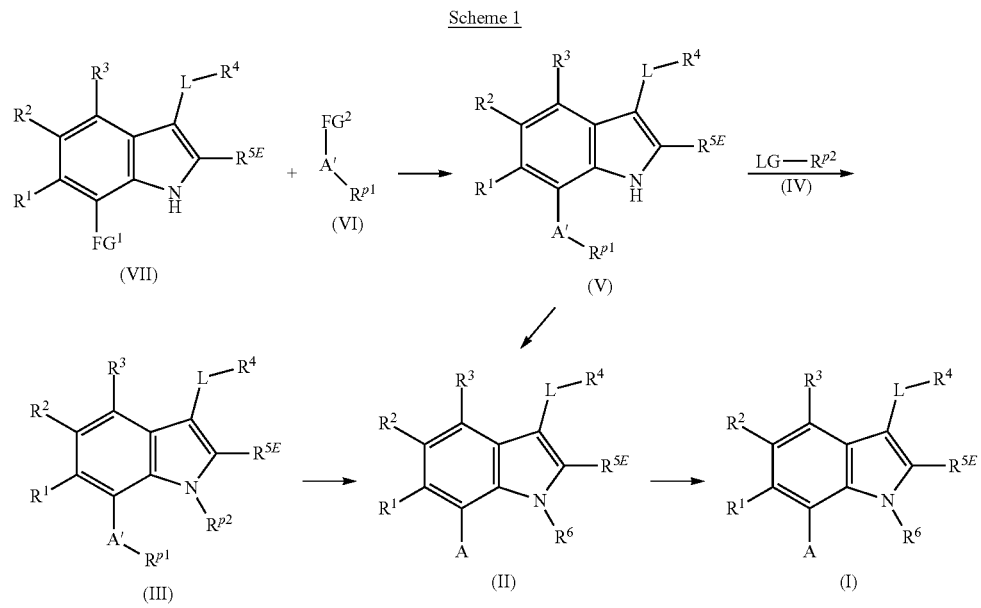

Compounds of general formula (I) can be synthesized according to the general synthesis route depicted in Scheme 1, encompassing a Suzuki coupling of starting materials of formulae (VII) and (VI) to give intermediates of formula (V), elaboration of the macrocyclic core by attachment of a group $R^{p2}$ to the indole nitrogen present in compounds of formula (V), by reaction with compounds of formula (IV), in which LG represents a leaving group as defined herein and $R^{p2}$ is discussed below, followed by (or together in one step with) macrocyclisation of the resulting intermediates of formula (III), e.g. by intramolecular nucleophilic substitution, to give macrocyclic intermediates of formula (II).

with the group $R^{p1}$ attached to it, represents a group suitable to act as precursor of a group A as defined for the compounds of general formula (I), to give compounds of formula (V). The group $R^4$, constituting the terminus of the side chain attached to C-3 of the indole core in formula (VII), can alternatively be established on later stage (see e.g. Scheme 2i and its discussion for details). Examples of groups A' are exemplified further below in this chapter.

In formulae (VI) and (VII), $FG^1$ in combination with $FG^2$ represents a pair of functional groups together enabling a Suzuki coupling; either $FG^1$ represents chloro, bromo, iodo or a trifluoromethanesulfonyl- group and $FG^2$ represents a group —B(OR$^B$)$_2$, or vice versa. Said group —(OR$^B$)$_2$ may be a boronic acid moiety (R$^B$=—H) or an alkyl ester of the boronic acid, e.g. its isopropyl ester (R$^B$=C$_1$-C$_4$-alkyl, e.g. —CH(CH$_3$)$_2$), or an ester derived from a diol such as pinacol in which the boronic acid intermediate forms a cyclic boronic ester, preferably a 4,4,5,5-tetramethyl-1,3,2-dioxaborolane (R$^B$—R$^B$=C$_2$-C$_6$-alkylene, preferably —(CH$_3$)$_2$—C(CH$_3$)$_2$—). Many boronic acids and their esters are commercially available and their synthesis is well-known to the person skilled in the art; see e.g. D. G. Hall, Boronic Acids, 2005 WILEY-VCH Verlag GmbH & Co. KGaA, Weinheim, ISBN 3-527-30991-8 and references cited therein, and Journal of Medicinal Chemistry, 2015, 58, 2180-2194. Alternatively to boronic acid derivatives, also tetrafluoroborates, in which —BF$_4$$^-$ replaces the —(OR$^B$)$_2$ moiety, can also be employed.

Said Suzuki coupling reaction can be catalysed by palladium catalysts, exemplified by but not limited to by Pd(0) catalysts such as e.g. tetrakis(triphenylphosphine)palladium (0) [Pd(PPh$_3$)$_4$], tris(dibenzylideneacetone)di-palladium(0) [Pd$_2$(dba)$_3$] in combination with a ligand, e.g. a phosphine such as e.g. triphenylphosphine, or by Pd(II) catalysts such as e.g. dichlorobis(triphenylphosphine)-palladium(II) [Pd (PPh$_3$)$_2$Cl$_2$], dichloropalladium-tricyclohexylphosphine (1:2), palladium(II) acetate in combination with a ligand, e.g. a phosphine such as e.g. triphenylphosphine, chloro(2-dicyclohexylphosphino-2',4',6'-triisopropyl-1,1'-biphenyl) [2-(2'-amino-1,1'-biphenyl)]palladium(II), (2-dicyclohexylphosphino-2',4',6'-triisopropyl-1,1'-biphenyl)[2-(2'-amino-1,1'-biphenyl)]palladium(II) methanesulfonate, or by [1,1'-bis(diphenylphosphino)ferrocene]-palladium dichloride, in free form [Pd(dppf)Cl$_2$] or as dichloromethane adduct [Pd(dppf)Cl$_2$×CH$_2$Cl$_2$].

The reaction is preferably carried out in solvents such as e.g. 1,2-dimethoxyethane, 1,4-dioxane, DMF, THF, toluene or n-propanol, or mixtures thereof, optionally also in mixture with water, and in the presence of a base such as e.g. aqueous potassium carbonate, aqueous sodium carbonate or aqueous potassium phosphate.

The reaction is performed at temperatures ranging from room temperature (i.e. 20° C.) to the boiling point of the solvent. Additionally, the reaction can be performed at temperatures above the boiling point using pressure tubes and a microwave oven. (for a review on Suzuki couplings see: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Synthetic approaches to starting materials of formulae (VI) and (VII) are discussed in context of chapter D, infra.

Compounds of formula (II) can be obtained using various methods described in more detail below, e.g. by reacting compounds of formula (V) with compounds of formula (IV) in which LG represents a leaving group, preferably bromo or iodo, and in which R$^{p2}$ represents a group suitable to act as a precursor for the group R$^6$ as defined for the compounds of general formula (I). The following paragraphs outline more specific examples of said conversion of compounds of formulae (Va), (Vb), (Ve), (Vh) and (Vj), all of them constituting sub-compartments of formula (V), into compounds of (IIa), (IIc), (IIe), (IIf), (IIh) and (IIj), all of them constituting sub-compartments of formula (II), some of which with the intermediacy of compounds of formulae (IIIb), (IIIc), (IIIf) and (IIIh), all of them constituting sub-compartments of formula (III), as discussed in the context of Scheme 1.

Said macrocyclic intermediates of formula (II) can finally be converted into the compounds of general formula (I) as described in further detail in context with Scheme 3, infra.

B. More Specific Synthesis Routes for Establishing the Macrocyclic Core, Schemes 2a- 2i:

Examples for R$^{p1}$ and R$^{p2}$ groups, as referred to in the general Synthesis Route of Scheme 1 above, are listed below and are put into their synthetic context in the more specific synthesis routes for establishing the macrocyclic core as present in advanced macrocyclic intermediates of formula (II), from compounds of formula (V), described further below. R$^{p1}$ groups are exemplified by but not limited to groups such as —C(=O)H, —X—OH, —X—(CH$_2$)$_b$—OH, —X—(CH$_2$)$_b$-LG$^2$, —X—(CH$_2$)$_{b\text{-}LG}$$^3$, —X—(CH$_2$)$_c$—OH, —X—(CH$_2$)$_c$—O—(CH$_2$)$_d$—CH=CH$_2$, —CH=CH—(CH$_2$)$_g$—OH, —(CH$_2$)$_{g+2}$-LG$^{10}$, —X—(CH$_2$)$_c$—NR$^{15}$(PG$^2$),

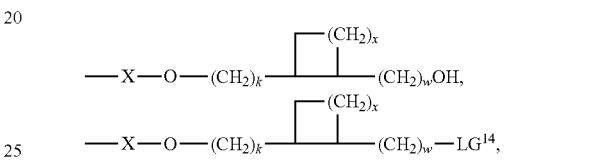

—X—O—(CH$_2$)$_k$—(CF$_2$)$_y$—(CH$_2$)$_2$—OH and —X—O—(CH$_2$)$_k$—(CF$_2$)$_y$—(CH$_2$)$_z$-LG$^{14}$, in which LG$^2$, LG$^3$ and LG$^{10}$, independently from each other, represent a leaving group as defined supra, preferably chloro, bromo or iodo, in which LG$^{14}$ represents a leaving group as defined supra, preferably chloro, bromo or iodo, or an alkylsulfonate or an arylsulfonate, preferably methanesulfonate, in which R$^{15}$ is as defined for the compounds of general formula (I), in which PG$^2$ represents a protective group, and in which indices "b", "c", "d", "g", "k", "w", "x", "y" and "z" are as defined infra, and R$^{p2}$ groups are exemplified by but not limited to groups such as —CH$_2$)$_a$—N(R$^{15}$)—PG$^1$,

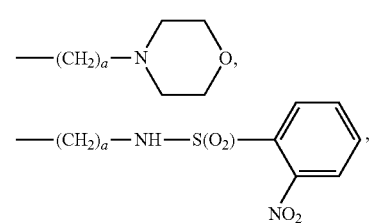

—(CH$_2$)$_e$—CH=CH$_2$, —(CH$_2$)$_f$-LG$^9$ or a hydrogen atom, in which R$^{15}$ is as defined for the compounds of general formula (I), PG$^1$ represents a hydrogen atom or a protective group, LG$^9$ represents a leaving group as defined supra, preferably chloro, bromo or iodo, and indices "a", "e" and "f" are as defined infra.

The reader is referred to the fact that the indices "a", "b", "c", "d", "e", "f", "g", "h", "i", "j", "k", "w", "x", "y" and "z" used within and in the context of the following Schemes 2a 2j have been introduced independently from the corresponding indices "n", "p", "q", "r", "t" and "v" used in the claims, in order to reflect diversity of chemotypes encompassed within the general formula (I), and of the various synthesis routes useful for their preparation. Said diversity encompasses inter alia the fact that whilst A contributes two carbon atoms to the macrocyclic core if being derived from pyrazole, A contributes three carbon atoms to the macrocyclic core if being derived from benzene;

the fact that inherently unstable formaldehyde aminals or hemiaminals result when "t" represents an integer 1 and a nitrogen or oxygen atom (but not a carbon atom), which is encoded for by $(B)_t$, is separated from the core indole nitrogen only by one carbon atom;

the fact that certain parts of precursor groups of —$R^6$-$R^7$ and —$R^6$-$R^{10}$, such as olefinic double bonds, have been drawn explicitly in some the Schemes for the sake of chemical clarity, mandating independent indices for the remaining parts of said precursor groups.

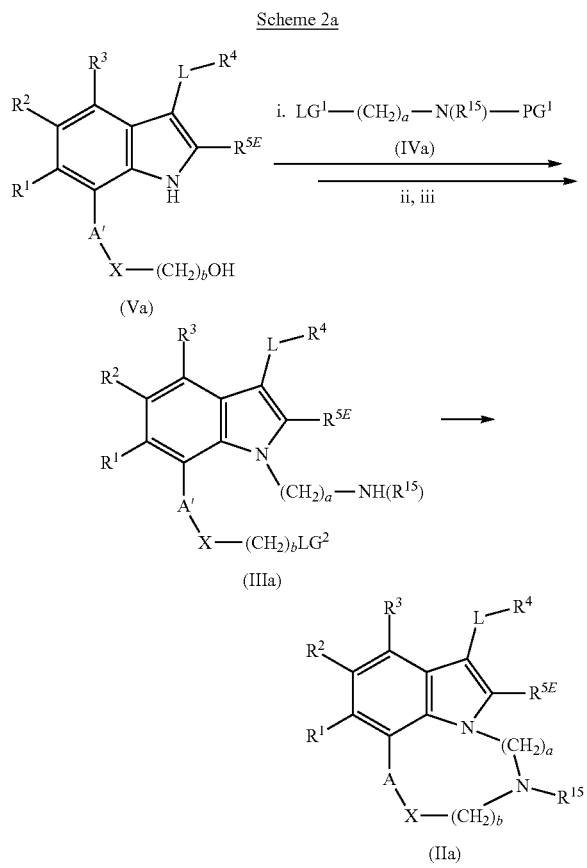

Scheme 2a

According to Scheme 2a, compounds of formula (IIa), in which $R^7$ (which is a feature of group A as defined for the compounds of general formula (I)) and $R^6$ together form a ##—X—$(CH_2)_b$—$N(R^{15})$—$(CH_2)_a$—# group, in which # represents the point of attachment to the indole nitrogen atom and ## represents the point of attachment to the pyrazole carbon atom bearing the $R^7$ substituent, can be obtained from compounds of formula (Va), in which X, $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $R^{P2}$ represents a hydrogen atom and $R^{P1}$ (see General Synthesis Route, Scheme 1) represents a —X—$(CH_2)_b$—OH group (in which the index "b" represents an integer selected from 0, 1, 2, 3, 4, 5, 6 and 7), by (i) reacting with compounds of formula (IVa), in which $R^{15}$ is as defined for the compounds of general formula (I), the index "a" represents an integer selected from 2, 3, 4, 5, 6, 7, 8, 9 and 10, with the proviso that the sum of the integers representing indices "a" and "b" is at least 2 and does not exceed 9, $LG^1$ represents a leaving group and $PG^1$ represents a hydrogen atom or a protective group, followed by (ii) conversion of said —X—$(CH_2)_b$—OH group into a —X—$(CH_2)_b$-$LG^2$ group, and (iii), if $PG^1$ represents a protective group, cleavage of said protective group, to give compounds of formula (IIIa), in which $R^{P1}$ represents a —X—$(CH_2)_b$-$LG^2$ group (in which in turn $LG^2$ represents a leaving group, preferably bromo), and in which $R^{P2}$ represents a —$(CH_2)_a$—$NH(R^{15})$ group. Dependent on the reaction and/or work-up conditions, compounds of the formula (IIIa) can be isolated as free bases or as salts, e.g. salts with hydrochloric acid. Subsequently, said compounds of formula (IIIa) can be subjected to an intramolecular nucleophilic substitution, giving rise to the corresponding macrocyclic intermediates of formula (IIa).

The abovementioned sequence of transformations can be advantageously accomplished by (step i) deprotonating a compound of formula (Va) with a suitable base, such as e.g. cesium carbonate, potassium tert-butoxide, or sodium hydride, in a suitable solvent, such as e.g. DMF, acetonitrile or THF, followed by addition of a compound of formula (IVa); subsequently (step ii) by halogenation of said —X—$(CH_2)_b$—OH group, e.g. by treatment with tetrabromomethane and triphenylphosphine in a halogenated hydrocarbon, such as e.g. dichloromethane, as a solvent, and (step iii), if $PG^1$ represents a protective group, by an appropriate deprotection method (see e.g. T. W. Greene and P. G. M. Wuts in Protective Groups in Organic Synthesis, $4^{th}$ edition, Wiley 2006), such as the cleavage of a tert-butoxycarbonyl group by hydrogen chloride in dioxane or by trifluoroacetic acid. The subsequent macrocyclization is favorably accomplished by reacting a compound of formula (IIIa) in the presence of a base such as an alkali carbonate or an alkali phosphate, preferably cesium carbonate, in a dipolar aprotic solvent such as e.g. dimethylformamide (DMF), dimethylacetamide or N-methyl pyrrolidin-2-one, preferably DMF, at a temperature between 20° C. and 120° C., preferably between 50° C. and 80° C.

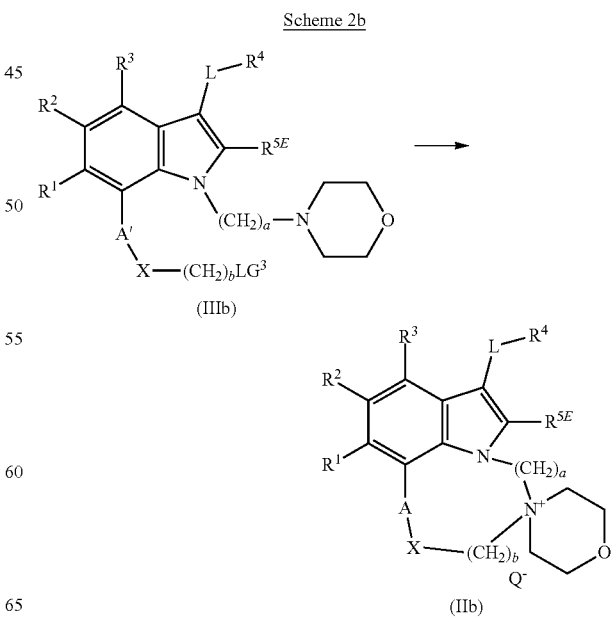

Scheme 2b

In an analogous fashion, and as outlined in Scheme 2b, compounds of formula (IIb), in which $R^7$ (which is a feature of group A as defined for the compounds of general formula (I)) and $R^6$ together form a

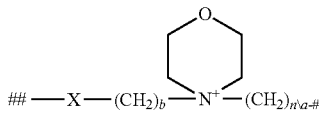

group, in which # represents the point of attachment to the indole nitrogen atom and ## represents the point of attachment to the pyrazole carbon atom bearing the $R^7$ substituent, and in which $Q^-$ represents an anion corresponding to a leaving group, preferably a halide ion such as a bromide ion, can be obtained from compounds of formula (IIIb), in which $R^1$, $R^2$, $R^3$, $R^4$ and L are as defined for the compounds of general formula (I), in which $R^{5E}$ represents a group suitable to act as a precursor of a —(=O)OH or a tetrazol-5-yl group, preferably a group —C(=O)O—$C_{1-4}$-alkyl, in which $R^{p1}$ (see General Synthesis Route, Scheme 1) represents a —X—$(CH_2)_b$-$LG^3$ group (in which the index "b" represents an integer selected from 0, 1, 2, 3, 4, 5, 6 and 7, and LG represents a leaving group, preferably bromo), and in which $R^{p2}$ (see General Synthesis Route, Scheme 1) represents a

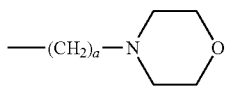

group (in which the index "a" represents an integer selected from 2, 3, 4, 5, 6, 7, 8, 9 and 10), by subjection to an intramolecular nucleophilic substitution, with the proviso that the sum of the integers representing indices "a" and "b" is at least 2 and does not exceed 9. Compounds of formula (IIIb) can be prepared in analogy to the approach outlined in Scheme 2a, supra.

Said intramolecular nucleophilic substitution can be favorably accomplished by reacting a compound of formula (IIIb) in the presence of a base such as an alkali carbonate or an alkali phosphate, preferably potassium carbonate, in a dipolar aprotic solvent such as e.g. dimethylformamide (DMF), dimethylacetamide (DMA) or N-methyl pyrrolidin-2-one, preferably DMA, at a temperature between 20° C. and 120° C., preferably between 40° C. and 70° C.

Scheme 2c

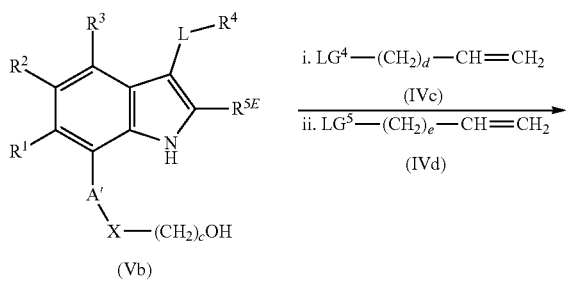

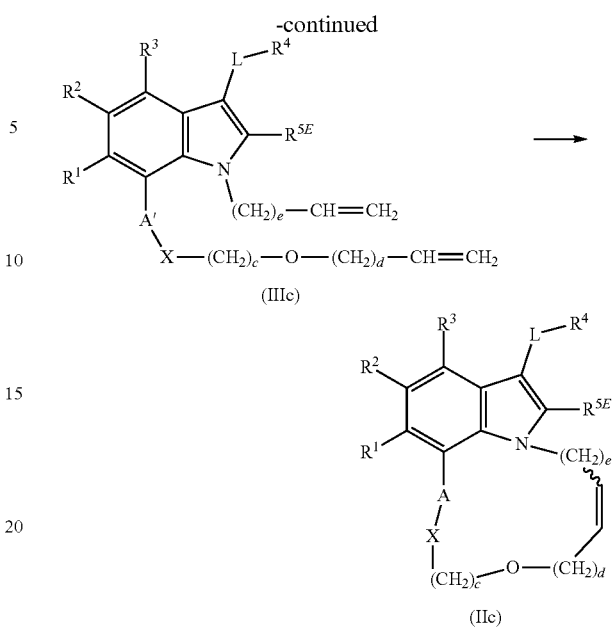

According to Scheme 2c, compounds of formula (IIc), in which $R^7$ (which is a feature of group A as defined for the compounds of general formula (I)) and $R^6$ together form a ##—X—$(CH_2)_c$—O—$(CH_2)_d$—CH=CH—$(CH_2)_e$—# group, in which # represents the point of attachment to the indole nitrogen atom and ## represents the point of attachment to the pyrazole carbon atom bearing the $R^7$ substituent, can be obtained from compounds of formula (Vb), in which $R^1$, $R^2$, $R^3$, $R^4$, L and X are as defined for the compounds of general formula (I), in which $R^{5E}$ represents a group suitable to act as a precursor of a —(=O)OH or a tetrazol-5-yl group, preferably a group —C(=O)O—$C_{1-4}$-alkyl, in which $R^{p2}$ represents a hydrogen atom and $R^{p1}$ (see General Synthesis Route, Scheme 1) represents a —X—$(CH_2)_c$—OH group, in which index "c" represents an integer selected from 0, 1 and 2, by reacting with compounds of formula (IVc), followed by compounds of formula (IVd), in which indices "d" and "e", independently from each other, represent an integer selected from 1, 2, 3, 4, 5 and 6, with the proviso that the sum of the integers representing indices "c", "d" and "e" does not exceed 7, and $LG^4$ and $LG^5$, independently from each other, represent a leaving group, to give compounds of formula (IIIc), in which $R^{p1}$ represents a —X—$(CH_2)_c$—O—$(CH_2)_d$—CH=CH$_2$ group, and in which $R^{p2}$ represents a —$(CH_2)_e$—CH=CH$_2$ group. Subsequently, said compounds of formula (IIIc) can be subjected to a ring closing metathesis (RCM) reaction (see e.g. Chem. Rev., 2009, 109 (8), pp 3783-3816), giving rise to the corresponding macrocyclic intermediates of formula (IIc).

The abovementioned sequence of transformations can be advantageously accomplished by deprotonating a compound of formula (Vb) with one equivalent of a suitable base, such as e.g. sodium hydride or cesium carbonate, in a suitable solvent, such as THF, dimethylformamide (DMF) or dimethylacetamide (DMA), followed by addition of a compound of formula (IVc), followed by the addition of one further equivalent of a suitable base, such as e.g. sodium hydride or cesium carbonate, followed by addition of a compound of formula (IVd). Whenever indices "d" and "e" are identical, said base can be added in one portion, followed by one reagent of formula (IVc) or (IVd). The subsequent macrocyclization is favorably accomplished by reacting a compound of formula (IIIc) in the presence of a catalyst suitable for the performance of a ring closing metathesis exemplified by but not limited to (1,3-bis(2,4,6-trimethylphenyl)-2-imidazolidinylidene) dichloro(phenylmethylene)(tricyclohexyl-phosphine)ruthenium or (1,3-bis-(2,4,6-trimethylphenyl)-2-imidazolidinylidene) dichloro(o-isopropoxyphenyl-methylene)ruthenium, in a halogenated hydrocarbon such as e.g. dichloromethane, chloroform, or 1,2-dichloroethane, preferably dichloromethane, at a temperature between 0° C. and 50° C., preferably between 20° C. and 30° C., using pressure tubes and a microwave oven if needed.

sodium iodide (to convert $LG^6$ and/or $LG^7$ into iodo in situ), in a solvent such as e.g. dimethylformamide (DMF), 1,2-dimethoxyethane, bis-(2-methoxymethyl) ether or acetonitrile, at a temperature between 0° C. and 100° C., preferably between 15° C. and 75° C.

In a preferred embodiment of the invention, said reaction is performed in the presence of one to three equivalents (relative to the compound of formula (IVe) of sodium iodide, in a solvent selected from acetonitrile and bis-(2-methoxymethyl) ether, initially at a temperature between 15° C. and 40° C. for a period of 2 to 30 hours, followed by a temperature between 50° C. and 80° C., for a period of 2 to 8 hours.

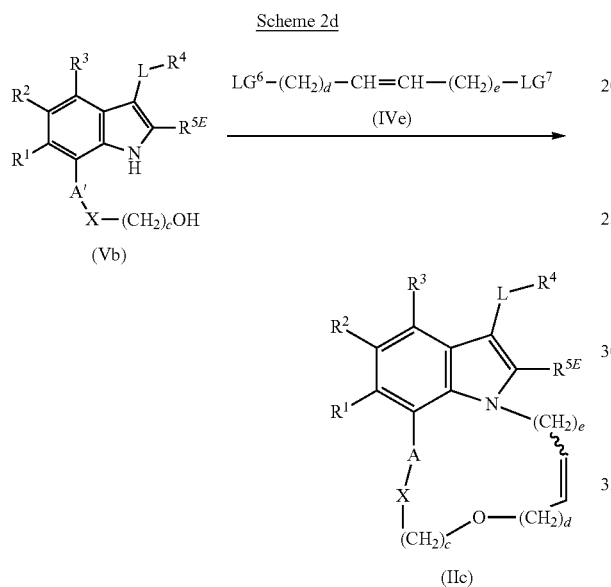

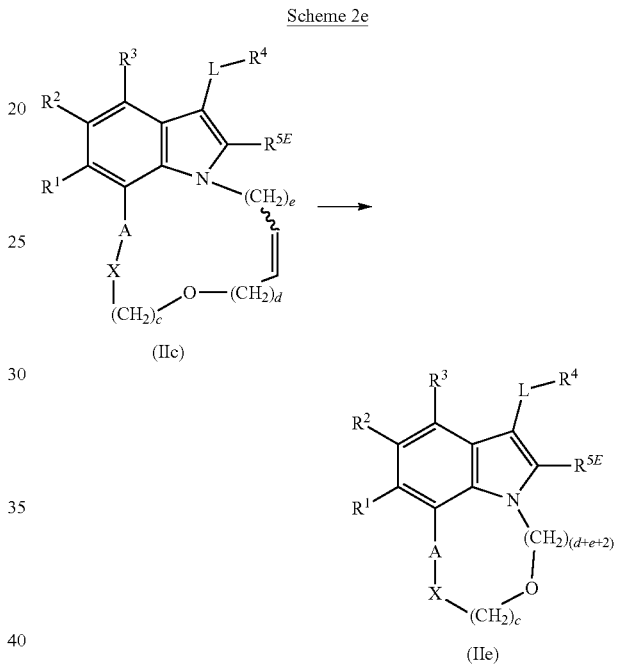

In an alternative approach outlined in Scheme 2d, compounds of the formula (IIc), as defined above in context of Scheme 2c, can be prepared in one synthetic step from compounds of formula (Vb), in which $R^1$, $R^2$, $R^3$, $R^4$, L and X are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{Pt}$ represents a hydrogen atom and $R^{P1}$ (see General Synthesis Route, Scheme 1) represents a —X—(CH$_2$)$_c$—OH group, in which in turn index "c" represents an integer selected from 0, 1 or 2, by reacting with compounds of formula (IVe), in which indices "d" and "e", independently from each other, represent an integer selected from 1, 2, 3, 4, 5 and 6, with the proviso that the sum of the integers representing indices "c", "d" and "e" does not exceed 87 and $LG^6$ and $LG^7$ represent, independently from each other, a leaving group, preferably chloro, bromo or iodo, giving rise to the corresponding macrocyclic intermediates of formula (IIc). If compounds of formula (IVe) are being employed as (Z)-alkenes, macrocyclic compounds of formulas (IIc) can be obtained as single (Z) double bond isomers.

Said reaction can be advantageously accomplished by reacting a compound of formula (Vb) with a compound of formula (IVe) in the presence of a base such as an alkali carbonate or an alkali phosphate, preferably cesium carbonate, preferably in the presence of an alkali iodide, preferably According to Scheme 2e, Compounds of formula (IIe), in which $R^7$ (which is a feature of group A as defined for the compounds of general formula (I)) and $R^6$ together form a $^{\#\#}$—X—(CH$_2$)$_c$—O—(CH$_2$)$_{(d+e+2)}$—$^{\#}$ group, in which $^{\#}$ represents the point of attachment to the indole nitrogen atom and $^{\#\#\#}$ represents the point of attachment to the pyrazole carbon atom bearing the $R^7$ substituent, can be obtained from compounds of formula (IIc), in which $R^1$, $R^2$, $R^3$, $R^4$, L and X are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $R^7$ and $R^6$ together form a —X—(CH$_2$)$_c$—O—(CH$_2$)$_d$—CH=CH—(CH$_2$)$_e$— group as defined in context of Schemes 2c and 2d, by hydrogenation of the olefinic double bond.

Said hydrogenation of the olefinic double bond can be advantageously accomplished by catalytic hydrogenation which is well known to the person skilled in the art, e.g. by reacting a solution of a compound of formula (IIc) in a solvent such as e.g. methanol, ethanol, THF or ethyl acetate, with an atmosphere of hydrogen under ambient or elevated pressure, in the presence of a hydrogenation catalyst such as e.g. palladium on carbon.

Scheme 2f

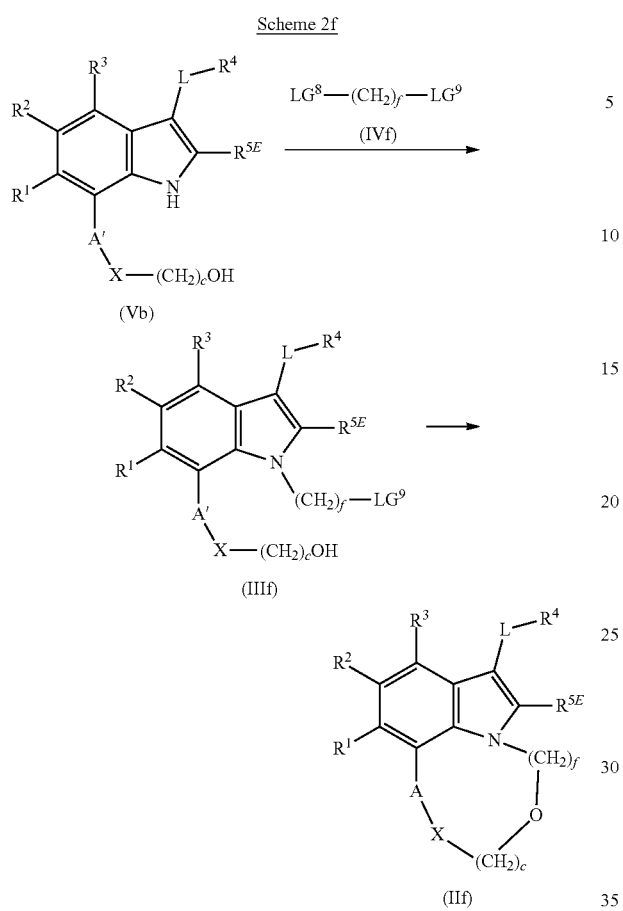

Scheme 2g

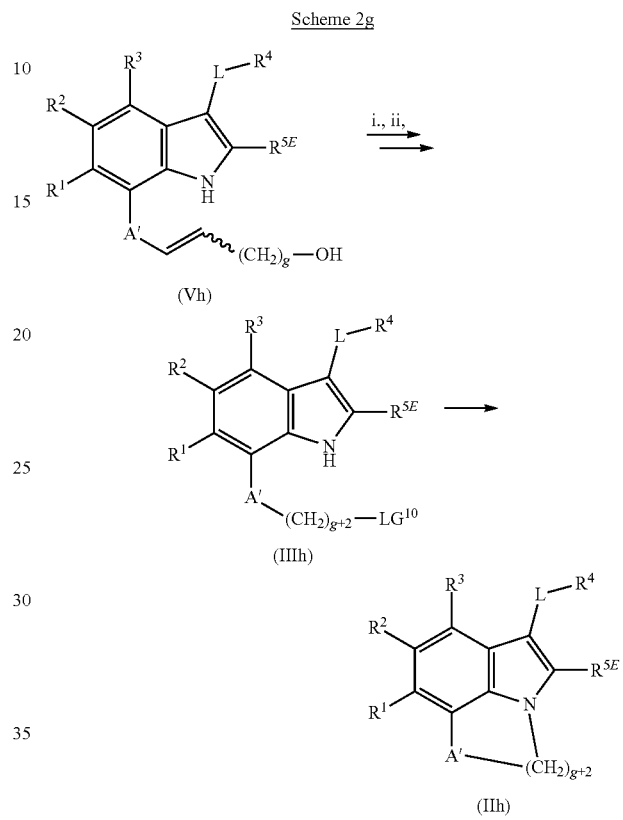

According to Scheme 2f, compounds of the formula (IIf), in which $R^7$ (which is a feature of group A as defined for the compounds of general formula (I)) and $R^6$ together form a ##—X—$(CH_2)_c$—O—$(CH_2)_f$—# group, in which # represents the point of attachment to the indole nitrogen atom and ## represents the point of attachment to the pyrazole carbon atom bearing the $R^7$ substituent, can be obtained from compounds of formula (Vb), in which $R^1$, $R^2$, $R^3$, $R^4$, L and X are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P2}$ represents a hydrogen atom and $R^{P1}$ (see General Synthesis Route, Scheme 1) represents a —X—$(CH_2)_c$—OH group, in which in turn index "c" represents an integer selected from 0, 1 or 2, by reacting with compounds of formula (IVf), in which index "f" represents an integer selected from 2, 3, 4, 5, 6, 7, 8 and 9, with the proviso that the sum of the integers representing indices "c" and "f" is at least 3 and does not exceed 9, and in which $LG^8$ and $LG^9$ represent, independently from each other, a leaving group, preferably bromo or iodo, giving rise to the corresponding macrocyclic intermediates of formula (IIf). Dependent on the reaction conditions and the choice of leaving groups $LG^8$ and $LG^9$, intermediate compounds of formula (IIIf) can be isolated and subsequently cyclised to the corresponding macrocyclic intermediates of formula (IIf).

Said reaction can be advantageously accomplished in one step by reacting a compound of formula (Vb) with a compound of formula (IVf), in which both $LG^8$ and $LG^9$ represent iodo, in the presence of a base such as an alkali carbonate or an alkali phosphate, preferably cesium carbonate, in a solvent such as e.g. dimethylformamide (DMF) or dimethylsulfoxide (DMSO), at a temperature between 0° C. and 100° C., preferably between 15° C. and 50° C.

As outlined in Scheme 2g, compounds of formula (IIh), in which $R^7$ (which is a feature of group A as defined for the compounds of general formula (I)) and $R^6$ together form a —$(CH_2)_{g+2}$— group, can be obtained from compounds of formula (Vh), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $R^{P2}$ represents a hydrogen atom and $R^{P1}$ (see General Synthesis Route, Scheme 1) represents a —CH=CH—$(CH_2)_g$—OH group (in which the index "g" represents an integer selected from 2, 3, 4, 5, 6, 7, 8 and 9), by (i) conversion of said —CH=CH—$(CH_2)_g$—OH group into a —$(CH_2)_{g+2}$—OH group by means of catalytic hydrogenation, and (ii) conversion of said —$(CH_2)_{g+2}$—OH group into a —$(CH_2)_{g+2}$-$LG^{10}$ group, to give compounds of formula (IIIh), in which $R^{P1}$ represents a —$(CH_2)_{g+2}$-$LG^{10}$ group (in which in turn $LG^{10}$ represents a leaving group, preferably bromo), and in which $R^{P2}$ represents a hydrogen atom. Subsequently, said compounds of formula (IIIh) can be subjected to an intramolecular nucleophilic substitution, giving rise to the corresponding macrocyclic intermediates of formula (IIh).

The abovementioned sequence of transformations can be advantageously accomplished by (step i) hydrogenating a compound of formula (Vh) in an atmosphere of hydrogen at a pressure between 1 and 20 bar, in ethanol as a solvent and in the presence of a palladium on charcoal hydrogenation catalyst, followed (step ii) by halogenation of the resulting —(CH$_2$)$_{g+2}$—OH group, e.g. by treatment with tetrabromomethane and triphenylphosphine in a halogenated hydrocarbon, such as e.g. dichloromethane, as a solvent. The subsequent macrocyclization can be favorably accomplished by reacting a compound of formula (IIIh) in the presence of a base such as e.g. potassium tert-butoxide, in an ethereal solvent such as e.g. 1,4-dioxane, THF or 1,2-dimethoxyethane, preferably 1,4-dioxane, at a temperature between 20° C. and 120° C., preferably between 60° C. and 100° C., using pressure tubes and a microwave oven if needed.

Starting materials of the formula (Vh) are available in analogy to Scheme 1, e.g. by employing a compound of formula (VI), in which FG$^2$ represents a halogen atom such as e.g. bromine, and in which R$^{p1}$ represents a —(CH$_2$)—OH group, which can be (a) oxidized by methods well known to the person skilled in the art, such as e.g. a Swern oxidation, to the corresponding aldehyde (in which R$^{p1}$ represents a —C(=O)H group), followed by (b) reacting said aldehyde in a well-known Wittig or Wadsworth-Horner-Emmons olefination reaction with a suitable phosphonium salt, and (c) subsequently establishing the terminal hydroxy group from a precursor group present in said phosphonium salt, e.g. by removal of a protective group or reduction of a corresponding carboxylic acid ester to give the corresponding hydroxyalkenyl compound of formula (VI) in which R$^{p1}$ represents a —CH=CH—(CH$_2$)$_g$—OH group, and finally (d) a Suzuki coupling with a compound of formula (VII) as outlined in Scheme 1.

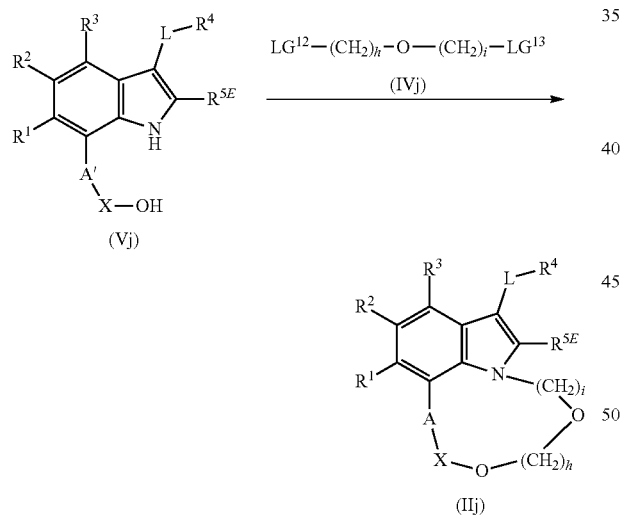

As outlined in Scheme 2h, compounds of formula (IIj), in which R$^7$ (which is a feature of group A as defined for the compounds of general formula (I)) and R$^6$ together form an $^{\#\#}$—X—O—(CH$_2$)$_h$—O—(CH$_2$)$_i$—$^{\#}$ group, in which $^{\#}$ represents the point of attachment to the indole nitrogen atom and $^{\#\#}$ represents the point of attachment to the pyrazole carbon atom bearing the R$^7$ substituent, can be obtained from compounds of formula (Vj), in which R$^1$, R$^2$, R$^3$, R$^4$, L and X are as defined for the compounds of general formula (I), in which R$^{5E}$ represents a group suitable to act as a precursor of a —C(=O)OH or a tetrazol-5-yl group, preferably a group —C(=O)O—C$_{1-4}$-alkyl, in which R$^{p2}$ represents a hydrogen atom and R$^{p1}$ (see general Synthesis Route, Scheme 1) represents a group —X—CH$_2$OH, which is a hydroxymethyl group, by reaction with compounds of formula (IVj), in which the indices "h" and "i", independently from each other, represent an integer selected from 2, 3, 4, 5 and 6, with the proviso that the sum of the integers representing indices "h" and "i" does not exceed 8, and in which LG$^{12}$ and LG$^{13}$, independently from each other, represent a leaving group, preferably iodo), to directly give the corresponding macrocyclic intermediates of formula (IIj). If said indices "h" and "i" are different from each other, regioisomeric mixtures (inverse arrangement of "h" and "i" in the reaction product) may result which may be separated by methods known to the person skilled in the art, such as preparative HPLC.

Said reaction can be favorably accomplished by reacting a compound of formula (Vj) with a compound of formula (IVj) in the presence of a base such as e.g. an alkali carbonate or an alkali phosphate, preferably cesium carbonate, in a solvent such bis-(2-methoxyethyl) ether, at a temperature between 15° C. and 100° C., preferably between 15° C. and 80° C.

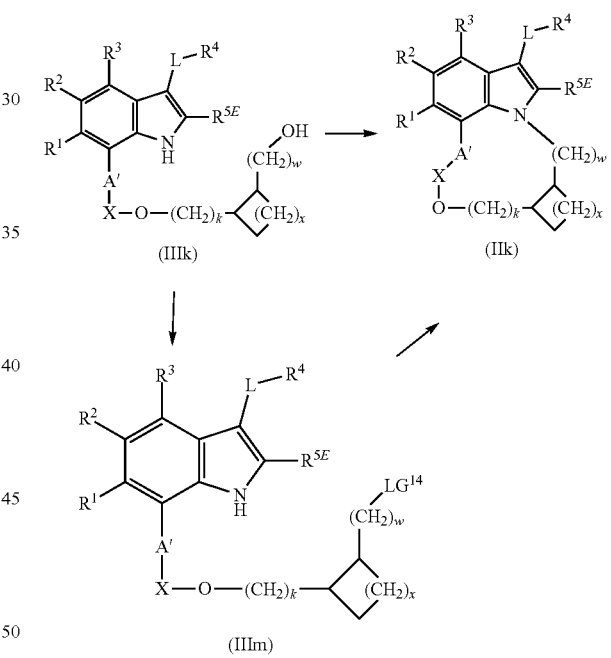

As outlined in Scheme 2i, compounds of formula (IIk), in which R$^7$ (which is a feature of group A as defined for the compounds of general formula (I)) and R$^6$ together form a

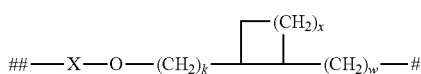

group, in which $^{\#}$ represents the point of attachment to the indole nitrogen atom and $^{\#\#}$ represents the point of attachment to the pyrazole carbon atom bearing the R$^7$ substituent, can be obtained from compounds of formula (IIIk), in which R$^1$, R$^2$, R$^3$, R$^4$, X and L are as defined for the compounds of general formula (I), in which R$^{5E}$ represents a group suitable to act as a precursor of a —C(=O)OH or a tetrazol-5-yl group, preferably a group —C(=O)O—$C_{1-4}$-alkyl, and in which $R^{p2}$ represents a hydrogen atom and $R^{p1}$ (see General Synthesis Route, Scheme 1) represents a

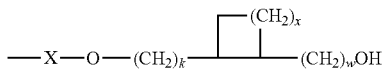

group (in which the index "x" represents an integer selected from 0, 1 and 2, and index "k" represents an integer selected from 1, 2, 3, 4, 5 and 6, in which the index "w" represents an integer selected from 1, 2, 3, 4, 5 and 6, with the proviso that the sum of the integers representing indices "k" and "w" does not exceed 7, by (i) conversion of said

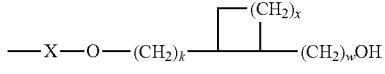

group of the a compound of general formula (III) into a group

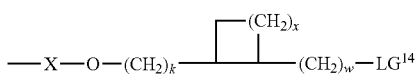

to yield a compound of general formula (IIIm), in which $LG^{14}$ represents a leaving group as defined supra, preferably chloro, bromo or iodo, or an alkylsulfonate or an arylsulfonate, preferably methanesulfonate, and (ii) subsequent cyclisation to yield a compound of general formula (IIk).

Alternatively a compound of general formula (IIIk) can be cyclized to deliver a compound of general formula (IIk).

The abovementioned sequence of transformations can be advantageously accomplished by (step i), reacting a compound of formula (IIIk) in the presence of a base such as e.g. a trialkylamine, preferably triethylamine, in a solvent such as e.g. dichloromethane, at a temperature between 0° C. and 40° C., with an arylsulfonyl chloride, or alkylsulfonyl chloride or alkylsulfonyl anhydride, preferably methanesulfonyl chloride, at a temperature between 0° C. and 40° C., preferably at room temperature, followed by (step ii), reacting a compound of formula (IIIm) in the presence of a base such as e.g. cesium carbonate, in a solvent such as e.g. N,N-dimethylformamide, at a temperature between 40° C. and 150° C., preferably between 80° C. and 130° C.

The macrocyclisation of a a compound of formula (IIIk) to deliver a compound of general formula (IIk) can be favorably accomplished by reacting a compound of formula (IIIk) in the presence of triphenylphosphine and di-tert-butyl azodicarboxylate, in a solvent such as e.g. tetrahydrofuran, at a temperature between −10° C. and 40° C., preferably at room temperature.

Starting materials of the formula (IIIk) are available in analogy to Scheme 1. Specific examples are given in the Experimental section, infra.

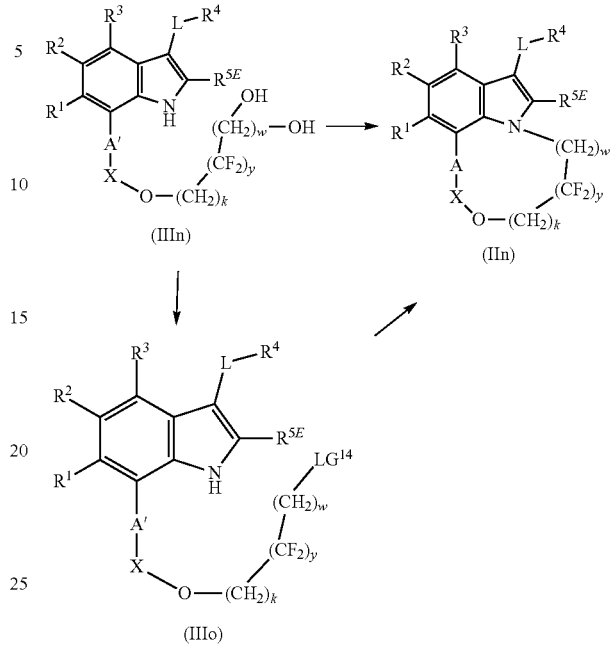

Scheme 2j

As outlined in Scheme 2j, compounds of formula (IIn), in which $R^7$ (which is a feature of group A as defined for the compounds of general formula (I)) and $R^6$ together form a ##—X—O—$(CH_2)_k$—$(CF_2)_y$—$(CH_2)_2$—# group, in which # represents the point of attachment to the indole nitrogen atom and ## represents the point of attachment to the pyrazole carbon atom bearing the $R^7$ substituent, can be obtained from compounds of formula (IIIn), in which $R^1$, $R^2$, $R^3$, $R^4$, X and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $R^{p2}$ represents a hydrogen atom and $R^{p1}$ (see General Synthesis Route, Scheme 1) represents a —X—O—$(CH_2)_k$—$(CF_2)_y$—$(CH_2)_2$—OH group (in which the index "k" represents an integer selected from 1, 2, 3, 4, 5 and 6, and index "y" represents an integer selected from 1, 2, 3, 4, 5 and 6, and index "z" represents an integer selected from 1, 2, 3, 4, 5 and 6, with the proviso that the sum of the integers representing indices "k", "y" and "z" does not exceed 9, by (i) conversion of said —X—O—$(CH_2)_k$—$(CF_2)_y$—$(CH_2)_2$—OH group of the a compound of general formula (IIIn) into a group —X—O—$(CH_2)_k$—$(CF_2)_y$—$(CH_2)_2$-$LG^{14}$ to yield a compound of general formula (IIIo), in which $LG^{14}$ represents a leaving group as defined supra, preferably chloro, bromo or iodo, or an alkylsulfonate or an arylsulfonate, preferably methanesulfonate, and (ii) subsequent cyclisation to yield a compound of general formula (IIn).

Alternatively a compound of general formula (IIIn) can be cyclised to deliver a compound of general formula (IIn).

The abovementioned sequence of transformations can be advantageously accomplished by (step i), reacting a compound of formula (IIIn) in the presence of a base such as e.g. a trialkylamine, preferably triethylamine, in a solvent such as e.g. dichloromethane, at a temperature between 0° C. and 40° C., with an arylsulfonyl chloride, or alkylsulfonyl chloride or alkylsulfonyl anhydride, preferably methanesulfonyl chloride, at a temperature between 0° C. and 40° C., preferably at room temperature, followed by (step ii), reacting a compound of formula (IIIo) in the presence of a base such as e.g. cesium carbonate, in a solvent such as e.g. N,N-dimethylformamide, at a temperature between 40° C. and 150° C., preferably between 80° C. and 130° C.

The macrocyclisation of a a compound of formula (IIIn) to deliver a compound of general formula (IIn) can be favorably accomplished by reacting a compound of formula (IIIn) in the presence of triphenylphosphine and di-tert-butyl azodicarboxylate, in a solvent such as e.g. tetrahydrofuran, at a temperature between −10° C. and 40° C., preferably at room temperature.

Starting materials of the formula (IIIn) are available in analogy to Scheme 1. Specific examples are given in the Experimental section, infra.

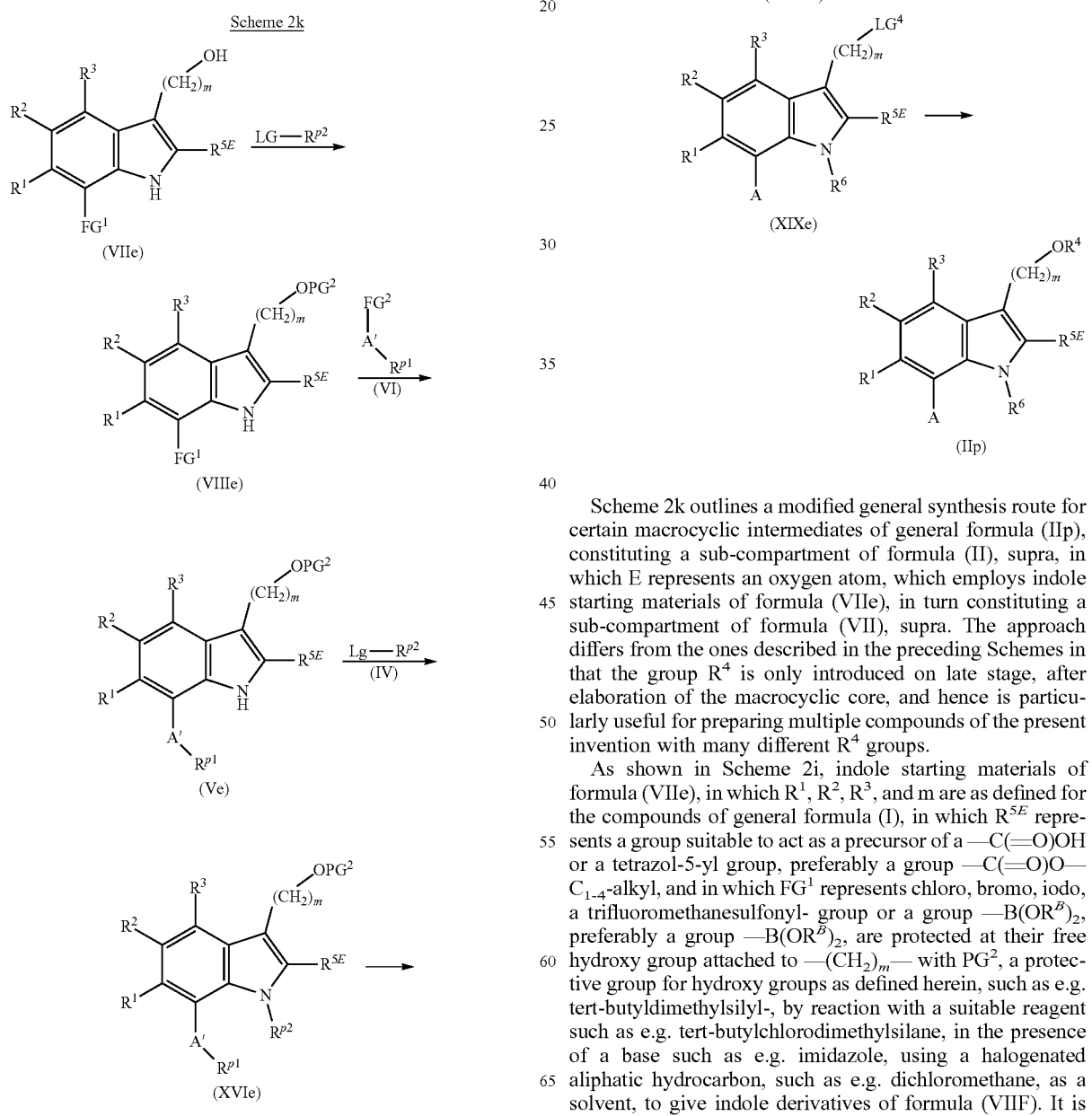

Scheme 2k outlines a modified general synthesis route for certain macrocyclic intermediates of general formula (IIp), constituting a sub-compartment of formula (II), supra, in which E represents an oxygen atom, which employs indole starting materials of formula (VIIe), in turn constituting a sub-compartment of formula (VII), supra. The approach differs from the ones described in the preceding Schemes in that the group $R^4$ is only introduced on late stage, after elaboration of the macrocyclic core, and hence is particularly useful for preparing multiple compounds of the present invention with many different $R^4$ groups.

As shown in Scheme 2i, indole starting materials of formula (VIIe), in which $R^1$, $R^2$, $R^3$, and m are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $FG^1$ represents chloro, bromo, iodo, a trifluoromethanesulfonyl- group or a group —B(OR$^B$)$_2$, preferably a group —B(OR$^B$)$_2$, are protected at their free hydroxy group attached to —(CH$_2$)$_m$— with PG$^2$, a protective group for hydroxy groups as defined herein, such as e.g. tert-butyldimethylsilyl-, by reaction with a suitable reagent such as e.g. tert-butylchlorodimethylsilane, in the presence of a base such as e.g. imidazole, using a halogenated aliphatic hydrocarbon, such as e.g. dichloromethane, as a solvent, to give indole derivatives of formula (VIIF). It is well possible to elaborate said —B(OR$^B$)$_2$ group, if not present already in the compounds of formula (VIIe), from bromo upon introduction of the protective group PG². Specific examples are given in the Experimental Section, infra. In formulae (VI), (VIIe) and (VIIIe), FG¹ in combination with FG² represents a pair of functional groups together enabling a Suzuki coupling; either FG¹ represents chloro, bromo, iodo or a trifluoromethanesulfonyl- group and FG² represents a group —B(OR$^B$)$_2$, or vice versa. Said group —B(OR$^B$)$_2$ may be a boronic acid moiety (R$^B$=—H) or an alkyl ester of the boronic acid, e.g. its isopropyl ester (R$^B$=C$_1$-C$_4$-alkyl, e.g. —CH(CH$_3$)$_2$), or an ester derived from a diol such as pinacol in which the boronic acid intermediate forms a cyclic boronic ester, preferably a 4,4,5,5-tetramethyl-1,3,2-dioxaborolane (R$^B$—R$^B$=C$_2$-C$_6$-alkylene, preferably —C(CH$_3$)$_2$—C(CH$_3$)$_2$).

Said indole derivatives of formula (VIIIe) can, in analogy to the methods discussed in the context of Scheme 1, be reacted in a well-known Suzuki coupling with compounds of formula (VI), in which FG² is as discussed above and in and in which A', together with the group R$^{p1}$ attached to it, represents a group suitable to act as precursor of a group A as defined for the compounds of general formula (I), to give compounds of formula (Ve). Said indole starting materials of formula (VIIe) are well known to the person skilled in the art and can be prepared as described infra.

In subsequent steps, the macrocyclic core can be elaborated using approaches such as those outlined and discussed in the context of Scheme 1 and Schemes 2a-2h to deliver compounds of general formula (XVIIe)

Said macrocyclic intermediate compounds of formula (XVIIe) can be subsequently subjected to a cleavage of the protective group PG², according to methods known to the person skilled in the art (see e.g. T. W. Greene and P. G. M. Wuts in Protective Groups in Organic Synthesis, 4$^{th}$ edition, Wiley 2006), to give compounds of the formula (XVIIIe). The hydroxy group present in said compounds of the formula (XVIIIe) can then be converted into LG⁴, representing a leaving group as defined herein, by methods known to the person skilled in the art, such as the reaction with tetrabromomethane in the presence of triphenylphosphane, in a suitable solvent such as a halogenated aliphatic hydrocarbon, e.g. dichloromethane, or by reaction with with an arylsulfonyl chloride, or alkylsulfonyl chloride or alkylsulfonyl anhydride, such as e.g. methanesulfonyl chloride, giving rise to compounds of the formula (XIXe). The group R⁴ can finally be introduced by reaction of said compounds of the formula (XIXe) with a compound of the formula R⁴—OH, in which R⁴ is as defined for the compounds of formula (I), in the presence of a base, such as e.g. sodium hydride or cesium carbonate, in a solvent such as e.g. tetrahydrofuran or N,N-dimethylformamide (DMF), to give compounds of formula (IIp).

Alternatively, the compounds of formula (IIp) can be obtained by reacting an alcohol R⁴—OH, in which R⁴ is as defined for the compounds of formula (I) and a compound of formula (XVIIIe) in the presence of triphenylphosphine and diisopropyl azodicarboxylate or di-tert-butyl azodicarboxylate, in a solvent such as e.g. tetrahydrofuran, at a temperature between −10° C. and 40° C., preferably at a temperature between −10° C. and room temperature.

Specific examples are given in the Experimental section, infra.

C. Conversion into Compounds of Formula (I), Scheme 3:

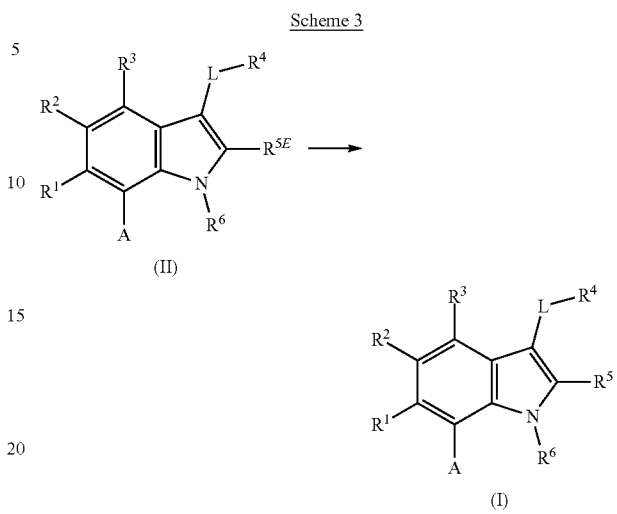

According to Scheme 3, compounds of formula (II) (such as the compounds of the formulae (IIa), (II), (IIc), (IIe), (IIf), (KIIh), (IIj), (IIk), (IIn) and (IIp)), in which R¹, R², R³, R⁴, R⁶, A and L are as defined for the compounds of general formula (I), and in which R$^{5E}$ represents a group suitable to act as precursor of a —C(=O)OH or a tetrazol-5-yl group, preferably a carboxylic ester group, such as e.g. a —C(=O) O—C$_{1-4}$-alkyl group or a benzyl ester, can be readily converted into compounds of formula (I) by transforming group R$^{5E}$ into group R⁵ as defined for the compounds of general formula (I), preferably by reacting with an alkali hydroxide, such as e.g. potassium hydroxide, sodium hydroxide, lithium hydroxide, preferably lithium hydroxide, in a mixture of water with THF and/or an aliphatic alcohol of the formula C$_1$-C$_3$-alkyl-OH, preferably methanol or ethanol, at a temperature between 0° C. and 100° C., and subsequent usual workup as known by the person skilled in the art and as for example disclosed in the experimental section.

Said compounds of general formula (I) may be obtained as free acids or converted into pharmaceutically acceptable salts thereof, such as alkali salts, e.g. sodium or potassium salts, earth alkali salts, e.g. magnesium or calcium salts, and ammonium salts, e.g. ammonium (NH$_4$⁺), diethylammonium (herein also referred to as N-ethylethanamine salts) or triethylammonium salts, by methods known to the person skilled in the art. Compounds of the invention featuring a basic nitrogen atom, such as some of those obtainable from macrocyclic intermediates of formula (IIc), can be isolated as salts with a counteranion of the basic nitrogen, such as e.g. trifluoroacetate, and the like, or as inner carboxylate salts. Further, compounds of formula (I) in which R⁵ represents a free carboxylic acid group can be optionally converted into an acylsulfonamide according to methods known to the person skilled in the art (see for example: *Bioorg. Med Chem. Lett.* 2006, 16, 3639-3641; *Bioorg. Med Chem. Lett.* 2012, 22, 713-717; *Org.*

*Lett.* 2012, 14(2), 556-559).

Further, single enantiomers of said compounds of general formula (I) may be obtained by methods known to the person skilled in the art, such as preparative HPLC on a chiral stationary phase, as described supra, and as exemplified in the Experimental Section, infra.

D. Synthesis Routes to Starting Materials of Formulae (VI) and (VII); Schemes 4a-4b:

As outlined in Schemes 4a and 4b below, several approaches, which are intended to illustrate but not to limit the synthetic routes available to the person skilled in the art for this purpose, can be followed in order to prepare starting materials of the formula (VI), as defined in the context of Scheme 1, supra, i.e. in which A', together with the group $R^{p1}$ attached to it, represents a group suitable to act as precursor of a group A as defined for the compounds of general formula (I), and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group and $FG^2$ represents a group $-B(OR^B)_2$ as defined supra, or vice versa. Preferably, $FG^2$ represents bromo. Conversion of compounds, in which $FG^2$ represents bromo, into compounds in which $FG^2$ represents a group $-B(OR^B)_2$, is possible on various steps of the outlined synthesis routes using methods well known to the person skilled in the art.

by reaction with hydrazines $HN(R^8)-NH_2$, in which $R^8$ is as defined for the compounds of general formula (I), to give regioisomeric mixtures of pyrazole derivatives of formulae (XIIa) and (XIIb), which can be separated on this step or on one of the steps described below. If unsubstituted hydrazine ($R^8$=H) is used, $R^8$ groups different from a hydrogen atom can be introduced into compounds of formulae (XIIa) and (XIIb) e.g. by suitable alkylating agents such as a $C_1$-$C_6$-alkyl halide or a di($C_1$-$C_6$-alkyl)sulfate in the presence of a base, such as e.g. sodium carbonate, in a solvent siuch as dichloromethane or N,N-dimethylformamide.

Said pyrazole derivatives of formulae (XIIa) and (XIIb) can subsequently reacted with reagents suitable to introduce $FG^2$, such as N-halo succinimides or solutions of elemental halogens, to give pyrazole derivatives of formulae (XIIIa) and (XIIIb); preferably, N-bromo succinimide in a halogenated hydrocarbon, such as e.g. 1,2-dichloroethane, as a solvent, or bromine in a solvent such as glacial acetic acid or a halogenated hydrocarbon, such as e.g. dichloromethane, can be used. Said pyrazole derivatives of formulae (XIIIa) and (XIIIb) can be subsequently reduced by a suitable

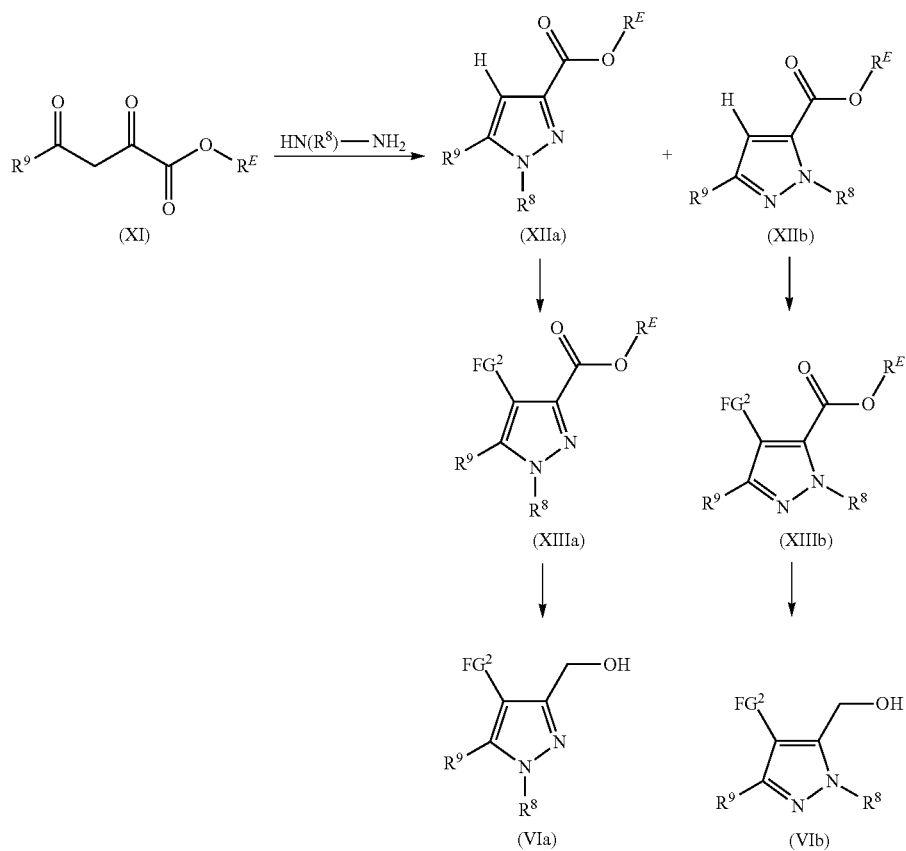

Scheme 4a

Scheme 4a illustrates the synthesis route enabling the preparation of compounds of formula (VI), in which A' is derived from pyrazole, namely compounds of formulae (VIa) and (VIb), both of them constituting sub-compartments for formula (VI).

Said compounds of formulae (VIa) and (VIb) can be prepared from well-known α,γ-diketoesters of formula (XI), in which $R^9$ is as defined for the compounds of general formula (I), and in which $R^E$ represents a $C_1$-$C_6$-alkyl group, reducing agent not interfering with the groups $FG^2$, such as e.g. lithium borohydride, in a solvent such as e.g. tetrahydrofuran, to give pyrazolyl methanols of formulae (VIa) and (VIb). Specific examples are given in the Experimental section, infra. It is readily recognised by the person skilled in the art that the $-CH_2OH$ group present in said pyrazolyl methanols of formulae (VIa) and (VIb) can be converted in various other $R^{p1}$ groups (see formula (VI)).

Scheme 4b

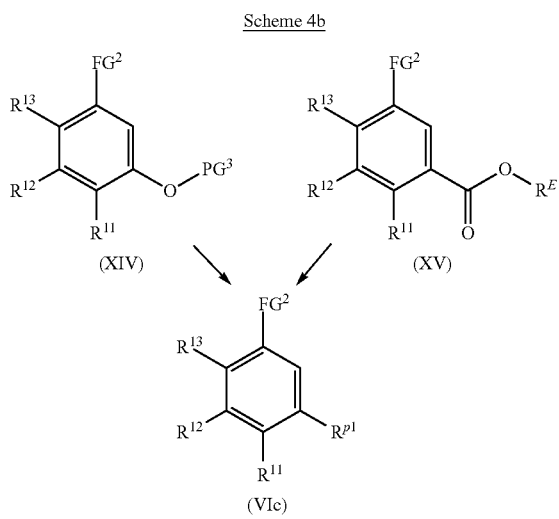

Scheme 4b illustrates synthesis routes enabling the preparation of compounds of formula (VI), in which A' is derived from phenyl, pyridinyl, pyrimidinyl or pyridazinyl, namely compounds of formula (VIc), constituting yet another sub-compartment of formula (VI).

Starting from compounds of formula (XIV), in which $R^{11}$, $R^{12}$, and $R^{13}$ are as defined for the compounds of general formula (I), and wherein one or two of the groups selected from $CR^{11}$, $CR^{12}$ or $CR^{13}$ may be replaced by a nitrogen atom, and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group and $FG^2$ represents a group $—B(OR^B)_2$ as defined supra, or vice versa, and in which $PG^3$ represents a protective group, compounds of formula (VIc), in which $R^{p1}$ represents a hydroxy group, can be readily obtained. Likewise, compounds of formula (XV), in which $R^{11}$, $R^{12}$, and $R^{13}$ are as defined for the compounds of general formula (I), and wherein one or two of the groups selected from $CR^{11}$, $CR^{12}$ or $CR^{13}$ may be replaced by a nitrogen atom, and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group and $FG^2$ represents a group $—B(OR^B)_2$ as defined supra, or vice versa, and $R^E$ represents a group $—C_1-C_6$-alkyl, can be converted into compounds of formula (VIc), in which $R^{p1}$ represents a $—CH_2—OH$ group, a $—C(=O)H$ group, or a $—CH_2-LG^5$ group, in which $LG^5$ represents a leaving group, preferably bromo, in analogy to methods known to the person skilled in the art.

Compounds of formulae (XIV) and (XV) are commercially available, and known to the person skilled in the art, in considerable variety. Using known methods, groups $R^{11}$, $R^{12}$ and $R^{13}$ can be broadly modified using known methods at various stages of the synthesis. Protective groups as present in compounds of formula (XIV), and methods of their removal, are well known to the person skilled in the art, see e.g. T. W. Greene and P. G. M. Wuts in Protective Groups in Organic Synthesis, 4$^{th}$ edition, Wiley 2006.

Indole based starting materials of formula (VII), in which $R^1$, $R^2$, $R^3$, $R^4$ and L are as defined for the compounds of general formula (I), in which $R^{5E}$ represents a group suitable to act as a precursor of a $—C(=O)OH$ or a tetrazol-5-yl group, preferably a group $—C(=O)O—C_{1-4}$-alkyl, and in which $FG^1$ represents chloro, bromo, iodo, a trifluoromethanesulfonyl- group or a group $—B(OR^B)_2$, preferably a group $—B(OR^B)_2$, can be prepared using methods well known to the person skilled in the art, see e.g. Journal of Medicinal Chemistry, 2015, 58, 2180-2194. Said group $—B(OR^B)_2$ may be a boronic acid moiety ($R^B$=—H) or an alkyl ester of the boronic acid, e.g. its isopropyl ester ($R^B$=$C_1-C_4$-alkyl, e.g. $—CH(CH_3)_2$), or an ester derived from a diol such as pinacol in which the boronic acid intermediate forms a cyclic boronic ester, preferably a 4,4,5,5-tetramethyl-1,3,2-dioxaborolane ($R^B$—$R^B$=$C_2-C_6$-alkylene, preferably $—C(CH_3)_2—C(CH_3)_2—$). Alternatively to boronic acid derivatives, also tetrafluoroborates, in which $—BF_4^-$ replaces the $—B(OR^B)_2$ moiety, can also be employed.

Modification of any of the substituents, such as $R^1$, $R^2$, $R^3$, $R^4$, $R^5$, $R^{5E}$, $R^6$, $R^7$, $R^8$, $R^9$, $R^{10}$, $R^{11}$, $R^{12}$, $R^{13}$, $R^{15}$, $R^{p1}$ and $R^{p2}$ can be achieved before and/or after the exemplified transformation. However, also other routes may be used to synthesise the target compounds, in accordance with common general knowledge of a person skilled in the art of organic synthesis. Also, suitable and optionally protected precursor groups of said substituents can be carried through the synthesis routes described in context of the Schemes above, to be elaborated into the actual substituents as defined for the general formula (I) on late stage, as exemplified in the Experimental Section below.

Said modifications can be such as the introduction of protective groups, cleavage of protective groups, reduction or oxidation of functional groups, formation or cleavage of esters or carboxamides, halogenation, metalation, substitution or other reactions known to a person skilled in the art. These transformations include those which introduce a functionality which allows for further interconversion of substituents. Appropriate protective groups and their introduction and cleavage are well-known to a person skilled in the art (see for example T. W. Greene and P. G. M. Wuts in Protective Groups in Organic Synthesis, 4$^{th}$ edition, Wiley 2006). Further, it is possible that two or more successive steps may be performed without work-up being performed between said steps, e.g. a "one-pot" reaction, as it is well-known to a person skilled in the art.

In accordance with a further aspect, the present invention provides a method of preparing a compound of general formula (I) according to any one of claims 1 to 5, said method comprising the step of allowing an intermediate compound of general formula (II):

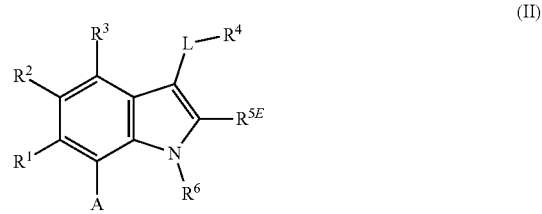

wherein $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester group,
with an alkali hydroxide in a mixture of water and THF and/or an aliphatic alcohol of formula $C_1-C_3$-alkyl-OH, at a temperature from 0° C. to 100° C., to transform the group $R^{5E}$ into a group $R^5$ as defined for the compounds of general formula (I), and subsequently optionally to convert the free acid group $R^5$ into a pharmaceutically acceptable salt thereof to obtain a compound of general formula (I)

(I)

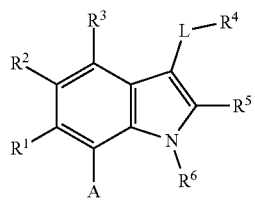

wherein $R^1$, $R^2$, $R^3$, $R^4$, $R^5$, $R^6$, A and L are as defined for the compound of general formula (I) according to any one of claims 1 to 5 or a stereoisomer, a tautomer, an N-oxide, a hydrate, a solvate, or a salt thereof, or a mixture of same and optionally separating enantiomers by means of preparative HPLC on a chiral stationary phase.

In accordance with a further aspect, the present invention covers a method of preparing compounds of general formula (I) according to any one of claims 1 to 5, said method comprising the step of reacting an intermediate compound of general formula (II)

(II)

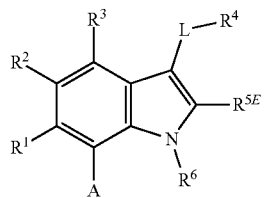

wherein $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester with an alkali hydroxide such as e.g. potassium hydroxide, sodium hydroxide, lithium hydroxide, preferably lithium hydroxide, in a mixture of water and THF and/or an aliphatic alcohol of the formula $C_1$-$C_3$-alkyl-OH, preferably methanol or ethanol, at a temperature from 0° C. to 100° C., preferably from 20° C. to 60° C., to transform the group $R^{5E}$ into a group $R^5$ as defined for the compounds of general formula (I), and subsequently optionally to convert the free acid group $R^5$ into a pharmaceutically acceptable salts thereof to obtain a compound of general formula (I)

(I)

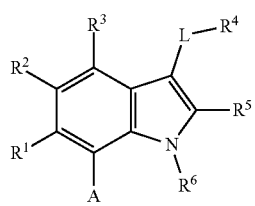

wherein $R^1$, $R^2$, $R^3$, $R^4$, $R^5$, $R^6$, A and L are as defined for the compound of general formula (I) according to any one of claims 1 to 5 or a stereoisomer, a tautomer, an N-oxide, a hydrate, a solvate, or a salt thereof, or a mixture of same and subsequently optionally separating enantiomers by means of preparative HPLC on a chiral stationary phase.

The present invention provides methods of preparing compounds of the present invention of general formula (I), said methods comprising the steps as described in the Experimental Section herein.

In accordance with a further aspect, the present invention provides intermediate compounds which are useful for the preparation of the compounds of general formula (I), supra.

Particularly, the invention provides the intermediate compounds of general formula (II)

(II)

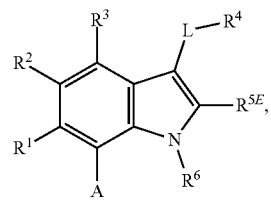

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl group.

In accordance with another aspect, the present invention provides the use of said intermediate compounds for the preparation of a compound of general formula (I) as defined supra.

In accordance with another aspect, the present invention provides a method of using the intermediate compound of general formula (II) for the preparation of a compound of general formula (I).

The present invention provides the intermediate compounds which are disclosed in the Example Section of this text, infra.

The present invention provides any sub-combination within any embodiment or aspect of the present invention of intermediate compounds of general formula (II), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Methods and Adminstration

Compounds of general formula (I) of the present invention demonstrate a valuable pharmacological spectrum of action and pharmacokinetic profile, both of which could not have been predicted. Compounds of the present invention have surprisingly been found to effectively inhibit MCL-1 activity, and it is possible therefore that said compounds can be used for the treatment or prophylaxis of diseases, preferably hyperproliferative disorders in humans and animals.

As used herein, "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

Compounds of the present invention can be utilized to inhibit, block, reduce, and/or decrease cell proliferation and/or cell division, and/or induce apoptosis. Disclosed methods include administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumours.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, basal cell carcinoma, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthalmol. Vis. Sci., 1996, 37, 855], neovascular glaucoma, psoriasis, retrolental fibroplasias, angiofibroma, inflammation, rheumatoid arthritis (RA), restenosis, in-stent restenosis, and vascular graft restenosis. In addition, the increased blood supply associated with cancerous and neoplastic tissue encourages growth, leading to rapid tumour enlargement and metastasis.

Moreover, the growth of new blood and lymph vessels in a tumour provides an escape route for rapidly dividing cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, and/or decreasing endothelial cell proliferation, or other pathways involved in angiogenesis, as well as causing cell death or apoptosis of such cell types.

These disorders have been well characterized in humans, but also exist with a similar etiology in other mammals, and can be treated by administering pharmaceutical compositions of the present invention.

By "subject" is meant a mammal, including, but not limited to, a human or non-human mammal, such as a bovine, equine, canine, ovine, or feline.

The term "treating" or "treatment" as stated throughout this document is used conventionally, for example the management or care of a subject for the purpose of combating, alleviating, reducing, relieving, and/or improving the condition of a disease or disorder, such as a carcinoma.

The compounds of the present invention can be used in particular in therapy and prevention, i.e., prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans, 5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In some embodiments of the present invention, the compounds of general formula (I) of the present invention may be used to sensitize a cell to radiation, i.e., treatment of a cell with a compound of the present invention prior to radiation treatment of the cell renders the cell more susceptible to DNA damage and cell death than the cell would be in the absence of any treatment with a compound of the present invention. In some embodiments, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In some embodiments, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e., after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g., cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In some embodiments, a compound of general formula (I) of the present invention is administered to a cell prior to the radiation or other induction of DNA damage in the cell. In some embodiments, a compound of general formula (I) of the present invention is administered to a cell concomitantly with the radiation or other induction of DNA damage in the cell. In some embodiments, a compound of general formula (I) of the present invention is administered to a cell immediately after radiation or other induction of DNA damage in the cell has begun.

In some embodiments, the cell is in vitro. In some embodiments, the cell is in vivo.

Thus in some embodiments, the present invention includes a method of inhibiting proliferation of a cell and/or the induction of apoptosis in a cell, comprising contacting the cell with a compound of formula (I) according to any one of claims 1-6.

Another aspect of the invention is a method for controlling cancer (e.g., through treatment and/or prophylaxis) in a subject (e.g., human, other mammal, such as rat, etc.) by administering an effective amount of at least one compound of general formula (I), or a pharmaceutically acceptable salt, polymorph, metabolite, hydrate, solvate or ester thereof to the subject.

In some embodiments, the subject may be administered a medicament, comprising at least one compound of general formula (I) and one or more pharmaceutically acceptable carriers, excipients, and/or diluents.

Furthermore in some embodiments, the present invention includes a method of using a compound of general formula (I) for the treatment of diseases.

Particularly in some embodiments, the present invention includes a method of treating a hyperproliferative disease, more particularly cancer, comprising administering an effective amount of at lest one compound of general formula (I) according to any one of claims 1-6.

In some embodimetns, the method of treatment and/or prophylaxis of a hyperproliferative disorder in a subject may comprise administering to the subject an effective amount of a compound of general formula (I). The hyperproliferative disorder may be, for example, cancer (e.g., breast cancer; leukemia, lung cancer; lymphoma, melanoma; multiple myeloma, pancreas cancer and ovarian cancer, etc.).

A method of inhibiting dihydroorotate dehydrogenase activity in a cancer cell is also provided, wherein the method comprises contacting a cancer cell with a compound of general formula (I). The cancer cell may be in vitro or in vivo.

Furthermore in some embodiments, the present invention includes a method of treating cancer, particularly breast cancer; leukemia, lung cancer; lymphoma, melanoma; multiple myeloma, pancreas cancer and ovarian cancer comprising administering an effective amount of at least one compound of formula (I) according to any one of claims 1-6.

Furthermore in some embodiments, the present invention includes a method of treating cancer, particularly multiple myeloma, ovarian carcinoma, acute monocytic leukemia, melanoma and lung cancer. comprising administering an effective amount of at least one compound of formula (I) according to any one of claims 1-6.

In some embodiments the present invention provides for compounds of general formula (I) for use in a method of treating cancer, particularly where the cancer disease is breast cancer; leukemia, lung cancer; lymphoma, melanoma; multiple myeloma, pancreas cancer and ovarian cancer.

Furthermore in some embodiments, the present invention includes a method of treating cancer, particularly breast cancer; endometrial cancer, leukemia, liver cancer, lung cancer; lymphoma, melanoma; and multiple myeloma comprising administering an effective amount of at least one compound of formula (I) according to any one of claims 1-6.

Furthermore in some embodiments, the present invention includes a method of treating cancer, particularly breast cancer; endometrial cancer, liver cancer, lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; pancreas cancer. GC-DLBCL means Germinal B-cell Diffuse Large B-Cell Lymphoma and  ABC-DLBCL means Activated B-cell Diffuse Large B-Cell Lymphoma comprising administering an effective amount of at least one compound of formula (I) according to any one of claims 1-6.

Furthermore in some embodiments, the present invention includes a method of treating cancer, particularly breast cancer; leukemia, lung cancer; lymphoma, melanoma; multiple myeloma, pancreas cancer and ovarian cancer comprising administering an effective amount of at least one compound of formula (I) according to any one of claims 1-6. Furthermore in accordance with another aspect, the present invention provides a compound of formula (I) for use of treating diseases.

In some embodiments, the present invention includes a compound of general formula (I) for use in a method of inhibiting proliferation of a cell and/or the induction of apoptosis in a cell, comprising contacting the cell with a compound of formula (I) according to any one of claims 1-6.

Furthermore in some embodiments, the present invention includes a method of treating [lymphoma] in a subject, the method comprising administering to the subject an effective amount of a compound of formula (I).

Particularly in some embodiments, the present invention includes compounds of general formula (I) for use in a method of treating a hyperproliferative disease, more particularly wherein the hyperproliferative disease is cancer, and yet even more particularly wherein the cancer disease breast cancer; leukemia, lung cancer; lymphoma, melanoma; multiple myeloma, pancreas cancer and ovarian cancer.

In yet some embodiments, the present invention includes compounds of general formula (I) for use in a method of treating a hyperproliferative disease, more particularly wherein the hyperproliferative disease is cancer, and yet even more particularly wherein the cancer disease is breast cancer; esophageal cancer, liver cancer, lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; pancreas cancer. GC-DLBCL means Germinal B-cell Diffuse Large B-Cell Lymphoma and  ABC-DLBCL means Activated B-cell Diffuse Large B-Cell Lymphoma In some embodiments, the present invention includes use of the compounds of general formula (I) for the manufacture of a medicament for the treatment of a hyperproliferative disease, particularly cancer and more particularly breast cancer; leukemia, lung cancer; lymphoma, melanoma; multiple myeloma, pancreas cancer and ovarian cancer.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, or otic route or as an implant or stent.

For these administration routes, it is possible for the compounds according to the invention to be administered in suitable administration forms.

For oral administration, it is possible to formulate the compounds according to the invention into dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatin capsules), sugar-coated tablets, granules, pellets, powders, emulsions, suspensions, aerosols or solutions. It is possible to incorporate the compounds according to the invention in crystalline and/or amorphous and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation (inter alia powder inhalers, nebulizers), nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example, cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example, polyethylene glycols, cacao butter, hard fat), solvents (for example, water, ethanol, isopropanol, glycerol, propylene glycol, medium chain-length triglycerides, fatty oils, liquid polyethylene glycols, paraffins), surfactants, emulsifiers, dispersants or wetters (for example, sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example, phosphates, carbonates, citric acid, acetic acid, hydrochloric acid, sodium hydroxide solution, ammonium carbonate, trometamol, triethanolamine), isotonicity agents (for example, glucose, sodium chloride), adsorbents (for example, highly-disperse silicas), viscosity-increasing agents, gel formers, thickeners and/or binders (for example, polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatin), disintegrants (for example, modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example, magnesium stearate, stearic acid, talc, highly-disperse silicas (such as, for example, Aerosit®)), coating materials (for example, sugar, shellac) and film formers for films or diffusion membranes which dissolve rapidly or in a modified manner (for example, polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example, gelatin, hydroxypropylmethylcellulose), synthetic polymers (for example, polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example, polyethylene glycols, propylene glycol, glycerol, triacetine, triacetyl citrate, dibutyl phthalate), penetration enhancers, stabilisers (for example, antioxidants such as, for example, ascorbic acid, ascorbyl palmitate, sodium ascorbate, butylhydroxyanisole, butylhydroxytoluene, propyl gallate), preservatives (for example, parabens, sorbic acid, thiomersal, benzalkonium chloride, chlorhexidine acetate, sodium benzoate), colourants (for example, inorganic pigments such as, for example, iron oxides, titanium dioxide), and flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In some embodiments, the present invention includes pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention includes a pharmaceutical combination, which comprises:

one or more first active ingredients, in particular compounds of general formula (I) as defined supra, and one or more further active ingredients, in particular for the treatment and/or prophylaxis of hyperproliferative disorder, particularly cancer.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent, or in combination with one or more other pharmaceutically active ingredients where the combination causes no unacceptable adverse effects. The present invention also includes such pharmaceutical combinations. For example, the compounds of the present invention can be combined with known anti-cancer agents.

Examples of Anti-Cancer Agents Include:

131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative diseases, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 40 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 3000 mg of active ingredient, and can be administered one or more times per day or less than once a day. The average daily dosage for administration by injection, including intravenous, intramuscular, subcutaneous and parenteral injections, and use of infusion techniques will preferably be from about 0.01 to about 200 mg/kg of total body weight. The average daily rectal dosage regimen will preferably be from about 0.01 to about 200 mg/kg of total body weight. The average daily vaginal dosage regimen will preferably be from about 0.01 to about 200 mg/kg of total body weight. The average daily topical dosage regimen will preferably be from about 0.1 to about 200 mg administered between one to four times daily. The transdermal concentration will preferably be that required to maintain a daily dose of from about 0.01 to about 200 mg/kg. The average daily inhalation dosage regimen will preferably be from about 0.01 to about 100 mg/kg of total body weight.

In one embodiment the average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from abut 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Experimental Section—NMR Spectra

To the extent NMR peak forms and multiplicities are specified, they are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), . . . , $δ_i$ (intensity$_i$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 01 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Experimental Section—Abbreviations

The following table lists the abbreviations used in this paragraph and in the Intermediates and Examples section as far as they are not explained within the text body. Other abbreviations have their meanings customary per se to the skilled person. A comprehensive list of the abbreviations utilized by organic chemists of ordinary skill in the art appears presented in the first issue of each volume of the Journal of Organic Chemistry; this list is typically presented in a table titled "Standard List of Abbreviations". In case of doubt, the abbreviations and/or their meaning according to the following table shall prevail.

TABLE 1

Abbreviations

| Abbreviation | Meaning |
| --- | --- |
| br. | broad signal (NMR) |
| d | doublet (NMR) |
| DAD | diode array detector |
| DCM | dichloromethane |
| dd | doublet of doublet (NMR) |
| ddd | doublet of doublet of doublet (NMR) |
| dt | doublet of triplet (NMR) |
| DMF | N,N-dimethylformamide |
| DMSO | dimethylsulfoxide |
| ESI | electrospray (ES) ionisation |
| h, hr (hrs) | hour(s) |
| HCl | hydrogen chloride, hydrochloric acid |
| HPLC | high performance liquid chromatography |
| LC-MS | liquid chromatography-mass spectrometry |
| m | multiplet (NMR) |
| min | minute(s) |
| MS | mass spectrometry |
| MWD | Multiple wavelength detector |
| NMR | nuclear magnetic resonance spectroscopy: chemical shifts (δ) are given in ppm. The chemical shifts were corrected by setting the DMSO signal to 2.50 ppm using unless otherwise stated. |
| q | quartet (NMR) |
| qd | quartet of doublet (NMR) |
| rt | room temperature |
| $R_t$, Rt | retention time |
| s | singulet (NMR) |
| SFC | Supercritical Fluid Chromatography |
| t | triplet (NMR) |
| td | triplet of doublet (NMR) |
| THF | tetrahydrofuran |
| TLC | thin layer chromatography |
| δ | chemical shift |
| XPhos Pd G2 | Chloro(2-dicyclohexylphosphino-2',4',6'-triisopropyl-1,1'-biphenyl)[2-(2'-amino-1,1'-biphenyl)]palladium(II) (Cas No: 1310584-14-5) |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate (Cas No: 1445085-55-1) |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art. Reactions were set up and started, e.g. by the addition of reagents, at temperatures as specified in the protocols; if no temperature is specified, the respective working step was performed at ambient temperature, i.e. between 18 and 25° C.

"Silicone filter" or "water resistant filter" refers to filter papers which are made hydrophobic (impermeable to water) by impregnation with a silicone. With the aid of these filters, water can be separated from water-immiscible organic solvents by means of a filtration (i.e. filter paper type MN 617 WA, Macherey-Nagel).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be removed by trituration using a suitable solvent or solvent mixture. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/ethanol. In flash column chromatography, unmodified ("regular") silica gel may be used as well as aminophase functionalized silica gel. As used herein, "Biotage SNAP cartridge silica" refers to the use of regular silica gel; "Biotage SNAP cartridge $NH_2$ silica" refers to the use of aminophase functionalized silica gel. If reference is made to flash column chromatography or to flash chromatography in the experimental section without specification of a stationary phase, regular silica gel was used. Further, column chromatography can also be used advantageously in the reversed-phase mode, using materilas such as C18 siliga gel as stationary phase, and using eluents such as gradients of water and acetonitrile which may contain additives such as trifluoroacetic acid, formic acid, diethylamine or aqueous ammonia. If reference is made to reversed phase column chromatography in the experimental section without specification of a stationary phase, C18 siliga gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid, diethylamine or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−).

Analytical UPLC Methods:
Method 1:

Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.

Method 2:

Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 3:

Instrument: Waters Alliance HT; Column: Waters Cortecs 30 mm×3 mm×2.7 µm; eluent A: Water (MilliQ)+0.01 vol % formic acid, eluent B: acetonitrile+0.01 vol % formic acid; gradient: 0-1.7 min 3-95% B, 1.7-2.2 min 95% B; 2.3-2.5 3% B; flow: 1.75 mL/mn; temperature: 45° C.; DAD scan: 200-500 nm.

Method 4:

Instrument: Waters Alliance HT; Column: Waters Cortecs 30 mm×3 mm×2.7 µm; eluent A: Water (MilliQ)+0.01 vol % formic acid, eluent B: acetonitrile+0.01 vol % formic acid; gradient: 0-6.8 min 5-95% B, 6.8-7.3 min 95% B; 7.3-7.5 5% B; flow: 1.75 mL/mn; temperature: 45° C.; DAD scan: 200-500 nm.

Preparative HPLC Methods:
Method P1:

Instrument: Waters Autopurification MS SingleQuad; Column: Waters XBrigde C18 5 µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm.

Method P2:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; solvent A: water+0.1 vol-% formic acid, solvent B: acetonitrile; gradient: 0.00-0.50 min 40% B (150 mL/min), 0.50-6.00 min 40-80% B (150 mL/min), 6.00-6.10 min 80-100% B (150 mL/min), 6.10-8.00 min 100% B (150 mL/min), UV-Detection.

Method P3:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; solvent A: water+0.1 vol-% formic acid, solvent B: acetonitrile; gradient: 0.00-0.50 min 65% B (150 mL/min), 0.50-6.00 min 65-100% B (150 mL/min), 6.00-8.00 min 100% B (150 mL/min), UV-Detection.

Method P4:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: XBridge, RP C18 5 µm, 100×30 mm; Solvent A: water+0.2 Vol-% ammonia (32%), Solvent B: acetonitrile, gradient: 0.00-2.00 min 10% B (60 mL/min), 2.00-14.00 min 10-50% B (60 mL/min), 14.00-14.10 min 50-100% B (60 mL/min), 14.10-17.00 min 100% B (60 mL/min), UV-Detection.

Specific Optial Rotation Methods:

Method O1: Instrument: JASCO P2000 Polarimeter; wavelength 589 nm; temperature: 20° C.; integration time 10 s; path length 100 mm.

Intermediates
Intermediate 1 di-tert-butyl (4-bromobutyl)-2-imidodicarbonate

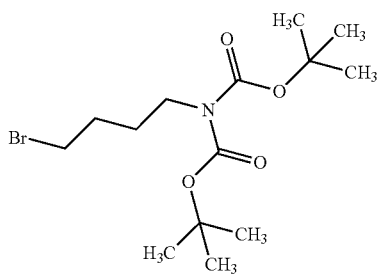 [SMILES: CC(C)(C)OC(=O)N(CCCCBr)C(=O)OC(C)(C)C]

Di-tert-butyl 2-imidodicarbonate (CAS 51779-32-9, 27.0 g, 124 mmol) was solved in 510 mL DMF and 500 mL THF and sodium hydride (4.97 g, 60% purity, 124 mmol) was added portionswise to the reaction mixture. After complete addition it was stirred at 65° C. for 2 hours. Then it was cooled to rt and 1,4-dibromobutane (CAS 110-52-1, 65 ml, 550 mmol) was added dropwise into the reaction mixture. It was stirred at 65° C. for 3 hours. Under cooling the mixture was diluted with methyl tert. butyl ether and water. The layers were separated and the aqueous layer was extracted with ether twice. The organic layers were dried using a water resistant filter. The clear filtrate was concentrated under reduced pressure. The crude product was purified using a 340 g silica column (Gradient: hexane/ethyl acetate 0-60) to provide the target compound in 95% purity: 41.6 g.

$^1$H-NMR (400 MHz, DMSO-d6): δ [ppm]=1.45 (s, 18H), 1.56-1.66 (m, 2H), 1.71-1.82 (m, 2H), 3.46-3.52 (m, 2H), 3.52-3.56 (m, 2H).

Intermediate 2 ethyl 7-bromo-3-(3-ethoxy-3-oxo-propyl)-6-fluoro-1H-indole-2-carboxylate

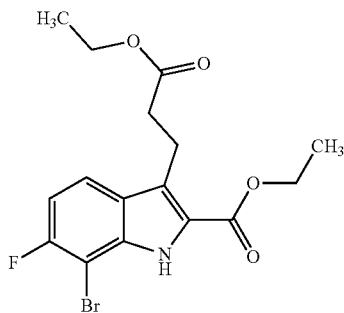 [SMILES: CCOC(=O)CCc1c(C(=O)OCC)[nH]c2c(Br)c(F)ccc12]

To a 0° C. stirred suspension of 2-bromo-3-fluoroaniline (40.0 g, 210 mmol, 1.00 eq.) in an aqueous hydrochloric acid solution (53.0 mL concentrated hydrochloric acid in 339 mL water, 630 mmol, 3.00 eq.) was added a 2.5 M solution of sodium nitrite in water (83.9 mL, 210 mmol, 1.00 eq.) via dropping funnel. After complete addition, 4.5 M sodium acetate (262 mL, 1.18 mol, 5.62 eq.) in water was added via dropping funnel, followed by addition of ethyl 2-oxocyclopentanecarboxylate (31.0 mL, 210 mmol, 1.00 eq.). The resulting yellow suspension was maintained at 0° C. for 15 minutes and then warmed to room temperature and stirred for 2 hours. The reaction mixture was extracted with dichloromethane (4×200 mL) and the combined organic extracts were dried (magnesium sulfate), filtered and concentrated under reduced pressure to give the crude hydrazone as a orange solid. The residue was re-suspended in ethanol (210 mL, 1.00 M), cooled to 0° C., followed by slow addition of concentrated sulfuric acid (27.9 mL, 525 mmol, 2.50 eq.). The dark red solution was heated at 95° C. for 13 days, cooled to room temperature and partially concentrated under reduced pressure. The dark brown solution was poured onto ice/water (500 mL) and extracted with dichloromethane (3×500 mL). The combined organic extracts were washed with saturated aqueous sodium bicarbonate (500 mL), dried (magnesium sulfate), filtered and concentrated under reduced pressure to give a brown solid. The residue was purified by flash column chromatography (20% ethyl acetate/hexanes) and then recrystallised from hot 10% ethyl acetate/hexanes to give the title compound as a white fluffy solid (40.8 g).

LC-MS (Method 3): $R_t$=1.62 min; (ESIpos): m/z=388 [M+H]$^+$ $^1$H NMR (300 MHz, Chloroform-d) δ [ppm]: 8.81 (0.78), 7.63 (1.03), 6.98 (1.02), 4.44 (2.08), 4.08 (2.08), 3.36 (2.07), 2.66 (2.08), 1.44 (3.27), 1.20 (3.61).

Intermediate 3 ethyl 7-bromo-6-fluoro-3-(3-hydroxypropyl)-1H-indole-2-carboxylate

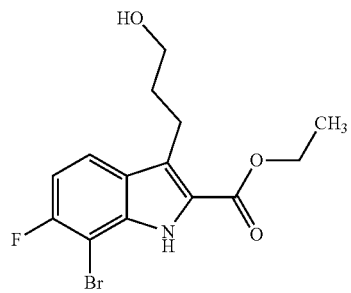 [SMILES: CCOC(=O)c1[nH]c2c(Br)c(F)ccc2c1CCCO]

To a 0° C. stirred solution of ethyl 7-bromo-3-(3-ethoxy-3-oxopropyl)-6-fluoro-1H-indole-2-carboxylate (see Intermediate 2, 24.0 g, 62.1 mmol, 1.00 eq.) in anhydrous tetrahydrofuran (621 mL, 0.10 M) was added borane dimethyl sulfide complex (23.4 mL, 248 mmol, 4.00 eq.). The resulting mixture was stirred at 0° C. for 30 minutes and then warmed to room temperature and stirred for 2 days. Methanol was added to the mixture to quench any remaining borane and the mixture was concentrated three times from methanol. The residue was purified by flash column chromatography (30-100% ethyl acetate/hexanes gradient) to give the title compound as a white solid (19.1 g).

LC-MS (Method 3): $R_t$=1.33 min; MS (ESIpos): m/z=346 [M+H]$^+$ $^1$H NMR (300 MHz, Chloroform-d) δ [ppm]: 1.45 (3.12), 1.93 (2.05), 2.28 (0.95), 3.21 (2.02), 3.57 (2.08), 4.46 (2.04), 6.98 (0.99), 7.59 (1.03), 8.73 (0.72).

Intermediate 4 ethyl 7-bromo-6-fluoro-3-[3-(1-naphthyloxy)propyl]-1H-indole-2-carboxylate

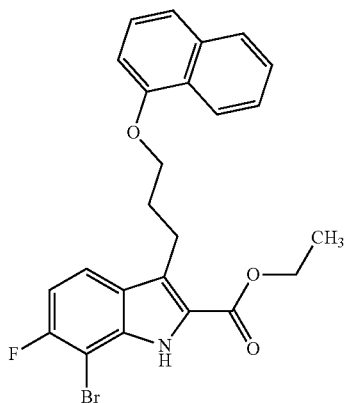 [SMILES: CCOC(=O)c1[nH]c2c(Br)c(F)ccc2c1CCCOc1cccc2ccccc12]

To a 0° C. stirred suspension of ethyl 7-bromo-6-fluoro-3-(3-hydroxypropyl)-1H-indole-2-carboxylate (see Intermediate 3, 11.7 g, 33.9 mmol, 1.00 eq.), 1-napthol (5.85 g, 40.6 mmol, 1.20 eq.) and triphenylphosphine (10.6 g, 40.6 mmol, 1.30 eq.) in anhydrous tetrahydrofuran (113 mL, 0.30 M) was carefully added di-tert-butyl azodicarboxylate (9.34 g, 40.6 mmol, 1.30 eq.) in small portions. After complete addition, the yellow solution was warmed to room temperature, stirred for 17 hours and then concentrated under reduced pressure. The residue was redissolved in dichloromethane (200 mL) and then washed with water (200 mL), saturated aqueous sodium bicarbonate (200 mL) and brine (200 mL). The organic layer was dried (magnesium sulfate), filtered and concentrated under reduced pressure. The residue was purified by flash column chromatography (10-20% ethyl actetae/hexanes gradient) and recrystallised from hot ethanol to give the title compound as an off white solid (12.3 g).

LC-MS (Method 3): $R_t$=2.04 min; MS (ESIpos): m/z=472 $[M+H]^+$ $^1$H-NMR (300 MHz, Chloroform-d) δ [ppm]: 1.39 (3.07), 2.32 (1.99), 3.38 (1.98), 4.16 (1.99), 4.39 (2.00), 6.71 (0.97), 6.85 (0.96), 7.33 (1.19), 7.41 (0.95), 7.48 (2.05), 7.55 (1.02), 7.80 (0.97), 8.25 (0.97), 8.80 (0.77).

Intermediate 5 ethyl 4-bromo-1,3-dimethyl-1H-pyrazole-5-carboxylate

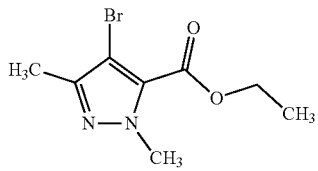

N-Bromosuccinimide (11.2 g, 62.4 mmol) was added to a solution of ethyl 1,3-dimethyl-1H-pyrazole-5-carboxylate (5.00 g, 29.7 mmol, CAS No: 5744-40-1) in 1,2-dichloroethane (100 ml) and the mixture was stirred for 15 h at 65-80° C. followed by 3 days at room temperature. For work-up, the mixture was diluted with ethyl acetate, washed with water and the organic phase was filtrated through a silicone filter and concentrated. The residue was purified by flash chromatography (Biotage SNAP cartridge silica, hexanes/dichloromethane gradient, 0%→100% dichloromethane) to give the title compound (6.69 g, 89% yield).

LC-MS (Method 2): $R_t$=1.15 min; MS (ESIpos): m/z=247 $[M+H]^+$ $^1$H-NMR (400 MHz, DMSO-d6) δ [ppm]: 1.308 (4.21), 1.325 (8.89), 1.343 (4.18), 2.155 (14.47), 3.862 (1.45), 4.008 (16.00), 4.302 (1.34), 4.320 (4.19), 4.337 (4.07), 4.355 (1.24).

Intermediate 6

(4-bromo-1,3-dimethyl-1H-pyrazol-5-yl)methanol

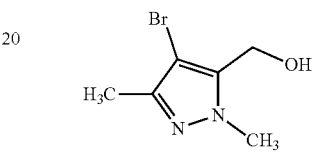

Lithium aluminium hydride (27 ml, 1.0 M in THF, 27 mmol) was added dropwise at 0° C. to a solution of ethyl 4-bromo-1,3-dimethyl-1H-pyrazole-5-carboxylate (see Intermediate 5, 6.69 g, 27.1 mmol) in THF (220 ml) and the mixture was stirred at 0° C. for 1.5 h. The reaction was quenched by dropwise addition of water (5.4 ml) followed by aqueous sodium hydroxide (5.4 ml, 2 M, 11 mmol) and again water (5.4 ml). The mixture was then filtrated through a pad of celite, eluted with THF and the filtrate was concentrated. The residue was purified by flash chromatography (Biotage SNAP cartridge silica 100 g, hexanes/ethyl acetate gradient, 20%→80% ethyl acetate) to give the title compound (3.77 g, 67% yield).

$^1$H-NMR (400 MHz, DMSO-d6) δ [ppm]: 2.083 (14.56), 3.334 (16.00), 4.422 (2.80), 4.435 (2.81), 5.311 (0.59), 5.325 (1.50), 5.337 (0.56).

Intermediate 7 ethyl 4-bromo-1,5-dimethyl-1H-pyrazole-3-carboxylate

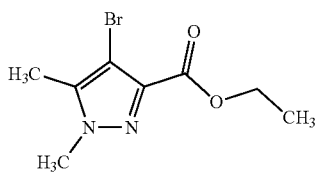

N-Bromosuccinimide (16.3 g, 90.5 mmol) was added to a solution of ethyl 1,5-dimethyl-1H-pyrazole-3-carboxylate (7.25 g, 43.1 mmol, CAS No 5744-51-4) in 1,2-dichloroethane (150 ml) and the mixture was stirred for 15 h at 80° C. For work-up, the mixture was diluted with dichloromethane, washed with water and the organic phase was filtrated through a silicone filter and concentrated. The residue was purified by flash chromatography (Biotage SNAP cartridge silica 340 g, hexanes/dichloromethane gradient, 0→100% dichloromethane) to give the title compound (6.49 g, 61% yield).

¹H-NMR (400 MHz, DMSO-d6) δ [ppm]: 1.261 (4.14), 1.278 (8.78), 1.296 (4.21), 2.268 (14.94), 2.518 (0.74), 2.523 (0.49), 3.857 (16.00), 4.229 (1.31), 4.247 (4.03), 4.264 (3.94), 4.282 (1.24).

Intermediate 8

(4-bromo-1,5-dimethyl-1H-pyrazol-3-yl)methanol

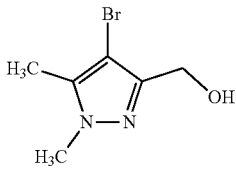

Lithium borohydride (711 mg, 32.6 mmol) was added to a solution of ethyl 4-bromo-1,5-dimethyl-1H-pyrazole-3-carboxylate (see see Intermediate 7, 6.45 g, 26.1 mmol) in THF (150 ml) and the mixture was stirred for 1 h at room temperature and 7 h at 60° C. The reaction was quenched by addition of saturated aqueous ammonium chloride solution and the mixture was extracted with ethyl acetate. The organic phase was filtrated through a silicone filter and concentrated. The residue was purified by flash chromatography (hexanes/ethyl acetate gradient, 50%->100% ethyl acetate) to give the title compound (4.07 g, 76% yield).

¹H-NMR (400 MHz, DMSO-d6) δ [ppm]: 2.205 (16.00), 2.518 (0.43), 3.330 (10.35), 4.285 (3.97), 4.299 (4.13), 4.933 (1.00), 4.946 (2.22), 4.960 (0.93).

Intermediate 9 ethyl 5-ethyl-1-methyl-1H-pyrazole-3-carboxylate

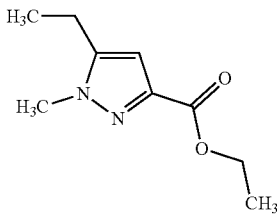

Ethyl 2,4-dioxohexanoate (CAS 13246-52-1, 5.00 g, 29.0 mmol) was dissolved in 20 mL of acetic acid. Under ice cooling methylhydrazine (1.5 mL, 29.0 mmol) was added and the mixture was stirred at rt for 23 hours. Methylhydrazine (0.5 mL, 10.0 mmol) was added and stirring was continued at rt for 24 hours. The reaction mixture was poured into ice water and extracted with ethyl acetate. The combined organic layers were washed with brine, dried using a waterresistant filter and concentrated under reduced pressure. The crude material was purified using silica gel (gradient hexane/ethyl acetate) to obtain of the title compound (2.13 g, 40% yield).

LC-MS (Method 1): R$_t$=0.92 min; MS (ESIpos): m/z=183 [M+H]$^+$

¹H-NMR (400 MHz, DMSO-d6) δ [ppm]: 1.170 (6.09), 1.188 (12.55), 1.208 (6.57), 1.245 (7.14), 1.263 (16.00), 1.280 (7.23), 2.601 (1.10), 2.602 (1.08), 2.619 (3.24), 2.621 (3.35), 2.638 (3.29), 2.640 (3.34), 2.657 (1.02), 2.659 (1.03), 3.331 (8.78), 4.200 (1.95), 4.218 (6.25), 4.236 (6.29), 4.254 (1.95), 5.759 (0.98), 6.518 (4.92).

Intermediate 10 ethyl 4-bromo-5-ethyl-1-methyl-1H-pyrazole-3-carboxylate

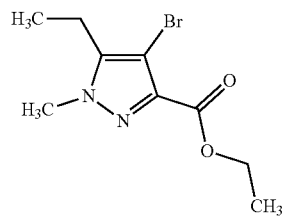

Ethyl 5-ethyl-1-methyl-1H-pyrazole-3-carboxylate (see Intermediate 9, 2.10 g, 11.5 mmol) was dissolved in 15 mL of acetic acid. A solution of bromine in acetic acid (23 mL, 1.0 M, 23 mmol) was added dropwise and the reaction mixture was stirred for 18 hours at rt. The mixture was poured into ice water and aqueous sodium thiosulfate solution (10%) was added. The mixture was extracted with ethyl acetate and the combined organic layers were washed with brine, dried using a water resistant filter and concentrated under reduced pressure to obtain 2.97 g of the title compound. The crude material was used without further purification in the next step.

LC-MS (Method 1): R$_t$=1.08 min; MS (ESIpos): m/z=261 [M+H]$^+$

¹H-NMR (400 MHz, DMSO-d6) δ [ppm]: 1.077 (2.69), 1.096 (6.29), 1.115 (2.81), 1.260 (3.48), 1.278 (7.87), 1.295 (3.68), 1.907 (1.63), 2.518 (0.62), 2.523 (0.41), 2.673 (0.89), 2.692 (2.71), 2.711 (2.65), 2.730 (0.75), 3.894 (16.00), 4.231 (1.11), 4.249 (3.60), 4.266 (3.59), 4.284 (1.10).

Intermediate 11

(4-bromo-5-ethyl-1-methyl-1H-pyrazol-3-yl)methanol

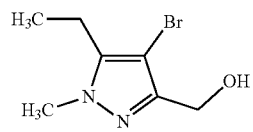

Ethyl 4-bromo-5-ethyl-1-methyl-1H-pyrazole-3-carboxylate (see Intermediate 10, 2.97 g) was dissolved in 45 mL of THF and the lithium borohydride (310 mg, 14.2 mmol) was added portionwise. This mixture was stirred for 20 hours at rt and for 22 hours at 60° C. Lithium borohydride (50 mg, 2.3 mmol) was added and stirring was continued for 24 hours at rt and 3 hours at 60° C. The reaction mixture was diluted with saturated aqueous ammonia chloride solution and extracted with with ethyl acetate. The combined organic layers were washed with brine, dried using a waterresistant filter and concentrated under reduced pressure to obtain the title compound (2.18 g). The crude material was used without further purification in the next step.

LC-MS (Method 1): R$_t$=0.79 min; MS (ESIpos): m/z=219 [M+H]$^+$

¹H-NMR (400 MHz, DMSO-d6) δ [ppm]: 1.068 (3.21), 1.087 (7.19), 1.105 (3.37), 2.518 (0.44), 2.609 (1.02), 2.628

(3.36), 2.647 (3.29), 2.666 (1.04), 3.761 (16.00), 4.287 (4.77), 4.301 (4.91), 4.941 (1.34), 4.955 (2.69), 4.969 (1.21).

Intermediate 12

(4-bromo-3-ethyl-1-methyl-1H-pyrazol-5-yl)methanol

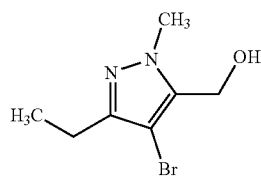

To a solution of ethyl 4-bromo-3-ethyl-1-methyl-1H-pyrazole-5-carboxylate (CAS, 128537-28-0, 200 g, 766 mmol, 1 eq) in 200 mL THF was added lithiumborohydride (83 g, 3.83 mol, 5 eq) slowly. The mixture was stirred at 60° C. for 3 h. The reaction mixture was quenched by addition of water (2000 mL) at 20° C., and then extracted with ethyl acetate (1000 mL) three times. The combined organic layers were washed with brine (800 mL), dried over sodium sulfate, filtered and concentrated under reduced pressure to give a residue. The residue was purified by triturating with PE (2000 mL) for 3 times to give the target compound (112 g, 99% purity) as a white solid.

$^1$H-NMR (400 MHz, Methanol-d4) δ [ppm]=4.60 (s, 2H), 3.86 (s, 3H), 2.58 (q, 2H), 1.20 (t, 3H).

Intermediate 13 ethyl 6-fluoro-3-[3-(naphthalen-1-yloxy)propyl]-7-(4,4,5,5-tetramethyl-1,3,2-dioxaborolan-2-yl)-1H-indole-2-carboxylate

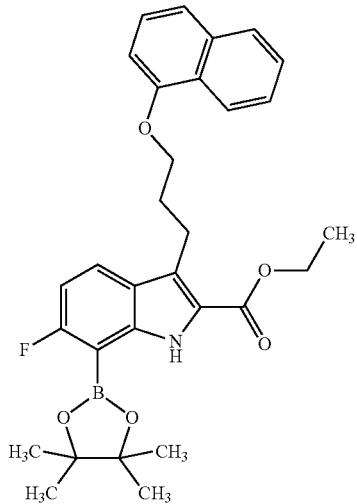 [SMILES: CCOC(=O)c1[nH]c2c(B3OC(C)(C)C(C)(C)O3)c(F)ccc2c1CCCOc1cccc2ccccc12]

To an oven dried flask under an argon atmosphere was added ethyl 7-bromo-6-fluoro-3-[3-(naphthalen-1-yloxy)propyl]-1H-indole-2-carboxylate (see Intermediate 4, 4.70 g, 10.0 mmol, 1.00 eq.), bis(pinicolato)diboron (3.05 g, 12.0 mmol, 1.20 eq.), potassium acetate (4.52 g, 46.0 mmol, 4.60 eq.) and [1,1'-bis(diphenylphosphino)ferrocene]dichloropalladium(II), complex with dichloromethane (408 mg, 0.50 mmol, 5.00 mol %). To this mixture was then added argon sparged 1,4-dioxane (60.0 mL) to give a 0.20 M solution. The red suspension were heated at 90° C. for 18 h and then cooled to room temperature. The mixture was filtered through a Celite plug (washing with ethyl acetate) and concentrated under reduced pressure to give a dark solid. Isolute HMN-R was added to the resulting residue, volatiles were removed under reduced pressure, and the residue was loaded onto a silica gel cartridge which was subjected to flash column chromatography (0-50% ethyl acetae/hexanes gradient) to give an inseparable mixture of the title compound and protodeborylated product (2.78 g). The mixture was used directly in the next step without further purification.

LC-MS (Method 1): R$_t$=1.84 min; MS (ESIpos): m/z=518 [M+H]$^+$ $^1$H-NMR (400 MHz, CHLOROFORM-d) delta [ppm]: 1.239 (0.60), 1.253 (1.51), 1.272 (16.00), 1.282 (5.57), 1.384 (1.38), 1.389 (0.70), 1.402 (2.81), 1.407 (0.51), 1.421 (1.51), 1.433 (10.34), 2.017 (0.78), 3.398 (0.64), 4.157 (0.74), 4.164 (0.53), 4.378 (1.08), 4.395 (1.32), 4.414 (0.69), 6.712 (0.41), 6.731 (0.51), 7.333 (0.45), 7.404 (0.42), 7.486 (0.53), 7.495 (0.71), 7.505 (0.61), 7.510 (0.46).

Intermediate 14

(rac)-ethyl 6-fluoro-7-[3-(hydroxymethyl)-1,5-dimethyl-1H-pyrazol-4-yl]-3-[3-(naphthalen-1-yloxy)propyl]-1H-indole-2-carboxylate

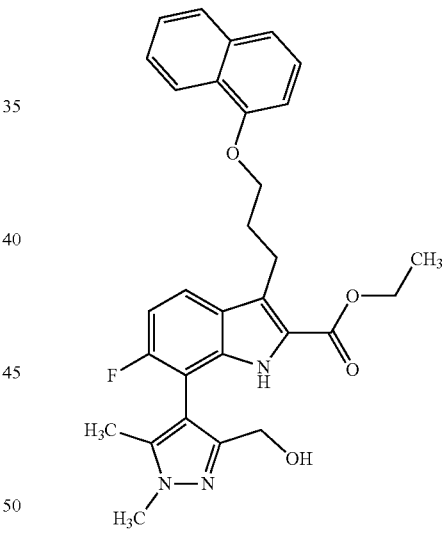

A mixture of ethyl 6-fluoro-3-[3-(naphthalen-1-yloxy)propyl]-7-(4,4,5,5-tetramethyl-1,3,2-dioxaborolan-2-yl)-1H-indole-2-carboxylate (see Intermediate 13, 5.17 g, 10.0 mmol, 1.00 eq.), (4-bromo-1,5-dimethyl-1H-pyrazol-3-yl)methanol (see intermediate 8, 2.46 g, 12.0 mmol, 1.20 eq.), XPhos Pd G3 (846 mg, 1.00 mmol, 10.0 mol %) and tripotassium phosphate (4.25 g, 20.0 mmol, 2.00 eq.) where placed under an argon atmosphere. To this mixture was then added argon degassed 1,4-dioxane (22.3 mL) and water (11.1 mL) to give a 0.30 M solution. The light brown suspension was heated at 40° C. for 16 hours, cooled to room temperature and concentrated under reduced pressure. The dark residue was suspended in water (100 mL) and extracted with dichloromethane (3×100 mL). The combined organic extracts were washed with 1.0 M aqueous hydrochloric acid (100 mL, dried (sodium sulfate), filtered and concentrated under reduced pressure. The residue was purified by flash column chromatography (20-100% ethyl acetate/dichloromethane with 1% methanol gradient) followed by reverse phase column chromatography (65-100% Acetonitrile/water with 0.1% formic acid) to give the title compound as a white solid (1.76 g).

LC-MS (Method 1): $R_t$=1.55 min; MS (ESIpos): m/z=516 $[M+H]^+$ $^1$H-NMR (400 MHz, DMSO-d6) δ [ppm]: 1.244 (4.45), 1.262 (9.57), 1.280 (4.71), 2.066 (8.95), 2.068 (9.28), 2.204 (1.27), 2.221 (1.76), 2.238 (1.34), 2.254 (0.54), 2.539 (1.51), 3.318 (1.54), 3.339 (16.00), 3.354 (1.79), 4.084 (0.99), 4.098 (1.06), 4.113 (1.25), 4.128 (1.22), 4.195 (1.73), 4.210 (3.74), 4.225 (2.19), 4.232 (4.63), 4.250 (4.17), 4.268 (1.41), 4.354 (1.22), 4.363 (1.37), 4.383 (1.15), 4.393 (1.07), 5.583 (1.19), 5.594 (1.69), 5.596 (1.65), 5.606 (1.23), 6.905 (2.04), 6.923 (2.21), 6.975 (1.36), 6.997 (1.77), 7.000 (1.76), 7.022 (1.40), 7.372 (1.19), 7.392 (2.55), 7.411 (1.96), 7.449 (2.91), 7.469 (1.62), 7.480 (0.60), 7.484 (0.69), 7.497 (1.57), 7.501 (1.54), 7.509 (1.71), 7.515 (3.19), 7.521 (1.87), 7.528 (1.71), 7.532 (1.76), 7.546 (0.75), 7.549 (0.57), 7.695 (1.24), 7.708 (1.36), 7.717 (1.35), 7.730 (1.26), 7.856 (1.72), 7.874 (1.63), 7.879 (1.49), 8.212 (1.47), 8.216 (1.55), 8.234 (1.53), 11.272 (3.07).

Intermediate 15

(rac)-ethyl (11Z)-4-fluoro-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate

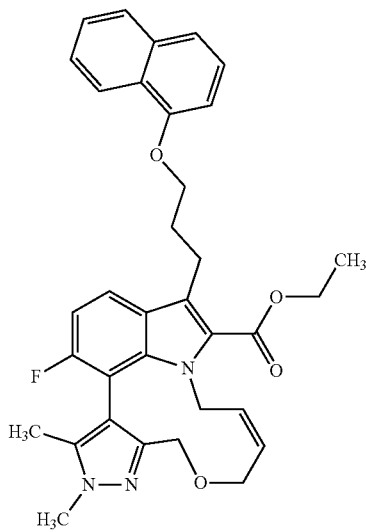 [SMILES: CCOC(=O)c1c(CCCOc2cccc3ccccc23)c2ccc(F)c3c2n1C/C=C\COCc1nn(C)c(C)c1-3]

To a room temperature stirred suspension of (rac)-ethyl 6-fluoro-7-[3-(hydroxymethyl)-1,5-dimethyl-1H-pyrazol-4-yl]-3-[3-(naphthalen-1-yloxy)propyl]-1H-indole-2-carboxylate (see Intermediate 14, 515 mg, 1.00 mmol, 1.00 eq.) in acetonitrile (10 mL, 0.10 M) was added cesium carbonate (1.62 g, 5.00 mmol, 5.00 eq.). After stirring for 10 minutes, cis-1,4-dichloro-2-butene (137 mg, 1.10 mmol, 1.10 eq.) and sodium iodide (300 mg, 2.00 mmol, 2.00 eq.) were sequentially added and the resulting mixture was then stirred at 40° C. for 24 hours and cooled to room temperature. The mixture was diluted with water (20 mL) and extracted with dichloromethane (3×20 mL). The combined organic extracts were washed with 1.0 M aqueous hydrochloric acid (20 mL). Isolute HMN-R was added to the resulting solution, volatiles were removed under reduced pressure, and the residue was loaded onto a Isolute HMN-R cartridge which was subjected to flash column chromatography (0-40% ethyl acetate/dichloromethane with 1% methanol gradient) to give the title compound as an off white foamy solid (268 mg).

LC-MS (Method 1): $R_t$=1.65 min; MS (ESIpos): m/z=568 $[M+H]^+$ $^1$H-NMR (400 MHz, CHLOROFORM-d) δ [ppm]: 1.375 (4.61), 1.392 (9.90), 1.410 (4.60), 1.575 (5.87), 1.955 (15.89), 2.326 (0.91), 2.342 (1.25), 2.359 (0.97), 3.322 (0.45), 3.339 (0.67), 3.356 (1.02), 3.376 (0.56), 3.391 (0.59), 3.410 (1.09), 3.429 (0.63), 3.444 (0.49), 3.783 (0.57), 3.796 (0.64), 3.814 (0.92), 3.827 (0.87), 3.921 (1.05), 3.942 (16.00), 3.979 (0.71), 4.217 (1.59), 4.232 (3.33), 4.247 (1.52), 4.319 (0.62), 4.329 (0.56), 4.337 (0.65), 4.347 (1.77), 4.354 (0.77), 4.364 (1.82), 4.372 (1.83), 4.382 (0.78), 4.390 (1.70), 4.399 (0.67), 4.408 (0.56), 4.417 (0.63), 4.434 (1.83), 4.467 (2.51), 4.579 (2.64), 4.613 (1.75), 4.846 (0.58), 4.872 (0.66), 4.884 (0.88), 4.911 (1.00), 5.030 (1.01), 5.069 (0.66), 5.236 (0.44), 5.243 (0.47), 5.263 (0.94), 5.270 (0.96), 5.290 (0.61), 5.297 (0.55), 5.392 (0.59), 5.404 (0.58), 6.781 (1.66), 6.798 (1.77), 6.882 (1.38), 6.904 (2.50), 6.926 (1.49), 7.348 (1.22), 7.369 (2.33), 7.388 (1.97), 7.431 (2.29), 7.451 (1.30), 7.483 (0.47), 7.495 (1.47), 7.501 (2.46), 7.511 (3.22), 7.520 (2.75), 7.525 (1.68), 7.537 (0.53), 7.641 (1.41), 7.654 (1.48), 7.663 (1.44), 7.676 (1.38), 7.816 (1.31), 7.819 (0.96), 7.826 (0.68), 7.831 (0.83), 7.834 (0.88), 7.839 (1.11), 8.341 (1.14), 8.348 (0.88), 8.354 (0.52), 8.355 (0.52), 8.365 (1.08).

Intermediate 16

(rac)-ethyl 4-fluoro-2,3-dimethyl-7-[3-(naphthalen-1-yloxy)propyl]-2,10,11,12,13,15-hexahydro-pyrazolo[4',3':9,10][1,6]oxazacycloundecino[8,7,6-hi]indole-8-carboxylate

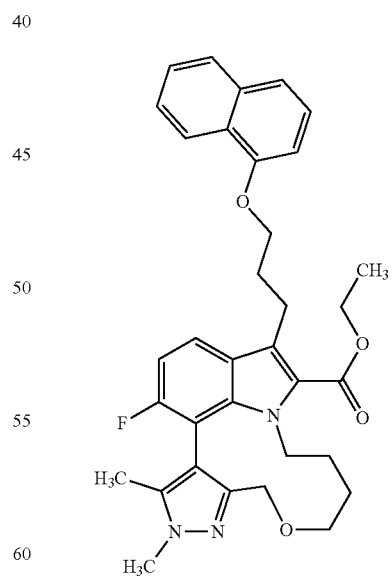

A stirred suspension of (rac)-ethyl (11Z)-4-fluoro-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 15, 164 mg, 289 µmol, 1.00 eq.) and Wilkinson's catalyst (536 mg, 578 µmol, 2.00 eq.) in ethanol (7.22 mL, 0.01 M) was placed under a hydrogen atmosphere and stirred for 6 h. The mixture was diluted with ethanol, filtered through a celite plug (washing with ethanol) and concentrated under reduced pressure. The residue was purified by reverse phase column chromatography (65-100% acetonitrile/water with 0.1% formic acid gradient) to give the title compound as a tan solid (130 mg).

LC-MS (Method 1): $R_t$=1.69 min; MS (ESIpos): m/z=570 [M+H]$^+$ $^1$H-NMR (400 MHz, CHLOROFORM-d) δ [ppm]: 1.201 (1.04), 1.225 (0.80), 1.366 (4.33), 1.384 (9.44), 1.402 (4.80), 1.421 (0.64), 1.437 (0.52), 1.446 (0.56), 1.461 (0.56), 1.582 (0.83), 1.925 (16.00), 2.299 (0.63), 2.306 (0.71), 2.316 (0.96), 2.323 (0.95), 2.335 (0.73), 2.342 (0.72), 3.245 (0.62), 3.255 (0.72), 3.275 (0.59), 3.281 (0.44), 3.292 (0.49), 3.309 (0.66), 3.325 (0.86), 3.345 (0.51), 3.373 (0.54), 3.392 (0.98), 3.410 (0.61), 3.426 (0.54), 3.443 (0.86), 3.452 (0.65), 3.463 (0.48), 3.468 (0.52), 3.478 (0.46), 3.886 (15.66), 4.001 (0.62), 4.011 (0.41), 4.024 (0.50), 4.188 (1.45), 4.203 (3.09), 4.218 (1.42), 4.294 (0.71), 4.303 (0.52), 4.312 (0.75), 4.321 (1.83), 4.329 (0.46), 4.338 (2.13), 4.343 (1.06), 4.357 (1.07), 4.361 (1.91), 4.371 (0.78), 4.379 (3.83), 4.388 (0.98), 4.397 (0.65), 4.406 (0.96), 4.411 (2.60), 4.656 (2.27), 4.687 (1.83), 6.768 (1.59), 6.786 (1.67), 6.869 (1.39), 6.892 (2.25), 6.914 (1.44), 7.345 (1.18), 7.365 (2.22), 7.384 (1.87), 7.426 (2.20), 7.447 (1.22), 7.489 (0.40), 7.501 (2.33), 7.506 (1.46), 7.511 (1.69), 7.514 (1.72), 7.519 (1.58), 7.525 (2.50), 7.536 (0.45), 7.611 (1.35), 7.625 (1.44), 7.633 (1.44), 7.647 (1.30), 7.813 (1.22), 7.818 (0.79), 7.825 (1.01), 7.829 (0.79), 7.837 (1.03), 8.364 (1.05), 8.373 (0.81), 8.376 (0.91), 8.384 (0.60), 8.388 (1.02).

Intermediate 17

(rac)-ethyl 7-[5-ethyl-3-(hydroxymethyl)-1-methyl-1H-pyrazol-4-yl]-6-fluoro-3-[3-(naphthalen-1-yloxy)propyl]-1H-indole-2-carboxylate

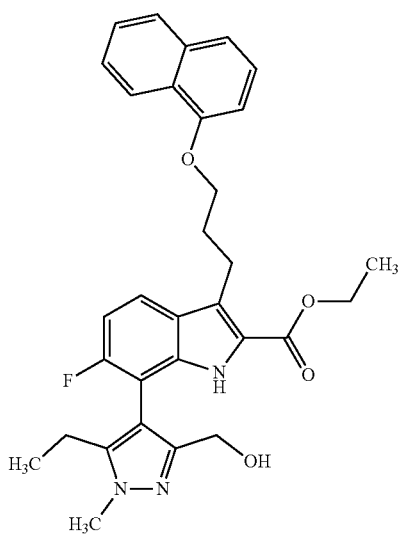 [SMILES: CCOC(=O)c1[nH]c2c(-c3c(CO)nn(C)c3CC)c(F)ccc2c1CCCOc1cccc2ccccc12]

A mixture of ethyl 6-fluoro-3-[3-(naphthalen-1-yloxy)propyl]-7-(4,4,5,5-tetramethyl-1,3,2-dioxaborolan-2-yl)-1H-indole-2-carboxylate (see Intermediate 13, 2.33 g, 4.50 mmol, 1.00 eq.), (4-bromo-5-ethyl-1-methyl-1H-pyrazol-3-yl)methanol (see Intermediate 11, 986 mg, 4.50 mmol, 1.00 eq.), XPhos Pd G3 (381 mg, 0.45 mmol, 10.0 mol %) and tripotassium phosphate (1.91 g, 9.00 mmol, 2.00 eq.) where placed under an argon atmosphere. To this mixture was then added argon degassed 1,4-dioxane (10.0 mL) and water (5.00 mL) to give a 0.30 M solution. The light brown suspension was heated at 40° C. for 3 h, cooled to room temperature and concentrated under reduced pressure. The dark residue was suspended in water (50 mL) and extracted with dichloromethane (3×50 mL). The combined organic extracts were washed with 1.0 M aqueous hydrochloric acid (50 mL), dried (sodium sulfate), filtered over a Celite plug and concentrated under reduced pressure. The residue was purified by flash column chromatography (0-20% ethanol/dichloromethne gradient) followed by reverse phase column (65-100% Acetonitrile/water with 0.1% formic acid gradient) to give the title compound as an off white solid (537 mg).

LC-MS (Method 1): $R_t$=1.57 min; MS (ESIpos): m/z=530 [M+H]$^+$ $^1$H-NMR (400 MHz, CHLOROFORM-d) δ [ppm]: 1.074 (2.88), 1.093 (6.58), 1.112 (3.04), 1.342 (4.78), 1.359 (10.58), 1.377 (5.04), 2.013 (0.62), 2.347 (1.04), 2.363 (1.44), 2.366 (1.45), 2.382 (1.12), 2.510 (0.42), 2.529 (0.75), 2.548 (1.16), 2.567 (1.03), 2.591 (1.02), 2.610 (1.12), 2.622 (2.87), 2.629 (0.77), 2.648 (0.40), 3.182 (0.43), 3.403 (1.62), 3.422 (2.91), 3.440 (1.47), 3.933 (16.00), 4.209 (1.75), 4.225 (3.73), 4.240 (1.67), 4.328 (0.80), 4.332 (0.99), 4.336 (0.78), 4.346 (2.60), 4.350 (2.82), 4.364 (2.70), 4.367 (2.96), 4.377 (0.64), 4.381 (1.16), 4.386 (1.27), 4.648 (0.88), 4.675 (0.72), 6.774 (1.73), 6.791 (1.82), 6.900 (1.45), 6.922 (1.74), 6.925 (1.69), 6.947 (1.55), 7.343 (1.27), 7.363 (2.45), 7.382 (2.07), 7.423 (2.39), 7.443 (1.32), 7.487 (0.45), 7.499 (2.23), 7.504 (1.60), 7.510 (1.87), 7.512 (1.99), 7.518 (1.68), 7.523 (2.42), 7.535 (0.48), 7.615 (1.14), 7.628 (1.19), 7.637 (1.18), 7.650 (1.11), 7.812 (1.34), 7.816 (0.87), 7.825 (1.23), 7.829 (0.84), 7.835 (1.13), 8.366 (1.17), 8.378 (0.98), 8.385 (0.60), 8.387 (0.67), 8.390 (1.10), 9.789 (1.22).

Intermediate 18

(rac)-ethyl(11Z)-3-ethyl-4-fluoro-2-methyl-7-[3-(naphthalen-1-yloxy)propyl]-2,10,13,15-tetrahydro-pyrazolo[4',3':9,10][1,6]oxazacycloundecino[8,7,6-hi]indole-8-carboxylate

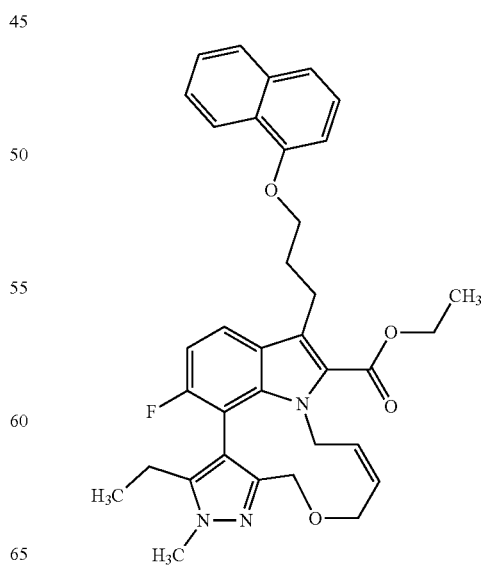

To a room temperature stirred suspension of (rac)-ethyl 7-[5-ethyl-3-(hydroxymethyl)-1-methyl-1H-pyrazol-4-yl]-6-fluoro-3-[3-(naphthalen-1-yloxy)propyl]-1H-indole-2-carboxylate (see Intermediate 17, 530 mg, 1.00 mmol, 1.00 eq.) in acetonitrile (10.0 mL, 0.10 M) was added cesium carbonate (1.63 g, 5.00 mmol, 5.00 eq.). After stirring for 10 minutes, cis-1,4-dichloro-2-butene (138 mg, 1.10 mmol, 1.10 eq.) and sodium iodide (300 mg, 2.00 mmol, 2.00 eq.) were sequentially added and the resulting mixture was then stirred at 40° C. for 18 h and cooled to room temperature. The mixture was diluted with dichloromethane (50 mL), filtered through a Celite plug (washing with dichloromethane) and concentrated under reduced pressure. The residue was purified by flash column chromatography (0-40% acetone/dichloromethane gradient) to give the title compound as an off white solid (345 mg).

LC-MS (Method 1): $R_t$=1.69 min; MS (ESIpos): m/z=583 [M+H]$^+$ $^1$H-NMR (400 MHz, CHLOROFORM-d) δ [ppm]: 0.938 (3.05), 0.957 (7.38), 0.976 (3.15), 1.373 (4.56), 1.390 (9.75), 1.408 (4.49), 1.594 (2.12), 2.297 (0.93), 2.316 (2.81), 2.335 (3.09), 2.343 (1.18), 2.354 (1.63), 2.363 (0.82), 2.368 (0.71), 3.342 (0.70), 3.360 (0.99), 3.380 (1.05), 3.398 (1.02), 3.416 (0.62), 3.776 (0.58), 3.789 (0.68), 3.806 (0.88), 3.819 (0.83), 3.927 (0.93), 3.955 (1.47), 3.967 (16.00), 3.984 (0.73), 4.219 (1.58), 4.235 (3.23), 4.250 (1.48), 4.317 (0.62), 4.326 (0.57), 4.335 (0.66), 4.344 (1.71), 4.352 (0.76), 4.362 (1.74), 4.369 (1.82), 4.380 (0.72), 4.387 (1.68), 4.397 (0.67), 4.406 (0.52), 4.414 (0.63), 4.431 (1.79), 4.464 (2.43), 4.580 (2.60), 4.613 (1.77), 4.838 (0.54), 4.865 (0.62), 4.877 (0.84), 4.904 (0.96), 5.017 (0.97), 5.055 (0.63), 5.224 (0.42), 5.231 (0.45), 5.250 (0.90), 5.257 (0.92), 5.278 (0.56), 5.284 (0.50), 5.394 (0.58), 5.407 (0.56), 6.781 (1.65), 6.798 (1.71), 6.879 (1.43), 6.901 (2.48), 6.923 (1.44), 7.348 (1.22), 7.368 (2.26), 7.387 (1.88), 7.431 (2.25), 7.452 (1.28), 7.484 (0.45), 7.496 (1.49), 7.501 (2.59), 7.511 (3.14), 7.520 (2.80), 7.525 (1.68), 7.537 (0.51), 7.641 (1.32), 7.654 (1.38), 7.663 (1.46), 7.676 (1.39), 7.816 (1.28), 7.820 (0.95), 7.827 (0.67), 7.831 (0.80), 7.834 (0.86), 7.839 (1.08), 8.345 (1.08), 8.352 (0.86), 8.357 (0.54), 8.360 (0.54), 8.369 (1.09).

Intermediate 19

(rac)-ethyl 3-ethyl-4-fluoro-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

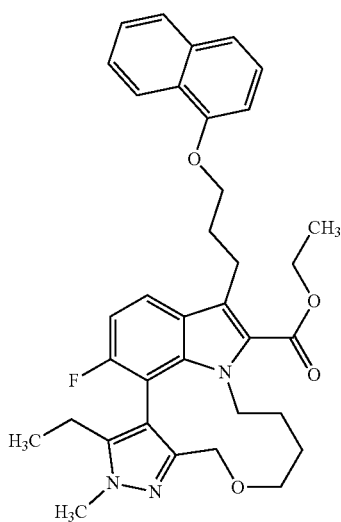 [SMILES: CCOC(=O)c1c(CCCOc2cccc3ccccc23)c2ccc(F)c3c2n1CCCCOCc1nn(C)c(CC)c1-3]

A stirred suspension of (rac)-ethyl (11Z)-3-ethyl-4-fluoro-2-methyl-7-[3-(naphthalen-1-yloxy) propyl]-2,10,13,15-tetrahydropyrazolo[4',3':9,10][1,6]oxazacycloundecino[8,7,6-hi]indole-8-carboxylate (see Intermediate 18, 282 mg, 485 μmol, 1.00 eq.) and Wilkinson's catalyst (900 mg, 970 μmol, 2.00 eq.) in ethanol (12.1 mL, 0.04 M) was placed under a hydrogen atmosphere and stirred for 3 d. The mixture was filtered through a silica plug (washing with ethanol) and concentrated under reduced pressure. The residue was purified by reverse phase column chromatography (65-100% acetonitrile/water with 0.1% ammonia gradient) to give the title compound as an off white solid (90.7 mg).

LC-MS (Method 1): $R_t$=1.71 min; MS (ESIpos): m/z=584 [M+H]$^+$ $^1$H-NMR (400 MHz, CHLOROFORM-d) δ [ppm]: 0.927 (2.83), 0.946 (6.78), 0.965 (2.91), 1.207 (0.82), 1.217 (0.72), 1.239 (0.58), 1.262 (1.11), 1.364 (4.09), 1.381 (9.14), 1.399 (4.50), 1.421 (0.46), 1.436 (0.57), 1.452 (0.44), 1.461 (0.54), 1.475 (0.49), 1.556 (6.13), 2.264 (0.61), 2.271 (0.51), 2.282 (1.50), 2.290 (1.45), 2.301 (1.79), 2.309 (1.64), 2.319 (1.32), 2.329 (1.07), 2.334 (1.02), 2.350 (0.66), 3.261 (0.58), 3.271 (0.66), 3.288 (0.44), 3.297 (0.69), 3.314 (0.65), 3.330 (0.82), 3.351 (0.59), 3.358 (0.56), 3.378 (0.88), 3.396 (0.56), 3.447 (0.55), 3.456 (0.55), 3.473 (0.46), 3.481 (0.43), 3.911 (16.00), 4.027 (0.64), 4.038 (0.40), 4.051 (0.45), 4.189 (1.20), 4.205 (2.50), 4.220 (1.18), 4.292 (0.93), 4.301 (0.64), 4.309 (1.26), 4.319 (1.64), 4.328 (0.68), 4.336 (1.76), 4.340 (0.86), 4.354 (0.73), 4.358 (1.72), 4.367 (0.58), 4.374 (2.37), 4.376 (2.15), 4.385 (0.75), 4.393 (0.50), 4.405 (2.59), 4.648 (2.14), 4.679 (1.77), 6.768 (1.46), 6.785 (1.55), 6.864 (1.30), 6.885 (2.13), 6.908 (1.35), 7.006 (0.42), 7.344 (1.11), 7.365 (2.09), 7.384 (1.72), 7.426 (2.04), 7.447 (1.15), 7.501 (2.25), 7.506 (1.44), 7.511 (1.58), 7.514 (1.64), 7.519 (1.48), 7.525 (2.43), 7.536 (0.43), 7.610 (1.30), 7.623 (1.33), 7.632 (1.34), 7.646 (1.31), 7.813 (1.15), 7.818 (0.73), 7.825 (0.89), 7.830 (0.79), 7.837 (0.98), 8.368 (1.01), 8.377 (0.77), 8.380 (0.82), 8.388 (0.55), 8.393 (0.95).

Intermediate 20

(rac)-ethyl 6-fluoro-7-(5-(hydroxymethyl)-1,3-dimethyl-1H-pyrazol-4-yl)-3-(3-(naphthalen-1-yloxy)propyl)-1H-indole-2-carboxylate

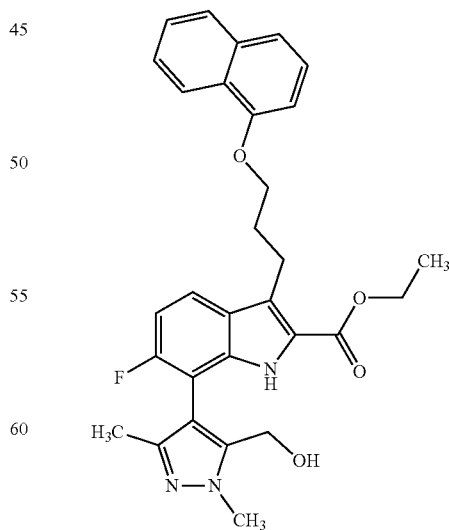

A flask was charged with ethyl 6-fluoro-3-(3-(naphthalen-1-yloxy)propyl)-7-(4,4,5,5-tetramethyl-1,3,2-dioxaborolan- 2-yl)-1H-indole-2-carboxylate (see Intermediate 13, 2.67 g, 5.16 mmol, 1.00 eq.), (4-bromo-1,3-dimethyl-1H-pyrazol-5-yl)methanol (see Intermediate 6, 1.26 g, 6.19 mmol, 1.20 eq.), XPhos Pd G3 (305 mg, 361 µmol, 7.00 mol %), tripotassium phosphate (2.18 mg, 10.3 mmol, 2.00 eq.) and then placed under an argon atmosphere. To this mixture was added argon sparged 1,4-dioxane (10.3 mL) and water (5.16 mL) to give a 0.33 M solution. The yellow suspension was heated at 40° C. for 20 hours and cooled to room temperature and then concentrated under reduced pressure. The residue was purified by flash column chromatography (0-100% ethyl acetate/hexanes gradient) to give the title compound as a white solid (233 mg).

LC-MS (Method 3): $R_t$=1.77 min; MS (ESIpos): m/z=516 [M+H]$^+$.

$^1$H-NMR (300 MHz, CHLOROFORM-d) δ [ppm]: 9.21 (0.74), 8.33 (1.10), 7.81 (1.29), 7.62 (1.01), 7.49 (2.17), 7.37 (2.27), 6.93 (0.99), 6.76 (1.00), 4.62 (2.08), 4.33 (2.850, 4.20 (2.43), 3.97 (2.62), 3.40 (2.10), 2.34 (3.42), 2.05 (1.10), 1.35 (2.26), 1.26 (2.24).

Intermediate 21

(rac)-ethyl (Z)-13-fluoro-10,12-dimethyl-1-(3-(naphthalen-1-yloxy)propyl)-4,7,9,10-tetrahydropyrazolo[4',3':9,10][1]oxa[6]azacycloundecino[8,7,6-hi]indole-2-carboxylate

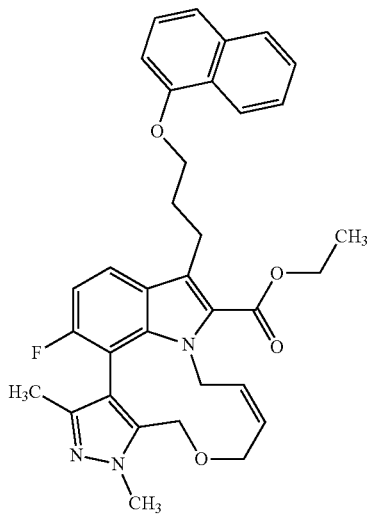 [SMILES: CCOC(=O)c1c(CCCOc2cccc3ccccc23)c2ccc(F)c3c2n1C/C=C\COCc1c-3c(C)nn1C]

To a room temperature stirred suspension of (rac)-ethyl 6-fluoro-7-(5-(hydroxymethyl)-1,3-dimethyl-1H-pyrazol-4-yl)-3-(3-(naphthalen-1-yloxy)propyl)-1H-indole-2-carboxylate (see Intermediate 20, 278 mg, 358 µmol, 1.00 eq.) in acetonitrile (3.57 mL, 0.10 M) was added cesium carbonate (579 mg, 1.78 mmol, 5.00 eq.). After stirring for 10 minutes, cis-1,4-dichloro-2-butene (41.3 µL, 393 µmol, 1.10 eq.) and sodium iodide (107 mg, 716 µmol, 2.00 eq.) were sequentially added and the resulting mixture was then stirred at 40° C. for 4 days and cooled to room temperature. The mixture was diluted with dichloromathane, filtered through a Celite plug (washing with dichloromethane) and concentrated under reduced pressure. The residue was purified by reverse phase flash column chromatography (50-100% acetonitrile/water with 0.1% formic acid gradient) to give the title compound as a colorless oil (140 mg).

LC-MS (Method 3): $R_t$=2.00 min; MS (ESIpos): m/z=568 [M+H]$^+$.

$^1$H-NMR (300 MHz, CHLOROFORM-d) δ [ppm]: 8.32 (0.96), 7.81 (1.09), 7.66 (1.00), 7.49 (2.16), 7.42 (1.02), 7.35 (1.01), 6.90 (1.03), 6.77 (0.91), 5.24 (0.72), 5.09 (1.85), 4.72 (2.09), 4.37 (2.91), 4.22 (2.10), 3.98 (2.67), 3.86 (1.37), 3.63 (0.92), 3.39 (2.06), 2.34 (2.20), 1.90 (2.68), 1.38 (3.03), 1.24 (2.04).

Intermediate 22

(rac)-ethyl 13-fluoro-10,12-dimethyl-1-(3-(naphthalen-1-yloxy)propyl)-4,5,6,7,9,10-hexahydro-pyrazolo[4',3':9,10][1]oxa[6]azacycloundecino[8,7,6-hi]indole-2-carboxylate A stirred suspension of (rac)-ethyl (Z)-13-fluoro-10,12-dimethyl-1-(3-(naphthalen-1-yloxy)-propyl)-4,7,9,10-tetrahydropyrazolo[4',3':9,10][1]oxa[6]azacycloundecino[8,7,6-hi]indole-2-carboxylate (see Intermediate 21, 74.7 mg, 131 µmol, 1.00 eq.) and Wilkinson's catalyst (242 mg, 262 µmol, 2.00 eq.) in ethanol (6.54 mL, 0.10 M) was placed under a hydrogen atmosphere and stirred for 7 hours. The mixture was diluted with ethanol, filtered through a celite plug (washing with ethanol) and concentrated under reduced pressure. The residue was purified by flash column chromatography (0-5% acetone/dichloromethane gradient) to give the title compound as a light brown solid (61.9 mg).

LC-MS (Method 3): $R_t$=1.98 min; MS (ESIpos): m/z=570 [M+H]$^+$.

$^1$H-NMR (300 MHz, CHLOROFORM-d) δ [ppm]: 8.35 (1.00), 7.81 (1.08), 7.67 (1.16), 7.50 (2.13), 7.43 (1.22), 7.35 (1.14), 6.88 (1.04), 6.77 (1.02), 4.60 (1.98), 4.30 (6.24), 3.95 (2.96), 3.40 (3.07), 2.91 (0.93), 2.32 (2.05), 1.98 (2.94), 1.37 (3.02), 1.23 (4.06).

139

Intermediate 23

(rac)-ethyl 7-(3-ethyl-5-(hydroxymethyl)-1-methyl-1H-pyrazol-4-yl)-6-fluoro-3-(3-(naphthalen-1-yloxy)propyl)-1H-indole-2-carboxylate

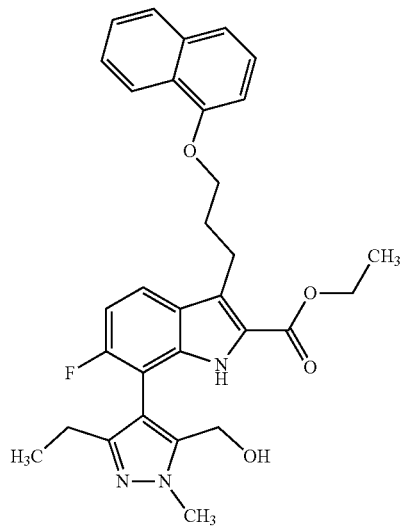 [SMILES: CCOC(=O)c1[nH]c2c(-c3c(CC)nn(C)c3CO)c(F)ccc2c1CCCOc1cccc2ccccc12]

A flask was charged with ethyl 6-fluoro-3-(3-(naphthalen-1-yloxy)propyl)-7-(4,4,5,5-tetramethyl-1,3,2-dioxaborolan-2-yl)-1H-indole-2-carboxylate (see Intermediate 13, 2.14 g, 744 µmol, 1.00 eq), (4-bromo-3-ethyl-1-methyl-1H-pyrazol-5-yl)methanol (see Intermediate 12, 195 mg, 892 µmol, 1.20 eq.), XPhos Pd G2 (58.5 mg, 74.4 µmol, 10.00 mol %), tripotassium phosphate (340 mg, 1.48 mmol, 2.00 eq.) and then placed under an argon atmosphere. To this mixture was added argon sparged 1,4-dioxane (5.00 mL) and water (2.50 mL) to give a 0.30 M solution. The yellow suspension was heated at 40° C. for 17 hours and cooled to room temperature and then concentrated under reduced pressure. The residue was purified by flash column chromatography (0-100% Ethyl acetate/hexanes gradient) to give the title compound as an off white solid (372 mg)

LC-MS (Method 3): $R_t$=1.83 min; MS (ESIpos): m/z=530 [M+H]$^+$.

$^1$H-NMR (300 MHz, CHLOROFORM-d) δ [ppm]: 8.94 (0.83), 8.33 (0.97), 7.81 (1.01), 7.62 (0.90), 7.50 (2.05), 7.42 (0.98), 7.35 (0.99), 6.93 (0.99), 6.76 (1.00), 4.47 (1.80), 4.35 (2.01), 4.21 (2.04), 4.01 (2.74), 3.41 (2.03), 2.51 (1.79), 2.35 (2.00), 1.83 (0.87), 1.35 (2.90), 1.12 (2.70).

140

Intermediate 24

(rac)-ethyl (Z)-12-ethyl-13-fluoro-10-methyl-1-(3-(naphthalen-1-yloxy)propyl)-4,7,9,10-tetrahydropyrazolo[4',3':9,10][1]oxa[6]azacycloundecino[8,7,6-hi]indole-2-carboxylate

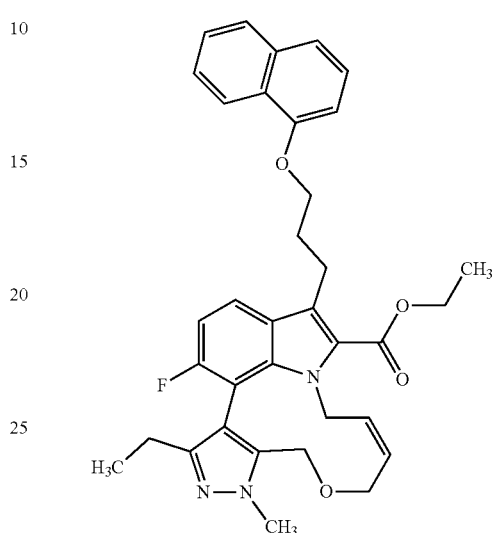

To a room temperature stirred suspension of (rac)-ethyl 7-(3-ethyl-5-(hydroxymethyl)-1-methyl-1H-pyrazol-4-yl)-6-fluoro-3-(3-(naphthalen-1-yloxy)propyl)-1H-indole-2-carboxylate (see Intermediate 23, 581 mg, 1.11 mmol, 1.00 eq.) in acetonitrile (11.0 mL, 0.10 M) was added cesium carbonate (1.77 g, 5.45 mmol, 5.00 eq.). After stirring for 10 minutes, cis-1,4-dichloro-2-butene (148 mg, 1.19 mmol, 1.10 eq.) and sodium iodide (326 mg, 2.18 mmol, 2.00 eq.) were sequentially added and the resulting mixture was then stirred at 40° C. for 21 hours and cooled to room temperature. The mixture was diluted with dichloromethane (50 mL), filtered through a Celite plug (washing with dichloromethane) and concentrated under reduced pressure. The residue was purified by flash column chromatography (0-40% acetone/dichloromethane gradient) to give the title compound as a colorless oil (298 mg).

LC-MS (Method 3): $R_t$=2.03 min; MS (ESIpos): m/z=582 [M+H]$^+$.

$^1$H-NMR (300 MHz, CHLOROFORM-d) δ [ppm]: 8.35 (1.01), 7.82 (1.05), 7.67 (0.99), 7.50 (2.12), 7.43 (1.03), 7.34 (1.05), 6.90 (1.00), 6.78 (0.97), 5.16 (3.02), 4.81 (0.96), 4.64 (0.93), 4.37 (3.00), 4.23 (2.02), 4.00 (2.95), 3.84 (0.94), 3.66 (0.91), 3.42 (2.09), 2.30 (3.99), 1.39 (3.00), 0.98 (2.92).

Intermediate 25

(rac)-ethyl 12-ethyl-13-fluoro-10-methyl-1-(3-(naphthalen-1-yloxy)propyl)-4,5,6,7,9,10-hexahydropyrazolo[4',3':9,10][1]oxa[6]azacycloundecino[8,7,6-hi]indole-2-carboxylate

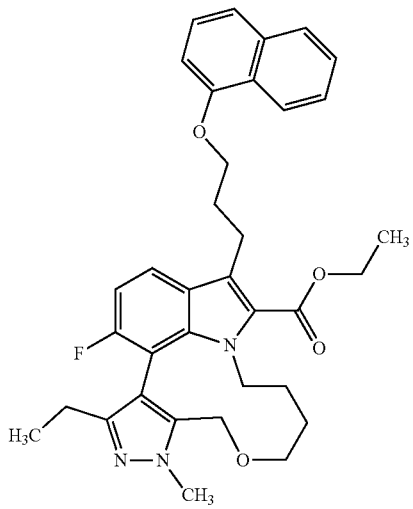 [SMILES: CCOC(=O)c1c(CCCOc2cccc3ccccc23)c2ccc(F)c3c2n1CCCCOCc1c-3c(CC)nn1C]

A stirred suspension of (rac)-ethyl (Z)-12-ethyl-13-fluoro-10-methyl-1-(3-(naphthalen-1-yloxy)propyl)-4,7,9,10-tetrahydropyrazolo[4',3':9,10][1]oxa[6]azacycloundecino[8,7,6-hi]indole-2-carboxylate (see Intermediate 24, 192 mg, 330 μmol, 1.00 eq.) and Wilkinson's catalyst (610 mg, 660 μmol, 2.00 eq.) in ethanol (3.30 mL, 0.1 M) was placed under a hydrogen atmosphere and stirred for 1 day. The mixture was diluted with ethanol, filtered through a celite plug (washing with ethanol) and concentrated under reduced pressure. The residue was purified by reverse phase column chromatography (65-100% acetonitrile/water with 0.1% formic acid gradient) to give the title compound as a brown solid (100.9 mg)

LC-MS (Method 3): $R_t$=2.03 min; MS (ESIpos): m/z=584 [M+H]$^+$.

$^1$H-NMR (300 MHz, CHLOROFORM-d) δ [ppm]: 8.37 (1.06), 7.82 (1.04), 7.68 (1.21), 7.52 (1.28), 7.43 (1.00), 7.35 (1.05), 6.89 (1.06), 6.77 (1.00), 4.61 (1.92), 4.36 (2.87), 4.20 (3.09), 3.97 (2.81), 3.42 (3.03), 2.94 (0.89), 2.34 (4.21), 1.38 (2.82), 1.24 (2.98), 1.02 (2.95).

Intermediate 26 ethyl 7-bromo-3-(3-((tert-butyldimethylsilyhoxy)propyl)-6-fluoro-1H-indole-2-carboxylate

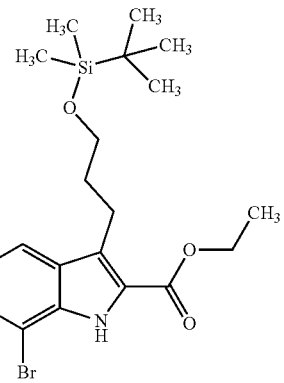

To a stirred solution of ethyl 7-bromo-6-fluoro-3-(3-hydroxypropyl)-1H-indole-2-carboxylate (see Intermediate 3, 18.4 g, 53.1 mmol, 1.00 eq.) in anhydrous dichloromethane (265 mL, 0.20 M) was added imidazole (5.41 g, 79.6 mmol, 1.50 eq.) and text-butylchlorodimethylsilane (CAS 18162-48-6, 9.60 g, 63.7 mmol, 1.20 eq.) at a temperature of 0° C. The resulting mixture was warmed to room temperature and stirred for 30 minutes. The mixture was diluted with water (200 mL) and extracted with dichloromethane thrice (100 mL each). The combined organic extracts were dried (magnesium sulfate), filtered and concentrated under reduced pressure. The residue was purified by flash column chromatography (0-20% ethyl acetate/hexanes gradient) to give the title compound as a white solid (23.2 g).

LC-MS (Method 3): $R_t$=2.21 min; MS (ESIpos): m/z=458 [M+H]$^+$.

$^1$H-NMR (300 MHz, CHLOROFORM-d) δ [ppm]: 8.77 (s, 1H), 7.61 (dd, 1H), 6.96 (t, 1H), 4.43 (q, 2H), 3.65 (t, 2H), 3.12 (m, 2H), 1.86 (m, 2H), 1.43 (t, 3H), 0.92 (s, 9H), 0.05 (s, 6H)

Intermediate 27 ethyl 3-(3-((tert-butyldimethylsilyl)oxy)propyl)-6-fluoro-7-(4,4,5,5-tetramethyl-1,3,2-dioxa-borolan-2-yl)-1H-indole-2-carboxylate

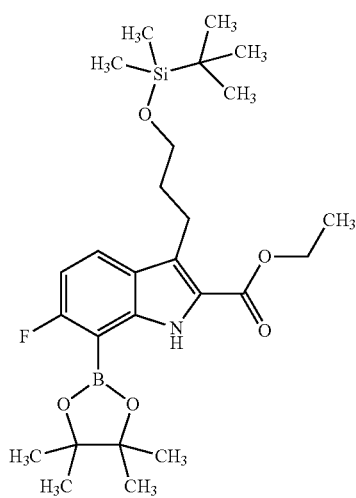 [SMILES: CCOC(=O)c1[nH]c2c(B3OC(C)(C)C(C)(C)O3)c(F)ccc2c1CCCO[Si](C)(C)C(C)(C)C]

To a mixture of ethyl 7-bromo-3-(3-((tert-butyldimethyl-silyhoxy)propyl)-6-fluoro-1H-indole-2-carboxylate (see Intermediate 26, 11.0 g, 24.0 mmol, 1.00 eq.), bis(pinacolato)diboron (7.28 g, 28.7 mmol, 1.20 eq.), potassium acetate (4.71 g, 48.0 mmol, 2.00 eq.) and [1,1'-bis-(diphenylphosphino)ferrocene]dichloropalladium(II), complex with dichloromethane (979 mg, 1.20 mmol, 5.00 mol %) under a nitrogen atmosphere was added nitrogen sparged 1,4-dioxane (48.0 mL, 0.50 M). The resulting red suspension was heated at 90° C. for 2 days and cooled to room temperature. Celite was added to the resulting suspension, volatiles were removed under reduced pressure, and the residue was loaded onto a silica gel cartridge which was subjected to flash column chromatography (5-20% ethyl acetate/hexanes gradient) to give the title compound as yellow solid. (12.1 g, >90% pure). The mixture was used directly in the next step.

LC-MS (Method 3): R$_t$=2.35 min; MS (ESIpos): m/z=506 [M+H]$^+$.

$^1$H-NMR (300 MHz, CHLOROFORM-d) δ [ppm]: 9.67 (s, 1H), 7.76 (m, 1H), 6.86 (dd, 1H), 4.41 (q, 2H), 3.65 (t, 2H), 3.12 (m, 2H), 1.86 (m, 2H), 1.42 (d, 14H), 1.26 (s, 3H), 0.92 (s, 9H), 0.05 (s, 6H).

Intermediate 28

(rac)-ethyl 3-(3-((tert-butyldimethylsilyhoxy)propyl)-6-fluoro-7-(3-(hydroxymethyl)-1,5-dimethyl-1H-pyrazol-4-yl)-1H-indole-2-carboxylate

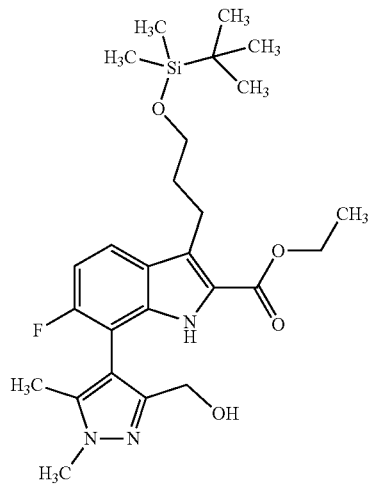 [SMILES: CCOC(=O)c1[nH]c2c(-c3c(CO)nn(C)c3C)c(F)ccc2c1CCCO[Si](C)(C)C(C)(C)C]

To a 50° C. stirred suspension of (4-bromo-1,5-dimethyl-1H-pyrazol-3-yl)methanol (see intermediate 8, 3.85 g, 18.8 mmol, 1.20 eq.), XPhos Pd G3 (922 mg, 1.09 mmol, 7.00 mol %) and potassium phosphate tribasic (6.64 g, 31.3 mmol, 2.00 eq.) in a 2:1 mixture of argon degassed 1,4-dioxane/water (45 mL, 0.33 M) was slowly added dropwise (~1 h), a solution of ethyl 3-(3-((tert-butyldimethylsilyhoxy)propyl)-6-fluoro-7-(4,4,5,5-tetramethyl-1,3,2-dioxaborolan-2-yl)-1H-indole-2-carboxylate (see Intermediate 27, 7.96 g, 15.7 mmol, 1.00 eq.) in argon degassed 1,4-dioxane (16 mL, 1.00 M). The resulting dark mixture was heated at 50° C. for a further 30 min, cooled to room temperature and concentrated under reduced pressure. The residue was dissolved in water (50 mL) and extracted with ethyl acetate (3×50 mL). The combined organic extracts were washed with brine (50 mL), dried (magnesium sulfate), filtered and concentrated under reduced pressure. The residue was purified by flash column chromatography (0-100% acetone/dichloromethane gradient) and then reverse phase column chromatography (10-100% acetonitrile/water gradient) to give the title compound as an off white solid (5.67 g).

LC-MS (Method 3): R$_t$=1.94 min; MS (ESIpos): m/z=502 [MH]$^-$ $^1$H-NMR (300 MHz, CHLOROFORM-d) δ [ppm]: 10.12 (s, 1H), 7.65 (dd, 2H), 6.99 (m, 2H), 4.70 (dt, 2H), 4.36 (m, 6H), 3.89 (s, 6H), 3.70 (m, 4H), 3.58 (m, 1H), 3.15 (dd, 4H), 2.17 (d, 6H), 1.92 (m, 4H), 1.37 (m, 6H), 0.93 (d, 19H), 0.07 (d, 12H).

Intermediate 29

(rac)-ethyl (Z)-1-(3-((tert-butyldimethylsilyl)oxy)propyl)-13-fluoro-11,12-dimethyl-4,7,9,11-tetrahydropyrazolo[4',3':9,10][1]oxa[6]azacycloundecino[8,7,6-hi]indole-2-carboxylate

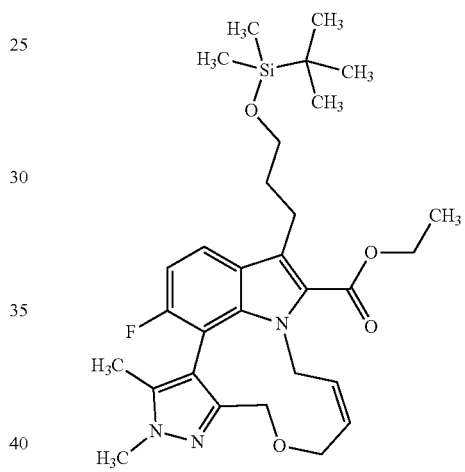

To a room temperature stirred solution of (rac)-ethyl 3-(3-((tert-butyldimethylsilyhoxy)propyl)-6-fluoro-7-(3-(hydroxymethyl)-1,5-dimethyl-1H-pyrazol-4-yl)-1H-indole-2-carboxylate (see Intermediate 28, 2.36 g, 4.68 mmol, 1.00 eq.) in anhydrous acetonitrile (46.8 mL, 0.10 M) was added cesium carbonate (7.62 g, 23.4 mmol, 5.00 eq.). After stirring for 10 minutes, 1,4-dichlorobutene (540 μL, 5.14 mmol, 1.10 eq.) and sodium iodide (1.40 g, 9.36 mmol, 2.00 eq.) was added to the mixture and the resulting yellow suspension was heated at 40° C. for 2 days. The mixture was cooled to room temperature and filtered through a Celite plug. Celite was added to the resulting suspension, volatiles were removed under reduced pressure, and the residue was loaded onto a silica gel cartridge which was subjected to flash column chromatography (20-100% ethyl acetate/hexanes gradient) to give the title compound as a light yellow solid (1.29 g).

LC-MS (Method 3): R$_t$=2.10 min; MS (ESIpos): m/z=556 [M+H]$^+$.

$^1$H-NMR (300 MHz, CHLOROFORM-d) δ [ppm]: 7.66 (dd, 1H), 6.95 (t, 1H), 5.38 (m, 1H), 5.24 (td, 1H), 5.03 (m, 1H), 4.83 (m, 1H), 4.59 (d, 1H), 4.39 (m, 3H), 3.93 (s, 4H), 3.79 (dd, 1H), 3.70 (t, 2H), 3.10 (m, 2H), 1.91 (m, 5H), 1.41 (t, 3H), 0.93 (s, 9H), 0.07 (d, 6H).

Intermediate 30

(rac)-ethyl 13-fluoro-1-(3-hydroxypropyl)-11,12-dimethyl-4,5,6,7,9,11-hexahydropyrazolo-[4',3':9,10][1]oxa[6]azacycloundecino[8,7,6-hi]indole-2-carboxylate

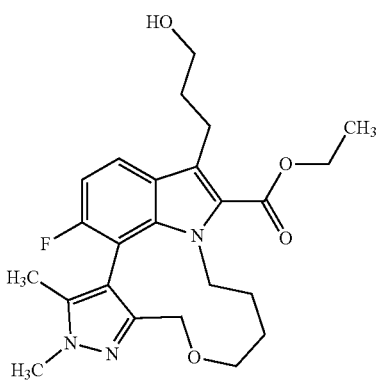 [SMILES: CCOC(=O)c1c(CCCO)c2ccc(F)c3c2n1CCCCOCc1nn(C)c(C)c1-3]

To a stirred solution of (rac)-ethyl (Z)-1-(3-((tert-butyldimethylsilyhoxy)propyl)-13-fluoro-11,12-dimethyl-4,7,9,11-tetrahydropyrazolo[4',3':9,10][1]oxa[6]azacycloundecino[8,7,6-hi]indole-2-carboxylate (see Intermediate 29, 1.28 g, 2.30 mmol, 1.00 eq.) in absolute ethanol (23.0 mL, 0.10 M) was added Wilkinson's catalyst (425 mg, 0.46 mmol, 0.20 eq.). The resulting dark suspension was evacuated and then placed under a hydrogen atmosphere and stirred for 10 hours at room temperature. Following complete reduction, the mixture was sparged with nitrogen to remove any residual hydrogen. Concentrated hydrochloric acid (188 µL, 2.30 mmol, 1.00 eq.) was added and the orange mixture was stirred for a further 15 minutes. Following complete deprotection the mixture was concentrated under reduced pressure to give a orange solid. The residue was purified by flash column chromatography (0-40% acetone/dichloromethane gradient) followed by reverse phase column chromatography (10-100% acetonitrile/water with 0.1% formic acid gradient) to give the title compound as a light yellow oil (718 mg, >90% purity). NMR and LCMS showed a small amount of triphenylphosphine oxide present. The mixture was used in the next step without further purification.

LC-MS (Method 3): $R_t$=2.92 min; MS (ESIpos): m/z=444 [M+H]$^+$.

$^1$H-NMR (300 MHz, CHLOROFORM-d) δ [ppm]: 7.61 (dd, 1H), 6.97 (t, 1H), 4.64 (d, 1H), 4.39 (m, 4H), 4.00 (ddd, 1H), 3.88 (s, 3H), 3.54 (m, 3H), 3.19 (m, 2H), 2.49 (s, 3H), 1.93 (m, 5H), 1.40 (t, 5H), 1.20 (m, 2H).

Intermediate 31

(rac)-ethyl 1-(3-bromopropyl)-13-fluoro-11,12-dimethyl-4,5,6,7,9,11-hexahydropyrazolo-[4',3':9,10][1]oxa[6]azacycloundecino[8,7,6-hi]indole-2-carboxylate

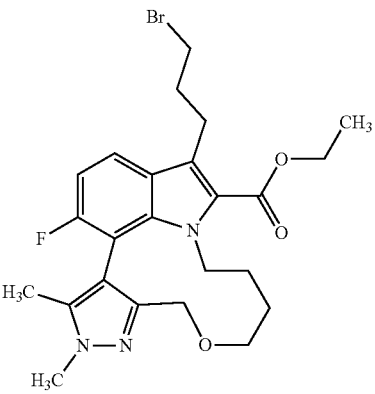 [SMILES: CCOC(=O)c1c(CCCBr)c2ccc(F)c3c2n1CCCCOCc1nn(C)c(C)c1-3]

To a 0° C. stirred solution of (rac)-ethyl 13-fluoro-1-(3-hydroxypropyl)-11,12-dimethyl-4,5,6,7,9,11-hexahydropyrazolo[4',3':9,10][1]oxa[6]azacycloundecino[8,7,6-hi]indole-2-carboxylate (see Intermediate 30, 718 mg, 1.61 mmol, 1.00 eq.) and triphenylphosphine (464 mg, 1.77 mmol, 1.10 eq.) in anhydrous DCM (16.0 mL, 0.10 M) was added carbon tetrabromide (586 g, 1.77 mmol, 1.10 eq.) in one portion. The resulting mixture was warmed to room temperature and stirred for 1 hour. Celite was added to the resulting mixture, volatiles were removed under reduced pressure, and the residue was loaded onto a silica gel cartridge which was subjected to flash column chromatography (0-20% acetone/dichloromethane gradient) to give the title compound as a oil (501 mg, >90% purity). NMR and LC-MS showed a small amount of triphenylphosphine oxide present. The mixture was used in the next step without further purification.

LC-MS (Method 3): $R_t$=4.33 min; MS (ESIpos): m/z=506 [M+H]$^+$.

$^1$H-NMR (300 MHz, CHLOROFORM-d) δ [ppm]: 7.64 (dd, 1H), 6.98 (t, 1H), 4.66 (d, 1H), 4.38 (m, 5H), 3.98 (m, 1H), 3.87 (s, 3H), 3.45 (m, 3H), 3.21 (m, 3H), 2.23 (m, 2H), 1.92 (s, 4H), 1.41 (m, 5H), 1.20 (m, 2H).

Intermediate 32

(rac)-ethyl 13-fluoro-1-(3-((6-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylate

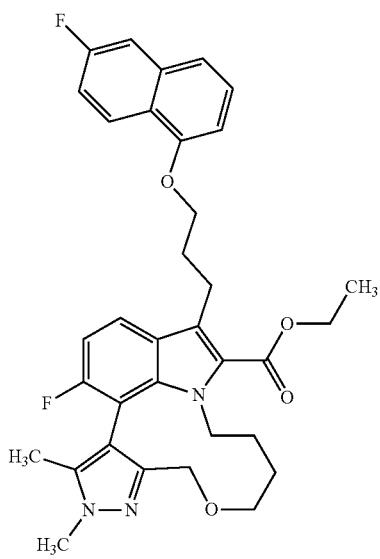 [SMILES: CCOC(=O)c1c(CCCOc2cccc3cc(F)ccc23)c2ccc(F)c3c2n1CCCCOCc1nn(C)c(C)c1-3]

Intermediate 33

(rac)-ethyl 13-fluoro-1-(3-((4-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylate

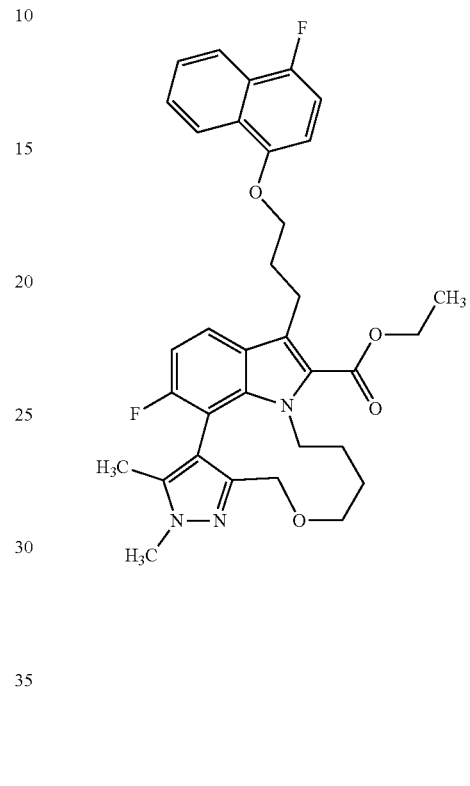

To a stirred solution of (rac)-ethyl 13-fluoro-1-(3-hydroxypropyl)-11,12-dimethyl-4,5,6,7,9,11-hexahydropyrazolo[4',3':9,10][1]oxa[6]azacycloundecino[8,7,6-hi]indole-2-carboxylate (see Intermediate 31, 127 mg, 248 µmol, 1.00 eq.) in anhydrous tetrahydrofuran (2.48 mL, 0.10 M) was added cesium carbonate (482 mg, 1.48 mmol, 6.00 eq.) and 6-fluoronaphthalen-1-ol (80.4 mg, 496 µmol, 2.00 eq.). The resulting suspension was heated at 55° C. for 12 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a yellow oil (146 mg).

LC-MS (Method 3): $R_t$=1.97 min; MS (ESIpos): m/z=588 [M+H]$^+$.

$^1$H-NMR (300 MHz, CHLOROFORM-d) δ [ppm]: 8.34 (dd, 1H), 7.60 (dd, 1H), 7.39 (m, 3H), 7.26 (m, 2H), 6.88 (dd, 1H), 6.71 (dd, 1H), 4.66 (d, 1H), 4.34 (m, 4H), 4.18 (m, 2H), 4.00 (m, 1H), 3.87 (s, 3H), 3.34 (m, 4H), 2.32 (m, 2H), 2.00 (s, 2H), 1.91 (s, 3H), 1.37 (t, 5H), 1.20 (m, 2H).

To a stirred solution of (rac)-ethyl 1-(3-bromopropyl)-13-fluoro-11,12-dimethyl-4,5,6,7,9,11-hexahydropyrazolo[4',3':9,10][1]oxa[6]azacycloundecino[8,7,6-hi]indole-2-carboxylate (see Intermediate 31, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 4-fluoronaphthalen-1-ol (64.8 mg, 0.40 mmol, 2.00 eq.). The resulting suspension was heated at 55° C. for 19 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a tan solid (110 mg).

LC-MS (Method 4): $R_t$=5.33 min; MS (ESIpos): m/z=588 [M+H]$^+$.

$^1$H-NMR (300 MHz, CHLOROFORM-d) δ [ppm]: 8.33 (m, 1H), 8.05 (m, 1H), 7.58 (m, 3H), 7.01 (dd, 1H), 6.88 (m, 1H), 6.62 (dd, 1H), 4.66 (d, 1H), 4.34 (m, 4H), 4.15 (t, 2H), 3.99 (ddd, 1H), 3.87 (s, 3H), 3.35 (m, 4H), 2.30 (m, 2H), 1.91 (s, 3H), 1.37 (m, 5H), 1.22 (dd, 2H).

Intermediate 34

(rac)-ethyl 13-fluoro-11,12-dimethyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylate

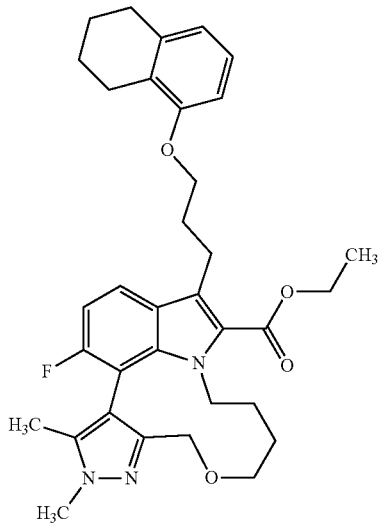 [SMILES: CCOC(=O)c1c(CCCOc2cccc3c2CCCC3)c2ccc(F)c3c2n1CCCCOCc1nn(C)c(C)c1-3]

To a stirred solution of (rac)-ethyl 1-(3-bromopropyl)-13-fluoro-11,12-dimethyl-4,5,6,7,9,11-hexahydropyrazolo[4',3':9,10][1]oxa[6]azacycloundecino[8,7,6-hi]indole-2-carboxylate (see Intermediate 31, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 5,6,7,8-tetrahydronaphthalen-1-ol (59.2 mg, 0.40 mmol, 2.00 eq.). The resulting suspension was heated at 55° C. for 19 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a tan solid (83.4 mg).

LC-MS (Method 4): $R_t$=5.64 min; MS (ESIpos): m/z=574 [M+H]$^+$.

$^1$H-NMR (300 MHz, CHLOROFORM-d) δ [ppm]: 7.61 (dd, 1H), 7.04 (t, 1H), 6.94 (t, 1H), 6.70 (dd, 1H), 6.61 (m, 1H), 4.67 (d, 1H), 4.36 (m, 3H), 4.01 (m, 3H), 3.88 (s, 3H), 3.45 (ddd, 1H), 3.23 (m, 3H), 2.76 (m, 4H), 2.15 (m, 2H), 1.92 (s, 3H), 1.79 (m, 4H), 1.40 (m, 5H), 1.21 (m, 2H).

Intermediate 35

(rac)-ethyl 1-(3-((2,3-dihydro-1H-inden-4-yl)oxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylate

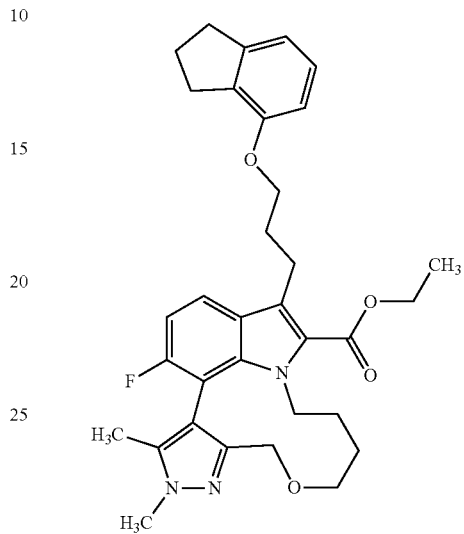

To a stirred solution of (rac)-ethyl 1-(3-bromopropyl)-13-fluoro-11,12-dimethyl-4,5,6,7,9,11-hexahydropyrazolo[4',3':9,10][1]oxa[6]azacycloundecino[8,7,6-hi]indole-2-carboxylate (see Intermediate 31, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 4-indanol (53.6 mg, 0.40 mmol, 2.00 eq.). The resulting suspension was heated at 55° C. for 19 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as an off white solid (85.6 mg).

LC-MS (Method 4): $R_t$=5.34 min; MS (ESIpos): m/z=560 [M+H]$^+$.

$^1$H-NMR (300 MHz, CHLOROFORM-d) δ [ppm]: 7.61 (dd, 1H), 7.09 (t, 1H), 6.94 (t, 1H), 6.85 (d, 1H), 6.62 (d, 1H), 4.67 (d, 1H), 4.36 (m, 4H), 4.03 (m, 3H), 3.88 (s, 3H), 3.45 (ddd, 1H), 3.24 (m, 3H), 2.94 (m, 4H), 2.11 (m, 4H), 1.92 (s, 3H), 1.40 (m, 5H), 1.22 (dd, 2H).

Intermediate 36

(rac)-ethyl 1-(3-(4-chloro-3,5-dimethylphenoxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylate

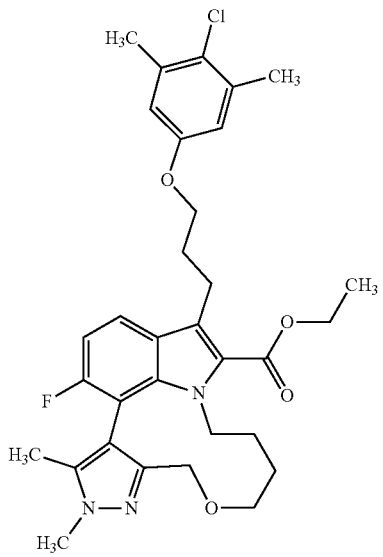 [SMILES: CCOC(=O)c1c(CCCOc2cc(C)c(Cl)c(C)c2)c2ccc(F)c3c2n1CCCCOCc1nn(C)c(C)c1-3]

To a stirred solution of (rac)-ethyl 1-(3-bromopropyl)-13-fluoro-11,12-dimethyl-4,5,6,7,9,11-hexahydropyrazolo[4',3':9,10][1]oxa[6]azacycloundecino[8,7,6-hi]indole-2-carboxylate (see Intermediate 31, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 4-chloro-3,5-dimethylphenol (62.6 mg, 0.40 mmol, 2.00 eq.). The resulting suspension was heated at 55° C. for 19 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as an off white solid (90.2 mg).

LC-MS (Method 4): $R_t$=5.54 min; MS (ESIpos): m/z=582 [M+H]$^+$.

$^1$H-NMR (300 MHz, CHLOROFORM-d) δ [ppm]: 7.59 (dd, 1H), 6.93 (t, 1H), 6.62 (s, 2H), 4.66 (d, 1H), 4.36 (m, 4H), 3.95 (m, 3H), 3.87 (s, 3H), 3.45 (m, 1H), 3.21 (m, 3H), 2.34 (s, 6H), 2.13 (m, 2H), 1.92 (s, 3H), 1.41 (m, 5H), 1.19 (m, 2H).

Intermediate 37

(rac)-ethyl 3-(3-((tert-butyldimethylsilyl)oxy)propyl)-7-(5-ethyl-3-(hydroxymethyl)-1-methyl-1H-pyrazol-4-yl)-6-fluoro-1H-indole-2-carboxylate

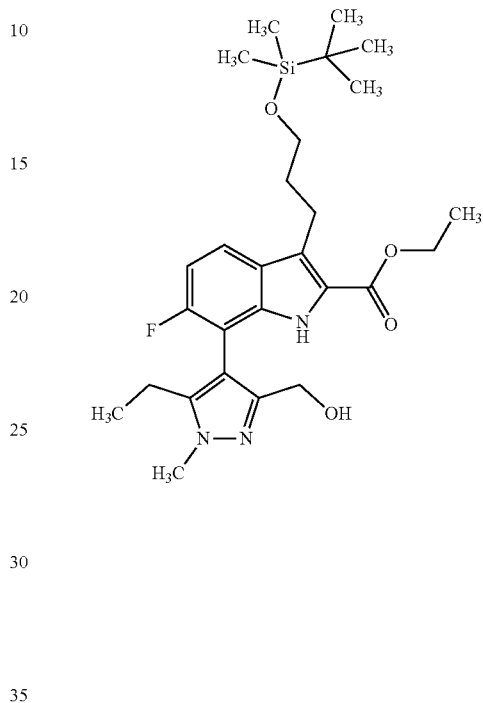

To a 50° C. stirred suspension of (4-bromo-5-ethyl-1-methyl-1H-pyrazol-3-yl)methanol (see Intermediate 11, 3.33 g, 15.2 mmol, 1.00 eq.), XPhos Pd G3 (752 mg, 0.89 mmol, 7.00 mol %) and potassium phosphate tribasic (5.39 g, 25.4 mmol, 2.00 eq.) in a 2:1 mixture of argon degassed 1,4-dioxane/water (38.1 mL,) was slowly added dropwise (~1 h), a solution of ethyl 3-(3-((tert-butyldimethylsilyl)oxy)propyl)-6-fluoro-7-(4,4,5,5-tetramethyl-1,3,2-dioxaborolan-2-yl)-1H-indole-2-carboxylate (see Intermediate 27, 6.42 g, 12.7 mmol, 1.00 eq.) in argon degassed 1,4-dioxane (12.7 mL, 1.00 M). The resulting dark mixture was heated at 50° C. for a further 30 minutes, cooled to room temperature and concentrated under reduced pressure. The residue was dissolved in water (50 mL) and extracted with ethyl acetate (3×50 mL). The combined organic extracts were washed with brine (50 mL), dried (magnesium sulfate), filtered and concentrated under reduced pressure. The residue was purified by flash column chromatography (0-100% acetone/dichloromethane gradient) and then reverse phase column chromatography (10-100% acetonitrile/water gradient) to give the title compound as a light yellow solid (3.37 g LC-MS (Method 3): $R_t$=1.99 min; MS (ESIpos): m/z=518 [M+H]$^+$.

$^1$H-NMR (300 MHz, CHLOROFORM-d) δ [ppm]: 9.60 (s, 1H), 7.64 (dd, 1H), 6.97 (dd, 1H), 4.63 (d, 1H), 4.36 (m, 3H), 3.92 (s, 3H), 3.70 (t, 2H), 3.15 (m, 2H), 2.57 (ddt, 2H), 1.91 (m, 2H), 1.37 (t, 3H), 1.08 (t, 3H), 0.93 (s, 9H), 0.07 (s, 6H).

Intermediate 38

(rac)-ethyl (Z)-1-(3-((tert-butyldimethylsilyl)oxy)propyl)-12-ethyl-13-fluoro-11-methyl-4,7,9,11-tetrahydropyrazolo[4',3':9,10][1]oxa[6]azacycloundecino[8,7,6-hi]indole-2-carboxylate

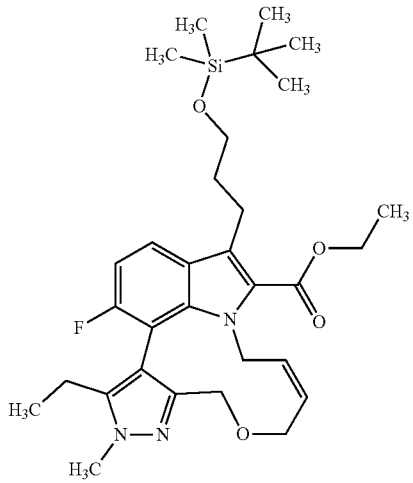 [SMILES: CCOC(=O)c1c(CCCO[Si](C)(C)C(C)(C)C)c2ccc(F)c3c2n1C/C=C\COCc1nn(C)c(CC)c1-3]

To a room temperature stirred solution of (rac)-ethyl 3-(3-((tert-butyldimethylsilyhoxy)propyl)-7-(5-ethyl-3-(hydroxymethyl)-1-methyl-1H-pyrazol-4-yl)-6-fluoro-1H-indole-2-carboxylate (see Intermediate 37, 3.35 g, 6.47 mmol, 1.00 eq.) in anhydrous acetonitrile (64.6 mL, 0.10 M) was added cesium carbonate (10.5 g, 32.3 mmol, 5.00 eq.). After stirring for 10 minutes, 1,4-dichlorobutene (747 µL, 7.11 mmol, 1.10 eq.) and sodium iodide (1.93 g, 12.9 mmol, 2.00 eq.) was added to the mixture and the resulting yellow suspension was heated at 40° C. for 2 days. The mixture was cooled to room temperature and filtered through a Celite plug. Celite was added to the resulting solution, volatiles were removed under reduced pressure, and the residue was loaded onto a silica gel cartridge which was subjected to flash column chromatography (0-100% ethyl acetate/hexanes gradient) to give the title compound as a light yellow oil (2.85 g).

LC-MS (Method 4): $R_t$=5.89 min; MS (ESIpos): m/z=570 [M+H]$^+$.

$^1$H-NMR (300 MHz, CHLOROFORM-d) δ [ppm]: 7.65 (dd, 1H), 6.95 (t, 1H), 5.38 (m, 1H), 5.23 (td, 1H), 5.01 (m, 1H), 4.83 (dd, 1H), 4.59 (d, 1H), 4.40 (m, 3H), 3.95 (m, 4H), 3.74 (m, 3H), 3.10 (m, 2H), 2.32 (q, 2H), 1.90 (m, 2H), 1.41 (t, 3H), 0.94 (m, 12H), 0.07 (s, 6H).

Intermediate 39

(rac)-ethyl 12-ethyl-13-fluoro-1-(3-hydroxypropyl)-11-methyl-4,5,6,7,9,11-hexahydropyrazolo-[4',3':9,10][1]oxa[6]azacycloundecino[8,7,6-hi]indole-2-carboxylate

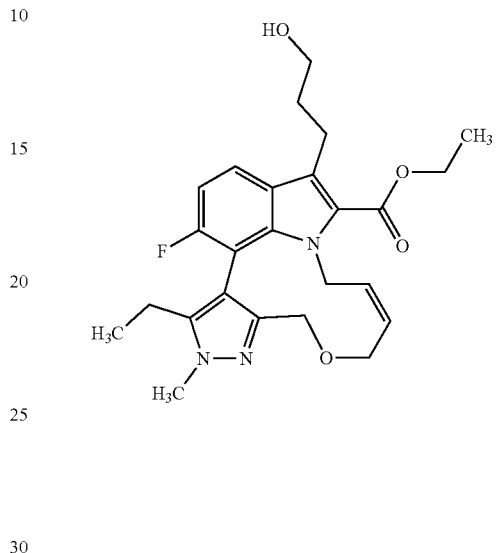

To a stirred solution of (rac)-ethyl (Z)-1-(3-((tert-butyldimethylsilyl)oxy)propyl)-12-ethyl-13-fluoro-11-methyl-4,7,9,11-tetrahydropyrazolo[4',3':9,10][1]oxa[6]azacycloundecino[8,7,6-hi]indole-2-carboxylate (see Intermediate 38, 2.70 g, 4.73 mmol, 1.00 eq.) in absolute ethanol (47.3 mL, 0.10 M) was added Wilkinson's catalyst (875 mg, 0.946 mmol, 0.20 eq.). The resulting dark suspension was evacuated and then placed under a hydrogen atmosphere and stirred for 8 hours at room temperature. Following complete reduction, the mixture was sparged with nitrogen to remove any residual hydrogen. Concentrated hydrochloric acid (386 µL, 4.73 mmol, 1.00 eq.) was added and the orange mixture was stirred for a further 15 minutes. Following complete deprotection and the mixture was diluted with dichloromethane. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a yellow solid (1.58 g).

LC-MS (Method 3): $R_t$=1.34 min; MS (ESIpos): m/z=458 [M+H]$^+$.

$^1$H-NMR (300 MHz, CHLOROFORM-d) δ [ppm]: 7.60 (dd, 1H), 6.97 (m, 1H), 4.64 (d, 1H), 4.39 (m, 3H), 4.19 (m, 1H), 4.03 (m, 1H), 3.90 (s, 3H), 3.54 (m, 3H), 3.20 (m, 3H), 2.31 (m, 2H), 1.98 (m, 2H), 1.40 (m, 5H), 1.21 (m, 2H), 0.96 (t, 3H).

Intermediate 40

(rac)-ethyl 1-(3-bromopropyl)-12-ethyl-13-fluoro-11-methyl-4,5,6,7,9,11-hexahydropyrazolo-[4',3':9,10][1]oxa[6]azacycloundecino[8,7,6-hi]indole-2-carboxylate

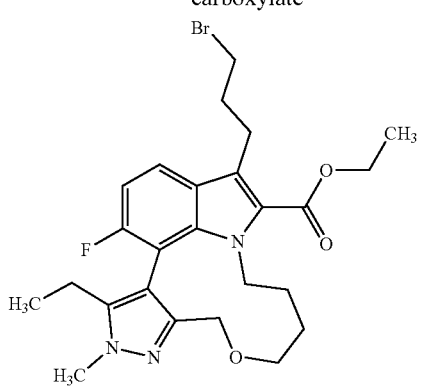

To a 0° C. stirred solution of (rac)-ethyl 12-ethyl-13-fluoro-1-(3-hydroxpropyl)-11-methyl-4,5,6,7,9,11-hexahydropyrazolo[4',3':9,10][1]oxa[6]azacycloundecino[8,7,6-hi]indole-2-carboxylate (see Intermediate 39, 1.58 g, 3.45 mmol, 1.00 eq.) and triphenylphosphine (994 mg, 3.79 mmol, 1.10 eq.) in anhydrous DCM (34.5 mL, 0.10 M) was added carbon tetrabromide (1.25 g, 3.79 mmol, 1.10 eq.) in one portion. The resulting mixture was warmed to room temperature and stirred for 1 hour. Celite was added to the resulting mixture, volatiles were removed under reduced pressure, and the residue was loaded onto a silica gel cartridge which was subjected to flash column chromatography (80 g HP silica, 0-15% acetone/dichloromethane gradient) to give the title compound as a colourless oil (1.45 g).

LC-MS (Method 3): $R_t$=1.77 min; MS (ESIpos): m/z=520 [M+H]$^+$.

$^1$H-NMR (300 MHz, CHLOROFORM-d) δ [ppm]: 7.64 (dd, 1H), 6.98 (t, 1H), 4.65 (d, 1H), 4.37 (m, 4H), 4.01 (ddd, 1H), 3.90 (s, 3H), 3.46 (m, 3H), 3.21 (m, 3H), 2.27 (m, 4H), 1.42 (m, 5H), 1.18 (m, 2H), 0.94 (t, 3H).

Intermediate 41

(rac)-ethyl 12-ethyl-13-fluoro-1-(3-((6-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylate

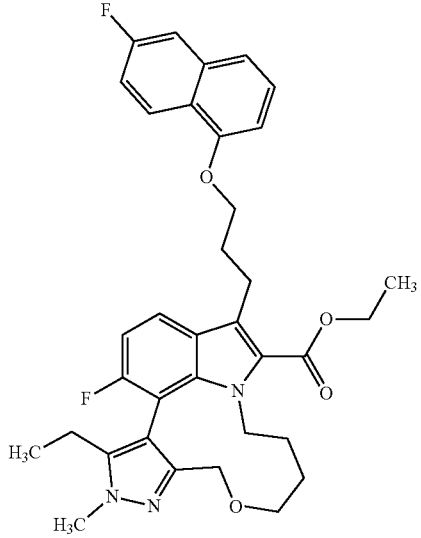

To a stirred solution of (rac)-ethyl 1-(3-bromopropyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate (see Intermediate 40, 167 mg, 0.32 mmol, 1.00 eq.) in anhydrous tetrahydrofuran (3.20 mL, 0.10 M) was added cesium carbonate (625 mg, 1.92 mmol, 6.00 eq.) and 6-fluoronaphthalen-1-ol (104 mg, 0.64 mmol, 2.00 eq.). The resulting suspension was heated at 55° C. for 2 days and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a brown solid (155 mg).

LC-MS (Method 3): $R_t$=2.03 min; MS (ESIpos): m/z=602 [M+H]$^+$.

$^1$H-NMR (300 MHz, CHLOROFORM-d) δ [ppm]: 8.35 (dd, 1H), 7.59 (dd, 1H), 7.38 (m, 3H), 7.26 (m, 3H), 6.88 (t, 1H), 6.71 (dd, 1H), 4.65 (d, 1H), 4.34 (m, 3H), 4.18 (t, 2H), 4.02 (ddd, 1H), 3.36 (m, 4H), 2.28 (m, 4H), 1.37 (t, 4H), 1.21 (m, 2H), 0.94 (t, 3H).

Intermediate 42

(rac)-ethyl 12-ethyl-13-fluoro-1-(3-((4-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylate

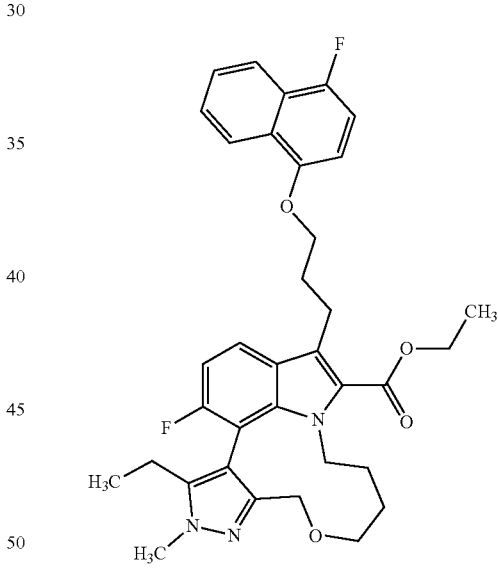

To a stirred solution of (rac)-ethyl 1-(3-bromopropyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate (see Intermediate 40, 167 mg, 0.32 mmol, 1.00 eq.) in anhydrous tetrahydrofuran (3.20 mL, 0.10 M) was added cesium carbonate (625 mg, 1.92 mmol, 6.00 eq.) and 4-fluoronaphthalen-1-ol (104 mg, 0.64 mmol, 2.00 eq.). The resulting suspension was heated at 55° C. for 2 days and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a brown solid (187 mg).

LC-MS (Method 3): $R_t$=2.05 min; MS (ESIpos): m/z=602 [M+H]$^+$.

$^1$H-NMR (300 MHz, CHLOROFORM-d) δ [ppm]: 8.34 (m, 1H), 8.06 (m, 1H), 7.58 (m, 3H), 7.01 (dd, 1H), 6.87 (t, 1H), 6.62 (dd, 1H), 4.65 (d, 1H), 4.33 (m, 3H), 4.15 (t, 2H), 4.01 (m, 1H), 3.90 (s, 3H), 3.35 (m, 4H), 2.28 (m, 3H), 1.37 (m, 5H), 1.21 (m, 2H), 0.93 (m, 3H).

Intermediate 43

(rac)-ethyl 12-ethyl-13-fluoro-11-methyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylate

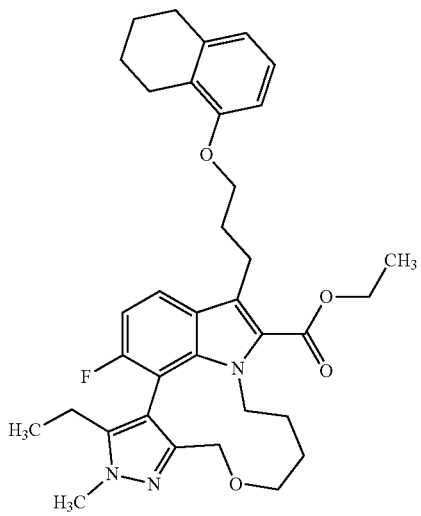

To a stirred solution of (rac)-ethyl 1-(3-bromopropyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate (see Intermediate 40, 156 mg, 0.30 mmol, 1.00 eq.) in anhydrous tetrahydrofuran (3.00 mL, 0.10 M) was added cesium carbonate (583 mg, 1.79 mmol, 6.00 eq.) and 5,6,7,8-tetrahydronaphthalen-1-ol (88.9 mg, 0.60 mmol, 2.00 eq.). The resulting suspension was heated at 55° C. for 19 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a light yellow solid (162 mg).

LC-MS (Method 3): $R_t$=2.14 min; MS (ESIpos): m/z=588 [M+H]$^+$.

$^1$H-NMR (300 MHz, CHLOROFORM-d) δ [ppm]: 7.61 (dd, 1H), 7.04 (t, 1H), 6.94 (t, 1H), 6.70 (m, 1H), 6.61 (m, 1H), 4.66 (d, 1H), 4.35 (m, 4H), 4.02 (m, 3H), 3.90 (s, 3H), 3.46 (dd, 1H), 3.23 (m, 3H), 2.75 (m, 4H), 2.29 (m, 2H), 2.16 (m, 2H), 1.80 (m, 5H), 1.39 (m, 5H), 1.20 (m, 2H), 0.94 (t, 3H).

Intermediate 44

(rac)-ethyl 1-(3-((2,3-dihydro-1H-inden-4-yl)oxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate

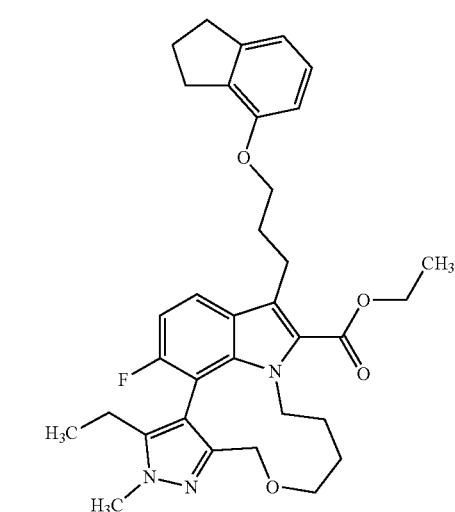

To a stirred solution of (rac)-ethyl 1-(3-bromopropyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate (see Intermediate 40, 156 mg, 0.30 mmol, 1.00 eq.) in anhydrous tetrahydrofuran (3.00 mL, 0.10 M) was added cesium carbonate (583 mg, 1.79 mmol, 6.00 eq.) and 4-indanol (80.5 mg, 0.60 mmol, 2.00 eq.). The resulting suspension was heated at 55° C. for 19 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a light yellow solid (167 mg).

LC-MS (Method 3): $R_t$=2.06 min; MS (ESIpos): m/z=574 [M+H]$^+$.

$^1$H-NMR (300 MHz, CHLOROFORM-d) δ [ppm]: 7.61 (dd, 1H), 7.09 (t, 1H), 6.93 (t, 1H), 6.85 (d, 1H), 6.62 (d, 1H), 4.66 (d, 1H), 4.36 (m, 4H), 4.04 (m, 3H), 3.90 (s, 3H), 3.46 (ddd, 1H), 3.23 (m, 3H), 2.94 (m, 4H), 2.20 (m, 5H), 1.40 (m, 6H), 1.21 (m, 2H), 0.94 (t, 3H).

Intermediate 45

(rac)-ethyl 1-(3-(4-chloro-3,5-dimethylphenoxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate

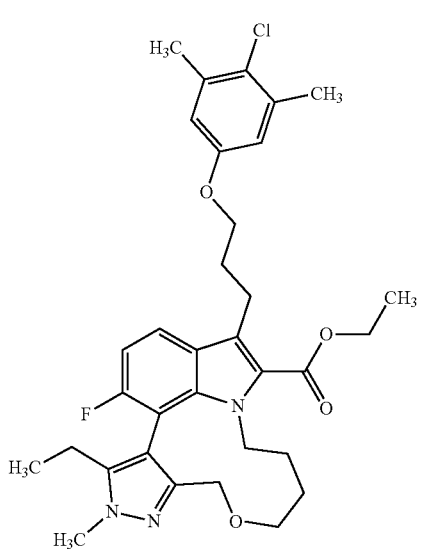

To a stirred solution of (rac)-ethyl 1-(3-bromopropyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate (see Intermediate 40, 156 mg, 0.30 mmol, 1.00 eq.) in anhydrous tetrahydrofuran (3.00 mL, 0.10 M) was added cesium carbonate (583 mg, 1.79 mmol, 6.00 eq.) and 4-chloro-3,5-dimethylphenol (93.9 mg, 0.60 mmol, 2.00 eq.). The resulting suspension was heated at 55° C. for 19 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a light yellow solid (171 mg).

LC-MS (Method 3): $R_t$=2.10 min; MS (ESIpos): m/z=596 [M+H]$^+$.

$^1$H-NMR (300 MHz, CHLOROFORM-d) δ [ppm]: 7.59 (dd, 1H), 6.92 (t, 1H), 6.63 (s, 2H), 4.66 (d, 1H), 4.36 (m, 4H), 3.92 (m, 6H), 3.46 (m, 1H), 3.24 (m, 3H), 2.30 (m, 8H), 2.12 (m, 2H), 1.41 (m, 5H), 1.20 (m, 3H), 0.94 (t, 3H).

Intermediate 46

(rac)-ethyl 3-(3-((tert-butyldimethylsilyl)oxy)propyl)-6-fluoro-7-(5-(hydroxymethyl)-1,3-dimethyl-1H-pyrazol-4-yl)-1H-indole-2-carboxylate

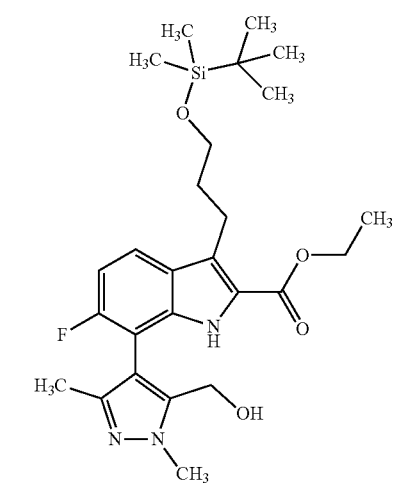

To a 50° C. stirred suspension of (4-bromo-1,3-dimethyl-1H-pyrazol-5-yl)methanol (see Intermediate 6, 3.89 g, 19.0 mmol, 1.00 eq.), XPhos Pd G3 (939 mg, 1.11 mmol, 7.00 mol %) and potassium phosphate tribasic (6.75 g, 31.8 mmol, 2.00 eq.) in a 2:1 mixture of argon degassed 1,4-dioxane/water (47.7 mL) was slowly added dropwise (~1 h), a solution of (rac)-ethyl 3-(3-((tert-butyldimethylsilyhoxy)propyl)-6-fluoro-7-(4,4,5,5-tetramethyl-1,3,2-dioxa-borolan-2-yl)-1H-indole-2-carboxylate (see Intermediate 27, 8.08 g, 15.9 mmol, 1.00 eq.) in argon degassed 1,4-dioxane (15.9 mL, 1.00 M). The resulting dark mixture was heated at 50° C. for further for further 30 minutes, cooled to room temperature and concentrated under reduced pressure. The residue was dissolved in water (50 mL) and extracted with ethyl acetate (3×50 mL). The combined organic extracts were washed with brine (50 mL), dried (magnesium sulfate) and filtered. Celite was added to the resulting solution, volatiles were removed under reduced pressure, and the residue was loaded onto a silica gel cartridge which was subjected to flash column chromatography (0-100% acetone/dichloromethane gradient) and then reverse phase column chromatography (10-100% acetonitrile/water gradient) to give the title compound as a light yellow solid (4.14 g).

LC-MS (Method 3): $R_t$=1.94 min; MS (ESIpos): m/z=504 [M+H]$^+$.

$^1$H-NMR (300 MHz, CHLOROFORM-d) δ [ppm]: 9.00 (s, 1H), 7.65 (m, 1H), 6.99 (dd, 1H), 4.52 (m, 2H), 4.35 (m, 2H), 3.99 (s, 3H), 3.70 (t, 2H), 3.14 (m, 2H), 1.90 (m, 3H), 1.38 (t, 3H), 0.92 (s, 9H), 0.07 (s, 6H).

Intermediate 47

(rac)-ethyl (Z)-1-(3-((tert-butyldimethylsilyl)oxy)propyl)-13-fluoro-10,12-dimethyl-4,7,9,10-tetrahydropyrazolo[4',3':9,10][1]oxa[6]azacycloundecino[8,7,6-hi]indole-2-carboxylate

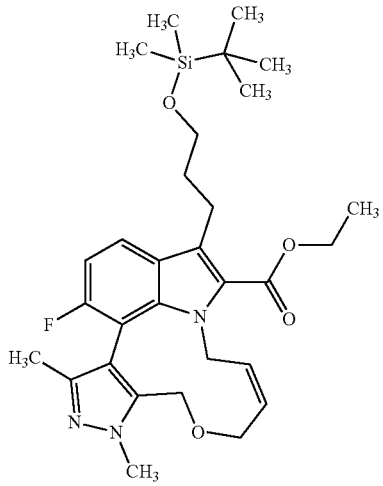 [SMILES: CCOC(=O)c1c(CCCO[Si](C)(C)C(C)(C)C)c2ccc(F)c3c2n1C/C=C\COCc1c-3c(C)nn1C]

To a room temperature stirred solution of (rac)-ethyl 3-(3-((tert-butyldimethylsilyl)oxy)propyl)-6-fluoro-7-(5-(hydroxymethyl)-1,3-dimethyl-1H-pyrazol-4-yl)-1H-indole-2-carboxylate (see Intermediate 46, 2.06 g, 4.08 mmol, 1.00 eq.) in argon degassed anhydrous acetonitrile (40.8 mL, 0.10 M) was added cesium carbonate (6.64 g, 20.4 mmol, 5.00 eq.). After stirring for 10 minutes, 1,4-dichlorobutene (470 µL, 4.48 mmol, 1.10 eq.) and sodium iodide (1.22 g, 8.16 mmol, 2.00 eq.) was added to the mixture and the resulting yellow suspension was heated at 40° C. for 16 hours. The mixture was cooled to room temperature and filtered through a Celite plug. Celite was added to the resulting solution, volatiles were removed under reduced pressure, and the residue was loaded onto a silica gel cartridge which was subjected to flash column chromatography (0-100% ethyl acetate/hexanes gradient) to give the title compound as a light yellow oil (1.63 g).

LC-MS (Method 4): $R_t$=5.96 min; MS (ESIpos): m/z=556 [M+H]$^+$.

$^1$H-NMR (300 MHz, CHLOROFORM-d) δ [ppm]: 7.67 (dd, 1H), 6.96 (t, 1H), 5.27 (m, 1H), 5.08 (m, 2H), 4.71 (m, 2H), 4.39 (m, 3H), 3.98 (s, 3H), 3.83 (dd, 1H), 3.68 (m, 3H), 3.13 (m, 2H), 1.90 (m, 5H), 1.41 (t, 3H), 0.93 (s, 9H), 0.07 (s, 6H).

Intermediate 48

(rac)-ethyl 13-fluoro-1-(3-hydroxypropyl)-10,12-dimethyl-4,5,6,7,9,10-hexahydropyrazolo-[4',3':9,10][1]oxa[6]azacycloundecino[8,7,6-hi]indole-2-carboxylate

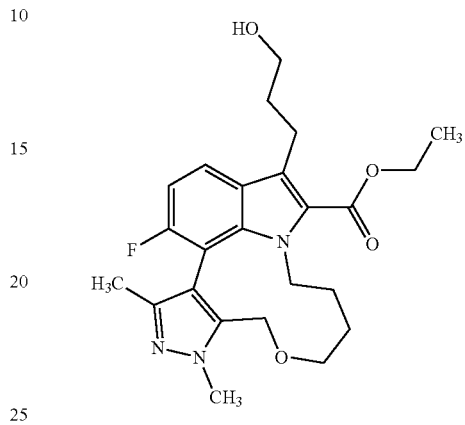

To a stirred solution of (rac)-ethyl (Z)-1-(3-((tert-butyldimethylsilyhoxy)propyl)-13-fluoro-10,12-dimethyl-4,7,9,10-tetrahydropyrazolo[4',3':9,10][1]oxa[6]azacycloundecino[8,7,6-hi]indole-2-carboxylate (see Intermediate 47, 1.61 g, 3.75 mmol, 1.00 eq.) in absolute ethanol (28.9 mL, 0.10 M) was added Wilkinson's catalyst (534 mg, 0.58 mmol, 0.20 eq.). The resulting dark suspension was evacuated and then placed under a hydrogen atmosphere and stirred for 22 hours at room temperature. Following complete reduction, the mixture was sparged with nitrogen to remove any residual hydrogen. Concentrated hydrochloric acid (235 µL, 2.89 mmol, 1.00 eq.) was added and the orange mixture was stirred for a further 15 minutes. Following complete deprotection celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) twice to give the title compound as a white solid (1.09 g).

LC-MS (Method 4): $R_t$=2.98 min; MS (ESIpos): m/z=444 [M+H]$^+$.

$^1$H-NMR (300 MHz, CHLOROFORM-d) δ [ppm]: 7.65 (dd, 1H), 6.96 (t, 1H), 4.60 (d, 1H), 4.41 (m, 4H), 4.13 (ddd, 1H), 3.95 (s, 3H), 3.57 (m, 3H), 3.19 (t, 2H), 2.94 (ddd, 1H), 2.43 (s, 1H), 1.97 (m, 5H), 1.36 (m, 7H).

Intermediate 49

(rac)-ethyl 1-(3-bromopropyl)-13-fluoro-10,12-dimethyl-4,5,6,7,9,10-hexahydropyrazolo-[4',3':9,10][1]oxa[6]azacycloundecino[8,7,6-hi]indole-2-carboxylate

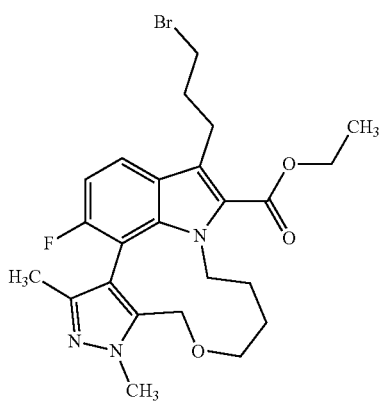 [SMILES: CCOC(=O)c1c(CCCBr)c2ccc(F)c3c2n1CCCCOCc1c-3c(C)nn1C]

To a 0° C. stirred solution of (rac)-ethyl 13-fluoro-1-(3-hydroxypropyl)-10,12-dimethyl-4,5,6,7,9,10-hexahydropyrazolo[4',3':9,10][1]oxa[6]azacycloundecino[8,7,6-hi]indole-2-carboxylate (see Intermediate 48, 1.05 g, 2.36 mmol, 1.00 eq.) and triphenylphosphine (679 mg, 2.59 mmol, 1.10 eq.) in anhydrous dichloromethane (23.5 mL, 0.10 M) was added carbon tetrabromide (858 mg, 2.59 mmol, 1.10 eq.) in one portion. The resulting mixture was warmed to room temperature and stirred for 1 hour. Celite was added to the resulting mixture, volatiles were removed under reduced pressure, and the residue was loaded onto a silica gel cartridge which was subjected to by flash column chromatography (0-15% acetone/dichloromethane gradient) to give the title compound as a white solid (923 mg).

LC-MS (Method 4): $R_t$=4.41 min; MS (ESIpos): m/z=506 [M+H]$^+$.

$^1$H-NMR (300 MHz, CHLOROFORM-d) δ [ppm]: 7.69 (dd, 1H), 6.97 (t, 1H), 4.60 (m, 2H), 4.40 (m, 3H), 4.11 (ddd, 1H), 3.95 (s, 3H), 3.49 (m, 3H), 3.23 (m, 2H), 2.90 (ddd, 1H), 2.26 (m, 2H), 1.98 (s, 3H), 1.42 (m, 4H), 1.23 (m, 3H).

Intermediate 50

(rac)-ethyl 13-fluoro-1-(3-((6-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylate

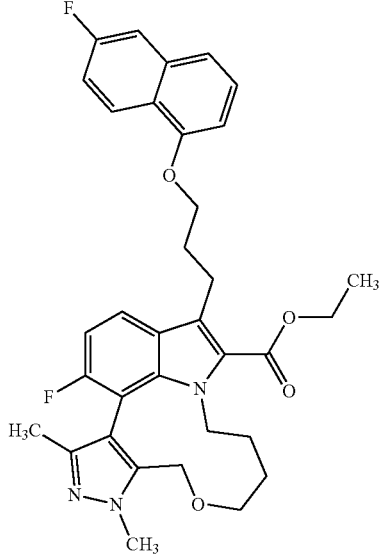 [SMILES: CCOC(=O)c1c(CCCOc2cccc3cc(F)ccc23)c2ccc(F)c3c2n1CCCCOCc1c-3c(C)nn1C]

To a stirred solution of (rac)-ethyl 1-(3-bromopropyl)-13-fluoro-10,12-dimethyl-4,5,6,7,9,10-hexahydropyrazolo[4',3':9,10][1]oxa[6]azacycloundecino[8,7,6-hi]indole-2-carboxylate (see Intermediate 49, 151 mg, 0.30 mmol, 1.00 eq.) in anhydrous tetrahydrofuran (3.00 mL, 0.10 M) was added cesium carbonate (583 mg, 1.79 mmol, 6.00 eq.) and 6-fluoronaphthalen-1-ol (97.2 mg, 0.60 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a orange solid (152 mg).

LC-MS (Method 4): $R_t$=5.35 min; MS (ESIpos): m/z=588 [M+H]$^+$.

$^1$H-NMR (300 MHz, CHLOROFORM-d) δ [ppm]: 8.33 (dd, 1H), 7.65 (dd, 1H), 7.38 (m, 3H), 7.25 (m, 3H), 6.89 (t, 1H), 6.71 (dd, 1H), 4.62 (m, 2H), 4.33 (m, 3H), 4.18 (m, 3H), 3.95 (s, 3H), 3.41 (m, 3H), 2.91 (td, 1H), 2.33 (m, 2H), 1.98 (s, 3H), 1.34 (m, 7H).

Intermediate 51

(rac)-ethyl 13-fluoro-1-(3-((4-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylate

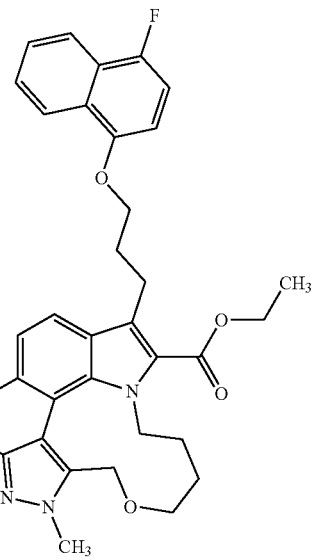

To a stirred solution of (rac)-ethyl 1-(3-bromopropyl)-13-fluoro-10,12-dimethyl-4,5,6,7,9,10-hexahydropyrazolo[4',3':9,10][1]oxa[6]azacycloundecino[8,7,6-hi]indole-2-carboxylate (see Intermediate 49, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 4-fluoronaphthalen-1-ol (64.8 mg, 0.40 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a tan solid (105 mg).

LC-MS (Method 4): $R_t$=5.40 min; MS (ESIpos): m/z=588 [M+H]$^+$.

$^1$H-NMR (300 MHz, CHLOROFORM-d) δ [ppm]: 8.33 (m, 1H), 8.05 (m, 1H), 7.60 (m, 3H), 7.01 (dd, 1H), 6.88 (t, 1H), 6.63 (dd, 1H), 4.61 (m, 2H), 4.34 (m, 3H), 4.15 (m, 3H), 3.95 (s, 3H), 3.41 (m, 3H), 2.91 (ddd, 1H), 2.32 (m, 2H), 1.99 (d, 4H), 1.34 (m, 7H).

Intermediate 52

(rac)-ethyl 13-fluoro-10,12-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylate

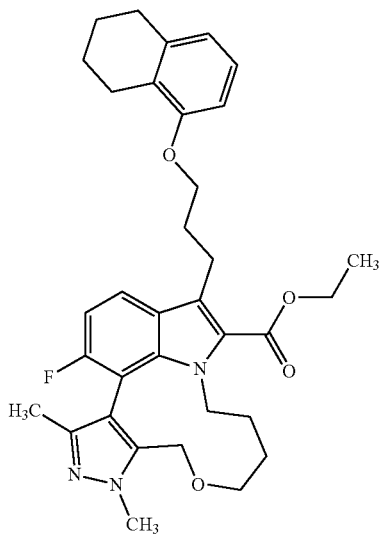 [SMILES: CCOC(=O)c1c(CCCOc2cccc3c2CCCC3)c2ccc(F)c3c2n1CCCCOCc1c-3c(C)nn1C]

To a stirred solution of (rac)-ethyl 1-(3-bromopropyl)-13-fluoro-10,12-dimethyl-4,5,6,7,9,10-hexahydropyrazolo[4',3':9,10][1]oxa[6]azacycloundecino[8,7,6-hi]indole-2-carboxylate (see Intermediate 49, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 5,6,7,8-tetrahydronaphthalen-1-ol (59.2 mg, 0.40 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a pink solid (90.0 mg).

LC-MS (Method 4): $R_t$=5.70 min; MS (ESIpos): m/z=574 [M+H]$^+$.

$^1$H-NMR (300 MHz, CHLOROFORM-d) δ [ppm]: 7.65 (dd, 1H), 7.04 (t, 1H), 6.93 (t, 1H), 6.70 (d, 1H), 6.61 (d, 1H), 4.63 (m, 2H), 4.37 (m, 3H), 4.05 (m, 3H), 3.95 (s, 3H), 3.52 (dt, 1H), 3.27 (m, 2H), 2.91 (m, 1H), 2.76 (m, 4H), 2.16 (m, 2H), 1.99 (s, 3H), 1.79 (m, 5H), 1.40 (m, 7H).

Intermediate 53

(rac)-ethyl 1-(3-((2,3-dihydro-1H-inden-4-yl)oxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylate

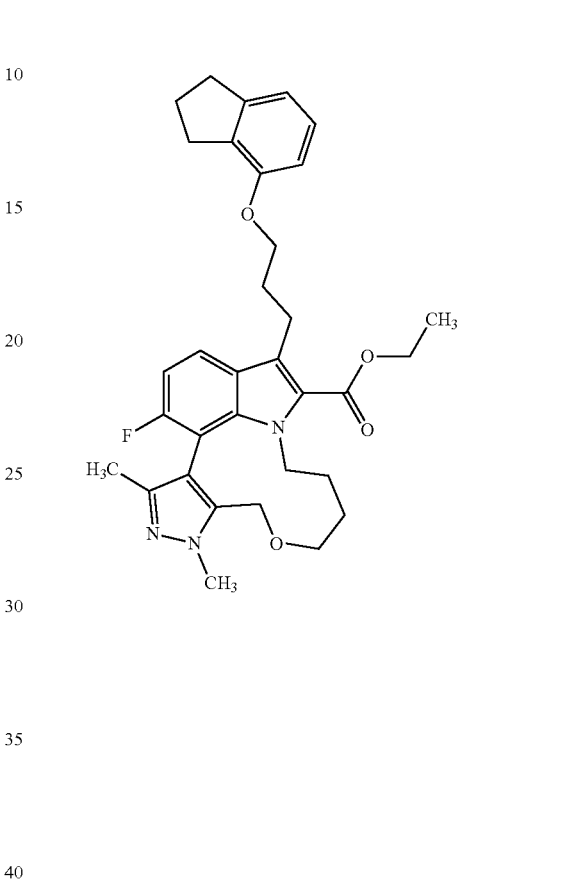

To a stirred solution of (rac)-ethyl 1-(3-bromopropyl)-13-fluoro-10,12-dimethyl-4,5,6,7,9,10-hexahydropyrazolo[4',3':9,10][1]oxa[6]azacycloundecino[8,7,6-hi]indole-2-carboxylate (see Intermediate 49, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 4-indanol (53.6 mg, 0.40 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a tan solid (82.5 mg).

LC-MS (Method 4): $R_t$=5.41 min; MS (ESIpos): m/z=560 [M+H]$^+$.

$^1$H-NMR (300 MHz, CHLOROFORM-d) δ [ppm]: 7.66 (dd, 1H), 7.10 (t, 1H), 6.90 (m, 2H), 6.63 (d, 1H), 4.62 (m, 2H), 4.36 (m, 3H), 4.07 (m, 3H), 3.95 (s, 3H), 3.52 (dt, 1H), 3.25 (m, 2H), 2.92 (m, 5H), 2.13 (m, 4H), 1.98 (s, 3H), 1.40 (m, 10H).

Intermediate 54

(rac)-ethyl 1-(3-(4-chloro-3,5-dimethylphenoxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylate

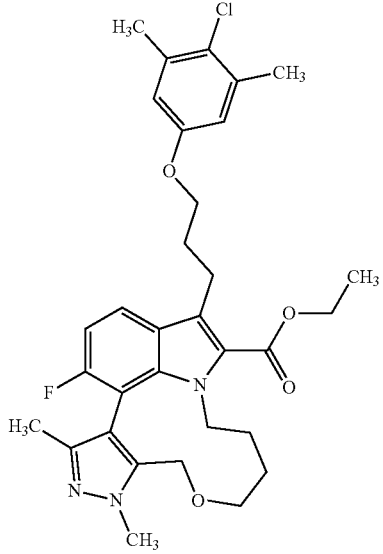 [SMILES: CCOC(=O)c1c(CCCOc2cc(C)c(Cl)c(C)c2)c2ccc(F)c3c2n1CCCCOCc1c-3c(C)nn1C]

To a stirred solution of (rac)-ethyl 1-(3-bromopropyl)-13-fluoro-10,12-dimethyl-4,5,6,7,9,10-hexahydropyrazolo[4',3':9,10][1]oxa[6]azacycloundecino[8,7,6-hi]indole-2-carboxylate (see Intermediate 49, 101 mg, 0.20 mmol, 1.00 eq.) in anhydrous tetrahydrofuran (2.00 mL, 0.10 M) was added cesium carbonate (390 mg, 1.20 mmol, 6.00 eq.) and 4-chloro-3,5-dimethylphenol (62.6 mg, 0.40 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as an off white solid (95.0 mg).

LC-MS (Method 4): $R_t$=5.61 min; MS (ESIpos): m/z=582 [M+H]$^+$.

$^1$H-NMR (300 MHz, CHLOROFORM-d) δ [ppm]: 7.64 (dd, 1H), 6.93 (t, 1H), 6.63 (s, 2H), 4.61 (m, 2H), 4.37 (m, 3H), 4.10 (m, 1H), 3.96 (m, 5H), 3.52 (dt, 1H), 3.23 (m, 2H), 2.91 (m, 1H), 2.34 (s, 6H), 2.14 (m, 2H), 1.98 (s, 3H), 1.41 (m, 7H).

Intermediate 55

(rac)-ethyl 3-(3-((tert-butyldimethylsilyl)oxy)propyl)-7-(3-ethyl-5-(hydroxymethyl)-1-methyl-1H-pyrazol-4-yl)-6-fluoro-1H-indole-2-carboxylate (SF0217-184)

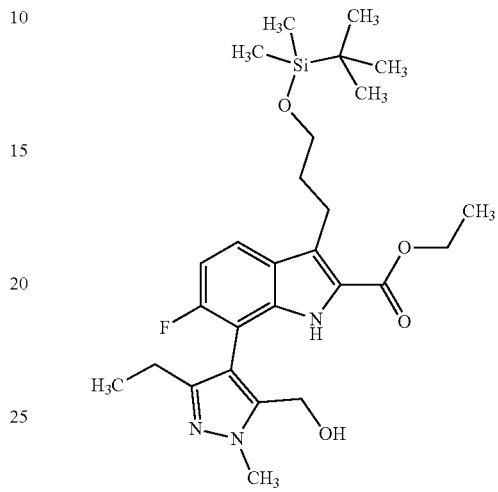

To a 50° C. stirred suspension of (4-bromo-3-ethyl-1-methyl-1H-pyrazol-5-yl)methanol (see Intermediate 12, 3.81 g, 17.4 mmol, 1.00 eq.), XPhos Pd G3 (854 mg, 1.01 mmol, 7.00 mol %) and potassium phosphate tribasic (6.15 g, 29.0 mmol, 2.00 eq.) in a 2:1 mixture of argon degassed 1,4-dioxane/water (43.5 mL) was slowly added dropwise (~1 h), a solution of ethyl 3-(3-((tert-butyldimethylsilyl)oxy)propyl)-6-fluoro-7-(4,4,5,5-tetramethyl-1,3,2-dioxaborolan-2-yl)-1H-indole-2-carboxylate (see Intermediate 27, 7.38 g, 14.5 mmol, 1.00 eq.) in argon degassed 1,4-dioxane (14.5 mL, 1.00 M). The resulting dark mixture was heated at 50° C. for further 30 minutes, cooled to room temperature and concentrated under reduced pressure. The residue was dissolved in water (50 mL) and extracted with ethyl acetate (3×50 mL). The combined organic extracts were washed with brine (50 mL), dried (magnesium sulfate) and filtered. Celite was added to the resulting solution, volatiles were removed under reduced pressure, and the residue was loaded onto a silica gel cartridge which was subjected to flash column chromatography (0-100% acetone/dichloromethane gradient) and then reverse phase column chromatography (10-100% acetonitrile/water gradient) to give the title compound as a yellow solid (4.79 g).

LC-MS (Method 3): $R_t$=2.01 min; MS (ESIpos): m/z=518 [M+H]$^+$.

$^1$H-NMR (300 MHz, CHLOROFORM-d) δ [ppm]: 8.88 (s, 1H), 7.65 (m, 1H), 6.99 (dd, 1H), 4.50 (q, 2H), 4.36 (q, 2H), 4.00 (s, 3H), 3.70 (t, 2H), 3.14 (m, 2H), 2.51 (qd, 2H), 1.91 (m, 3H), 1.38 (t, 3H), 1.11 (t, 3H), 0.92 (s, 9H), 0.07 (s, 6H).

Intermediate 56

(rac)-ethyl (Z)-1-(3-((tert-butyldimethylsilyl)oxy)propyl)-12-ethyl-13-fluoro-10-methyl-4,7,9,10-tetrahydropyrazolo[4',3':9,10][1]oxa[6]azacycloundecino[8,7,6-hi]indole-2-carboxylate (SF0217-198)

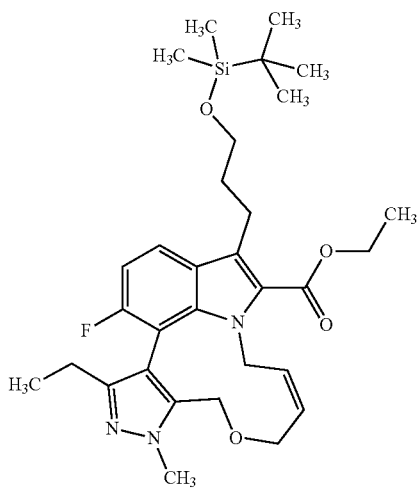 [SMILES: CCOC(=O)c1c(CCCO[Si](C)(C)C(C)(C)C)c2ccc(F)c3c2n1C/C=C\COCc1c-3c(CC)nn1C]

To a room temperature stirred solution of (rac)-ethyl 3-(3-((tert-butyldimethylsilyhoxy)propyl)-7-(3-ethyl-5-(hydroxymethyl)-1-methyl-1H-pyrazol-4-yl)-6-fluoro-1H-indole-2-carboxylate (see Intermediate 55, 2.58 g, 5.00 mmol, 1.00 eq.) in argon degassed anhydrous acetonitrile (50.0 mL, 0.10 M) was added cesium carbonate (8.14 g, 25.0 mmol, 5.00 eq.). After stirring for 10 minutes, 1,4-dichlorobutene (578 µL, 5.50 mmol, 1.10 eq.) and sodium iodide (1.49 g, 10.0 mmol, 2.00 eq.) was added to the mixture and the resulting yellow suspension was heated at 40° C. for 24 hours. The mixture was cooled to room temperature and filtered through a Celite plug. Celite was added to the resulting solution, volatiles were removed under reduced pressure, and the residue was loaded onto a silica gel cartridge which was subjected to flash column chromatography (0-100% ethyl acetate/hexanes gradient) to give the title compound as a colourless oil (2.14 g).

LC-MS (Method 3): $R_t$=2.23 min; MS (ESIpos): m/z=570 [M+H]$^+$.

$^1$H-NMR (300 MHz, CHLOROFORM-d) δ [ppm]: 7.67 (dd, 1H), 6.95 (t, 1H), 5.27 (m, 1H), 5.09 (m, 2H), 4.76 (m, 1H), 4.63 (d, 1H), 4.38 (m, 3H), 3.99 (s, 3H), 3.83 (dd, 1H), 3.69 (m, 3H), 3.12 (m, 2H), 2.25 (m, 2H), 1.91 (m, 2H), 1.41 (t, 3H), 0.94 (m, 12H), 0.07 (s, 6H).

Intermediate 57

(rac)-ethyl 12-ethyl-13-fluoro-1-(3-hydroxypropyl)-10-methyl-4,5,6,7,9,10-hexahydropyrazolo-[4',3':9,10][1]oxa[6]azacycloundecino[8,7,6-hi]indole-2-carboxylate (SF0217-207)

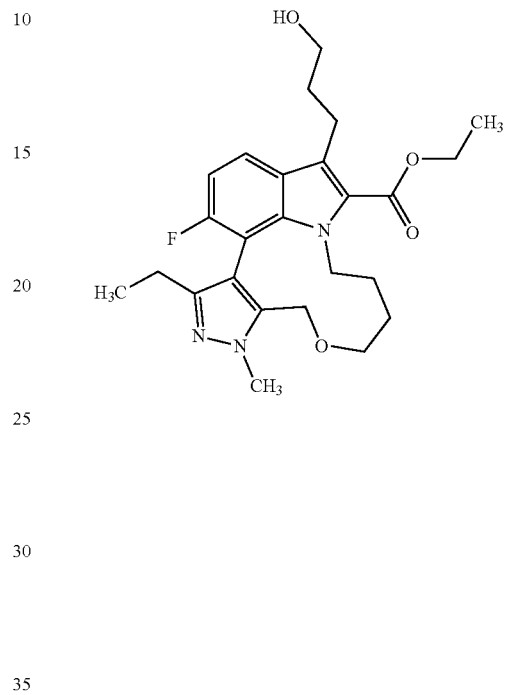

To a stirred solution of (rac)-ethyl (Z)-1-(3-((tert-butyldimethylsilyl)oxy)propyl)-12-ethyl-13-fluoro-10-methyl-4,7,9,10-tetrahydropyrazolo[4',3':9,10][1]oxa[6]azacycloundecino[8,7,6-hi]indole-2-carboxylate (see Intermediate 56, 2.14 g, 3.75 mmol, 1.00 eq.) in absolute ethanol (37.5 mL, 0.10 M) was added Wilkinson's catalyst (693 mg, 0.75 mmol, 0.20 eq.). The resulting dark suspension was evacuated and then placed under a hydrogen atmosphere and stirred for 10 hours at room temperature. Following complete reduction, the mixture was sparged with nitrogen to remove any residual hydrogen. Concentrated hydrochloric acid (305 µL, 3.75 mmol, 1.00 eq.) was added and the orange mixture was stirred for a further 15 minutes. Following complete deprotection the mixture was concentrated under reduced pressure. The residue was purified by flash column chromatography (0-40% acetone/dichloromethane gradient) followed by reverse phase column chromatography (10-100% acetonitrile/water with 0.1% formic acid gradient) to give the title compound as an off white solid (932 mg).

LC-MS (Method 4): $R_t$=3.18 min; MS (ESIpos): m/z=458 [M+H]$^+$.

$^1$H-NMR (300 MHz, CHLOROFORM-d) δ [ppm]: 7.65 (dd, 1H), 6.96 (t, 1H), 4.59 (d, 1H), 4.40 (m, 4H), 4.15 (ddd, 1H), 3.96 (s, 3H), 3.57 (m, 3H), 3.19 (m, 2H), 2.96 (ddd, 1H), 2.35 (qd, 3H), 1.98 (m, 2H), 1.40 (m, 4H), 1.19 (m, 3H), 1.01 (t, 3H).

Intermediate 58

(rac)-ethyl 1-(3-bromopropyl)-12-ethyl-13-fluoro-10-methyl-4,5,6,7,9,10-hexahydropyrazolo-[4',3':9,10][1]oxa[6]azacycloundecino[8,7,6-hi]indole-2-carboxylate (SF0217-216)

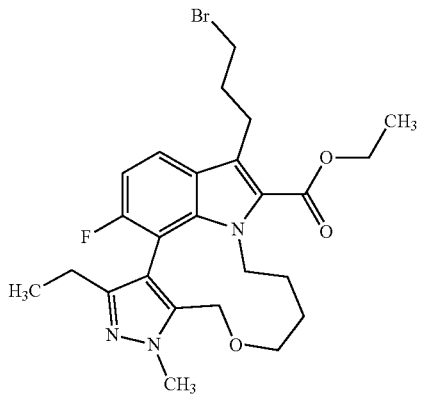 [SMILES: CCOC(=O)c1c(CCCBr)c2ccc(F)c3c2n1CCCCOCc1c-3c(CC)nn1C]

To a 0° C. stirred solution of (rac)-ethyl 12-ethyl-13-fluoro-1-(3-hydroxpropyl)-10-methyl-4,5,6,7,9,10-hexahydropyrazolo[4',3':9,10][1]oxa[6]azacycloundecino[8,7,6-hi]indole-2-carboxylate (see Intermediate 57, 931 mg, 2.03 mmol, 1.00 eq.) and triphenylphosphine (584 mg, 2.23 mmol, 1.10 eq.) in anhydrous dichloromethane (20.2 mL, 0.10 M) was added carbon tetrabromide (739 g, 2.23 mmol, 1.10 eq.) in one portion. The resulting mixture was warmed to room temperature and stirred for 1 hour. Celite was added to the resulting mixture, volatiles were removed under reduced pressure, and the residue was loaded onto a silica gel cartridge which was subjected to flash column chromatography (0-20% acetone/dichloromethane gradient) to give the title compound as a oil (925 mg).

LC-MS (Method 4): $R_t$=4.63 min; MS (ESIpos): m/z=520 [M+H]$^+$.

$^1$H-NMR (300 MHz, CHLOROFORM-d) δ [ppm]: 7.69 (dd, 1H), 6.97 (t, 1H), 4.59 (m, 2H), 4.40 (m, 3H), 4.13 (ddd, 1H), 3.96 (s, 3H), 3.50 (m, 3H), 3.22 (m, 2H), 2.92 (ddd, 1H), 2.31 (m, 4H), 1.42 (m, 4H), 1.23 (m, 3H), 1.01 (t, 3H).

Intermediate 59

(rac)-ethyl 12-ethyl-13-fluoro-10-methyl-1-(3-(naphthalen-1-yloxy)propyl)-4,5,6,7,9,10-hexahydropyrazolo[4',3':9,10][1]oxa[6]azacycloundecino[8,7,6-hi]indole-2-carboxylate

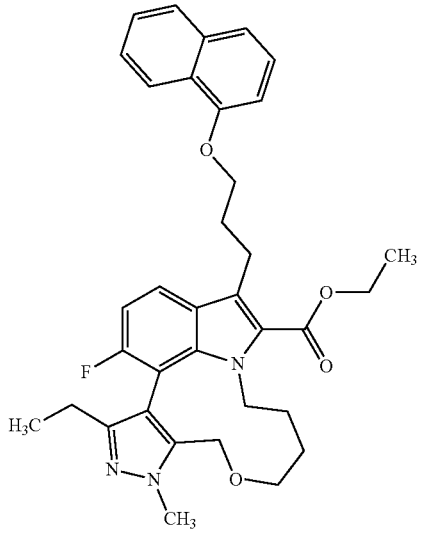 [SMILES: CCOC(=O)c1c(CCCOc2cccc3ccccc23)c2ccc(F)c3c2n1CCCCOCc1c-3c(CC)nn1C]

To a stirred solution of (rac)-ethyl 1-(3-bromopropyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 58, 156 mg, 0.30 mmol, 1.00 eq.) in anhydrous tetrahydrofuran (3.00 mL, 0.10 M) was added cesium carbonate (583 mg, 1.79 mmol, 6.00 eq.) and naphthalen-1-ol (86.5 mg, 0.60 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a tan solid (159 mg).

LC-MS (Method 4): $R_t$=5.49 min; MS (ESIpos): m/z=584 [M+H]$^+$.

$^1$H-NMR (300 MHz, CHLOROFORM-d) δ [ppm]: 8.36 (m, 1H), 7.82 (m, 1H), 7.67 (dd, 1H), 7.45 (m, 4H), 6.88 (t, 1H), 6.77 (dd, 1H), 4.60 (d, 2H), 4.33 (m, 6H), 3.97 (s, 3H), 3.42 (m, 3H), 2.93 (m, 1H), 2.35 (m, 4H), 1.34 (m, 7H), 1.01 (t, 3H).

Intermediate 60

(rac)-ethyl 12-ethyl-13-fluoro-1-(3-((6-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylate

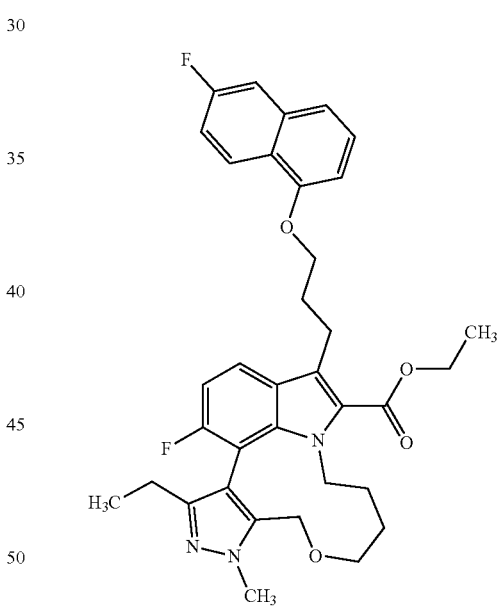

To a stirred solution of (rac)-ethyl 1-(3-bromopropyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 58, 156 mg, 0.30 mmol, 1.00 eq.) in anhydrous tetrahydrofuran (3.00 mL, 0.10 M) was added cesium carbonate (583 mg, 1.79 mmol, 6.00 eq.) and 6-fluoronaphthalen-1-ol (97.2 mg, 0.60 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a tan solid (157 mg).

LC-MS (Method 4): $R_t$=5.55 min; MS (ESIpos): m/z=602 [M+H]$^+$.

$^1$H-NMR (300 MHz, CHLOROFORM-d) δ [ppm]: 8.34 (dd, 1H), 7.65 (dd, 1H), 7.38 (m, 3H), 7.26 (s, 4H), 6.88 (t, 1H), 6.71 (dd, 1H), 4.59 (m, 2H), 4.30 (m, 6H), 3.96 (s, 3H), 3.42 (m, 3H), 2.93 (ddd, 1H), 2.34 (m, 4H), 1.33 (m, 7H), 1.01 (t, 3H).

Intermediate 61

(rac)-ethyl 12-ethyl-13-fluoro-1-(3-((4-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylate

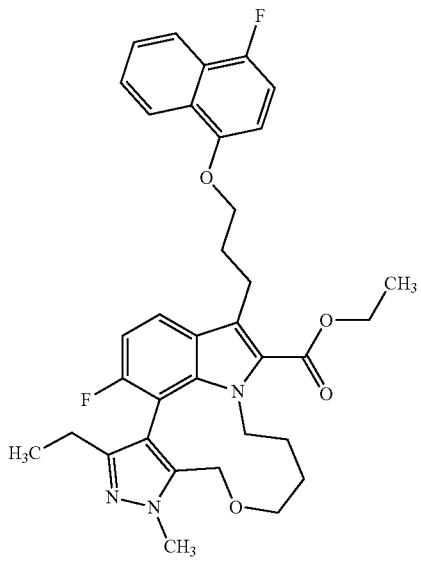 [SMILES: CCOC(=O)c1c(CCCOc2ccc(F)c3ccccc23)c2ccc(F)c3c2n1CCCCOCc1c-3c(CC)nn1C]

To a stirred solution of (rac)-ethyl 1-(3-bromopropyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 58, 156 mg, 0.30 mmol, 1.00 eq.) in anhydrous tetrahydrofuran (3.00 mL, 0.10 M) was added cesium carbonate (583 mg, 1.79 mmol, 6.00 eq.) and 4-fluoronaphthalen-1-ol (97.2 mg, 0.60 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as an orange solid (146 mg).

LC-MS (Method 4): $R_t$=5.60 min; MS (ESIpos): m/z=602 [M+H]$^+$.

$^1$H-NMR (300 MHz, CHLOROFORM-d) δ [ppm]: 8.33 (m, 1H), 8.06 (m, 1H), 7.60 (m, 3H), 7.01 (dd, 1H), 6.87 (t, 1H), 6.63 (dd, 1H), 4.59 (m, 2H), 4.35 (m, 3H), 4.16 (m, 3H), 3.96 (s, 3H), 3.41 (m, 3H), 2.93 (ddd, 1H), 2.33 (m, 4H), 1.34 (m, 7H), 1.01 (t, 3H).

Intermediate 62

(rac)-ethyl 12-ethyl-13-fluoro-10-methyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylate

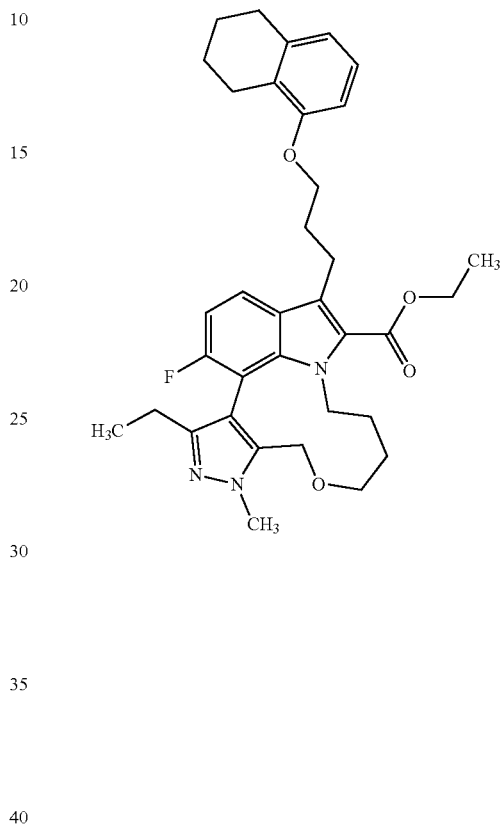

To a stirred solution of (rac)-ethyl 1-(3-bromopropyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 58, 78.0 mg, 0.15 mmol, 1.00 eq.) in anhydrous tetrahydrofuran (1.50 mL, 0.10 M) was added cesium carbonate (293 mg, 0.90 mmol, 6.00 eq.) and 5,6,7,8-tetrahydronaphthalen-1-ol (44.4 mg, 0.30 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a light pink solid (77.0 mg).

LC-MS (Method 4): $R_t$=5.92 min; MS (ESIpos): m/z=588, [M+H]$^+$.

$^1$H-NMR (300 MHz, CHLOROFORM-d) δ [ppm]: 7.65 (dd, 1H), 7.04 (t, 1H), 6.93 (t, 1H), 6.70 (d, 1H), 6.62 (m, 1H), 4.60 (m, 2H), 4.38 (m, 3H), 4.13 (ddd, 1H), 4.03 (t, 2H), 3.96 (s, 3H), 3.54 (dt, 1H), 3.26 (m, 2H), 2.93 (ddd, 1H), 2.77 (m, 4H), 2.35 (m, 2H), 2.18 (m, 2H), 1.79 (m, 4H), 1.36 (m, 7H), 1.01 (t, 3H).

Intermediate 63

(rac)-ethyl 1-(3-((2,3-dihydro-1H-inden-4-yl)oxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate

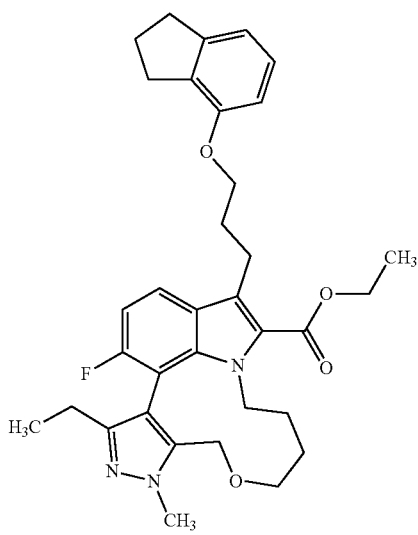 [SMILES: CCOC(=O)c1c(CCCOc2cccc3c2CCC3)c2ccc(F)c3c2n1CCCCOCc1c-3c(CC)nn1C]

To a stirred solution of (rac)-ethyl 1-(3-bromopropyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 58, 78.0 mg, 0.15 mmol, 1.00 eq.) in anhydrous tetrahydrofuran (1.50 mL, 0.10 M) was added cesium carbonate (293 mg, 0.90 mmol, 6.00 eq.) and 4-indanol (40.2 mg, 0.30 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as a tan solid (75.3 mg).

LC-MS (Method 4): $R_t$=5.63 min; MS (ESIpos): m/z=574 [M+H]$^+$.

$^1$H-NMR (300 MHz, CHLOROFORM-d) δ [ppm]: 7.66 (dd, 1H), 7.09 (t, 1H), 6.90 (m, 2H), 6.63 (d, 1H), 4.60 (m, 2H), 4.36 (m, 3H), 4.08 (m, 3H), 3.96 (s, 3H), 3.54 (dt, 1H), 3.25 (m, 2H), 2.94 (m, 5H), 2.35 (m, 2H), 2.11 (m, 4H), 1.40 (m, 7H), 1.01 (t, 3H).

Intermediate 64

(rac)-ethyl 1-(3-(4-chloro-3,5-dimethylphenoxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate

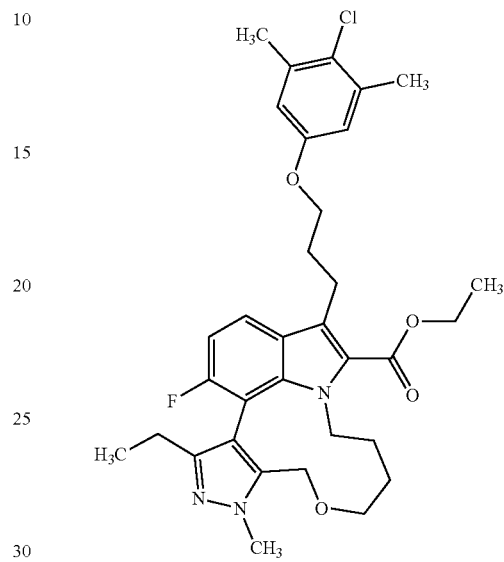

To a stirred solution of (rac)-ethyl 1-(3-bromopropyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 58, 78.0 mg, 0.15 mmol, 1.00 eq.) in anhydrous tetrahydrofuran (1.50 mL, 0.10 M) was added cesium carbonate (293 mg, 0.90 mmol, 6.00 eq.) and 4-chloro-3,5-dimethylphenol (46.9 mg, 0.30 mmol, 2.00 eq.). The resulting suspension was heated at 55° C. for 20 hours and cooled to room temperature. Celite was added to the resulting suspension, volatiles were removed under reduced pressure, and the residue was loaded onto a silica gel cartridge which was subjected to reverse phase column chromatography (10-100% acetonitrile/water with 0.1% formic acid gradient) to give the title compound as an off white solid (77.2 mg).

LC-MS (Method 4): $R_t$=5.81 min; MS (ESIpos): m/z=596 [M+H]$^+$.

$^1$H-NMR (300 MHz, CHLOROFORM-d) δ [ppm]: 7.64 (dd, 1H), 6.92 (t, 1H), 6.63 (s, 2H), 4.60 (m, 2H), 4.36 (m, 3H), 4.12 (m, 1H), 3.96 (m, 5H), 3.54 (m, 1H), 3.23 (m, 2H), 2.94 (m, 1H), 2.33 (m, 8H), 2.14 (m, 2H), 1.37 (m, 7H), 1.01 (t, 3H).

Intermediate 65

(rac)-ethyl 1-{4-[bis(tert-butoxycarbonyl)amino]butyl}-6-fluoro-7-[3-(hydroxymethyl)-1,5-dimethyl-1H-pyrazol-4-yl]-3-{3-[(naphthalen-1-yl)oxy]propyl}-1H-indole-2-carboxylate

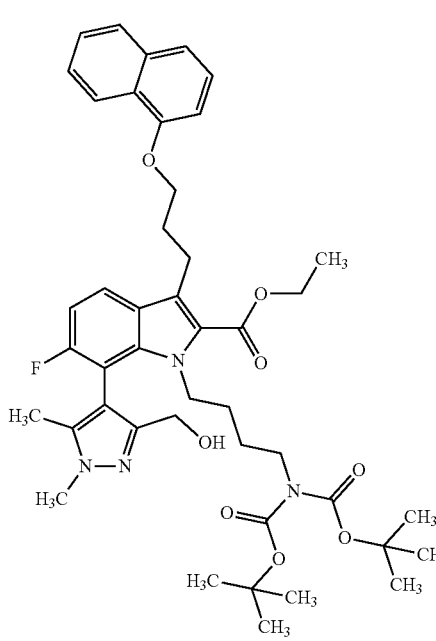

To a room temperature stirred suspension of (rac)-ethyl 6-fluoro-7-[3-(hydroxymethyl)-1,5-dimethyl-1H-pyrazol-4-yl]-3-[3-(naphthalen-1-yloxy)propyl]-1H-indole-2-carboxylate (see Intermediate 14, 1.45 g) in anhydrous N,N-dimethylformamide (35.1 mL, 0.08 M) was added cesium carbonate (4.58 g). After stirring for 30 minutes, a 1.0 M solution of di-tert-butyl (4-bromobutyl)-2-imidodicarbonate (Intermediate 1, 1.19 g) in anhydrous N,N-dimethylformamide (3.38 mL) was added dropwise to the mixture. Following complete addition, the resulting light yellow suspension was stirred at room temperature for 7 days and then concentrated under reduced pressure. Water (50 mL) was added to the residue and extracted with ethyl acetate (3×50 mL). The combined organic extracts were washed with water (50 mL), brine (50 mL), dried (sodium sulfate), filtered and concentrated under reduced pressure. Celite was added to the residue, volatiles were removed under reduced pressure, and the residue was loaded onto a isolute HMN-R cartridge which was subjected to flash chromatographyonto (3-30% acetone/dichloromethane gradient) to give the title compound as a white solid (1.40 g).

LC-MS (Method 1): $R_t$=1.77 min; MS (ESIpos): m/z=787 [M+H]$^+$ $^1$H-NMR (400 MHz, CHLOROFORM-d) δ [ppm]: 1.367 (0.79), 1.386 (1.60), 1.403 (0.78), 1.465 (16.00), 1.514 (2.41), 2.139 (2.23), 3.889 (2.28), 4.214 (0.75), 4.340 (0.66), 4.358 (0.63), 4.491 (0.66), 7.428 (0.43), 7.502 (0.40), 7.525 (0.42).

Intermediate 66

(rac)-ethyl 1-{4-[bis(tert-butoxycarbonyl)amino]butyl}-7-[3-(bromomethyl)-1,5-dimethyl-1H-pyrazol-4-yl]-6-fluoro-3-{3-[(naphthalen-1-yl)oxy]propyl}-1H-indole-2-carboxylate

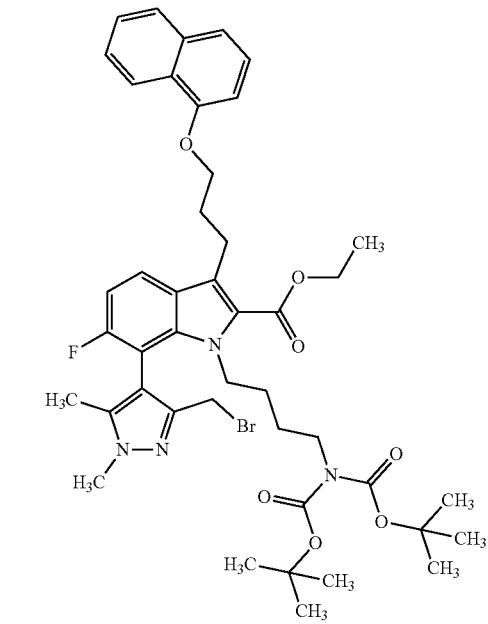 [SMILES: CCOC(=O)c1c(CCCOc2cccc3ccccc23)c2ccc(F)c(-c3c(CBr)nn(C)c3C)c2n1CCCCN(C(=O)OC(C)(C)C)C(=O)OC(C)(C)C]

To a 0° C. stirred solution of (rac)-ethyl 1-{4-[bis(tert-butoxycarbonyl)amino]butyl}-6-fluoro-7-[3-(hydroxymethyl)-1,5-dimethyl-1H-pyrazol-4-yl]-3-{3-[(naphthalen-1-yl)oxy]propyl}-1H-indole-2-carboxylate (see Intermediate 65, 1.40 g) in anhydrous dichloromethane (35.6 mL, 0.05 M) triphenylphosphine (700 mg, 2.67 mmol, 1.50 eq.) was added. After stirring for 10 minutes, carbon tetrabromide (885 mg, 2.67 mmol, 1.50 eq.) was added to the mixture and the resulting solution was warmed to room temperature, stirred for 2 hours and then concentrated under reduced pressure. Celite was added to the residue, volatiles were removed under reduced pressure, and the residue was loaded onto Isolute HMN-R which was subjected to flash chromatography (7-60% ethyl acetate/hexanes gradient) to give the title compound as a white solid (1.22 g).

LC-MS (Method 1): $R_t$=1.88 min; MS (ESIpos): m/z=849 [M+H]$^+$ $^1$H-NMR (400 MHz, CHLOROFORM-d) δ [ppm]: 1.372 (0.83), 1.391 (1.69), 1.408 (0.83), 1.462 (16.00), 1.579 (0.61), 2.174 (2.52), 3.319 (0.41), 3.912 (2.74), 4.221 (0.62), 4.280 (0.67), 4.298 (0.68), 4.348 (0.40), 4.361 (0.41), 7.429 (0.43), 7.502 (0.42), 7.525 (0.44).

Intermediate 67

(rac)-ethyl 1-(4-aminobutyl)-7-[3-(bromomethyl)-1,5-dimethyl-1H-pyrazol-4-yl]-6-fluoro-3-{3-[(naphthalen-1-yl)oxy]propyl}-1H-indole-2-carboxylate-hydrochloric acid salt

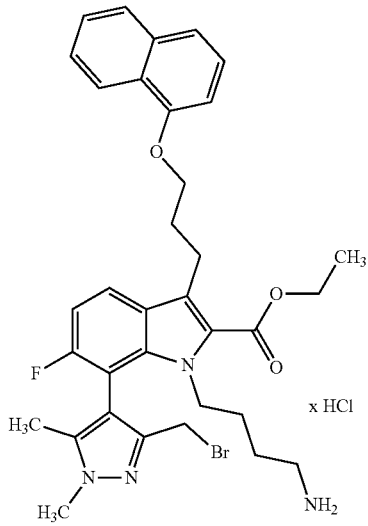 [SMILES: CCOC(=O)c1c(CCCOc2cccc3ccccc23)c2ccc(F)c(-c3c(CBr)nn(C)c3C)c2n1CCCCN ; "x HCl"]

To a 0° C. stirred solution of (rac)-ethyl 1-{4-[bis(tert-butoxycarbonyl)amino]butyl}-7-[3-(bromo-methyl)-1,5-dimethyl-1H-pyrazol-4-yl]-6-fluoro-3-{3-[(naphthalen-1-yl)oxy]propyl}-1H-indole-2-carboxylate (see Intermediate 66, 1.22 g) in methanol (14.4 mL, 0.10 M) a 4.0 M hydrochloric acid in dioxanes solution (1.79 mL, 7.18 mmol) was added. The resulting mixture was warmed to room temperature, stirred for 3 hours and then concentrated under reduced pressure to give a white solid (1.06 g). The crude product was used directly in the next step without further purification.

LC-MS (Method 1): $R_t$=1.32 min; MS (ESIpos): m/z=649 [M+H]$^+$ $^1$H-NMR (400 MHz, CHLOROFORM-d) δ [ppm]: 1.200 (1.78), 1.284 (0.53), 1.373 (2.03), 1.390 (4.04), 1.408 (2.39), 1.420 (5.28), 1.584 (0.64), 1.635 (9.59), 1.813 (0.98), 2.160 (0.84), 2.233 (2.72), 2.320 (1.42), 2.335 (1.13), 2.917 (0.75), 3.225 (0.58), 3.346 (1.07), 3.364 (1.79), 3.381 (0.99), 3.715 (16.00), 3.945 (1.12), 4.124 (0.41), 4.195 (2.48), 4.208 (4.01), 4.222 (2.54), 4.312 (0.78), 4.343 (2.02), 4.360 (2.20), 4.461 (0.44), 4.490 (0.53), 4.522 (0.45), 6.771 (1.49), 6.789 (1.60), 6.891 (0.65), 6.914 (1.22), 6.936 (0.65), 7.342 (0.91), 7.362 (1.84), 7.381 (1.41), 7.425 (2.31), 7.446 (1.33), 7.480 (0.43), 7.492 (1.43), 7.497 (2.31), 7.506 (2.62), 7.516 (2.46), 7.520 (1.72), 7.532 (0.49), 7.711 (0.48), 7.721 (0.79), 7.733 (0.91), 7.743 (0.78), 7.756 (0.54), 7.812 (1.34), 7.822 (0.80), 7.829 (0.99), 7.835 (1.14), 8.332 (1.32), 8.339 (1.20), 8.346 (1.10), 8.356 (1.65), 8.372 (0.98), 8.386 (0.98).

Intermediate 68

(rac)-ethyl 4-fluoro-2,3-dimethyl-7-{3-[(naphthalen-1-yl)oxy]propyl}-10,11,12,13,14,15-hexa-hydro-2H-pyrazolo[3',4':8,9][1,6]diazacycloundecino[10,11,1-hi]indole-8-carboxylate

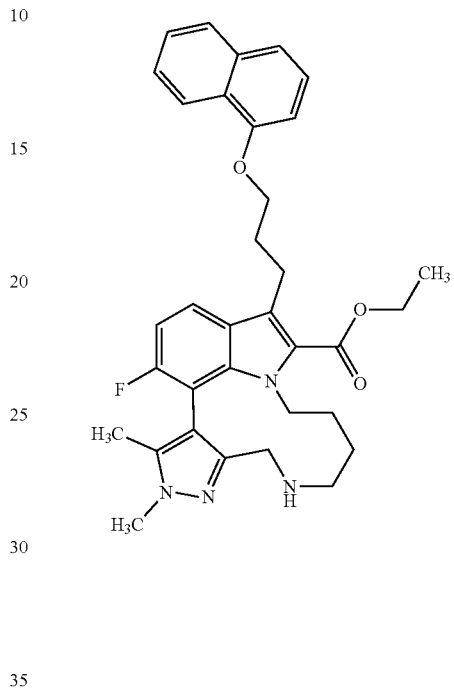

To a stirred solution of (rac)-ethyl 1-(4-aminobutyl)-7-[3-(bromomethyl)-1,5-dimethyl-1H-pyrazol-4-yl]-6-fluoro-3-{3-[(naphthalen-1-yl)oxy]propyl}-1H-indole-2-carboxylate-hydrochloric acid salt (see Intermediate 67, 1.04 g) in anhydrous N,N-dimethylformamide (144 mL, 0.01 M) cesium carbonate (2.34 g, 7.18 mmol) was added. The resulting suspension was heated at 65° C. for 17 hours, cooled to room temperature and concentrated under reduced pressure. Water (20 mL) was added to the residue and extracted with ethyl acetate (3×20 mL). The combined organic extracts were washed with water (20 mL), brine (20 mL), dried (sodium sulfate), filtered and concentrated under reduced pressure. The residue was purified by flash column chromatography (7-60% acetone/dichloromethane gradient followed by 0-100% methanol/dichloromethane gradient) to give the title compound as an off white solid (398 mg).

LC-MS (Method 2): $R_t$=1.61 min; MS (ESIpos): m/z=569 [M+H]$^+$ $^1$H-NMR (400 MHz, CHLOROFORM-d) δ [ppm]: 1.099 (1.39), 1.368 (7.28), 1.385 (9.81), 1.402 (5.74), 1.978 (13.53), 2.102 (0.61), 2.262 (1.84), 2.332 (3.83), 2.717 (1.56), 2.898 (1.01), 3.321 (1.71), 3.338 (2.00), 3.416 (1.83), 3.432 (1.53), 3.447 (1.23), 3.790 (1.81), 3.826 (3.20), 3.895 (16.00), 3.934 (2.22), 4.078 (1.54), 4.095 (1.40), 4.218 (5.53), 4.327 (2.45), 4.343 (2.78), 4.354 (2.77), 4.372 (2.34), 4.571 (1.57), 4.605 (1.46), 6.779 (2.76), 6.797 (2.88), 6.867 (1.50), 6.889 (2.60), 6.911 (1.52), 7.348 (1.51), 7.367 (2.84), 7.386 (2.15), 7.427 (3.51), 7.447 (2.30), 7.512 (4.87), 7.644 (1.73), 7.663 (2.18), 7.676 (1.69), 7.815 (2.45), 7.827 (2.50), 8.374 (2.43).

Intermediate 69

8-(ethoxycarbonyl)-4-fluoro-2,3,14,14-tetramethyl-7-[3-(1-naphthyloxy)propyl]-10,11,12,13,14,15-hexahydro-2H-pyrazolo[3',4':8,9][1,6]diazacycloundecino[10,11,1-hi]indol-14-ium-trifluroacetate

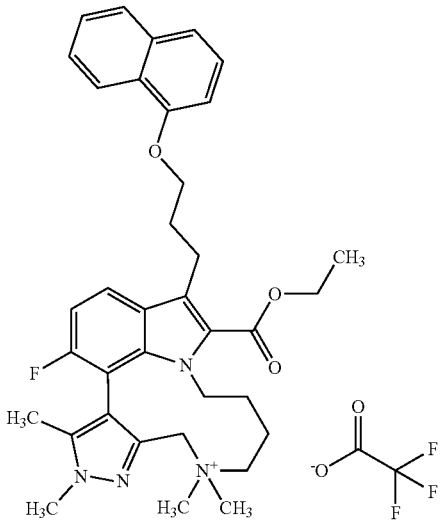

To a 0° C. stirred solution of (rac)-ethyl 4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylate (see Intermediate 68, 113 mg) in anhydrous N,N-dimethylformamide (2.00 mL, 0.10 M) was carefully added sodium hydride (60%, 23.8 mg, 0.60 mmol). Iodomethane (61.8 µL, 1.00 mmol, 5.00 eq.) was added to the mixture and the resulting solution was warmed to room temperature and stirred for 1 hour. The mixture was diluted with dimethyl sulfoxide, filtered and then purified by reverse phase column chromatography (10-100% acetonitrile/water with 0.1% trifluoroacetic acid gradient) to give the title compound as a white solid (54.3 mg).

LC-MS (Method 3): $R_t$=1.50 min; MS (ESIpos): m/z=597 [M+H]$^+$.

$^1$H-NMR (300 MHz, CHLOROFORM-d) δ [ppm]: 8.32 (d, 1H), 7.82 (d, 1H), 7.76 (dd, 1H), 7.49 (m, 2H), 7.43 (d, 1H), 7.36 (t, 1H), 6.92 (t, 1H), 6.78 (d, 1H), 4.84 (d, 1H), 4.36 (m, 2H), 4.23 (m, 3H), 4.01 (d, 1H), 3.95 (s, 3H), 3.85 (t, 1H), 3.60 (s, 3H), 3.41 (m, 3H), 3.06 (s, 3H), 2.55 (t, 1H), 2.33 (m, 2H), 2.02 (s, 3H), 1.58 (m, 2H), 1.39 (t, 3H), 1.30 (m, 1H), 0.92 (m, 1H).

Intermediate 70 tert-butyl (4-bromobutyl)methylcarbamate

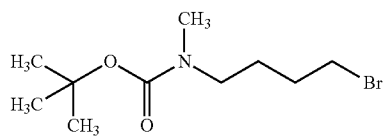

Tert-butyl (4-hydroxybutyl)methylcarbamate (CAS 99207-32-6, 10.6 g, 95% purity, 49.3 mmol) and triphenylphosphane (17.5 g, 66.6 mmol) were provided in 200 mL of dichloromethane at 0° C. and tetrabromomethane (21.5 g, 64.1 mmol) was added slowly and in portions. The mixture was stirred overnight at rt and concentrated under reduced pressure. The residue was triturated with hexane, the solid material was isolated by filtration and dried under reduced pressure to give the title compound (15.5 g).

$^1$H-NMR (400 MHz, DMSO-d6) δ [ppm]: 1.388 (16.00), 2.748 (0.68), 3.157 (0.57), 3.174 (1.09), 3.192 (0.55), 3.532 (0.81), 3.549 (1.66), 3.565 (0.80), 7.698 (1.28).

Intermediate 71

(rac)-ethyl 1-(4-{[(tert-butoxy)carbonyl](methyl)amino}butyl)-3-{3-[(tert-butyldimethylsilyl)oxy]propyl}-7-[5-ethyl-3-(hydroxymethyl)-1-methyl-1H-pyrazol-4-yl]-6-fluoro-1H-indole-2-carboxylate

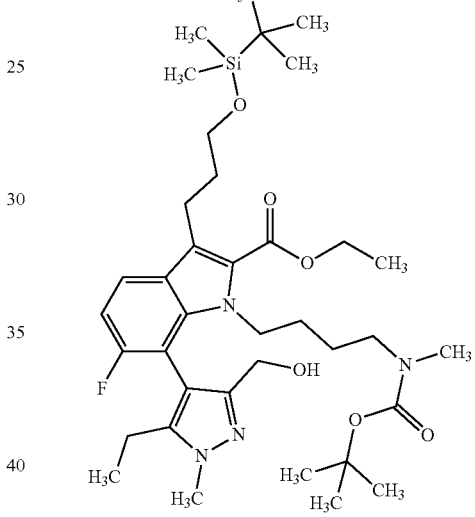

To a room temperature stirred solution of (rac)-ethyl 3-(3-((tert-butyldimethylsilyhoxy)propyl)-7-(5-ethyl-3-(hydroxymethyl)-1-methyl-1H-pyrazol-4-yl)-6-fluoro-1H-indole-2-carboxylate (see Intermediate 37, 4.14 g, 8.00 mmol, 1.00 eq.) in anhydrous N,N-dimethylformamide (80.0 mL, 0.10 M) was added cesium carbonate (13.1 g, 40.0 mmol, 10.0 eq.). After stirring for 10 minutes, tert-butyl (4-bromobutyl)(methyl)carbamate (see Intermediate 70, 2.55 g, 9.60 mmol, 1.20 eq.) was added and the resulting orange suspension was then stirred at room temperature for 5 days. Water (100 mL) was added to the reaction mixture and then extracted with ethyl acetate (3×50 mL). The combined organic extracts were washed with water (3×50 mL), brine (50 mL), dried (magnesium sulfate), filtered and concentrated under reduced pressure. The residue was purified by reverse phase column chromatography (10-100% acetonitrile/water with 0.1% ammonium hydroxide) followed by flash column chromatography (0-100% ethyl acetate/hexanes gradient) to give the title compound as a light yellow oil (2.59 g).

LC-MS (Method 4): Rt=6.02 min; MS (ESIpos): m/z=703 [M+H]$^+$.

$^1$H NMR (300 MHz, Chloroform-d) δ 7.66 (dd, J=8.8, 5.5 Hz, 1H), 6.96 (t, J=9.1 Hz, 1H), 4.47 (s, 2H), 4.36 (q, J=7.1

Hz, 2H), 4.24-4.04 (m, 2H), 3.91 (s, 3H), 3.69 (t, J=6.3 Hz, 2H), 3.16-2.79 (m, 4H), 2.73 (s, 3H), 2.66-2.32 (m, 2H), 1.96-1.73 (m, 2H), 1.46-1.14 (m, 15H), 1.11-0.95 (m, 5H), 0.93 (s, 9H), 0.07 (s, 6H).

Intermediate 72

(rac)-ethyl 7-[3-(bromomethyl)-5-ethyl-1-methyl-1H-pyrazol-4-yl]-1-(4-{[(tert-butoxy)carbonyl](methyl)amino}butyl)-3-{3-[(tert-butyldimethylsilyl)oxy]propyl}-6-fluoro-1H-indole-2-carboxylate

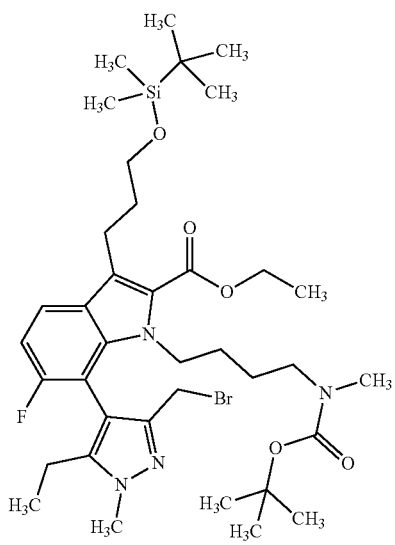 [SMILES: CCOC(=O)c1c(CCCO[Si](C)(C)C(C)(C)C)c2ccc(F)c(-c3c(CBr)nn(C)c3CC)c2n1CCCCN(C)C(=O)OC(C)(C)C]

To a 0° C. stirred solution of (rac)-ethyl 1-(4-{[(tert-butoxy)carbonyl](methyl)amino}butyl)-3-{3-[(tert-butyldimethylsilyl)oxy]propyl}-7-[5-ethyl-3-(hydroxymethyl)-1-methyl-1H-pyrazol-4-yl]-6-fluoro-1H-indole-2-carboxylate (see Intermediate 71, 2.59 g, 3.68 mmol, 1.00 eq.) in anhydrous dichloromethane (73.6 mL, 0.05 M) was added triphenylphosphine (1.44 g, 5.52 mmol, 1.50 eq.). After stirring for 10 minutes, tetrabromomethane (1.83 g, 5.52 mmol, 1.50 eq.) was added in one portion. The resulting mixture was warmed to room temperature, stirred for 2 hours and then dry loaded onto Celite. The residue was purified by flash column chromatography (0-20% acetone/dichloromethane gradient) to give the title compound as a colourless oil (2.46 g, >90% purity).

LC-MS (Method 4): Rt=6.69 min; MS (ESIpos): m/z=765 [M+H]⁺.

1H NMR (300 MHz, Chloroform-d) δ 7.69 (dd, J=8.8, 5.5 Hz, 1H), 6.97 (t, J=9.1 Hz, 1H), 4.36 (q, J=7.1 Hz, 2H), 4.28 (s, 2H), 3.92 (s, 3H), 3.69 (t, J=6.3 Hz, 2H), 3.15-2.80 (m, 4H), 2.73 (s, 3H), 2.68-2.39 (m, 2H), 1.94-1.80 (m, 2H), 1.41 (dq, J=7.2, 3.8 Hz, 15H), 1.23-0.99 (m, 6H), 0.93 (s, 9H), 0.07 (s, 6H).

Intermediate 73

(rac)-ethyl 3-ethyl-4-fluoro-7-(3-hydroxpropyl)-2,14-dimethyl-10,11,12,13,14,15-hexahydro-2H-pyrazolo[3',4':8,9][1,6]diazacycloundecino[10,11,1-hi]indole-8-carboxylate

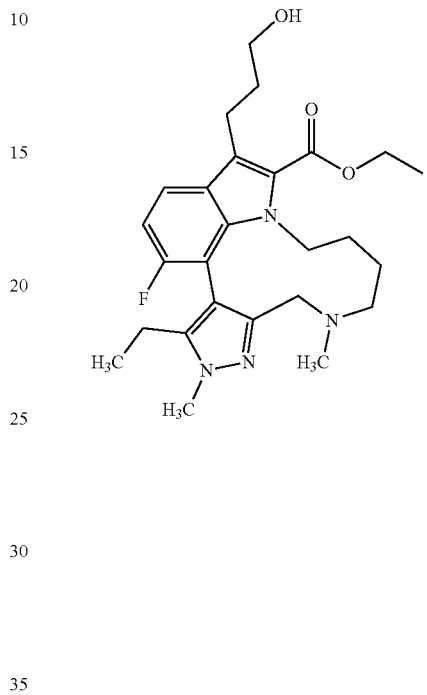

To a stirred solution of (rac)-ethyl 7-[3-(bromomethyl)-5-ethyl-1-methyl-1H-pyrazol-4-yl]-1-(4-{[(tert-butoxy)carbonyl](methyl)amino}butyl)-3-{3-[(tert-butyldimethylsilyl)oxy]propyl}-6-fluoro-1H-indole-2-carboxylate (see Intermediate 72, 2.46 g, 3.21 mmol, 1.00 eq.) in acetonitrile (64.1 mL, 0.05 M) was added a 4.0 M aqueous solution of hydrochloric acid (8.02 mL, 32.1 mmol, 10.0 eq.). The mixture was heated at 60° C. for 2 hours, after which cesium carbonate (15.7 g, 48.1 mmol, 15.0 eq.) was carefully added. The resulting suspension was heated at 60° C. for a further 6 hours, cooled to room temperature and concentrated. Water (100 mL) was added to the mixture and extracted with ethyl acetate (3×50 mL). The combined organic extracts were washed with brine (100 mL), dried (magnesium sulfate), filtered and concentrated under reduced pressure. The residue was purified by flash column chromatography (1-5% methanol/dichloromethane with 1% ammonia) followed by reverse phase column chromatography (10-100% acetonitrile/water with 0.1% ammonium hydroxide) to give the title compound as a white solid (695 mg).

LC-MS (Method 4): Rt=1.92 min; MS (ESIpos): m/z=471 [M+H]⁺.

1H NMR (300 MHz, Chloroform-d) δ 7.59 (dd, J=8.7, 5.4 Hz, 1H), 6.95 (t, J=9.0 Hz, 1H), 4.52-4.26 (m, 2H), 4.27-4.14 (m, 1H), 4.12-3.97 (m, 1H), 3.88 (s, 3H), 3.70-3.51 (m, 3H), 3.41 (d, J=12.7 Hz, 1H), 3.29-3.06 (m, 2H), 2.54 (s, 1H), 2.48-2.33 (m, 1H), 2.33-2.17 (m, 2H), 2.17-1.85 (m, 7H), 1.40 (t, J=7.1 Hz, 3H), 1.35-1.00 (m, 4H), 0.94 (t, J=7.6 Hz, 3H).

Intermediate 74

(rac)-ethyl 7-[3-(2,3-dihydro-1H-inden-4-yloxy)propyl]-3-ethyl-4-fluoro-2,14-dimethyl-10,11,12,13,14,15-hexahydro-2H-pyrazolo[3',4':8,9][1,6]diazacycloundecino[10,11,1-hi]indole-8-carboxylate

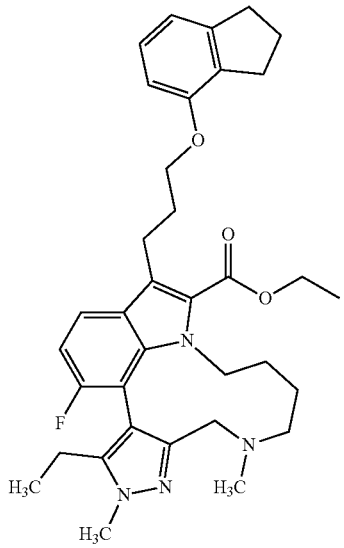 [SMILES: CCOC(=O)c1c(CCCOc2cccc3c2CCC3)c2ccc(F)c3c2n1CCCCN(C)Cc1nn(C)c(CC)c1-3]

To a room temperature stirred solution of (rac)-ethyl 3-ethyl-4-fluoro-7-(3-hydroxypropyl)-2,14-dimethyl-10,11,12,13,14,15-hexahydro-2H-pyrazolo[3',4':8,9][1,6]diazacycloundecino[10,11,1-hi]indole-8-carboxylate (see Intermediate 73, 94.1 mg, 0.20 mmol, 1.00 eq.), 4-indanol (40.2 mg, 0.30 mmol, 1.50 eq.) and triphenylphosphine (78.6 mg, 0.30 mmol, 1.50 eq.) in anhydrous tetrahydrofuran (2.50 mL, 0.08 M) was added di-tert-butyl azodicarboxylate (69.0 mg, 0.30 mmol, 1.50 eq.) in one portion. The resulting yellow solution was stirred at room temperature for 22 hours and then dry loaded onto Celite. The residue was purified by reverse phase flash column chromatography (acetonitrile/water with 0.1% ammonium hydroxide gradient) to give the title compound as a white solid (60.0 mg).

LC-MS (Method 4): Rt=3.43 min; MS (ESIpos): m/z=587 [M+H]$^+$.

1H NMR (300 MHz, DMSO-d6) δ 7.70 (dd, J=8.8, 5.5 Hz, 1H), 7.12-6.95 (m, 2H), 6.80 (d, J=7.3 Hz, 1H), 6.65 (d, J=8.0 Hz, 1H), 4.39-4.08 (m, 3H), 4.08-3.86 (m, 3H), 3.81 (s, 3H), 3.48 (d, J=12.4 Hz, 1H), 3.31-3.00 (m, 3H), 2.92-2.74 (m, 4H), 2.41-2.09 (m, 3H), 2.10-1.93 (m, 7H), 1.88-1.72 (m, 1H), 1.30 (t, J=7.1 Hz, 3H), 1.26-0.89 (m, 4H), 0.83 (t, J=7.5 Hz, 3H).

Intermediate 75

(rac)-ethyl 3-ethyl-4-fluoro-2,14-dimethyl-7-[3-(5,6,7,8-tetrahydronaphthalen-1-yloxy)propyl]-10,11,12,13,14,15-hexahydro-2H-pyrazolo[3',4':8,9][1,6]diazacycloundecino[10,11,1-hi]indole-8-carboxylate

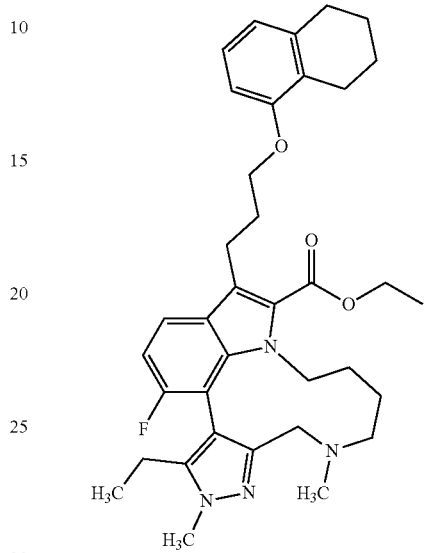

To a room temperature stirred solution of (rac)-ethyl 3-ethyl-4-fluoro-7-(3-hydroxypropyl)-2,14-dimethyl-10,11,12,13,14,15-hexahydro-2H-pyrazolo[3',4':8,9][1,6]diazacycloundecino[10,11,1-hi]indole-8-carboxylate (see Intermediate 73, 94.1 mg, 0.20 mmol, 1.00 eq.), 5,6,7,8-tetrahydronaphthalen-1-ol (44.4 mg, 0.30 mmol, 1.50 eq.) and triphenylphosphine (78.6 mg, 0.30 mmol, 1.50 eq.) in anhydrous tetrahydrofuran (2.50 mL, 0.08 M) was added di-tert-butyl azodicarboxylate (69.0 mg, 0.30 mmol, 1.50 eq.) in one portion. The resulting yellow solution was stirred at room temperature for 22 hours and then dry loaded onto Celite. The residue was purified by reverse phase flash column chromatography (60-100% acetonitrile/water gradient buffered with 0.1% ammonium hydroxide) to give the title compound as a white solid (51.2 mg).

LC-MS (Method 4): Rt=3.61 min; MS (ESIpos): m/z=601 [M+H]$^+$.

1H NMR (300 MHz, DMSO-d6) δ 7.70 (dd, J=8.8, 5.5 Hz, 1H), 7.05-6.78 (m, 2H), 6.63 (d, J=7.9 Hz, 2H), 4.38-4.09 (m, 3H), 4.06-3.85 (m, 3H), 3.81 (s, 3H), 3.48 (d, J=12.4 Hz, 1H), 3.31-3.04 (m, 3H), 2.76-2.57 (m, 4H), 2.43-1.93 (m, 9H), 1.89-1.61 (m, 5H), 1.29 (t, J=7.1 Hz, 3H), 1.28-0.88 (m, 5H), 0.83 (t, J=7.5 Hz, 3H).

Intermediate 76

(rac)-ethyl 3-ethyl-4-fluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indole-8-carboxylate

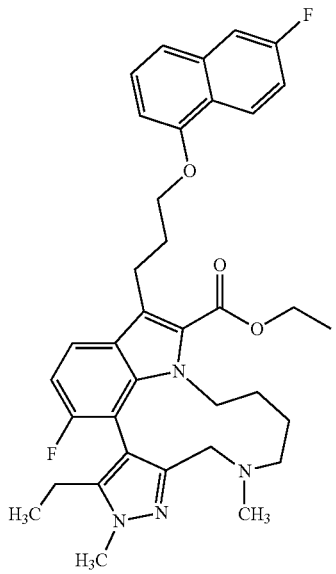 [SMILES: CCOC(=O)c1c(CCCOc2cccc3cc(F)ccc23)c2ccc(F)c3c2n1CCCCN(C)Cc1nn(C)c(CC)c1-3]

To a 0° C. stirred solution of (rac)-ethyl 3-ethyl-4-fluoro-7-(3-hydroxypropyl)-2,14-dimethyl-10,11,12,13,14,15-hexahydro-2H-pyrazolo[3',4':8,9][1,6]diazacycloundecino[10,11,1-hi]indole-8-carboxylate (see Intermediate 73, 101 mg, 0.21 mmol, 1.00 eq.) and 6-fluoronaphthalen-1-ol (41.7 mg, 0.26 mmol, 1.20 eq.) in anhydrous tetrahydrofuran (7.15 mL, 0.08 M) was added triphenylphosphine (84.4 mg, 0.32 mmol, 1.50 eq.). After stirring for 10 minutes, di-tert-butyl azodicarboxylate (74.1 mg, 0.32 mmol, 1.50 eq.) was added in one portion. The resulting mixture was warmed to room temperature, stirred for 1 hour and then dry loaded onto Celite. The residue was purified by reverse phase column chromatography (10-100% acetonitrile/water with 0.1% ammonium hydroxide gradient) to give the title compound as a white solid (115 mg, >80% purity). The material was used as is directly in the next step without further purification.

LC-MS (Method 4): Rt=3.81 min; MS (ESIpos): m/z=615 [M+H]⁺.

1H NMR (300 MHz, Chloroform-d) δ 8.36 (dd, J=9.2, 5.8 Hz, 1H), 7.63-7.54 (m, 1H), 7.46-7.30 (m, 2H), 7.30-7.17 (m, 2H), 6.88 (t, J=9.0 Hz, 1H), 6.71 (dd, J=6.1, 2.6 Hz, 1H), 4.45-4.24 (m, 3H), 4.20 (t, J=6.2 Hz, 2H), 4.13-3.96 (m, 1H), 3.89 (s, 3H), 3.58 (d, J=12.7 Hz, 1H), 3.50-3.17 (m, 3H), 2.50-2.18 (m, 5H), 2.18-1.96 (m, 4H), 1.74-1.41 (m, 4H), 1.43-1.03 (m, 10H), 0.93 (t, J=7.6 Hz, 3H).

Intermediate 77

(rac)-ethyl 3-ethyl-4-fluoro-2,14-dimethyl-7-[3-(1-naphthyloxy)propyl]-10,11,12,13,14,15-hexahydro-2H-pyrazolo[3',4':8,9][1,6]diazacycloundecino[10,11,1-hi]indole-8-carboxylate

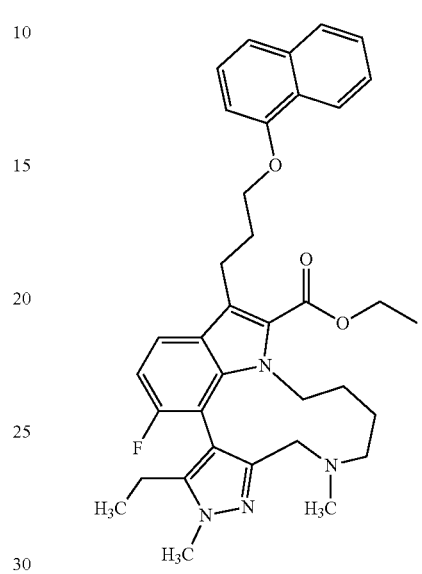

To a room temperature stirred solution of (rac)-ethyl 3-ethyl-4-fluoro-7-(3-hydroxypropyl)-2,14-dimethyl-10,11,12,13,14,15-hexahydro-2H-pyrazolo[3',4':8,9][1,6]diazacycloundecino[10,11,1-hi]indole-8-carboxylate (see Intermediate 73, 141 mg, 0.30 mmol, 1.00 eq.), naphthalen-1-ol (47.5 mg, 0.33 mmol, 1.05 eq.) and triphenylphosphine (118 mg, 0.45 mmol, 1.50 eq.) in anhydrous tetrahydrofuran (3.74 mL, 0.08 M) was added di-tert-butyl azodicarboxylate (103 mg, 0.45 mmol, 1.50 eq.) in one portion. The resulting yellow solution was stirred at room temperature for 16 hours and then dry loaded onto Celite. The residue was purified by reverse phase flash column chromatography (60-100% acetonitrile/water with 0.1% ammonium hydroxide gradient) to give the title compound as a colourless oil (87.4 mg, >95% purity).

LC-MS (Method 4): Rt=3.66 min; MS (ESIpos): m/z=597 [M+H]⁺.

1H NMR (300 MHz, Chloroform-d) δ 8.46-8.32 (m, 1H), 7.88-7.75 (m, 1H), 7.63 (dd, J=8.7, 5.4 Hz, 1H), 7.55-7.46 (m, 2H), 7.45-7.31 (m, 2H), 6.88 (t, J=9.0 Hz, 1H), 6.81-6.73 (m, 1H), 4.47-4.25 (m, 3H), 4.22 (t, J=6.2 Hz, 2H), 4.12-3.95 (m, 1H), 3.89 (s, 3H), 3.73-3.56 (m, 1H), 3.56-3.20 (m, 3H), 2.54-2.03 (m, 9H), 1.38 (t, J=7.1 Hz, 3H), 1.34-1.07 (m, 4H), 0.93 (t, J=7.6 Hz, 3H).

EXAMPLES

Example 1

(rac)-(11Z)-4-fluoro-2,3-dimethyl-7-[3-(naphthalen-1-yloxy)propyl]-2,10,13,15-tetrahydro-pyrazolo[4',3':9,10][1,6]oxazacycloundecino[8,7,6-hi]indole-8-carboxylic acid

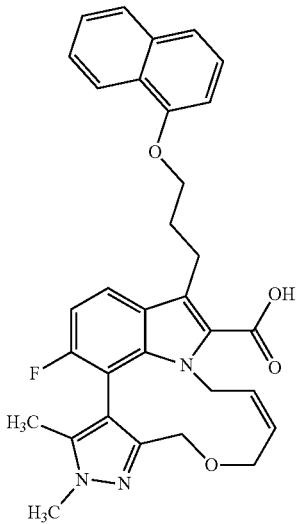 [SMILES: Cc1c2c(nn1C)COC/C=C\Cn1c(C(=O)O)c(CCCOc3cccc4ccccc34)c3ccc(F)c-2c31]

To a stirred solution of (rac)-ethyl (11Z)-4-fluoro-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 15, 105 mg, 185 µmol, 1.00 eq.) in ethanol (0.23 mL, 0.80 M) was added a 2.0 M solution of sodium hydroxide in water (0.23 mL, 462 µmol, 2.50 eq.). The resulting white suspension was heated at 70° C. for 17 h and then cooled to room temperature. The reaction mixture was diluted with water (5.00 mL), acidified to pH 2.0 with 1.0 M aqueous hydrochloric acid and extracted with ethyl acetate (3×10 mL). The combined organic extracts was washed with brine (10.0 mL), dried (sodium sulfate), filtered and concentrated under reduced pressure. The residue was purified by reverse phase column chromatography (65-100% Acetonitrile/water with 0.1% formic acid gradient) to give the title compound as a white solid (78.3 mg).

LC-MS (Method 1): $R_t$=1.42 min; MS (ESIneg): m/z=538 [M–H]⁻

¹H-NMR (400 MHz, CHLOROFORM-d) δ [ppm]: 1.960 (15.78), 2.347 (0.91), 2.363 (1.28), 2.382 (0.96), 3.427 (0.63), 3.446 (1.16), 3.470 (1.17), 3.489 (0.59), 3.774 (0.56), 3.787 (0.65), 3.805 (0.94), 3.818 (0.88), 3.901 (0.95), 3.929 (1.36), 3.946 (16.00), 3.959 (0.89), 4.205 (1.49), 4.220 (3.12), 4.235 (1.45), 4.442 (1.70), 4.474 (2.36), 4.595 (2.48), 4.628 (1.75), 4.838 (0.57), 4.864 (0.66), 4.877 (0.82), 4.903 (0.90), 5.071 (0.97), 5.110 (0.70), 5.270 (0.44), 5.277 (0.43), 5.297 (0.95), 5.303 (0.93), 5.323 (0.66), 5.330 (0.62), 5.369 (0.42), 5.380 (0.44), 5.396 (0.62), 5.408 (0.60), 6.757 (1.73), 6.775 (1.87), 6.909 (1.37), 6.931 (2.59), 6.953 (1.42), 7.328 (1.23), 7.348 (2.33), 7.367 (1.95), 7.409 (2.45), 7.430 (1.37), 7.457 (0.53), 7.466 (3.26), 7.475 (2.53), 7.482 (2.85), 7.490 (3.50), 7.499 (0.64), 7.684 (1.25), 7.697 (1.34), 7.706 (1.38), 7.719 (1.29), 7.791 (1.33), 7.799 (0.90), 7.807 (1.24), 7.815 (1.14), 8.334 (1.20), 8.343 (1.03), 8.350 (0.95), 8.358 (1.08).

Example 2

(rac)-4-fluoro-2,3-dimethyl-7-[3-(naphthalen-1-yloxy)propyl]-2,10,11,12,13,15-hexahydro-pyrazolo[4',3':9,10][1,6]oxazacycloundecino[8,7,6-hi]indole-8-carboxylic acid

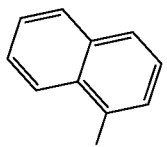
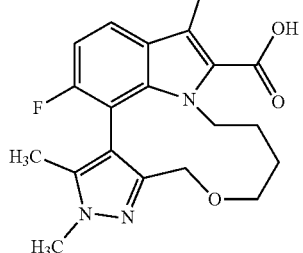

To a stirred solution of (rac)-ethyl 4-fluoro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 16, 126 mg, 221 µmol, 1.00 eq.) in ethanol (0.28 mL, 0.80 M) was added a 2.0 M solution of sodium hydroxide in water (0.28 mL, 553 µmol, 2.50 eq.). The resulting white suspension was heated at 70° C. for 2 days and cooled to room temperature. The mixture was diluted with water (10 mL), acidified to pH 2.0 with 1.0 M aqueous hydrochloric acid and extracted with ethyl acetate (3×10 mL). The combined organic extracts were washed with brine (10 mL), dried (sodium sulfate), filtered and concentrated under reduced pressure. The residue was dissolved in dimethyl sulfoxide, filtered through a PTFE filter and purified by reverse phase column chromatography (65-100% Acetonitrile/water with 0.1% formic acid gradient) to give the title compound as a white solid (86.2 mg).

LC-MS (Method 1): $R_t$=1.45 min; MS (ESIpos): m/z=542 [M+H]⁺

¹H-NMR (400 MHz, DMSO-d6) δ [ppm]: 1.025 (0.46), 1.035 (0.46), 1.145 (0.49), 1.173 (1.05), 1.185 (1.09), 1.197 (1.00), 1.209 (0.71), 1.353 (0.51), 1.844 (15.37), 2.182 (1.12), 2.199 (1.75), 2.216 (1.19), 2.233 (0.41), 2.518 (9.60), 2.523 (6.15), 2.539 (1.12), 3.075 (0.78), 3.089 (0.68), 3.245 (0.51), 3.259 (0.73), 3.278 (1.65), 3.298 (1.82), 3.816 (16.00), 3.844 (0.51), 3.855 (0.78), 3.866 (0.49), 3.878 (0.49), 4.172 (1.36), 4.186 (4.43), 4.203 (1.43), 4.217 (2.58), 4.282 (0.58), 4.301 (0.66), 4.320 (0.51), 4.425 (2.29), 4.456 (1.92), 6.878 (1.90), 6.896 (2.04), 6.959 (1.31), 6.982 (2.21), 7.005 (1.36), 7.364 (1.29), 7.385 (2.53), 7.404 (2.02), 7.446 (2.75), 7.467 (1.56), 7.495 (0.53), 7.508 (1.60), 7.514 (2.38), 7.523 (3.48), 7.533 (2.72), 7.538 (1.82), 7.550 (0.66), 7.734 (1.17), 7.748 (1.26), 7.756 (1.29), 7.769 (1.17), 7.855 (1.56), 7.864 (0.83), 7.873 (1.17), 7.878 (1.36), 8.224 (1.36), 8.230 (1.17), 8.239 (0.66), 8.248 (1.34).

The title compound (80 mg) was separated into enantiomers by preparative chiral HPLC to give enantiomer 1 (30 mg, see Example 3) and enantiomer 2 (30 mg, see Example 4).
Preparative Chiral HPLC Method:
Instrument: Sepiatec: Prep SFC100; column: Chiralpak IG 5 μm 250×30 mm; Eluent A: CO2, Eluent B: 2-Propanol+ 0.4 Vol-% Diethylamine (99%); Isokratic: 30% B; flow 100.0 ml/min Temperature: 40° C.; BPR: 150 bar; MWD @ 220 nm
Analytical Chiral HPLC Method:
Instrument: Agilent: 1260, Aurora SFC-Modul; column: Chiralpak IG 5 μm 100×4.6 mm; Eluent A: CO2, Eluent B: 2-Propanol+0.2 Vol-% Diethylamine (99%); Isokratic: 30% B; flow 4.0 ml/min; Temperature: 37.5° C.; BPR: 100 bar; MWD @ 220 nm Example 3

4-fluoro-2,3-dimethyl-7-[3-(naphthalen-1-yloxy) propyl]-2,10,11,12,13,15-hexahydropyrazolo-[4',3': 9,10][1,6]oxazacycloundecino[8,7,6-hi]indole-8-carboxylic acid-N-ethylethanamine salt (enantiomer 1)

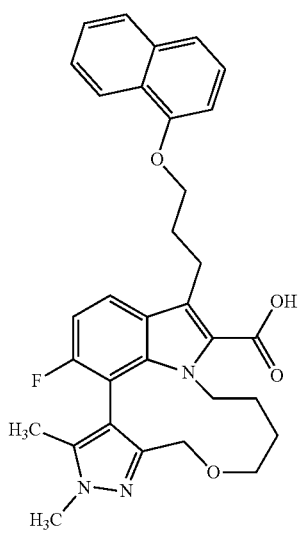 [SMILES: Cc1c2c(nn1C)COCCCCn1c(C(=O)O)c(CCCOc3cccc4ccccc34)c3ccc(F)c-2c31]

For the preparation of the racemic titled compound see Example 2. Separation of enantiomers by preparative chiral HPLC (method see Example 2) gave the titled compound (30 mg).
Analytical Chiral HPLC (method see Example 2): $R_t$=1.22 min.
LC-MS (Method 1): $R_t$=1.45 min; MS (ESIpos): m/z=542 [M+H]$^+$
$^1$H-NMR (400 MHz, DMSO-d6) δ [ppm]: 1.026 (4.43), 1.042 (4.37), 1.137 (8.47), 1.155 (16.00), 1.173 (7.87), 1.312 (0.62), 1.850 (13.92), 2.173 (1.19), 2.191 (1.82), 2.208 (1.27), 2.225 (0.42), 2.327 (0.55), 2.331 (0.41), 2.523 (2.22), 2.665 (0.44), 2.669 (0.57), 2.673 (0.43), 2.824 (2.05), 2.843 (6.15), 2.860 (6.03), 2.879 (1.96), 3.045 (0.50), 3.069 (0.94), 3.092 (0.83), 3.105 (0.57), 3.145 (0.62), 3.162 (0.97), 3.178 (1.09), 3.195 (1.50), 3.214 (1.15), 3.271 (3.22), 3.288 (3.59), 3.302 (4.36), 3.697 (0.48), 3.709 (0.57), 3.730 (0.78), 3.739 (0.66), 3.754 (0.74), 3.770 (0.56), 3.785 (0.45), 3.809 (14.95), 4.144 (0.80), 4.161 (1.75), 4.173 (1.78), 4.186 (2.66), 4.217 (2.55), 4.378 (2.38), 4.409 (1.85), 4.464 (0.57), 4.478 (0.56), 4.496 (0.54), 6.827 (1.23), 6.850 (3.70), 6.871 (2.58), 7.343 (1.15), 7.363 (2.33), 7.382 (1.73), 7.429 (2.63), 7.450 (1.55), 7.483 (0.50), 7.496 (1.47), 7.503 (2.05), 7.512 (3.10), 7.520 (2.23), 7.527 (1.70), 7.539 (0.62), 7.555 (1.07), 7.569 (1.16), 7.576 (1.16), 7.590 (1.03), 7.845 (1.55), 7.854 (0.80), 7.863 (1.21), 7.869 (1.31), 8.224 (1.30), 8.230 (1.18), 8.239 (0.68), 8.248 (1.28).

Example 4

4-fluoro-2,3-dimethyl-7-[3-(naphthalen-1-yloxy) propyl]-2,10,11,12,13,15-hexahydropyrazolo-[4',3': 9,10][1,6]oxazacycloundecino[8,7,6-hi]indole-8-carboxylic acid-N-ethylethanamine salt (enantiomer 2)

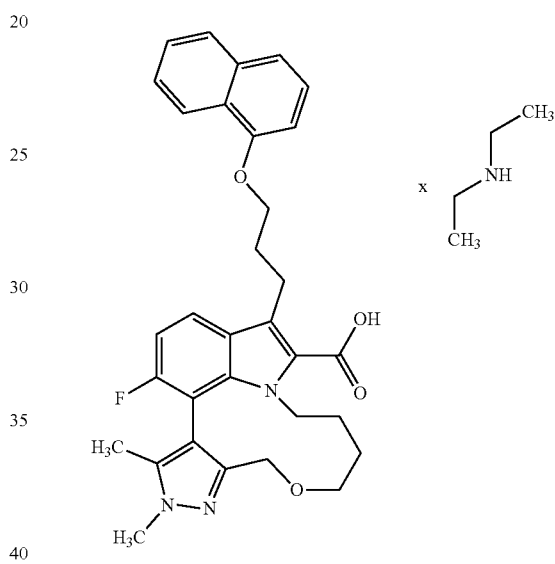

For the preparation of the racemic titled compound see Example 2. Separation of enantiomers by preparative chiral HPLC (method see Example 2) gave the titled compound (30 mg).
Analytical Chiral HPLC (method see Example 2): $R_t$=1.90 min.
LC-MS (Method 1): $R_t$=1.45 min; MS (ESIpos): m/z=542 [M+H]$^+$
$^1$H-NMR (400 MHz, DMSO-d6) δ [ppm]: 1.027 (8.51), 1.042 (8.67), 1.102 (1.23), 1.127 (1.79), 1.138 (2.22), 1.156 (5.62), 1.173 (10.66), 1.192 (5.29), 1.332 (0.79), 1.845 (16.00), 2.163 (0.48), 2.180 (1.51), 2.197 (2.32), 2.214 (1.72), 2.230 (0.60), 2.539 (0.69), 2.857 (1.33), 2.875 (3.89), 2.893 (3.81), 2.911 (1.33), 3.045 (0.55), 3.058 (0.60), 3.070 (1.13), 3.081 (0.94), 3.095 (0.90), 3.180 (0.54), 3.199 (0.93), 3.214 (1.06), 3.231 (1.56), 3.250 (1.00), 3.275 (1.80), 3.292 (2.25), 3.306 (1.70), 3.325 (1.22), 3.343 (0.76), 3.453 (0.48), 3.740 (0.62), 3.755 (1.36), 3.770 (1.58), 3.779 (1.18), 3.785 (1.55), 4.168 (2.37), 4.174 (2.47), 4.186 (3.70), 4.217 (3.09), 4.398 (3.54), 4.419 (0.97), 4.429 (2.87), 4.452 (0.50), 6.854 (2.26), 6.873 (2.70), 6.900 (2.62), 6.923 (1.59), 7.342 (1.20), 7.362 (2.62), 7.381 (1.82), 7.429 (3.17), 7.450 (1.91), 7.483 (0.56), 7.495 (1.74), 7.500 (2.72), 7.511 (3.31), 7.519 (3.04), 7.537 (0.68), 7.623 (1.36), 7.636 (1.49), 7.645 (1.54), 7.659 (1.36), 7.844 (1.85), 7.853 (0.97), 7.860 (1.39), 7.867 (1.56), 8.224 (1.59), 8.230 (1.43), 8.237 (0.89), 8.247 (1.64).

Example 5

(rac)-(11Z)-3-ethyl-4-fluoro-2-methyl-7-[3-(naphthalen-1-yloxy)propyl]-2,10,13,15-tetrahydro-pyrazolo[4',3':9,10][1,6]oxazacycloundecino[8,7,6-hi]indole-8-carboxylic acid

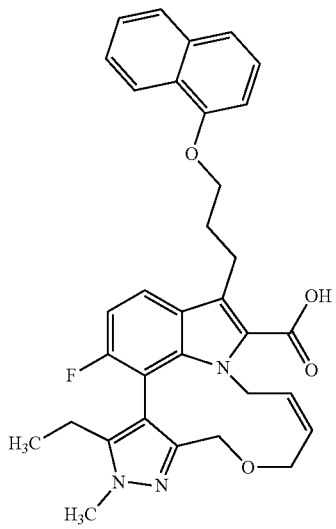 [SMILES: CCc1c2c(nn1C)COC/C=C\Cn1c(C(=O)O)c(CCCOc3cccc4ccccc34)c3ccc(F)c-2c31]

To a stirred solution of (rac)-ethyl (11Z)-3-ethyl-4-fluoro-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 18, 58.2 mg, 100 μmol, 1.00 eq.) in ethanol (0.13 mL, 0.80 M) was added a 2.0 M solution of sodium hydroxide in water (0.13 mL, 250 μmol, 2.50 eq.). The resulting white suspension was heated at 70° C. for 3 h and then cooled to room temperature. The mixture was diluted with water (5.00 mL), acidified to pH 2.0 with 1.0 M aqueous hydrochloric acid and extracted with ethyl acetate (3×10 mL). The combined organic layers were washed with brine (10 mL), dried (sodium sulfate) filtered and concentrated under reduced pressure. The residue was purified by reverse phase column chromatography (65-100% acetonitrile in water with 0.1% formic acid gradient) to give the title compound as an off white solid (42.3 mg).

LC-MS (Method 1): $R_t$=1.47 min; MS (ESIpos): m/z=554 [M+H]$^+$ $^1$H-NMR (400 MHz, CHLOROFORM-d) δ [ppm]: 0.938 (3.35), 0.957 (7.44), 0.976 (3.53), 2.300 (1.07), 2.319 (2.88), 2.338 (3.18), 2.358 (2.18), 2.366 (2.05), 2.383 (1.46), 2.645 (0.58), 3.437 (1.26), 3.450 (1.96), 3.466 (1.23), 3.768 (0.75), 3.780 (0.88), 3.798 (1.23), 3.811 (1.13), 3.908 (1.13), 3.937 (1.73), 3.969 (16.00), 4.205 (1.95), 4.219 (3.83), 4.235 (1.92), 4.433 (1.84), 4.466 (2.61), 4.589 (2.69), 4.622 (1.86), 4.840 (0.69), 4.866 (0.86), 4.879 (1.05), 4.905 (1.10), 5.060 (1.35), 5.099 (0.96), 5.265 (0.57), 5.270 (0.57), 5.291 (1.25), 5.297 (1.22), 5.318 (0.84), 5.323 (0.77), 5.372 (0.58), 5.384 (0.64), 5.398 (0.90), 5.411 (0.86), 5.425 (0.43), 6.756 (2.12), 6.774 (2.26), 6.903 (1.33), 6.926 (2.58), 6.948 (1.39), 7.328 (1.21), 7.348 (2.50), 7.367 (1.88), 7.411 (2.85), 7.432 (1.68), 7.468 (3.14), 7.475 (2.33), 7.478 (2.35), 7.483 (2.59), 7.492 (3.35), 7.682 (1.36), 7.695 (1.50), 7.704 (1.47), 7.717 (1.32), 7.795 (1.58), 7.801 (1.14), 7.806 (1.15), 7.810 (1.46), 7.818 (1.34), 8.336 (1.40), 8.344 (1.37), 8.353 (1.01), 8.360 (1.32).

Example 6

(rac)-3-ethyl-4-fluoro-2-methyl-7-[3-(naphthalen-1-yloxy)propyl]-2,10,11,12,13,15-hexahydro-pyrazolo[4',3':9,10][1,6]oxazacycloundecino[8,7,6-hi]indole-8-carboxylic acid

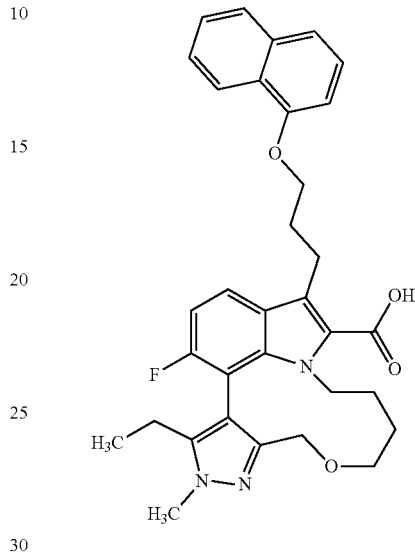

To a stirred solution of (rac)-ethyl 3-ethyl-4-fluoro-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 19, 90.0 mg, 154 μmol, 1.00 eq.) in ethanol (0.19 mL, 0.80 M) was added a 2.0 M solution of NaOH in water (0.19 mL, 385 μmol, 2.50 eq.). The resulting white suspension was heated at 70° C. for 24 h and then cooled to room temperature. The mixture was diluted with water (5 mL), acidified to pH 2.0 with 1.0 M aqueous hydrochloric acid I and extracted with ethyl acetate (3×10 mL). The combined organic layers were washed with brine (10 mL), dried (sodium sulfate) filtered and concentrated under reduced pressure. The residue was purified by reverse phase column chromatography (65-100% Acetonitrile/water with 0.1% formic acid gradient) to give the title compound as a white solid (47.9 mg).

LC-MS (Method 1): $R_t$=1.51 min; MS (ESIpos): m/z=556 [M+H]$^+$ $^1$H-NMR (400 MHz, CHLOROFORM-d) δ [ppm]: 0.929 (3.22), 0.948 (7.34), 0.967 (3.29), 1.210 (1.56), 1.234 (1.27), 1.252 (0.76), 1.262 (1.02), 1.270 (1.25), 1.288 (0.51), 1.424 (0.62), 1.436 (0.73), 1.451 (0.63), 1.466 (0.47), 1.535 (0.82), 2.057 (1.48), 2.265 (0.75), 2.284 (1.71), 2.293 (1.69), 2.303 (1.69), 2.312 (1.90), 2.331 (1.59), 2.349 (1.54), 3.239 (0.48), 3.263 (0.84), 3.283 (0.56), 3.402 (0.95), 3.421 (1.56), 3.432 (1.65), 3.439 (1.49), 3.446 (1.48), 3.457 (1.13), 3.484 (0.75), 3.913 (16.00), 4.001 (0.47), 4.027 (0.83), 4.053 (0.58), 4.179 (1.49), 4.193 (2.93), 4.209 (1.46), 4.328 (0.70), 4.348 (0.64), 4.362 (0.65), 4.381 (2.44), 4.413 (2.53), 4.663 (2.42), 4.695 (2.00), 6.749 (1.92), 6.767 (2.06), 6.886 (1.37), 6.909 (2.56), 6.931 (1.43), 7.328 (1.22), 7.348 (2.46), 7.367 (1.91), 7.413 (2.63), 7.433 (1.52), 7.483 (3.13), 7.490 (2.04), 7.493 (2.20), 7.497 (2.19), 7.501 (2.01), 7.507 (3.15), 7.518 (0.50), 7.648 (1.34), 7.661 (1.46), 7.669 (1.47), 7.683 (1.32), 7.799 (1.46), 7.807 (1.35), 7.811 (1.00), 7.817 (0.97), 7.822 (1.24), 8.366 (1.33), 8.382 (1.15), 8.390 (1.19).

The title compound (39 mg) was separated into enantiomers by preparative chiral HPLC to give enantiomer 1 (24 mg, see Example 7) and enantiomer 2 (20 mg, see Example 8).

Preparative Chiral HPLC Method:

Instrument: Labomatic HD5000, Labocord-5000; Gilson GX-241, Labcol Vario 4000, Column: YMC Amylose SA 5µ 250×30 mm; Eluent A: Hexane+0.1 Vol-% Diethylamine (99%); Eluent B: Ethanol; Isokratic: 20% B; Flow 40.0 mL/min; UV 254 nm Analytical Chiral HPLC Method:

Instrument: Agilent HPLC 1260; Column: YMC Amylose SA 3µ 100×4.6 mm; Eluent A: Hexane+0.1 Vol-% Diethylamine (99%); Eluent B: Ethanol; Isokratic: 20% B; Flow 1.4 mL/min; Temperature: 25° C.; DAD 254 nm Example 7

3-ethyl-4-fluoro-2-methyl-7-{3-[(naphthalen-1-yl) oxy]propyl}-2,10,11,12,13,15-hexahydro-pyrazolo [4',3':9,10][1,6]oxazacycloundecino[8,7,6-hi]indole-8-carboxylic acid-N-ethylethanamine salt (enantiomer 1)

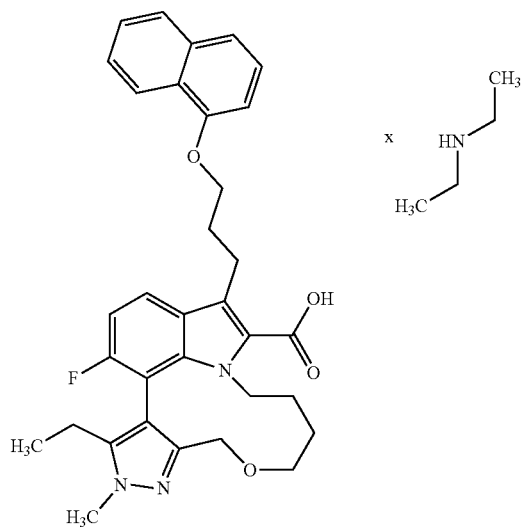

For the preparation of the racemic title compound see Example 6. Separation of enantiomers by preparative chiral HPLC (method see Example 6) gave the title compound (24 mg).

Analytical Chiral HPLC (method see Example 6): $R_t$=1.45 min.

LC-MS (Method 1): $R_t$=1.51 min; MS (ESIpos): m/z=556 [M+H]$^+$

Specific Optical Rotation (Method O1): 22.6° (c=10 mg/mL, DMSO)

$^1$H-NMR (400 MHz, DMSO-d6) δ [ppm]: 0.828 (1.15), 0.847 (2.70), 0.865 (1.19), 1.130 (7.10), 1.148 (16.00), 1.166 (7.53), 1.205 (0.65), 1.900 (0.92), 1.959 (0.54), 2.185 (0.42), 2.202 (0.96), 2.214 (0.76), 2.231 (0.70), 2.249 (0.50), 2.518 (1.41), 2.522 (0.96), 2.840 (1.95), 2.858 (5.93), 2.876 (6.01), 2.895 (1.82), 3.207 (0.42), 3.226 (0.68), 3.239 (0.58), 3.253 (0.85), 3.273 (0.99), 3.841 (6.22), 4.165 (0.63), 4.180 (1.30), 4.211 (0.93), 4.381 (0.85), 4.413 (0.73), 6.841 (0.55), 6.845 (0.72), 6.864 (1.34), 6.885 (0.45), 7.342 (0.53), 7.362 (0.95), 7.381 (0.74), 7.431 (0.96), 7.452 (0.58), 7.498 (0.58), 7.502 (0.57), 7.506 (0.74), 7.514 (1.34), 7.522 (0.76), 7.525 (0.64), 7.530 (0.65), 7.848 (0.57), 7.865 (0.46), 7.871 (0.47), 8.226 (0.51), 8.233 (0.44), 8.250 (0.46).

Example 8

3-ethyl-4-fluoro-2-methyl-7-{3-[(naphthalen-1-yl) oxy]propyl}-2,10,11,12,13,15-hexahydro-pyrazolo [4',3':9,10][1,6]oxazacycloundecino[8,7,6-hi]indole-8-carboxylic acid-N-ethylethanamine salt (enantiomer 2)

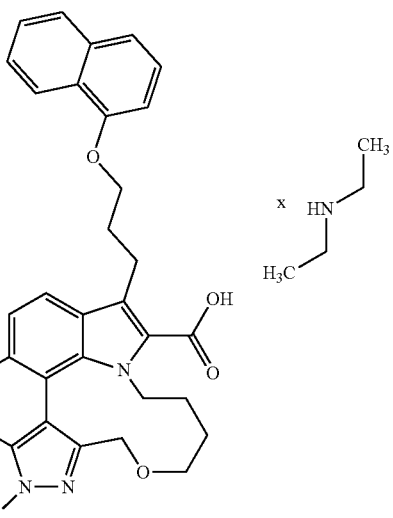

For the preparation of the racemic title compound see Example 6. Separation of enantiomers by preparative chiral HPLC (method see Example 6) gave the title compound (20 mg).

Analytical Chiral HPLC (method see Example 6): $R_t$=3.64 min.

LC-MS (Method 1): $R_t$=1.51 min; MS (ESIpos): m/z=556 [M+H]$^+$

Specific Optical Rotation (Method O1): −31.9° (c=10 mg/mL, DMSO)

$^1$H-NMR (400 MHz, DMSO-d6) δ [ppm]: 0.827 (2.03), 0.846 (4.76), 0.865 (2.13), 1.114 (0.58), 1.128 (7.47), 1.147 (16.00), 1.164 (7.49), 1.901 (0.71), 2.181 (0.76), 2.198 (1.31), 2.215 (1.56), 2.233 (1.17), 2.249 (0.87), 2.266 (0.41), 2.518 (2.40), 2.522 (1.59), 2.822 (1.83), 2.840 (5.81), 2.858 (5.67), 2.876 (1.68), 3.086 (0.50), 3.202 (0.55), 3.220 (0.95), 3.247 (1.08), 3.265 (0.93), 3.280 (1.32), 3.841 (10.51), 4.147 (0.47), 4.163 (1.12), 4.179 (2.27), 4.193 (0.49), 4.210 (1.65), 4.380 (1.50), 4.411 (1.29), 6.836 (0.77), 6.847 (1.25), 6.859 (1.25), 6.864 (1.42), 6.881 (0.76), 7.341 (0.93), 7.362 (1.69), 7.381 (1.34), 7.430 (1.69), 7.451 (1.02), 7.497 (1.09), 7.502 (1.07), 7.504 (1.40), 7.513 (2.39), 7.521 (1.48), 7.528 (1.18), 7.541 (0.41), 7.567 (0.59), 7.581 (0.63), 7.589 (0.63), 7.603 (0.56), 7.846 (0.98), 7.849 (0.76), 7.856 (0.50), 7.864 (0.76), 7.870 (0.82), 8.227 (0.90), 8.233 (0.77), 8.243 (0.42), 8.251 (0.82).

Example 9

(rac)-(Z)-13-fluoro-10,12-dimethyl-1-(3-(naphthalen-1-yloxy)propyl)-4,7,9,10-tetrahydro-pyrazolo[4',3':9,10][1]oxa[6]azacycloundecino[8,7,6-hi]indole-2-carboxylic acid

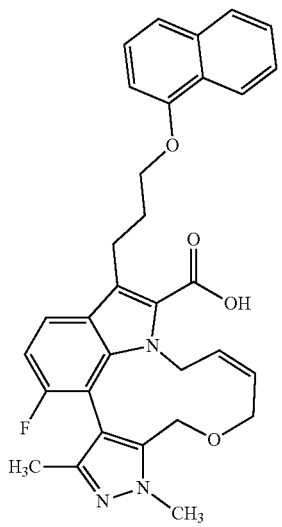 [SMILES: Cc1nn(C)c2c1-c1c(F)ccc3c(CCCOc4cccc5ccccc45)c(C(=O)O)n(c13)C/C=C\COC2]

To a stirred solution of (rac)-ethyl (Z)-13-fluoro-10,12-dimethyl-1-(3-(naphthalen-1-yloxy)propyl)-4,7,9,10-tetrahydropyrazolo[4',3':9,10][1]oxa[6]azacycloundecino[8,7,6-hi]indole-2-carboxylate (see Intermediate 21, 41.0 mg, 72.2 μmol, 1.00 eq.) in ethanol (90.2 μL) was added a 2.0 M solution of sodium hydroxide in water (90.0 μL, 180 μmol, 2.50 eq.). The resulting white suspension was heated at 70° C. for 5 hours and cooled to room temperature. The mixture was diluted with water (10 mL), acidified to pH 2.0 with 1.0 M aqueous hydrochloric acid and extracted with ethyl acetate (3×10 mL). The combined organic extracts were dried (magnesium sulfate), filtered and concentrated under reduced pressure. The residue was purified by reverse phase chromatography (65-100% acetonitrile/water with 0.1% trifluoroacetic acid) to give the title compound as an off white solid (28.4 mg).

LC-MS (Method 3): $R_t$=1.69 min; MS (ESIpos): m/z=540 [M+H]$^+$.

$^1$H-NMR (300 MHz, CHLOROFORM-d) δ [ppm]: 8.31 (m, 1H), 7.79 (m, 1H), 7.72 (dd, 1H), 7.47 (m, 2H), 7.41 (d, 1H), 7.34 (m, 1H), 6.93 (t, 1H), 6.75 (dd, 1H), 5.20 (m, 2H), 5.07 (t, 1H), 4.70 (m, 2H), 4.43 (d, 1H), 4.21 (m, 2H), 4.03 (s, 3H), 3.83 (dd, 1H), 3.60 (t, 1H), 3.46 (m, 2H), 2.37 (m, 2H), 1.95 (s, 3H).

Example 10

(rac)-13-fluoro-10,12-dimethyl-1-(3-(naphthalen-1-yloxy)propyl)-4,5,6,7,9,10-hexahydro-pyrazolo[4',3':9,10][1]oxa[6]azacycloundecino[8,7,6-hi]indole-2-carboxylic acid

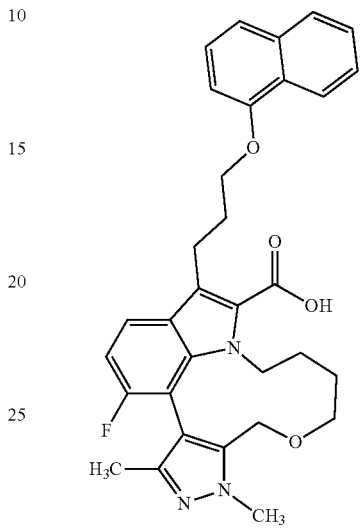

To a stirred solution of (rac)-ethyl 13-fluoro-10,12-dimethyl-1-(3-(naphthalen-1-yloxy)propyl)-4,5,6,7,9,10-hexahydropyrazolo[4',3':9,10][1]oxa[6]azacycloundecino[8,7,6-hi]indole-2-carboxylate (see Intermediate 22, 61.9 mg, 108 μmol, 1.00 eq.) in ethanol (0.14 mL) was added a 2.0 M solution of sodium hydroxide in water (0.14 mL, 270 μmol, 2.50 eq.). The resulting white suspension was heated at 70° C. for 21 hours and cooled to room temperature. The mixture was diluted with water (10 mL), acidified to pH 2.0 with 1.0 M aqueous hydrochloric acid and extracted with ethyl acetate (3×10 mL). The combined organic extracts were dried over magnesium sulfate, filtered and concentrated under reduced pressure. The residue was purified by flash column chromatography (0-10% methanol/dichloromethane gradient) to give the acid as a colorless oil (48.2 mg).

LC-MS (Method 3): $R_t$=1.69 min; MS (ESIpos): m/z=542 [M+H]$^+$.

$^1$H-NMR (300 MHz, CHLOROFORM-d) δ [ppm]: 8.35 (1.02), 7.79 (1.01), 7.71 (1.19), 7.47 (2.32), 7.40 (1.08), 7.33 (1.04), 6.90 (1.00), 6.74 (0.98), 4.62 (2.01), 4.43 (0.98), 4.19 (3.14), 3.96 (3.05), 3.46 (3.14), 2.89 (0.97), 2.36 (2.03), 2.00 (4.20), 1.51 (0.96), 1.18 (3.44).

Example 11

(rac)-(Z)-12-ethyl-13-fluoro-10-methyl-1-(3-(naphthalen-1-yloxy)propyl)-4,7,9,10-tetrahydro-pyrazolo[4',3':9,10][1]oxa[6]azacycloundecino[8,7,6-hi]indole-2-carboxylic acid

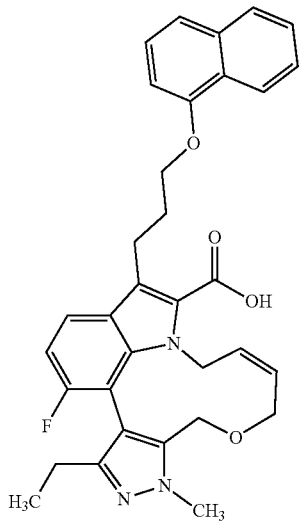 [SMILES: CCc1nn(C)c2c1-c1c(F)ccc3c(CCCOc4cccc5ccccc45)c(C(=O)O)n(c13)C/C=C\COC2]

To a stirred solution of (rac)-ethyl (Z)-12-ethyl-13-fluoro-10-methyl-1-(3-(naphthalen-1-yloxy)propyl)-4,7,9,10-tetrahydropyrazolo[4',3':9,10][1]oxa[6]azacycloundecino[8,7,6-hi]indole-2-carbon/late (see Intermediate 24, 66.4 mg, 114 μmol, 1.00 eq.) in ethanol (0.142 mL) was added a 2.0 M solution of sodium hydroxide in water (0.142 mL, 285 μmol, 2.50 eq.). The resulting white suspension was heated at 70° C. for 2 hours and cooled to room temperature. The mixture was diluted with water (10 mL), acidified to pH 2.0 with 1.0 M aqueous hydrochloric acid and extracted with ethyl acetate (3×10 mL). The combined organic extracts were dried (magnesium sulfate), filtered and concentrated under reduced pressure. The residue was purified by flash column chromatography (0-5% methanol/dichloromethane gradient) to give the title compound as a white solid (44.3 mg).

LC-MS (Method 3): $R_t$=1.75 min; MS (ESIpos): m/z=552 [MH]⁻

¹H-NMR (300 MHz, CHLOROFORM-d) δ [ppm]: 8.32 (m, 1H), 7.76 (m, 2H), 7.47 (m, 2H), 7.36 (m, 2H), 6.92 (t, 1H), 6.74 (dd, 1H), 5.17 (m, 3H), 4.79 (dd, 1H), 4.64 (d, 1H), 4.42 (d, 1H), 4.21 (m, 2H), 4.02 (s, 3H), 3.82 (dd, 1H), 3.62 (t, 1H), 3.47 (m, 2H), 2.30 (m, 2H), 2.05 (s, 2H), 0.98 (t, 3H).

Example 12

(rac)-13-fluoro-1-(3-((6-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylic acid

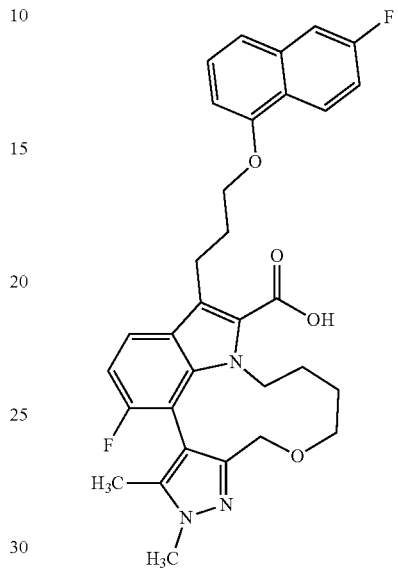

To a stirred solution of (rac)-ethyl 13-fluoro-1-(3-((6-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylate (see Intermediate 32, 153 mg, 254 μmol, 1.00 eq.) in ethanol (1.01 mL, 0.25 M) was added a 2.0 M solution of sodium hydroxide in water (317 μL, 635 μmol, 2.50 eq.). The resulting yellow solution was heated at 70° C. for 16 hours, cooled to room temperature. The mixture was diluted with water (10 mL), acidified to pH 2.0 with 1.0 M aqueous hydrochloric acid and extracted with ethyl acetate (3×10 mL). The combined organic extracts were dried (magnesium sulfate), filtered and concentrated under reduced pressure. Celite was added to the resulting mixture, volatiles were removed under reduced pressure, and the residue was loaded onto a silica gel cartridge which was subjected to reverse phase column chromatography (40-100% acetonitrile/water with 0.1% formic acid gradient) to give the title compound as an off white solid (105 mg).

LC-MS (Method 3): $R_t$=1.69 min; MS (ESIpos): m/z=558 [MH]⁻

¹H-NMR (300 MHz, CHLOROFORM-d) δ [ppm]: 8.34 (dd, 1H), 7.66 (dd, 1H), 7.37 (m, 3H), 7.22 (m, 1H), 6.93 (t, 1H), 6.69 (dd, 1H), 4.68 (d, 1H), 4.45 (d, 1H), 4.34 (dd, 1H), 4.17 (m, 2H), 3.93 (m, 4H), 3.44 (m, 3H), 3.19 (m, 1H), 2.32 (m, 2H), 1.95 (s, 3H), 1.35 (m, 5H).

The title compound (93 mg) was separated into enantiomers by preparative chiral HPLC to give enantiomer 1 (26 mg, see Example 13) and enantiomer 2 (23 mg, see Example 14).
Preparative Chiral HPLC Method:
Instrument: Labomatic HD5000, Labocord-5000; Gilson GX-241, Labcol Vario 4000, Column: Chiralpak IG SA 5μ 250×30 mm; Eluent A: Hexane+0.1 Vol-% Diethylamine (99%); Eluent B: 2-Propanol; Gradient: 20-50% B in 20 min; Flow 40.0 mL/min; UV 254 nm Analytical Chiral HPLC Method:
Instrument: Agilent HPLC 1260; Column: Chiralpak IG 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 254 nm Example 13

4-fluoro-7-{3-[(6-fluoronaphthalen-1-yl)oxy]propyl}-2,3-dimethyl-2,10,11,12,13,15-hexahydro-pyrazolo[4',3':9,10][1,6]oxazacycloundecino[8,7,6-hi]indole-8-carboxylic acid-N-ethylethanamine salt (enantiomer 1)

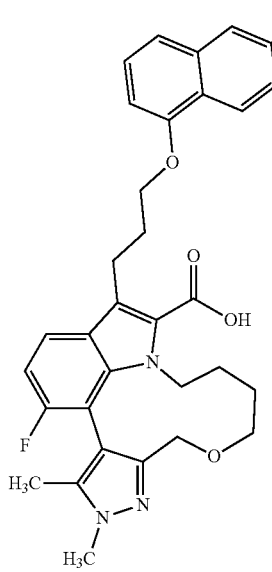

For the preparation of the racemic title compound see Example 12. Separation of enantiomers by preparative chiral HPLC (method see Example 12) gave the title compound (26 mg).

Analytical Chiral HPLC (method see Example 12): $R_t$=2.32 min.

LC-MS (Method 1): $R_t$=1.48 min; MS (ESIpos): m/z=560 [M+H]$^+$

Specific Optical Rotation (Method O1): 44.9° (c=10 mg/mL, DMSO)

$^1$H-NMR (400 MHz, DMSO-d6) δ [ppm]: 1.132 (6.97), 1.150 (13.01), 1.168 (6.24), 1.307 (0.51), 1.846 (12.87), 2.169 (1.07), 2.185 (1.63), 2.202 (1.11), 2.331 (0.60), 2.518 (3.67), 2.523 (2.30), 2.539 (16.00), 2.669 (0.86), 2.673 (0.63), 2.832 (1.69), 2.850 (5.00), 2.868 (4.96), 2.886 (1.57), 3.043 (0.43), 3.067 (0.83), 3.091 (0.67), 3.152 (0.51), 3.171 (0.84), 3.185 (0.96), 3.204 (1.37), 3.222 (1.07), 3.245 (1.46), 3.262 (2.77), 3.719 (0.44), 3.742 (0.61), 3.764 (0.47), 3.810 (13.46), 4.151 (0.79), 4.166 (1.59), 4.175 (1.63), 4.186 (2.44), 4.217 (2.26), 4.384 (2.01), 4.415 (1.81), 4.443 (0.47), 4.458 (0.47), 6.831 (1.16), 6.837 (1.21), 6.848 (1.91), 6.853 (1.44), 6.870 (1.57), 6.894 (0.93), 7.355 (0.70), 7.362 (0.77), 7.377 (1.21), 7.384 (1.39), 7.400 (0.84), 7.409 (2.16), 7.421 (2.54), 7.426 (4.63), 7.441 (0.44), 7.575 (0.76), 7.588 (0.87), 7.595 (0.84), 7.609 (0.74), 7.631 (1.36), 7.638 (1.37), 7.657 (1.33), 7.664 (1.31), 8.247 (1.17), 8.262 (1.23), 8.270 (1.20), 8.285 (1.10).

Example 14

4-fluoro-7-{3-[(6-fluoronaphthalen-1-yl)oxy]propyl}-2,3-dimethyl-2,10,11,12,13,15-hexahydro-pyrazolo[4',3':9,10][1,6]oxazacycloundecino[8,7,6-hi]indole-8-carboxylic acid-N-ethylethanamine salt (enantiomer 2)

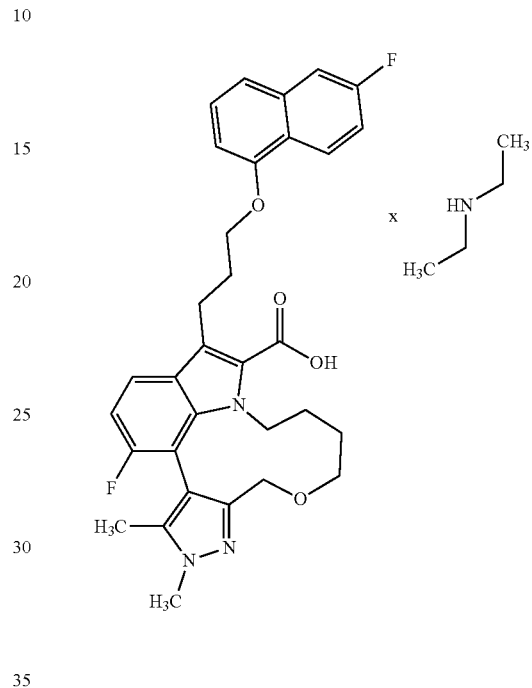

For the preparation of the racemic title compound see Example 12. Separation of enantiomers by preparative chiral HPLC (method see Example 12) gave the title compound (23 mg).

Analytical Chiral HPLC (method see Example 12): $R_t$=3.62 min.

LC-MS (Method 1): $R_t$=1.48 min; MS (ESIpos): m/z=560 [M+H]$^+$

Specific Optical Rotation (Method O1): −41.0° (c=10 mg/mL, DMSO)

$^1$H-NMR (400 MHz, DMSO-d6) δ [ppm]: 1.127 (8.59), 1.146 (16.00), 1.163 (7.38), 1.229 (0.40), 1.303 (0.67), 1.847 (15.00), 2.168 (1.25), 2.185 (1.90), 2.202 (1.28), 2.218 (0.40), 2.327 (1.04), 2.331 (0.74), 2.518 (4.14), 2.523 (2.61), 2.669 (1.06), 2.673 (0.76), 2.822 (2.01), 2.840 (5.97), 2.858 (5.79), 2.876 (1.87), 3.067 (0.93), 3.090 (0.77), 3.146 (0.55), 3.164 (0.92), 3.178 (1.04), 3.197 (1.50), 3.215 (1.11), 3.240 (1.55), 3.259 (2.82), 3.712 (0.51), 3.732 (0.69), 3.754 (0.53), 3.810 (15.35), 4.149 (0.86), 4.165 (1.80), 4.174 (1.87), 4.186 (2.69), 4.217 (2.61), 4.381 (2.34), 4.412 (1.88), 4.438 (0.56), 4.455 (0.55), 4.471 (0.51), 6.830 (1.43), 6.837 (1.88), 6.846 (1.46), 6.851 (1.58), 6.861 (1.83), 6.884 (1.07), 7.355 (0.81), 7.362 (0.90), 7.377 (1.43), 7.384 (1.65), 7.400 (1.02), 7.408 (2.75), 7.420 (2.92), 7.424 (5.37), 7.440 (0.53), 7.561 (0.90), 7.575 (1.00), 7.582 (0.99), 7.596 (0.84), 7.631 (1.57), 7.637 (1.60), 7.657 (1.57), 7.663 (1.55), 8.248 (1.34), 8.263 (1.43), 8.271 (1.39), 8.285 (1.30).

Example 15

(rac)-13-fluoro-1-(3-((4-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylic acid

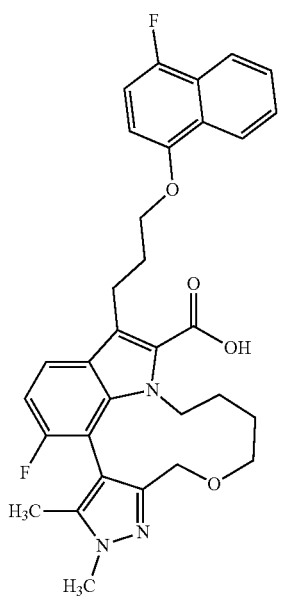 [SMILES: Cc1c2c(nn1C)COCCCCn1c(C(=O)O)c(CCCOc3ccc(F)c4ccccc34)c3ccc(F)c-2c31]

To a stirred solution of (rac)-ethyl 13-fluoro-1-(3-((4-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylate (see Intermediate 33, 107 mg, 182 µmol, 1.00 eq.) in ethanol (0.73 mL, 0.25 M) was added a 2.0 M solution of sodium hydroxide in water (227 µL, 455 µmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to by reverse phase column chromatography (10-100% acetonitrile/water with 0.1% formic acid gradient) to give the title compound as a white solid (53.7 mg).

LC-MS (Method 4): $R_t$=4.39 min; MS (ESIpos): m/z=560 [M+H]$^+$.

$^1$H-NMR (300 MHz, DMSO-d) δ [ppm]: 13.13 (s, 1H), 8.27 (m, 1H), 7.99 (m, 1H), 7.75 (dd, 1H), 7.65 (m, 2H), 7.20 (dd, 1H), 6.98 (t, 1H), 6.82 (dd, 1H), 4.44 (d, 1H), 4.21 (m, 4H), 3.82 (m, 3H), 3.29 (m, 3H), 3.08 (m, 1H), 2.18 (m, 2H), 1.84 (s, 3H), 1.17 (m, 4H).

The title compound (40 mg) was separated into enantiomers by preparative chiral HPLC to give enantiomer 1 (26 mg, see Example 16) and enantiomer 2 (26 mg, see Example 17).

Preparative Chiral HPLC Method:
Instrument: Labomatic HD5000, Labocord-5000; Gilson GX-241, Labcol Vario 4000, Column: Chiralpak IA 5µ 250×30 mm; Eluent: Hexane+0.1 Vol-% trifluoroacetic acid (99%)/2-Propanol 80:20; Flow 40.0 mL/min; UV 254 nm Analytical Chiral HPLC Method:
Instrument: Waters Alliance 2695Agilent HPLC 1260; Column: Chiralpak IA 3µ 100×4, 6 mm; Eluent A: Hexane+ 0.1 Vol-% trifluoroacetic acid (99%); Eluent B: 2-Propanol; Gradient: 20-50% B in 7 min; Flow 1.4 mL/min; Temperature: 25° C.; DAD 254 nm

Example 16

4-fluoro-7-{3-[(4-fluoronaphthalen-1-yl)oxy]propyl}-2,3-dimethyl-2,10,11,12,13,15-hexahydro-pyrazolo[4',3':9,10][1,6]oxazacycloundecino[8,7,6-hi]indole-8-carboxylic acid (enantiomer 1)

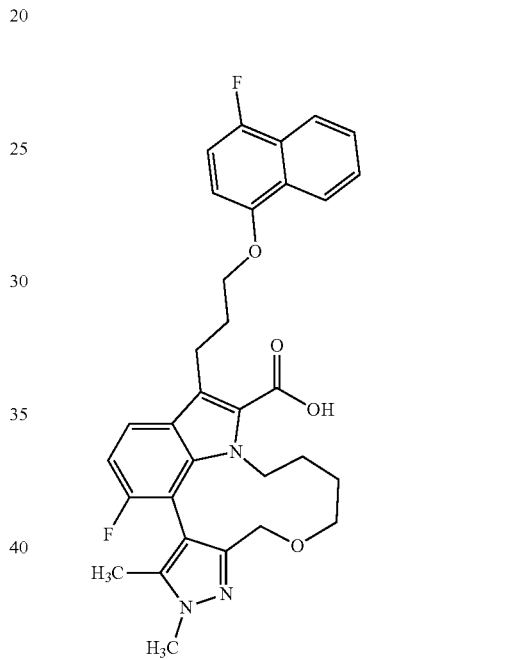

For the preparation of the racemic title compound see Example 15. Separation of enantiomers by preparative chiral HPLC (method see Example 15) gave the title compound (26 mg).

Analytical Chiral HPLC (method see Example 15): $R_t$=1.60 min.

LC-MS (Method 1): $R_t$=1.49 min; MS (ESIpos): m/z=560 [M+H]$^+$

Specific Optical Rotation (Method O1): 31.1° (c=10 mg/mL, DMSO)

$^1$H-NMR (400 MHz, DMSO-d6) δ [ppm]: 1.106 (16.00), 1.153 (0.84), 1.172 (0.52), 1.838 (2.29), 2.518 (0.67), 2.523 (0.47), 3.815 (2.43), 4.184 (0.47).

Example 17

4-fluoro-7-{3-[(4-fluoronaphthalen-1-yl)oxy]propyl}-2,3-dimethyl-2,10,11,12,13,15-hexahydro-pyrazolo[4',3':9,10][1,6]oxazacycloundecino[8,7,6-hi]indole-8-carboxylic acid (enantiomer 2)

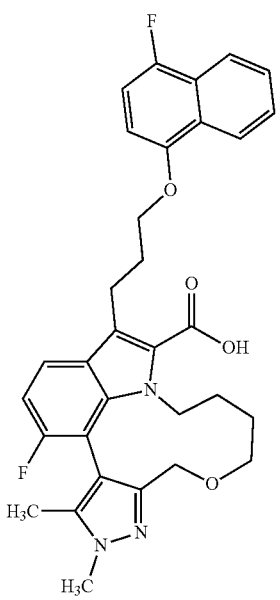

For the preparation of the racemic title compound see Example 15. Separation of enantiomers by preparative chiral HPLC (method see Example 15) gave the title compound (26 mg).

Analytical Chiral HPLC (method see Example 15): $R_t$=2.01 min.

LC-MS (Method 3): $R_t$=1.49 min; MS (ESIpos): m/z=560 [M+H]$^+$

Specific Optical Rotation (Method O1): −32.7° (c=10 mg/mL, DMSO)

$^1$H-NMR (400 MHz, DMSO-d6) δ [ppm]: 1.107 (16.00), 1.839 (1.82), 2.518 (0.45), 3.855 (0.56), 3.879 (0.66), 3.889 (0.66).

Example 18

(rac)-13-fluoro-11,12-dimethyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylic acid

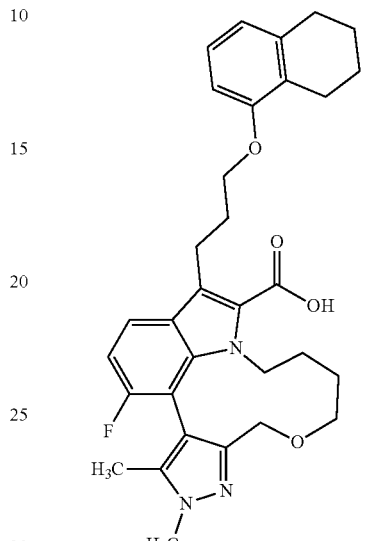

To a stirred solution of (rac)-ethyl 13-fluoro-11,12-dimethyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylate (see Intermediate 34, 81.7 mg, 142 μmol, 1.00 eq.) in ethanol (0.57 mL, 0.25 M) was added a 2.0 M solution of sodium hydroxide in water (178 μL, 356 μmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (58.7 mg).

LC-MS (Method 4): $R_t$=4.60 min; MS (ESIpos): m/z=546 [M+H]$^+$.

$^1$H-NMR (300 MHz, DMSO-d) δ [ppm]: 13.05 (s, 1H), 7.71 (dd, 1H), 7.01 (m, 2H), 6.62 (dd, 2H), 4.45 (d, 1H), 4.22 (m, 2H), 3.96 (m, 2H), 3.82 (m, 4H), 3.25 (m, 4H), 2.64 (m, 4H), 2.04 (m, 2H), 1.85 (s, 3H), 1.70 (m, 5H), 1.16 (m, 5H).

Example 19

(rac)-1-(3-((2,3-dihydro-1H-inden-4-yl)oxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylic acid

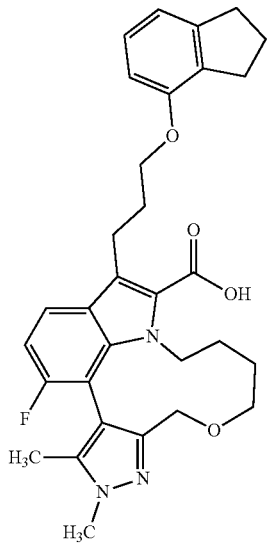 [SMILES: Cc1c2c(nn1C)COCCCCn1c(C(=O)O)c(CCCOc3cccc4c3CCC4)c3ccc(F)c-2c31]

To a stirred solution of (rac)-ethyl 1-(3-((2,3-dihydro-1H-inden-4-yl)oxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylate (see Intermediate 35, 83.8 mg, 149 µmol, 1.00 eq.) in ethanol (0.60 mL, 0.25 M) was added a 2.0 M solution of sodium hydroxide in water (187 µL, 374 µmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (24.8 mg).

LC-MS (Method 4): $R_t$=4.33 min; MS (ESIpos): m/z=532 [M+H]$^+$.

$^1$H-NMR (300 MHz, DMSO-d) δ [ppm]: 13.05 (s, 1H), 7.71 (dd, 1H), 7.03 (m, 2H), 6.79 (d, 1H), 6.63 (d, 1H), 4.45 (d, 1H), 4.20 (m, 2H), 3.98 (m, 2H), 3.82 (s, 4H), 3.23 (m, 5H), 2.82 (dt, 4H), 2.03 (m, 4H), 1.85 (s, 3H), 1.16 (m, 4H).

Example 20

(rac)-1-(3-(4-chloro-3,5-dimethylphenoxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylic acid

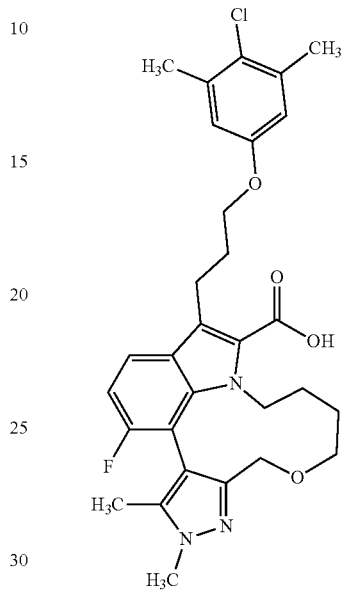

To a stirred solution of (rac)-ethyl 1-(3-(4-chloro-3,5-dimethylphenoxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylate (see Intermediate 36, 88.3 mg, 152 µmol, 1.00 eq.) in ethanol (0.61 mL, 0.25 M) was added a 2.0 M solution of sodium hydroxide in water (189 µL, 379 µmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (23.9 mg).

LC-MS (Method 4): $R_t$=4.54 min; MS (ESIpos): m/z=554 [M+H]$^+$.

$^1$H-NMR (300 MHz, DMSO-d) δ [ppm]: 13.03 (s, 1H), 7.72 (dd, 1H), 7.03 (m, 1H), 6.73 (s, 2H), 4.44 (d, 1H), 4.22 (m, 2H), 3.88 (m, 6H), 3.21 (m, 6H), 2.26 (s, 6H), 2.02 (m, 2H), 1.85 (s, 3H), 1.13 (m, 4H).

Example 21

(rac)-12-ethyl-13-fluoro-1-(3-((6-fluoronaphthalen-1-yl)oxy)propyl)-11-methyl-4,5,6,7,9,11-hexahydro-pyrazolo[4',3':9,10][1]oxa[6]azacycloundecino[8,7,6-hi]indole-2-carboxylic acid

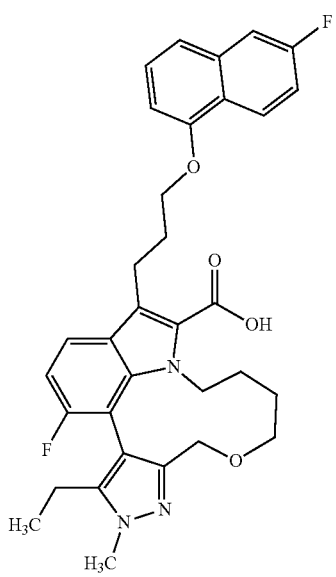 [SMILES: CCc1c2c(nn1C)COCCCCn1c(C(=O)O)c(CCCOc3cccc4cc(F)ccc34)c3ccc(F)c-2c31]

To a stirred solution of (rac)-ethyl 12-ethyl-13-fluoro-1-(3-((6-fluoronaphthalen-1-yl)oxy)propyl)-11-methyl-4,5,6,7,9,11-hexahydropyrazolo[4',3':9,10][1]oxa[6]azacycloun-decino[8,7,6-hi]-indole-2-carboxylate (see Intermediate 41, 153 mg, 254 μmol, 1.00 eq.) in ethanol (1.01 mL, 0.25 M) was added a 2.0 M solution of sodium hydroxide in water (317 μL, 635 μmol, 2.50 eq.). The resulting yellow solution was heated at 70° C. for 16 hours, cooled to room temperature and then acidified to pH 2.0 with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as an off white solid (122 mg).

LC-MS (Method 4): $R_t$=4.54 min; MS (ESIpos): m/z=574 [M+H]$^+$.

$^1$H-NMR (300 MHz, DMSO-d) δ [ppm]: 13.12 (s, 1H), 8.26 (dd, 1H), 7.75 (dd, 1H), 7.66 (dd, 1H), 7.41 (m, 3H), 6.98 (t, 1H), 6.86 (dd, 1H), 4.44 (d, 1H), 4.20 (m, 4H), 3.85 (m, 4H), 3.30 (m, 3H), 3.10 (m, 1H), 2.22 (m, 4H), 1.25 (m, 4H), 0.84 (t, 3H).

The title compound (103 mg) was separated into enantiomers by preparative chiral HPLC to give enantiomer 1 (39 mg, see Example 22) and enantiomer 2 (37 mg, see Example 23).

Preparative Chiral HPLC Method:
Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B: Ethanol; Isokratic: 42% B; Flow 45.0 mL/min; UV 220 nm Analytical Chiral HPLC Method:
Instrument: Agilent HPLC 1260; Column: Chiralpak IG 3 μ 100×4, 6 mm; Eluent A: Hexane+0.1 Vol-% Diethylamine (99%); Eluent B: Ethanol; Isokratic: 30% B; Flow 1.4 mL/min; Temperature: 25° C.; DAD 254 nm The title compound (792 mg) was separated into enantiomers by preparative chiral HPLC to give enantiomer 1 (382 mg, see Example 24) and enantiomer 2 (391 mg, see Example 25).

Preparative Chiral HPLC Method:
Instrument: Labomatic HD5000, Labocord-5000; Gilson GX-241, Labcol Vario 4000, Column: Chiralpak IA 5μ 250×30 mm; Eluent A: Hexane+0.1 Vol-% trifluoroacetic acid (99%); Eluent B: 2-Propanol; Isokratic 85% A+15% B; Flow 50.0 mL/min; UV 254 nm Analytical Chiral HPLC Method:
Instrument: Waters Alliance 2695 Agilent HPLC 1260; Column: Chiralpak IA 3μ 100×4, 6 mm; Eluent A: Hexane+0.1 Vol-% trifluoroacetic acid (99%); Eluent B: 2-Propanol; Gradient: 20-50% B in 7 min; Flow 1.4 mL/min; Temperature: 25° C.; DAD 254 nm

Example 22

3-ethyl-4-fluoro-7-{3-[(6-fluoronaphthalen-1-yl)oxy]propyl}-2-methyl-2,10,11,12,13,15-hexahydro-pyrazolo[4',3':9,10][1,6]oxazacycloundecino[8,7,6-hi]indole-8-carboxylic acid-N-ethylethanamine salt (enantiomer 1)

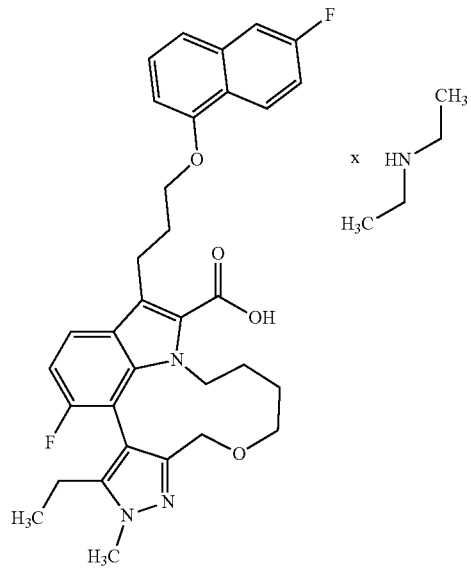

For the preparation of the racemic title compound see Example 21. Separation of enantiomers by preparative chiral HPLC (method see Example 21) gave the title compound (39 mg).

Analytical Chiral HPLC (method see Example 21): $R_t$=1.28 min.

LC-MS (Method 1): $R_t$=1.52 min; MS (ESIpos): m/z=574 [M+H]$^+$

Specific Optical Rotation (Method O1): 38.1° (c=10 mg/mL, DMSO)

$^1$H-NMR (400 MHz, DMSO-d6) δ [ppm]: 0.821 (3.21), 0.840 (6.96), 0.859 (3.23), 1.103 (0.93), 1.128 (8.08), 1.146 (15.87), 1.164 (7.65), 1.340 (0.54), 2.159 (0.42), 2.176 (1.31), 2.194 (2.17), 2.209 (2.52), 2.226 (2.06), 2.243 (1.44), 2.261 (0.65), 2.518 (3.78), 2.522 (2.51), 2.820 (1.88), 2.838

(5.81), 2.857 (5.57), 2.874 (1.77), 3.058 (0.43), 3.083 (0.89), 3.107 (0.69), 3.186 (0.67), 3.200 (1.05), 3.218 (2.06), 3.236 (2.24), 3.254 (1.68), 3.737 (0.46), 3.762 (0.69), 3.783 (0.50), 3.839 (16.00), 4.148 (0.81), 4.163 (1.79), 4.179 (3.45), 4.191 (0.86), 4.200 (0.62), 4.210 (2.60), 4.380 (2.36), 4.412 (2.12), 4.441 (0.51), 4.455 (0.50), 6.820 (1.25), 6.825 (1.25), 6.838 (2.28), 6.861 (1.87), 6.884 (1.12), 7.354 (0.80), 7.360 (0.91), 7.376 (1.45), 7.382 (1.96), 7.403 (2.24), 7.419 (4.26), 7.438 (0.62), 7.562 (0.88), 7.575 (1.01), 7.583 (0.99), 7.597 (0.86), 7.629 (1.55), 7.636 (1.58), 7.655 (1.55), 7.662 (1.52), 8.248 (1.28), 8.262 (1.34), 8.271 (1.31), 8.285 (1.25).

Example 23

3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2)

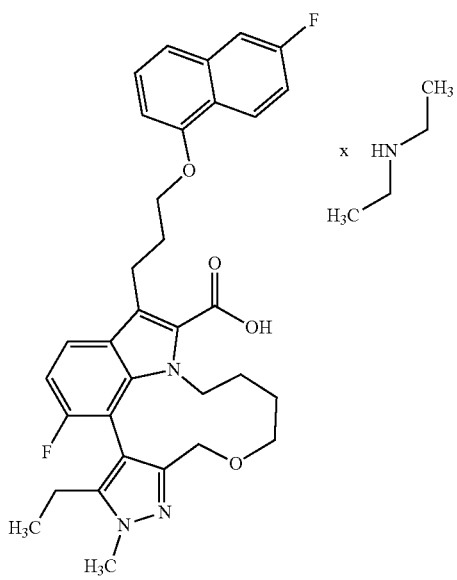

For the preparation of the racemic title compound see Example 21. Separation of enantiomers by preparative chiral HPLC (method see Example 21) gave the title compound (37 mg).

Analytical Chiral HPLC (method see Example 21): $R_t$=2.13 min.

LC-MS (Method 1): $R_t$=1.52 min; MS (ESIpos): m/z=574 $[M+H]^+$

Specific Optical Rotation (Method O1): −35.3° (c=10 mg/mL, DMSO)

$^1$H-NMR (400 MHz, DMSO-d6) δ [ppm]: 0.814 (0.48), 0.823 (2.95), 0.842 (6.55), 0.861 (3.09), 1.121 (7.98), 1.139 (16.00), 1.157 (8.06), 1.335 (0.53), 2.175 (1.37), 2.193 (2.33), 2.211 (2.49), 2.225 (1.69), 2.230 (1.69), 2.244 (1.34), 2.261 (0.63), 2.322 (0.68), 2.326 (0.95), 2.331 (0.71), 2.522 (5.51), 2.664 (0.74), 2.668 (0.98), 2.673 (0.74), 2.805 (1.85), 2.823 (5.44), 2.841 (5.44), 2.859 (1.79), 3.082 (0.80), 3.107 (0.64), 3.177 (0.53), 3.192 (0.84), 3.210 (1.79), 3.229 (1.92), 3.248 (1.21), 3.728 (0.42), 3.751 (0.61), 3.773 (0.47), 3.839 (14.23), 4.147 (0.74), 4.163 (1.72), 4.178 (3.27), 4.191 (0.87), 4.200 (0.64), 4.210 (2.40), 4.375 (2.14), 4.406 (1.74), 4.435 (0.52), 4.452 (0.50), 4.467 (0.52), 6.820 (1.30), 6.826 (2.03), 6.837 (1.40), 6.842 (1.53), 6.849 (1.84), 6.872 (1.06), 7.355 (0.72), 7.361 (0.82), 7.377 (1.32), 7.383 (1.85), 7.403 (2.24), 7.420 (4.15), 7.438 (0.60), 7.545 (0.84), 7.559 (0.95), 7.567 (0.95), 7.581 (0.84), 7.630 (1.38), 7.636 (1.46), 7.656 (1.42), 7.662 (1.42), 8.250 (1.19), 8.264 (1.27), 8.273 (1.27), 8.287 (1.16).

Example 24

3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1)

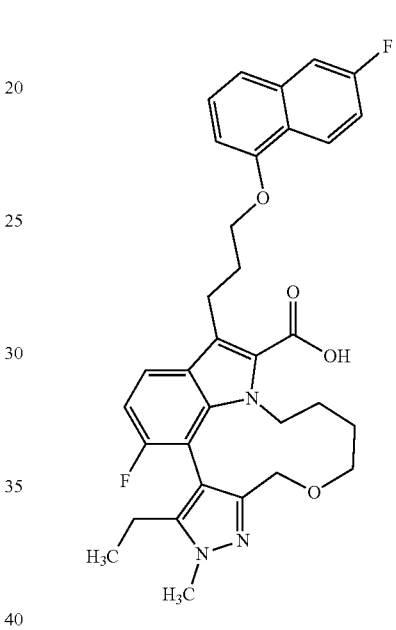

For the preparation of the racemic title compound see Example 21. Separation of enantiomers by preparative chiral HPLC (method see Example 21) gave the title compound (382 mg).

Analytical Chiral HPLC (method see Example 21): $R_t$=1.48 min.

LC-MS (Method 2): $R_t$=0.89 min; MS (ESIpos): m/z=574 $[M+H]^+$

Specific Optical Rotation (Method O1): 25.5° (c=10 mg/mL, DMSO)

$^1$H-NMR (400 MHz, DMSO-d6) δ [ppm]: 0.818 (1.41), 0.837 (3.29), 0.856 (1.49), 1.107 (16.00), 1.154 (0.42), 1.213 (0.44), 1.225 (0.49), 2.172 (0.47), 2.190 (0.85), 2.203 (0.70), 2.209 (0.83), 2.231 (0.62), 2.250 (0.52), 2.518 (2.05), 2.522 (1.31), 3.267 (0.50), 3.287 (0.97), 3.306 (0.73), 3.846 (7.71), 4.173 (0.60), 4.183 (1.36), 4.188 (1.27), 4.204 (0.60), 4.214 (1.16), 4.423 (1.01), 4.454 (0.83), 6.850 (0.57), 6.856 (0.58), 6.865 (0.51), 6.871 (0.62), 6.962 (0.68), 6.984 (1.03), 7.007 (0.69), 7.367 (0.43), 7.383 (0.59), 7.390 (0.64), 7.405 (0.59), 7.412 (0.47), 7.426 (1.05), 7.435 (1.17), 7.441 (2.60), 7.641 (0.69), 7.648 (0.71), 7.667 (0.70), 7.674 (0.70), 7.731 (0.61), 7.745 (0.65), 7.753 (0.67), 7.766 (0.60), 8.239 (0.61), 8.253 (0.63), 8.262 (0.61), 8.277 (0.59).

Example 25

3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 2)

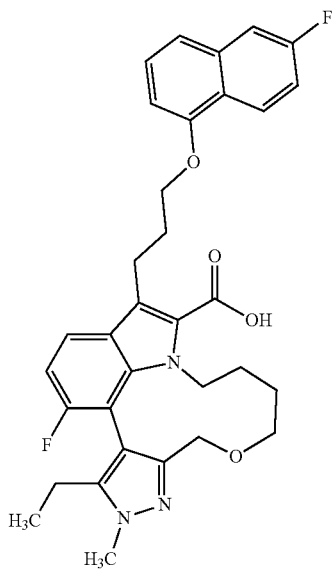 [SMILES: CCc1c2c(nn1C)COCCCCn1c(C(=O)O)c(CCCOc3cccc4cc(F)ccc34)c3ccc(F)c-2c31]

For the preparation of the racemic title compound see Example 21. Separation of enantiomers by preparative chiral HPLC (method see Example 21) gave the title compound (391 mg).

Analytical Chiral HPLC (method see Example 21): $R_t$=1.94 min.

LC-MS (Method 2): $R_t$=0.88 min; MS (ESIpos): m/z=574 [M+H]$^+$

Specific Optical Rotation (Method O1): −30.3° (c=10 mg/mL, DMSO)

$^1$H-NMR (400 MHz, DMSO-d6) δ [ppm]: 0.818 (1.50), 0.837 (3.52), 0.856 (1.58), 1.107 (16.00), 1.213 (0.46), 1.225 (0.50), 2.172 (0.50), 2.190 (0.90), 2.202 (0.75), 2.209 (0.88), 2.231 (0.65), 2.250 (0.55), 2.518 (1.86), 2.522 (1.20), 2.539 (0.73), 3.266 (0.52), 3.287 (1.00), 3.306 (0.75), 3.846 (8.34), 4.173 (0.62), 4.183 (1.44), 4.188 (1.34), 4.204 (0.63), 4.214 (1.23), 4.423 (1.08), 4.454 (0.89), 6.850 (0.61), 6.856 (0.63), 6.864 (0.55), 6.871 (0.65), 6.962 (0.73), 6.984 (1.09), 7.007 (0.74), 7.361 (0.42), 7.367 (0.46), 7.383 (0.62), 7.390 (0.68), 7.405 (0.63), 7.412 (0.51), 7.426 (1.11), 7.435 (1.25), 7.441 (2.79), 7.641 (0.73), 7.648 (0.76), 7.667 (0.75), 7.674 (0.75), 7.731 (0.65), 7.745 (0.69), 7.753 (0.71), 7.767 (0.64), 8.239 (0.65), 8.253 (0.68), 8.262 (0.65), 8.277 (0.63).

Example 26

(rac)-12-ethyl-13-fluoro-1-(3-((4-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylic acid

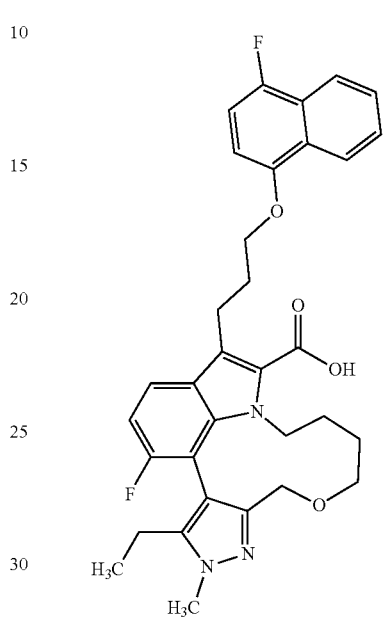

To a stirred solution of (rac)-ethyl 12-ethyl-13-fluoro-1-(3-((4-fluoronaphthalen-1-yl)oxy)propyl)-11-methyl-4,5,6,7,9,11-hexahydropyrazolo[4',3':9,10][1]oxa[6]azacycloundecino[8,7,6-hi]-indole-2-carboxylate (see Intermediate 42, 185 mg) in ethanol (1.22 mL) a 2.0 M solution of sodium hydroxide in water (384 μL, 768 μmol) was added. The resulting yellow solution was heated at 70° C. for 16 hours, cooled to room temperature and then acidified to pH 2.0 with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as an off white solid (146 mg).

LC-MS (Method 4): $R_t$=4.58 min; MS (ESIpos): m/z=574 [M+H]$^+$.

$^1$H-NMR (300 MHz, DMSO-d) δ [ppm]: 13.11 (s, 1H), 8.26 (dt, 1H), 7.99 (m, 1H), 7.75 (dd, 1H), 7.65 (m, 2H), 7.20 (dd, 1H), 6.98 (t, 1H), 6.82 (dd, 1H), 4.44 (d, 1H), 4.19 (m, 4H), 3.85 (m, 4H), 3.31 (m, 6H), 3.10 (m, 1H), 2.22 (m, 4H), 1.20 (m, 4H), 0.84 (t, 3H).

The title compound (123 mg) was separated into enantiomers by preparative chiral HPLC to give enantiomer 1 (55 mg, see Example 27) and enantiomer 2 (61 mg, see Example 28).

Preparative Chiral HPLC Method:

Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B: Ethanol; Isokratic: 42% B; Flow 45.0 mL/min; UV 220 nm Analytical Chiral HPLC Method:
Instrument: Agilent HPLC 1260; Column: Chiralpak IG 3μ 100×4, 6 mm; Eluent A: Hexane+0.1 Vol-% Diethylamine (99%); Eluent B: Ethanol; Isokratic: 30% B; Flow 1.4 mL/min; Temperature: 25° C.; DAD 254 nm

Example 27

3-ethyl-4-fluoro-7-{3-[(4-fluoronaphthalen-1-yl)oxy]propyl}-2-methyl-2,10,11,12,13,15-hexahydro-pyrazolo[4',3':9,10][1,6]oxazacycloundecino[8,7,6-hi]indole-8-carboxylic acid-N-ethylethanamine salt (enantiomer 1)

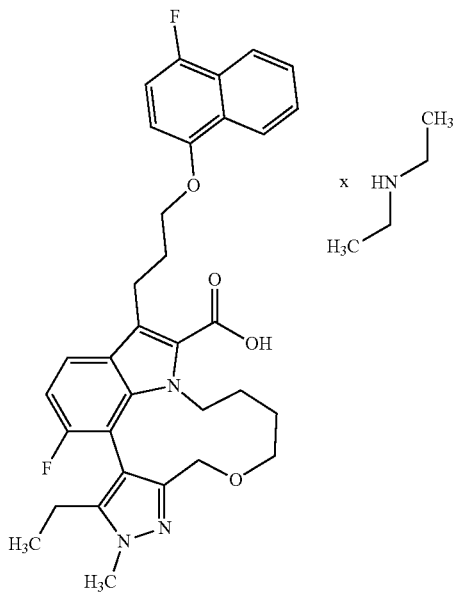

For the preparation of the racemic title compound see Example 26. Separation of enantiomers by preparative chiral HPLC (method see Example 26) gave the title compound (55 mg).
Analytical Chiral HPLC (method see Example 26): $R_t$=1.27 min.
LC-MS (Method 1): $R_t$=1.54 min; MS (ESIpos): m/z=574 [M+H]$^+$
Specific Optical Rotation (Method O1): 38.5° (c=10 mg/mL, DMSO)
$^1$H-NMR (400 MHz, DMSO-d6) δ [ppm]: 0.822 (3.23), 0.841 (7.21), 0.860 (3.32), 1.106 (1.04), 1.128 (8.36), 1.147 (16.00), 1.165 (8.01), 1.339 (0.59), 2.154 (0.46), 2.171 (1.47), 2.189 (2.37), 2.208 (2.51), 2.224 (2.02), 2.242 (1.50), 2.260 (0.68), 2.322 (0.64), 2.326 (0.89), 2.331 (0.67), 2.522 (4.88), 2.664 (0.65), 2.668 (0.89), 2.673 (0.68), 2.819 (1.97), 2.837 (5.89), 2.855 (5.89), 2.874 (1.88), 3.058 (0.42), 3.082 (0.90), 3.107 (0.71), 3.179 (0.61), 3.193 (0.92), 3.211 (1.62), 3.235 (1.87), 3.254 (1.39), 3.269 (1.82), 3.737 (0.47), 3.761 (0.71), 3.783 (0.53), 3.839 (15.69), 4.130 (0.83), 4.146 (1.81), 4.158 (1.85), 4.177 (2.65), 4.208 (2.57), 4.377 (2.40), 4.408 (2.15), 4.438 (0.58), 4.453 (0.56), 6.777 (1.05), 6.786 (1.14), 6.797 (1.32), 6.808 (1.29), 6.832 (1.10), 6.855 (1.84), 6.878 (1.14), 7.156 (1.26), 7.177 (1.30), 7.183 (1.42), 7.203 (1.14), 7.559 (0.92), 7.572 (1.08), 7.580 (1.05), 7.594 (0.96), 7.599 (0.77), 7.603 (0.76), 7.616 (1.44), 7.620 (1.42), 7.635 (2.33), 7.638 (2.48), 7.653 (1.50), 7.657 (1.66), 7.671 (0.73), 7.674 (0.58), 7.972 (1.69), 7.990 (1.65), 7.995 (1.42), 8.253 (1.56), 8.258 (1.02), 8.271 (1.26).

Example 28

3-ethyl-4-fluoro-7-{3-[(4-fluoronaphthalen-1-yl)oxy]propyl}-2-methyl-2,10,11,12,13,15-hexahydro-pyrazolo[4',3':9,10][1,6]oxazacycloundecino[8,7,6-hi]indole-8-carboxylic acid-N-ethylethanamine salt (enantiomer 2)

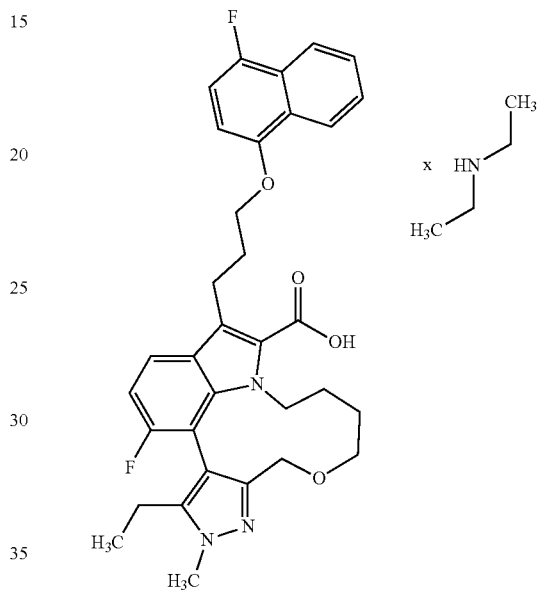

For the preparation of the racemic title compound see Example 26. Separation of enantiomers by preparative chiral HPLC (method see Example 26) gave the title compound (61 mg).
Analytical Chiral HPLC (method see Example 26): $R_t$=1.95 min.
LC-MS (Method 1): $R_t$=1.53 min; MS (ESIpos): m/z=574 [M+H]$^+$
Specific Optical Rotation (Method O1): −33.5° (c=10 mg/mL, DMSO)
$^1$H-NMR (400 MHz, DMSO-d6) δ [ppm]: 0.823 (2.73), 0.843 (5.99), 0.861 (2.78), 1.122 (7.71), 1.140 (16.00), 1.158 (7.43), 1.337 (0.49), 2.170 (1.12), 2.188 (1.76), 2.205 (1.65), 2.211 (1.72), 2.223 (1.52), 2.230 (1.35), 2.243 (1.21), 2.261 (0.54), 2.322 (0.52), 2.326 (0.71), 2.331 (0.54), 2.522 (2.54), 2.664 (0.59), 2.668 (0.75), 2.804 (1.88), 2.822 (5.60), 2.840 (5.50), 2.858 (1.72), 3.082 (0.76), 3.107 (0.59), 3.170 (0.51), 3.185 (0.72), 3.204 (1.25), 3.230 (1.42), 3.248 (1.04), 3.749 (0.59), 3.771 (0.42), 3.839 (13.18), 4.130 (0.71), 4.145 (1.56), 4.157 (1.56), 4.178 (2.17), 4.209 (2.16), 4.372 (2.01), 4.404 (1.61), 4.438 (0.50), 4.456 (0.49), 4.471 (0.50), 6.775 (0.95), 6.784 (1.00), 6.796 (1.17), 6.806 (1.12), 6.820 (0.99), 6.843 (1.60), 6.865 (0.99), 7.155 (1.20), 7.176 (1.18), 7.181 (1.27), 7.203 (1.04), 7.540 (0.84), 7.554 (0.94), 7.562 (0.94), 7.576 (0.81), 7.603 (0.54), 7.617 (1.21), 7.620 (1.18), 7.635 (1.98), 7.639 (2.08), 7.653 (1.23), 7.657 (1.32), 7.670 (0.57), 7.972 (1.47), 7.991 (1.36), 7.995 (1.17), 8.254 (1.35), 8.272 (1.07).

Example 29

(rac)-12-ethyl-13-fluoro-11-methyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylic acid

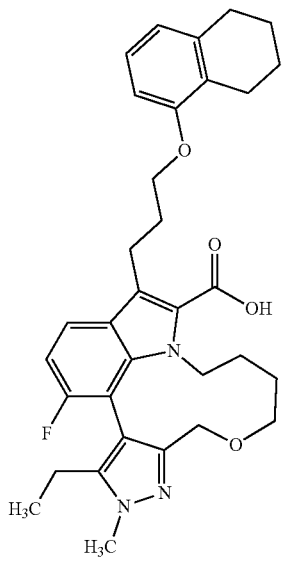 [SMILES: CCc1c2c(nn1C)COCCCCn1c(C(=O)O)c(CCCOc3cccc4c3CCCC4)c3ccc(F)c-2c31]

To a stirred solution of (rac)-ethyl 12-ethyl-13-fluoro-11-methyl-1-(3-((5,6,7,8-tetrahydro-naphthalen-1-yl)oxy)propyl)-4,5,6,7,9,11-hexahydropyrazolo[4',3':9,10][1]oxa[6]azacycloundecino[8,7,6-hi]indole-2-carboxylate (see Intermediate 43, 160 mg) in ethanol (1.08 mL, 0.25 M) was added a 2.0 M solution of sodium hydroxide in water (340 μL, 681 μmol). The resulting yellow solution was heated at 70° C. for 3 days, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (121 mg).

LC-MS (Method 4): $R_t$=4.80 min; MS (ESIpos): m/z=560 [M+H]$^+$.

$^1$H-NMR (300 MHz, DMSO-d) δ [ppm]: 13.05 (s, 1H), 7.71 (dd, 1H), 7.01 (m, 2H), 6.62 (m, 2H), 4.44 (d, 1H), 4.21 (m, 2H), 3.90 (d, 6H), 3.27 (m, 5H), 2.68 (t, 2H), 2.61 (t, 2H), 2.23 (m, 2H), 2.06 (m, 2H), 1.70 (m, 4H), 1.25 (m, 3H), 0.99 (m, 1H), 0.84 (t, 3H).

Example 30

(rac)-1-(3-((2,3-dihydro-1H-inden-4-yl)oxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylic acid

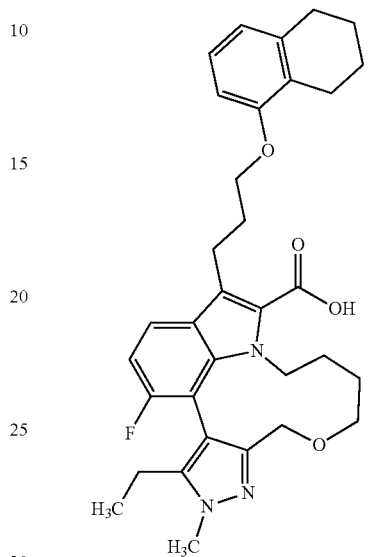

To a stirred solution of (rac)-ethyl 1-(3-((2,3-dihydro-1H-inden-4-yl)oxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate (see Intermediate 44, 165 mg) in ethanol (1.15 mL, 0.25 M) a 2.0 M solution of sodium hydroxide in water (359 μL, 719 μmol) was added. The resulting yellow solution was heated at 70° C. for 3 days, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (121 mg).

LC-MS (Method 4): $R_t$=4.52 min; MS (ESIpos): m/z=546 [M+H]$^+$.

$^1$H-NMR (300 MHz, DMSO-d) δ [ppm]: 13.04 (s, 1H), 7.71 (dd, 1H), 7.02 (m, 2H), 6.79 (d, 1H), 6.62 (d, 1H), 4.44 (d, 1H), 4.21 (m, 2H), 3.92 (m, 6H), 3.19 (m, 4H), 2.82 (m, 4H), 2.23 (m, 2H), 2.02 (m, 3H), 1.23 (m, 3H), 0.99 (m, 1H), 0.84 (t, 3H).

Example 31

(rac)-1-(3-(4-chloro-3,5-dimethylphenoxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylic acid

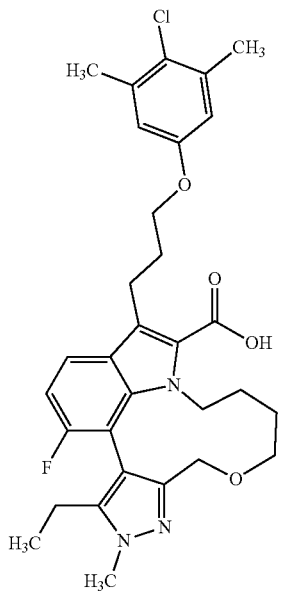 [SMILES: CCc1c2c(nn1C)COCCCCn1c(C(=O)O)c(CCCOc3cc(C)c(Cl)c(C)c3)c3ccc(F)c-2c31]

To a stirred solution of (rac)-ethyl 1-(3-(4-chloro-3,5-dimethylphenoxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylate (see Intermediate 45, 169 mg, 283 μmol, 1.00 eq.) in ethanol (1.13 mL, 0.25 M) was added a 2.0 M solution of sodium hydroxide in water (354 μL, 709 μmol, 2.50 eq.). The resulting yellow solution was heated at 70° C. for 24 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (140 mg).

LC-MS (Method 4): $R_t$=4.73 min; MS (ESIpos): m/z=568 [M+H]$^+$.

$^1$H-NMR (300 MHz, DMSO-d) δ [ppm]: 13.04 (s, 1H), 7.72 (dd, 1H), 7.03 (t, 1H), 6.73 (s, 2H), 4.44 (d, 1H), 4.21 (m, 2H), 3.89 (m, 6H), 3.33 (m, 2H), 3.12 (m, 3H), 2.26 (m, 9H), 2.04 (m, 2H), 1.24 (m, 3H), 0.99 (m, 1H), 0.84 (t, 3H).

Example 32

(rac)-13-fluoro-1-(3-((6-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylic acid

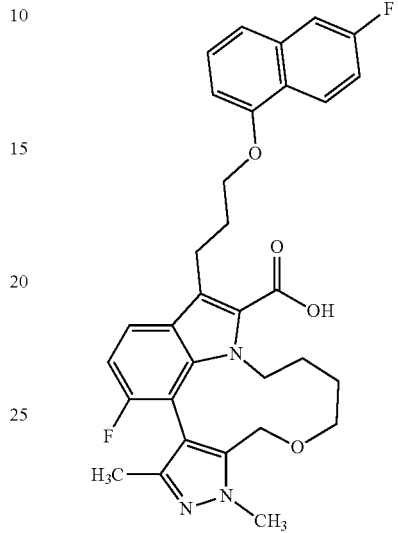

To a stirred solution of (rac)-ethyl 13-fluoro-1-(3-((6-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylate (see Intermediate 50, 148 mg, 252 μmol, 1.00 eq.) in ethanol (1.00 mL, 0.25 M) was added a 2.0 M solution of sodium hydroxide in water (314 μL, 630 μmol, 2.50 eq.). The resulting yellow solution was heated at 70° C. for 14 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to by reverse phase column chromatography (10-100% acetonitrile/water with 0.1% formic acid gradient) to give the title compound as an off white solid (130 mg).

LC-MS (Method 4): $R_t$=4.41 min; MS (ESIpos): m/z=560 [M+H]$^+$.

$^1$H-NMR (300 MHz, DMSO-d) δ [ppm]: 13.21 (s, 1H), 8.26 (m, 1H), 7.79 (dd, 1H), 7.65 (dd, 1H), 7.41 (m, 3H), 7.00 (t, 1H), 6.87 (dd, 1H), 4.66 (d, 1H), 4.52 (dt, 1H), 4.21 (q, 3H), 3.96 (dt, 1H), 3.85 (s, 3H), 3.35 (m, 4H), 2.79 (dt, 1H), 2.20 (m, 2H), 1.81 (s, 3H), 1.26 (m, 2H), 1.04 (s, 2H).

Example 33

(rac)-13-fluoro-1-(3-((4-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylic acid

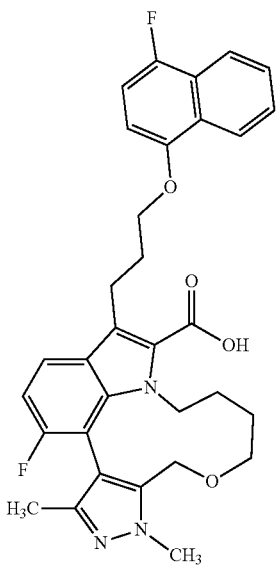 [SMILES: Cc1nn(C)c2c1-c1c(F)ccc3c(CCCOc4ccc(F)c5ccccc45)c(C(=O)O)n(c13)CCCCOC2]

To a stirred solution of (rac)-ethyl 13-fluoro-1-(3-((4-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylate (see Intermediate 51, 102 mg, 173 μmol, 1.00 eq.) in ethanol (0.69 mL, 0.25 M) was added a 2.0 M solution of sodium hydroxide in water (216 μL, 433 μmol, 2.50 eq.). The resulting yellow solution was heated at 70° C. for 14 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (81.0 mg).

LC-MS (Method 4): $R_t$=4.44 min; MS (ESIpos): m/z=560 [M+H]$^+$.

$^1$H-NMR (300 MHz, DMSO-d) δ [ppm]: 13.19 (s, 1H), 8.24 (dt, 1H), 7.99 (dd, 1H), 7.80 (dd, 1H), 7.63 (m, 2H), 7.21 (dd, 1H), 7.00 (t, 1H), 6.83 (dd, 1H), 4.66 (d, 1H), 4.51 (dt, 1H), 4.19 (m, 3H), 3.96 (dt, 1H), 3.85 (s, 3H), 3.30 (m, 5H), 2.80 (m, 1H), 2.19 (m, 2H), 1.81 (s, 3H), 1.28 (s, 2H), 1.05 (s, 2H).

Example 34

(rac)-13-fluoro-10,12-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid

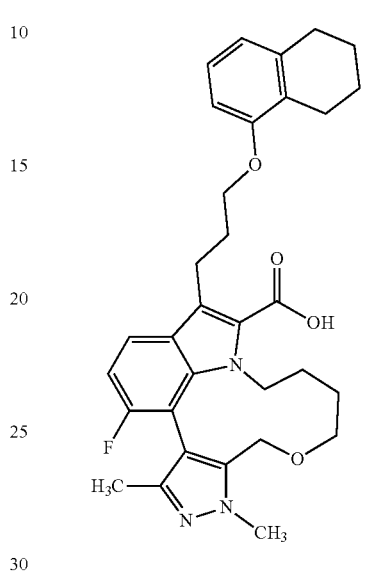

To a stirred solution of (rac)-ethyl 13-fluoro-10,12-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylate (see Intermediate 52, 88.2 mg, 154 μmol, 1.00 eq.) in ethanol (0.61 mL, 0.25 M) was added a 2.0 M solution of sodium hydroxide in water (192 μL, 384 μmol, 2.50 eq.). The resulting yellow solution was heated at 70° C. for 14 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (70.4 mg).

LC-MS (Method 4): $R_t$=4.67 min; MS (ESIpos): m/z=546 [M+H]$^+$.

$^1$H-NMR (300 MHz, DMSO-d) δ [ppm]: 13.12 (s, 1H), 7.74 (dd, 1H), 7.01 (m, 2H), 6.63 (d, 2H), 4.67 (d, 1H), 4.51 (dt, 1H), 4.24 (d, 1H), 3.97 (m, 3H), 3.86 (s, 3H), 3.45 (dt, 1H), 3.22 (m, 1H), 2.80 (m, 1H), 2.64 (m, 4H), 2.06 (m, 2H), 1.82 (s, 3H), 1.70 (m, 4H), 1.26 (m, 2H), 1.07 (s, 2H).

Example 35

(rac)-1-(3-((2,3-dihydro-1H-inden-4-yl)oxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylic acid

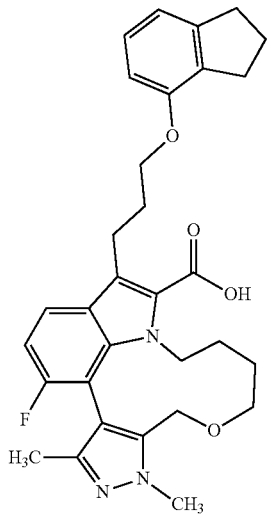 [SMILES: Cc1nn(C)c2c1-c1c(F)ccc3c(CCCOc4cccc5c4CCC5)c(C(=O)O)n(c13)CCCCOC2]

To a stirred solution of (rac)-ethyl 1-(3-((2,3-dihydro-1H-inden-4-yl)oxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylate (see Intermediate 53, 80.8 mg, 144 µmol, 1.00 eq.) in ethanol (0.58 mL, 0.25 M) was added a 2.0 M solution of sodium hydroxide in water (180 µL, 361 µmol, 2.50 eq.). The resulting yellow solution was heated at 70° C. for 14 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (64.9 mg).

LC-MS (Method 4): $R_t$=4.39 min; MS (ESIpos): m/z=532 [M+H]$^+$.

$^1$H-NMR (300 MHz, DMSO-d) δ [ppm]: 13.12 (s, 1H), 7.75 (dd, 1H), 7.03 (td, 2H), 6.80 (d, 1H), 6.64 (d, 1H), 4.67 (d, 1H), 4.50 (dt, 1H), 4.24 (d, 1H), 3.99 (q, 3H), 3.86 (s, 3H), 3.45 (dt, 1H), 3.18 (m, 2H), 2.81 (m, 5H), 2.03 (m, 4H), 1.82 (s, 3H), 1.26 (m, 2H), 1.07 (m, 2H).

Example 36

(rac)-1-(3-(4-chloro-3,5-dimethylphenoxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylic acid

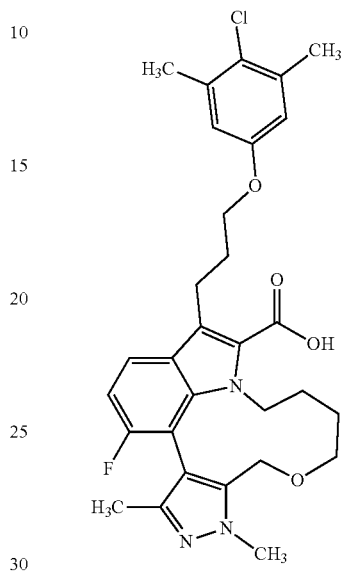

To a stirred solution of (rac)-ethyl 1-(3-(4-chloro-3,5-dimethylphenoxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylate (see Intermediate 54, 93.1 mg, 160 µmol, 1.00 eq.) in ethanol (0.64 mL, 0.25 M) was added a 2.0 M solution of sodium hydroxide in water (199 µL, 400 µmol, 2.50 eq.). The resulting yellow solution was heated at 70° C. for 14 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (79.1 mg).

LC-MS (Method 4): $R_t$=4.60 min; MS (ESIpos): m/z=554 [M+H]$^+$.

$^1$H-NMR (300 MHz, DMSO-d) δ [ppm]: 13.13 (s, 1H), 7.75 (dd, 1H), 7.03 (t, 1H), 6.74 (s, 2H), 4.67 (d, 1H), 4.50 (dt, 1H), 4.24 (d, 1H), 3.90 (m, 6H), 3.45 (dt, 1H), 3.17 (m, 2H), 2.80 (dt, 1H), 2.27 (s, 6H), 2.03 (m, 2H), 1.82 (s, 3H), 1.26 (m, 2H), 1.07 (m, 2H).

Example 37

(rac)-12-ethyl-13-fluoro-10-methyl-1-(3-(naphthalen-1-yloxy)propyl)-4,5,6,7,9,10-hexahydro-pyrazolo[4',3':9,10][1]oxa[6]azacycloundecino[8,7,6-hi]indole-2-carboxylic acid

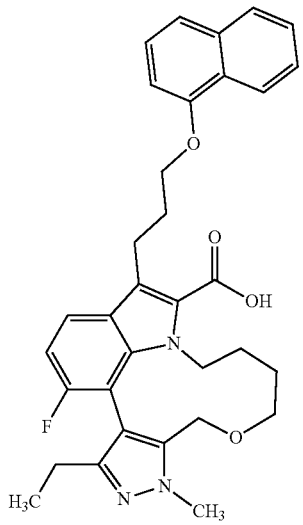 [SMILES: CCc1nn(C)c2c1-c1c(F)ccc3c(CCCOc4cccc5ccccc45)c(C(=O)O)n(c13)CCCCOC2]

To a stirred solution of (rac)-ethyl 12-ethyl-13-fluoro-10-methyl-1-(3-(naphthalen-1-yloxy)propyl)-4,5,6,7,9,10-hexahydropyrazolo[4',3':9,10][1]oxa[6]azacycloundecino[8,7,6-hi]-indole-2-carboxylate (see Intermediate 59, 155 mg, 266 μmol, 1.00 eq.) in ethanol (1.06 mL, 0.25 M) was added a 2.0 M solution of sodium hydroxide in water (331 μL, 664 μmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (140 mg).

LC-MS (Method 4): $R_t$=4.50 min; MS (ESIpos): m/z=556 [M+H]$^+$.

$^1$H-NMR (300 MHz, DMSO-d) δ [ppm]: 13.20 (s, 1H), 8.22 (m, 1H), 7.83 (m, 2H), 7.47 (m, 4H), 6.99 (t, 1H), 6.88 (dd, 1H), 4.65 (d, 1H), 4.49 (dt, 1H), 4.20 (m, 3H), 3.98 (m, 1H), 3.87 (s, 3H), 3.38 (m, 4H), 2.81 (m, 1H), 2.18 (m, 4H), 1.26 (m, 2H), 1.06 (m, 2H), 0.89 (t, 3H).

Example 38

(rac)-12-ethyl-13-fluoro-1-(3-((6-fluoronaphthalen-1-yl)oxy)propyl)-10-methyl-4,5,6,7,9,10-hexahydro-pyrazolo[4',3':9,10][1]oxa[6]azacycloundecino[8,7,6-hi]indole-2-carboxylic acid

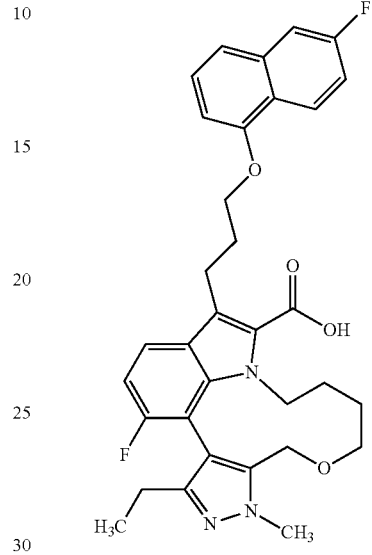

To a stirred solution of (rac)-ethyl 12-ethyl-13-fluoro-1-(3-((6-fluoronaphthalen-1-yl)oxy)propyl)-10-methyl-4,5,6,7,9,10-hexahydropyrazolo[4',3':9,10][1]oxa[6]azacycloundecino[8,7,6-hi]-indole-2-carboxylate (see Intermediate 60, 153 mg, 254 μmol, 1.00 eq.) in ethanol (1.01 mL, 0.25 M) was added a 2.0 M solution of sodium hydroxide in water (317 μL, 709 μmol, 2.50 eq.). The resulting yellow solution was heated at 70° C. for 3 days, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (119 mg).

LC-MS (Method 4): $R_t$=4.58 min; MS (ESIpos): m/z=574 [M+H]$^+$.

$^1$H-NMR (300 MHz, DMSO-d) δ [ppm]: 13.21 (s, 1H), 8.25 (dd, 1H), 7.79 (dd, 1H), 7.65 (dd, 1H), 7.40 (m, 3H), 6.99 (t, 1H), 6.86 (m, 1H), 4.65 (d, 1H), 4.49 (dt, 1H), 4.20 (m, 3H), 3.98 (m, 1H), 3.87 (s, 3H), 3.35 (m, 4H), 2.81 (m, 1H), 2.17 (m, 4H), 1.27 (m, 2H), 1.05 (d, 2H), 0.89 (t, 3H).

The title compound (101 mg) was separated into enantiomers by preparative chiral HPLC to give enantiomer 1 (40 mg, see Example 39) and enantiomer 2 (39 mg, see Example 40).

Preparative Chiral HPLC Method:
Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B:
Ethanol; Gradient: 20-50% B in 20 min; Flow 40.0 mL/min; UV 254 nm
Analytical Chiral HPLC Method:
Instrument: Agilent HPLC 1260; Column: Chiralpak IG 3μ 100×4, 6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 254 nm

Example 39

3-ethyl-4-fluoro-7-{3-[(6-fluoronaphthalen-1-yl)oxy]propyl}-1-methyl-1,10,11,12,13,15-hexahydro-pyrazolo[4',3':9,10][1,6]oxazacycloundecino[8,7,6-hi]indole-8-carboxylic acid-N-ethylethanamine salt (enantiomer 1)

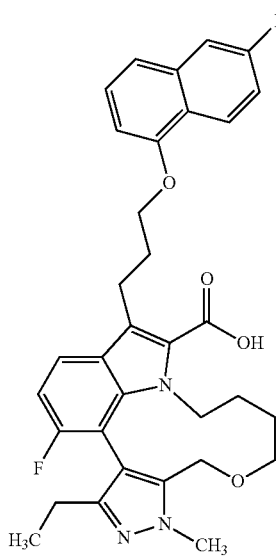

For the preparation of the racemic title compound see Example 38. Separation of enantiomers by preparative chiral HPLC (method see Example 38) gave the title compound (40 mg).

Analytical Chiral HPLC (method see Example 38): $R_t$=4.23 min.

LC-MS (Method 1): $R_t$=1.53 min; MS (ESIpos): m/z=574 [M+H]$^+$

Specific Optical Rotation (Method O1): 82.5° (c=10 mg/mL, DMSO)

$^1$H-NMR (400 MHz, DMSO-d6) δ [ppm]: 0.889 (4.11), 0.908 (9.38), 0.927 (4.22), 0.984 (0.49), 1.006 (0.56), 1.047 (0.46), 1.068 (0.41), 1.099 (0.56), 1.126 (7.69), 1.144 (16.00), 1.162 (7.87), 2.144 (0.83), 2.162 (2.15), 2.180 (3.19), 2.198 (2.42), 2.216 (0.90), 2.518 (4.64), 2.522 (2.72), 2.760 (0.49), 2.773 (0.44), 2.826 (1.96), 2.844 (6.02), 2.862 (5.87), 2.881 (1.82), 3.134 (0.46), 3.149 (0.51), 3.167 (0.74), 3.242 (0.56), 3.261 (1.06), 3.279 (1.02), 3.295 (1.46), 3.404 (0.60), 3.419 (0.79), 3.438 (0.64), 3.450 (0.67), 3.813 (0.58), 3.850 (14.52), 4.161 (1.25), 4.176 (3.48), 4.193 (1.25), 4.208 (1.69), 4.622 (1.87), 4.655 (2.17), 4.690 (0.51), 6.830 (1.64), 6.836 (1.45), 6.846 (1.20), 6.853 (2.05), 6.877 (0.88), 7.345 (0.74), 7.352 (0.85), 7.367 (1.16), 7.374 (1.29), 7.390 (0.88), 7.396 (0.93), 7.408 (1.96), 7.418 (2.33), 7.424 (4.94), 7.439 (0.44), 7.580 (0.65), 7.594 (0.76), 7.601 (0.76), 7.615 (0.65), 7.630 (1.41), 7.636 (1.41), 7.656 (1.38), 7.663 (1.38), 8.239 (1.20), 8.254 (1.23), 8.262 (1.22), 8.277 (1.16).

Example 40

3-ethyl-4-fluoro-7-{3-[(6-fluoronaphthalen-1-yl)oxy]propyl}-1-methyl-1,10,11,12,13,15-hexahydro-pyrazolo[4',3':9,10][1,6]oxazacycloundecino[8,7,6-hi]indole-8-carboxylic acid-N-ethylethanamine salt (enantiomer 2)

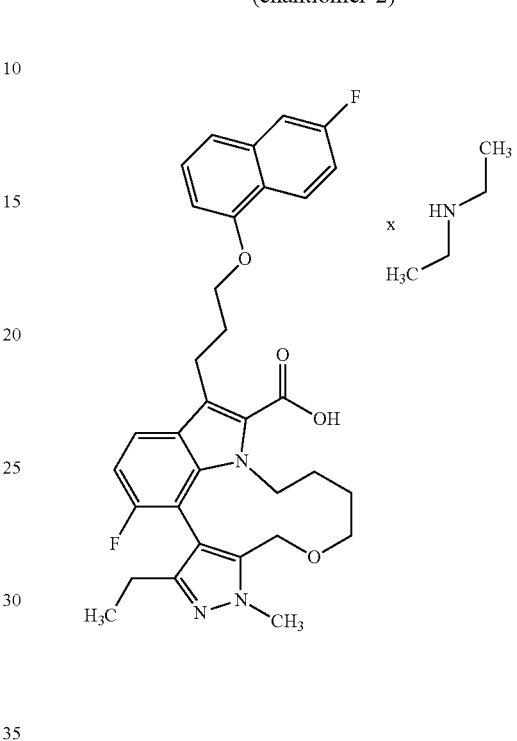

For the preparation of the racemic title compound see Example 38. Separation of enantiomers by preparative chiral HPLC (method see Example 38) gave the title compound (39 mg).

Analytical Chiral HPLC (method see Example 38): $R_t$=5.50 min.

LC-MS (Method 1): $R_t$=1.53 min; MS (ESIpos): m/z=574 [M+H]$^+$

Specific Optical Rotation (Method O1): −74.2° (c=10 mg/mL, DMSO)

$^1$H-NMR (400 MHz, DMSO-d6) δ [ppm]: 0.888 (4.18), 0.907 (9.67), 0.926 (4.38), 0.987 (0.54), 1.006 (0.64), 1.033 (0.43), 1.046 (0.46), 1.068 (0.40), 1.083 (0.40), 1.102 (0.51), 1.130 (7.21), 1.148 (16.00), 1.166 (7.16), 2.144 (0.82), 2.161 (2.06), 2.180 (2.95), 2.197 (2.30), 2.215 (0.90), 2.234 (0.41), 2.518 (3.62), 2.522 (2.22), 2.761 (0.51), 2.774 (0.44), 2.831 (1.76), 2.850 (5.56), 2.868 (5.35), 2.886 (1.66), 3.137 (0.46), 3.153 (0.53), 3.171 (0.76), 3.245 (0.57), 3.264 (1.07), 3.281 (1.04), 3.298 (1.43), 3.402 (0.61), 3.420 (0.80), 3.432 (0.64), 3.450 (0.67), 3.817 (0.60), 3.850 (14.48), 4.161 (1.26), 4.176 (3.59), 4.193 (1.24), 4.208 (1.66), 4.622 (1.87), 4.655 (2.23), 4.689 (0.51), 6.829 (1.26), 6.835 (2.07), 6.845 (1.19), 6.851 (1.43), 6.857 (1.62), 6.880 (0.94), 7.344 (0.74), 7.351 (0.86), 7.367 (1.17), 7.374 (1.27), 7.389 (0.90), 7.396 (0.90), 7.407 (1.97), 7.418 (2.34), 7.423 (4.86), 7.438 (0.43), 7.584 (0.71), 7.598 (0.80), 7.605 (0.80), 7.619 (0.71), 7.630 (1.43), 7.636 (1.44), 7.656 (1.37), 7.662 (1.37), 8.239 (1.19), 8.253 (1.23), 8.262 (1.20), 8.276 (1.16).

Example 41

(rac)-12-ethyl-13-fluoro-1-(3-((4-fluoronaphthalen-1-yl)oxy)propyl)-10-methyl-4,5,6,7,9,10-hexahydro-pyrazolo[4',3':9,10][1]oxa[6]azacycloundecino[8,7,6-hi]indole-2-carboxylic acid

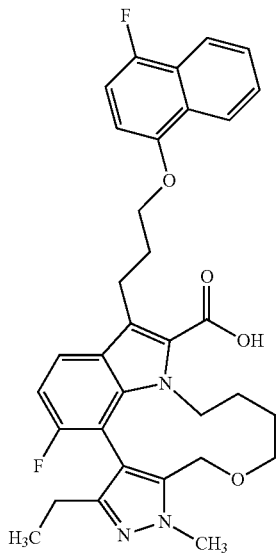 [SMILES: CCc1nn(C)c2c1-c1c(F)ccc3c(CCCOc4ccc(F)c5ccccc45)c(C(=O)O)n(c13)CCCCOC2]

To a stirred solution of (rac)-ethyl 12-ethyl-13-fluoro-1-(3-((4-fluoronaphthalen-1-yl)oxy)propyl)-10-methyl-4,5,6,7,9,10-hexahydropyrazolo[4',3':9,10][1]oxa[6]azacycloundecino[8,7,6-hi]-indole-2-carboxylate (see Intermediate 61, 143 mg, 238 µmol, 1.00 eq.) in ethanol (0.95 mL, 0.25 M) was added a 2.0 M solution of sodium hydroxide in water (297 µL, 594 µmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (112 mg).

LC-MS (Method 4): $R_t$=4.61 min; MS (ESIpos): m/z=574 [M+H]$^+$.

$^1$H-NMR (300 MHz, DMSO-d) δ [ppm]: 13.20 (s, 1H), 8.24 (m, 1H), 7.99 (dd, 1H), 7.79 (dd, 1H), 7.64 (m, 2H), 7.20 (dd, 1H), 6.99 (t, 1H), 6.82 (dd, 1H), 4.65 (d, 1H), 4.48 (dt, 1H), 4.19 (m, 3H), 3.98 (m, 1H), 3.87 (s, 3H), 3.35 (m, 4H), 2.82 (m, 1H), 2.16 (m, 4H), 1.28 (m, 2H), 1.05 (m, 2H), 0.89 (t, 3H).

The title compound (106 mg) was separated into enantiomers by preparative chiral HPLC to give enantiomer 1 (44 mg, see Example 42) and enantiomer 2 (36 mg, see Example 43).

Preparative Chiral HPLC Method:

Instrument: Sepiatec: Prep SFC100; Column: Chiralpak IG 5 µm 250×30 mm; Eluent A: CO2, Eluent B: Ethanol+0.2 Vol-% aqueous ammonia (32%); Isokratic: 21% B; Flow 100.0 mL/min Temperature: 40° C.; BPR: 150 bar; MWD @ 220 nm Analytical Chiral HPLC Method:

Instrument: Agilent: 1260, Aurora SFC-Modul; Column: Chiralpak IG 5 µm 100×4.6 mm; Eluent A: CO2, Eluent B: Ethanol+0.2 Vol-% aqueous ammonia (32%); Isokratic: 21% B; Flow 4.0 mL/min; Temperature: 37.5° C.; BPR: 100 bar; MWD @ 220 nm

Example 42

3-ethyl-4-fluoro-7-{3-[(4-fluoronaphthalen-1-yl)oxy]propyl}-1-methyl-1,10,11,12,13,15-hexahydro-pyrazolo[4',3':9,10][1,6]oxazacycloundecino[8,7,6-hi]indole-8-carboxylic acid (enantiomer 1)

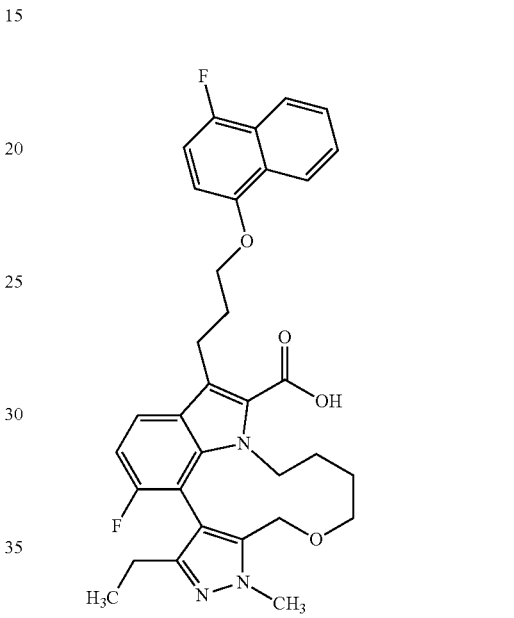

For the preparation of the racemic title compound see Example 41. Separation of enantiomers by preparative chiral HPLC (method see Example 41) gave the title compound (44 mg).

Analytical Chiral HPLC (method see Example 41): $R_t$=1.31 min.

LC-MS (Method 1): $R_t$=1.54 min; MS (ESIpos): m/z=574 [M+H]$^+$

Specific Optical Rotation (Method O1): 88.7° (c=10 mg/mL, DMSO)

$^1$H-NMR (400 MHz, DMSO-d6) δ [ppm]: 0.859 (0.55), 0.875 (4.63), 0.894 (10.48), 0.913 (4.75), 0.967 (1.15), 0.994 (0.44), 1.009 (0.74), 1.037 (1.14), 1.107 (12.16), 1.139 (1.90), 1.143 (0.97), 1.158 (3.94), 1.175 (1.96), 1.208 (1.18), 1.229 (0.56), 1.323 (0.47), 2.130 (0.83), 2.141 (0.78), 2.149 (1.96), 2.160 (2.14), 2.168 (2.41), 2.179 (2.48), 2.187 (1.82), 2.197 (1.54), 2.208 (1.09), 2.331 (0.62), 2.518 (3.34), 2.523 (2.08), 2.673 (0.63), 2.780 (0.65), 2.792 (0.55), 2.808 (0.69), 2.876 (0.49), 2.894 (1.46), 2.912 (1.45), 2.931 (0.47), 3.214 (0.62), 3.230 (0.81), 3.247 (1.21), 3.268 (1.05), 3.409 (0.86), 3.426 (1.09), 3.440 (0.87), 3.456 (0.89), 3.472 (0.47), 3.861 (16.00), 3.929 (0.62), 3.952 (0.41), 4.155 (1.48), 4.170 (3.01), 4.189 (2.60), 4.223 (1.87), 4.514 (0.65), 4.548 (0.61), 4.626 (2.13), 4.659 (1.92), 6.800 (1.14), 6.810 (1.20), 6.822 (1.39), 6.831 (1.31), 6.928 (1.05), 6.950 (1.82), 6.973 (1.03), 7.174 (1.55), 7.195 (1.49), 7.200 (1.59), 7.221 (1.30), 7.595 (0.61), 7.598 (0.68), 7.612 (1.40), 7.615 (1.54), 7.632 (1.62), 7.636 (2.52), 7.640 (1.61), 7.657 (1.52), 7.660 (1.49),

Example 43

3-ethyl-4-fluoro-7-{3-[(4-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 2)

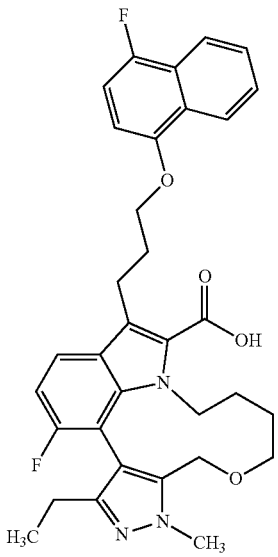 [SMILES: CCc1nn(C)c2c1-c1c(F)ccc3c(CCCOc4ccc(F)c5ccccc45)c(C(=O)O)n(c13)CCCCOC2]

For the preparation of the racemic title compound see Example 41. Separation of enantiomers by preparative chiral HPLC (method see Example 41) gave the title compound (36 mg).

Analytical Chiral HPLC (method see Example 41): $R_t$=2.56 min.

LC-MS (Method 1): $R_t$=1.54 min; MS (ESIpos): m/z=574 [M+H]$^+$

Specific Optical Rotation (Method O1): −84.9° (c=10 mg/mL, DMSO)

$^1$H-NMR (400 MHz, DMSO-d6) δ [ppm]: 0.858 (0.60), 0.872 (4.73), 0.891 (10.43), 0.909 (4.71), 0.966 (1.30), 0.993 (0.40), 1.008 (0.62), 1.041 (1.27), 1.107 (14.60), 1.139 (0.66), 1.143 (0.95), 1.156 (1.23), 1.175 (0.62), 1.207 (1.03), 1.249 (0.58), 1.258 (0.59), 1.303 (0.57), 2.128 (0.83), 2.137 (0.77), 2.146 (1.94), 2.156 (2.19), 2.164 (2.21), 2.175 (2.78), 2.183 (1.45), 2.194 (2.16), 2.211 (1.33), 2.229 (0.42), 2.331 (0.50), 2.518 (2.49), 2.523 (1.57), 2.539 (0.47), 2.673 (0.50), 2.788 (0.72), 2.800 (0.57), 2.817 (0.76), 2.904 (0.42), 2.922 (0.40), 3.217 (0.43), 3.235 (0.72), 3.250 (0.98), 3.269 (1.52), 3.412 (0.87), 3.429 (1.14), 3.442 (0.90), 3.459 (0.93), 3.475 (0.47), 3.864 (16.00), 3.946 (0.45), 3.957 (0.69), 3.969 (0.45), 3.980 (0.46), 4.159 (1.49), 4.174 (3.01), 4.194 (2.43), 4.227 (1.95), 4.483 (0.75), 4.494 (0.46), 4.506 (0.43), 4.517 (0.69), 4.628 (2.19), 4.661 (1.97), 6.803 (1.14), 6.813 (1.19), 6.825 (1.38), 6.834 (1.32), 6.952 (1.30), 6.974 (2.27), 6.997 (1.35), 7.177 (1.56), 7.199 (1.50), 7.204 (1.59), 7.226 (1.35), 7.597 (0.61), 7.600 (0.69), 7.614 (1.41), 7.617 (1.56), 7.634 (1.59), 7.638 (2.54), 7.642 (1.64), 7.659 (1.57), 7.662 (1.53), 7.676 (0.77), 7.679 (0.63), 7.754 (1.07), 7.768 (1.18), 7.775 (1.17), 7.790 (1.04), 7.976 (1.82), 7.995 (1.66), 8.229 (1.51), 8.248 (1.28).

Example 44

(rac)-12-ethyl-13-fluoro-10-methyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid

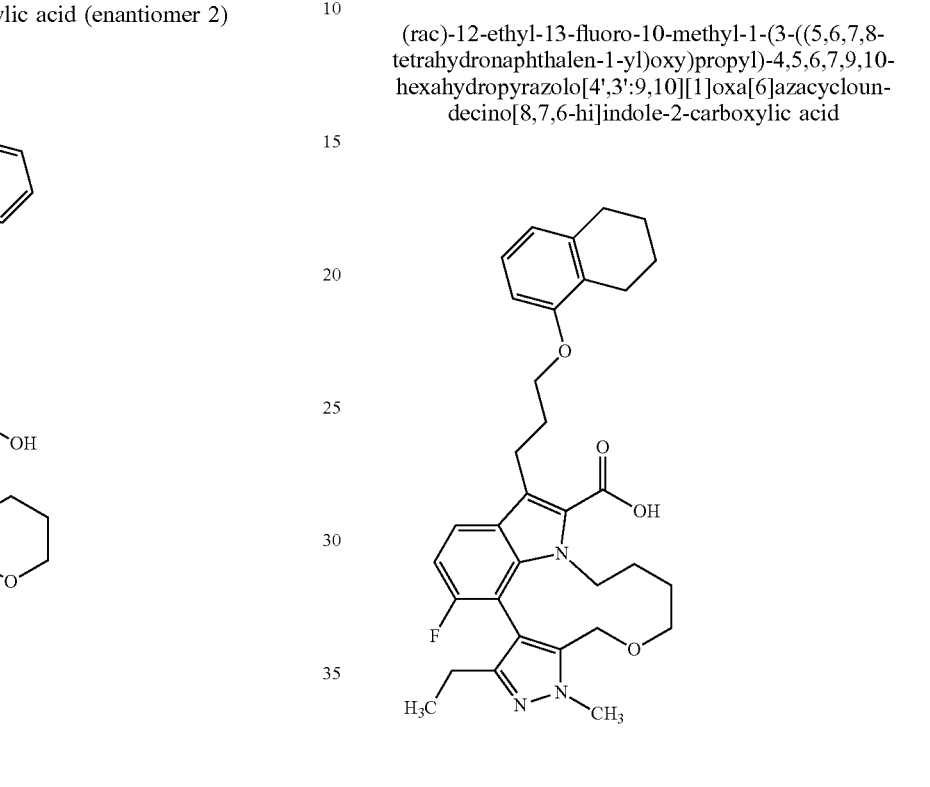

To a stirred solution of (rac)-ethyl 12-ethyl-13-fluoro-10-methyl-1-(3-((5,6,7,8-tetrahydro-naphthalen-1-yl)oxy)propyl)-4,5,6,7,9,10-hexahydropyrazolo[4',3':9,10][1]oxa[6]azacycloundecino[8,7,6-hi]indole-2-carboxylate (see Intermediate 62, 75.4 mg, 128 μmol, 1.00 eq.) in ethanol (0.51 mL, 0.25 M) was added a 2.0 M solution of sodium hydroxide in water (160 μL, 320 μmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as an off white solid (58.3 mg).

LC-MS (Method 4): $R_t$=4.85 min; MS (ESIpos): m/z=560 [M+H]$^+$.

$^1$H-NMR (300 MHz, DMSO-d) δ [ppm]: 13.13 (s, 1H), 7.74 (dd, 1H), 7.00 (m, 2H), 6.62 (d, 2H), 4.66 (d, 1H), 4.48 (dt, 1H), 4.24 (d, 1H), 3.98 (m, 3H), 3.87 (s, 3H), 3.47 (dt, 1H), 3.19 (m, 2H), 2.82 (m, 1H), 2.64 (m, 4H), 2.18 (m, 2H), 2.06 (m, 2H), 1.71 (m, 4H), 1.28 (m, 2H), 1.09 (m, 2H), 0.90 (t, 3H).

Example 45

(rac)-1-(3-((2,3-dihydro-1H-inden-4-yl)oxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylic acid

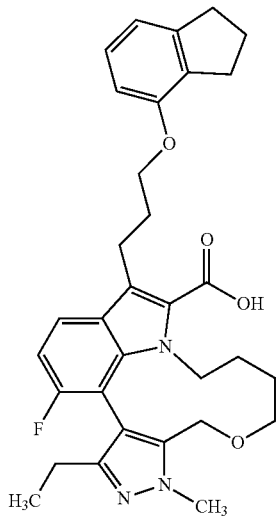 [SMILES: CCc1nn(C)c2c1-c1c(F)ccc3c(CCCOc4cccc5c4CCC5)c(C(=O)O)n(c13)CCCCOC2]

To a stirred solution of (rac)-ethyl 1-(3-((2,3-dihydro-1H-inden-4-yl)oxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 63, 73.7 mg, 128 μmol, 1.00 eq.) in ethanol (0.51 mL, 0.25 M) was added a 2.0 M solution of sodium hydroxide in water (160 μL, 320 μmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (45.7 mg).

LC-MS (Method 4): $R_t$=4.56 min; MS (ESIpos): m/z=546 [M+H]$^+$.

$^1$H-NMR (300 MHz, DMSO-d) δ [ppm]: 13.12 (s, 1H), 7.75 (dd, 1H), 7.03 (td, 2H), 6.80 (d, 1H), 6.63 (d, 1H), 4.66 (d, 1H), 4.47 (dt, 2H), 4.24 (d, 1H), 3.98 (q, 3H), 3.87 (s, 3H), 3.47 (dt, 1H), 3.18 (m, 2H), 2.82 (m, 5H), 2.18 (m, 2H), 2.02 (m, 4H), 1.27 (m, 2H), 1.08 (m, 2H), 0.90 (t, 3H).

Example 46

(rac)-1-(3-(4-chloro-3,5-dimethylphenoxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylic acid

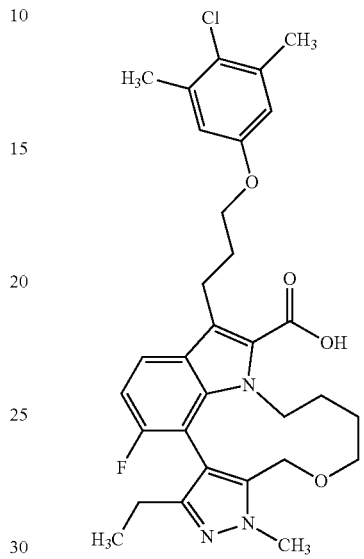

To a stirred solution of (rac)-ethyl 1-(3-(4-chloro-3,5-dimethylphenoxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylate (see Intermediate 64, 73.7 mg, 124 μmol, 1.00 eq.) in ethanol (0.49 mL, 0.25 M) was added a 2.0 M solution of sodium hydroxide in water (154 μL, 310 μmol, 2.50 eq.). The resulting yellow solution was heated at 70° C. for 20 hours, cooled to room temperature and then acidified with 1.0 M aqueous hydrochloric acid. Celite was added to the resulting mixture, volatiles were removed under reduced pressure, and the residue was loaded onto a silica gel cartridge which was subjected to reverse phase column chromatography (10-100% acetonitrile/water with 0.1% formic acid gradient) to give the title compound as a white solid (59.8 mg).

LC-MS (Method 4): $R_t$=4.77 min; MS (ESIpos): m/z=568 [M+H]$^+$.

$^1$H-NMR (300 MHz, DMSO-d) δ [ppm]: 13.11 (s, 1H), 7.75 (dd, 1H), 7.02 (t, 1H), 6.73 (s, 2H), 4.66 (d, 1H), 4.47 (dt, 1H), 4.24 (d, 1H), 3.96 (m, 3H), 3.87 (s, 3H), 3.47 (dt, 1H), 3.17 (m, 2H), 2.82 (dt, 1H), 2.23 (m, 8H), 2.05 (m, 2H), 1.27 (m, 2H), 1.08 (m, 2H), 0.90 (t, 3H).

Example 47

(rac)-4-fluoro-2,3-dimethyl-7-[3-(1-naphthyloxy)propyl]-10,11,12,13,14,15-hexahydro-2H-pyrazolo[3',4':8,9][1,6]diazacycloundecino[10,11,1-hi]indole-8-carboxylic acid trifluoroacetic acid salt

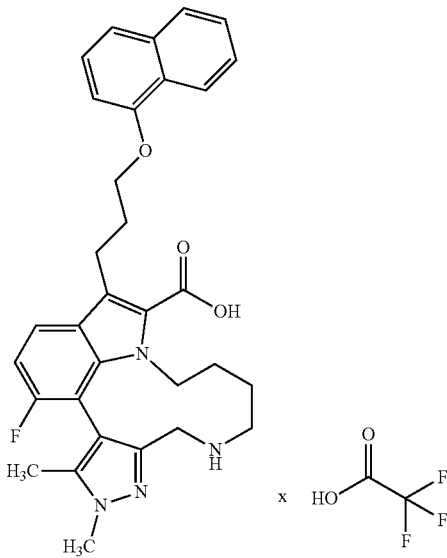 [SMILES: Cc1c2c(nn1C)CNCCCCn1c(C(=O)O)c(CCCOc3cccc4ccccc34)c3ccc(F)c-2c31 ; O=C(O)C(F)(F)F]

To a stirred solution of (rac)-ethyl 4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylate (see Intermediate 68, 56.8 mg) in ethanol (400 μL, 0.25 M) was added a 2.0 M solution of sodium hydroxide in water (125 μL, 250 μmol). The resulting yellow solution was heated at 70° C. for 8 hours, cooled to room temperature and then acidified to pH 2.0 with trifluoroacetic acid. The mixture was diluted with dimethyl sulfoxide and then purified by reverse phase column chromatography (10-100% acetonitrile/water with 0.1% trifluoroacetic acid) to give the title compound as a white solid (52.0 mg).

LC-MS (Method 3): $R_t$=1.19 min; MS (ESIpos): m/z=541 [M+H]$^+$.

$^1$H-NMR (300 MHz, CHLOROFORM-d) δ [ppm]: 10.89 (s, 1H), 8.50 (s, 1H), 8.39 (d, 1H), 7.79 (m, 1H), 7.74 (d, 1H), 7.40 (dt, 4H), 6.98 (t, 1H), 6.79 (d, 1H), 4.76 (d, 1H), 4.20 (m, 3H), 3.95 (m, 1H), 3.73 (t, 1H), 3.63 (s, 3H), 3.43 (m, 1H), 2.94 (m, 1H), 2.44 (m, 1H), 2.24 (m, 2H), 1.98 (s, 3H), 1.43 (m, 2H), 1.15 (m, 2H).

The title compound (27 mg) was separated into enantiomers by preparative chiral HPLC to give enantiomer 1 (7 mg, see Example 48) and enantiomer 2 (8 mg, see Example 49).

Preparative Chiral HPLC Method:
Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B:
Ethanol; Isokratic: 42% B; Flow 45.0 mL/min; UV 254 nm
Analytical Chiral HPLC Method:
Instrument: Agilent HPLC 1260; Column: Chiralpak IG 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 254 nm

Example 48

4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid (enantiomer 1)

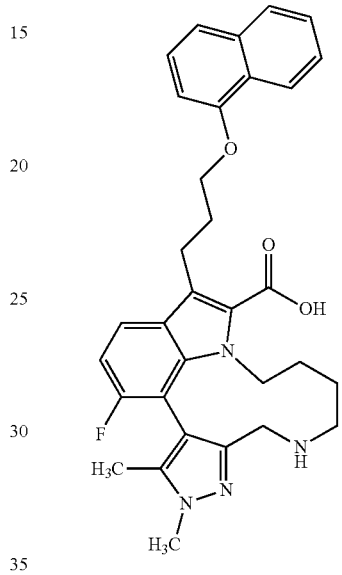

For the preparation of the racemic title compound see Example 47. Separation of enantiomers by preparative chiral HPLC (method see Example 47) gave the title compound (7 mg).

Analytical Chiral HPLC (method see Example 47): $R_t$=2.88 min.

LC-MS (Method 1): $R_t$=1.13 min; MS (ESIpos): m/z=541 [M+H]$^+$ $^1$H-NMR (400 MHz, DMSO-d6) δ [ppm]: 0.851 (0.53), 0.865 (0.53), 0.888 (0.53), 1.106 (0.68), 1.131 (2.37), 1.149 (4.45), 1.167 (2.20), 1.231 (1.19), 1.352 (0.62), 1.905 (1.93), 1.913 (14.31), 2.038 (0.42), 2.060 (0.71), 2.084 (0.47), 2.142 (1.22), 2.160 (1.81), 2.178 (1.31), 2.195 (0.45), 2.318 (0.62), 2.322 (1.25), 2.327 (1.69), 2.331 (1.25), 2.336 (0.56), 2.518 (6.35), 2.523 (4.16), 2.612 (0.50), 2.659 (0.83), 2.665 (1.45), 2.669 (1.84), 2.673 (1.34), 2.849 (0.50), 2.867 (1.42), 2.885 (1.42), 2.903 (0.47), 3.115 (0.71), 3.130 (0.74), 3.148 (0.98), 3.167 (0.59), 3.279 (2.85), 3.550 (1.40), 3.585 (1.57), 3.723 (0.42), 3.749 (0.71), 3.771 (0.47), 3.841 (16.00), 3.877 (0.80), 4.142 (1.45), 4.158 (2.91), 4.174 (1.40), 4.648 (0.56), 4.683 (0.53), 6.841 (1.28), 6.860 (2.55), 6.863 (2.49), 6.877 (2.26), 6.887 (1.37), 7.348 (1.42), 7.369 (2.70), 7.388 (2.14), 7.429 (2.94), 7.450 (1.66), 7.476 (0.45), 7.481 (0.65), 7.493 (1.72), 7.498 (1.63), 7.502 (1.99), 7.510 (3.71), 7.517 (1.99), 7.522 (1.78), 7.526 (1.84), 7.539 (0.71), 7.543 (0.45), 7.592 (1.04), 7.606 (1.13), 7.614 (1.13), 7.627 (1.01), 7.844 (1.72), 7.852 (0.95), 7.862 (1.54), 7.868 (1.45), 8.222 (1.48), 8.227 (1.42), 8.246 (1.42).

Example 49

4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid (enantiomer 2)

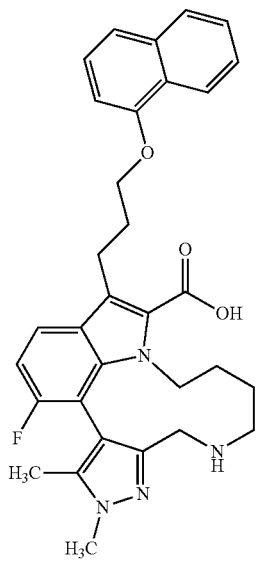 [SMILES: Cc1c2c(nn1C)CNCCCCn1c(C(=O)O)c(CCCOc3cccc4ccccc34)c3ccc(F)c-2c31]

For the preparation of the racemic title compound see Example 47. Separation of enantiomers by preparative chiral HPLC (method see Example 47) gave the title compound (8 mg).

Analytical Chiral HPLC (method see Example 47): $R_t$=4.22 min.

LC-MS (Method 1): $R_t$=1.13 min; MS (ESIpos): m/z=541 [M+H]$^+$ $^1$H-NMR (400 MHz, DMSO-d6) δ [ppm]: 0.863 (0.57), 0.888 (0.57), 1.101 (0.91), 1.137 (2.26), 1.155 (3.80), 1.173 (1.82), 1.230 (1.18), 1.348 (0.61), 1.906 (1.04), 1.918 (15.45), 2.036 (0.44), 2.060 (0.76), 2.084 (0.51), 2.135 (1.31), 2.152 (1.92), 2.169 (1.37), 2.322 (0.89), 2.327 (1.20), 2.331 (0.89), 2.336 (0.42), 2.518 (4.65), 2.523 (2.98), 2.659 (0.93), 2.665 (1.37), 2.669 (1.69), 2.673 (1.37), 2.860 (0.42), 2.878 (1.23), 2.896 (1.18), 2.914 (0.40), 3.097 (0.46), 3.116 (0.82), 3.131 (0.85), 3.149 (1.12), 3.169 (0.72), 3.282 (3.15), 3.566 (1.39), 3.601 (1.52), 3.718 (0.53), 3.744 (0.78), 3.770 (0.55), 3.847 (16.00), 3.896 (1.06), 3.932 (0.89), 4.134 (1.61), 4.150 (3.21), 4.166 (1.56), 4.662 (0.66), 4.696 (0.61), 6.851 (2.79), 6.872 (4.44), 6.894 (1.39), 7.344 (1.50), 7.365 (2.90), 7.384 (2.24), 7.427 (3.19), 7.447 (1.82), 7.472 (0.53), 7.477 (0.72), 7.490 (1.84), 7.494 (1.71), 7.500 (2.05), 7.507 (3.89), 7.514 (2.05), 7.519 (1.88), 7.524 (2.01), 7.536 (0.80), 7.541 (0.53), 7.605 (1.16), 7.618 (1.29), 7.626 (1.27), 7.640 (1.12), 7.842 (1.90), 7.850 (1.08), 7.860 (1.80), 7.866 (1.59), 8.218 (1.65), 8.224 (1.59), 8.243 (1.54).

Example 50

8-carboxy-4-fluoro-2,3,14,14-tetramethyl-7-[3-(1-naphthyloxy)propyl]-10,11,12,13,14,15-hexa-hydro-2H-pyrazolo[3',4':8,9][1,6]diazacycloundecino[10,11,1-hi]indol-14-ium trifluroacetate

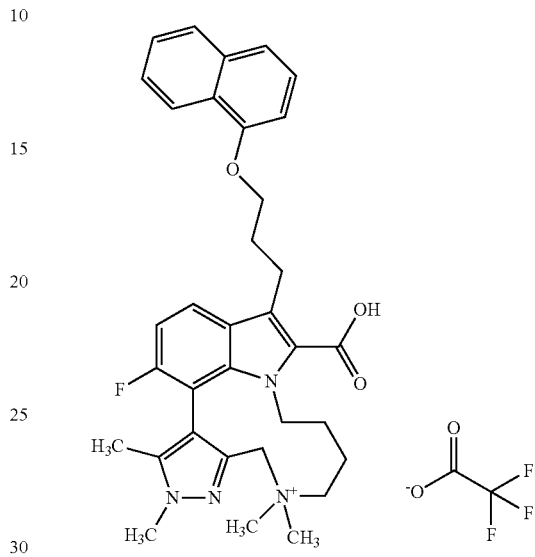

To a stirred solution of 8-(ethoxycarbonyl)-4-fluoro-2,3,14,14-tetramethyl-7-[3-(1-naphthyl-oxy)propyl]-10,11,12,13,14,15-hexahydro-2H-pyrazolo[3',4':8,9][1,6]diazacycloundecino-[10,11,1-hi]indol-14-ium trifluroacetate (see Intermediate 69, 52.0 mg) in ethanol (292 μL, 0.25 M) was added a 2.0 M solution of sodium hydroxide in water (128 μL, 256 μmol). The resulting yellow solution was heated at 70° C. for 16 h, cooled to room temperature and then acidified with trifluoroacetic acid. The mixture was purified by reverse phase column chromatography (10-100% acetonitrile/water with 0.1% trifluoroacetic acid gradient) to give the title compound as a white solid (38.6 mg).

LC-MS (Method 4): $R_t$=3.25 min; MS (ESIpos): m/z=569 [M+H]$^+$.

$^1$H-NMR (300 MHz, DMSO-d) δ [ppm]: 13.30 (s, 1H), 8.24 (d, 1H), 7.87 (m, 2H), 7.53 (m, 2H), 7.47 (m, 1H), 7.40 (t, 1H), 4.75 (d, 1H), 4.51 (d, 1H), 4.22 (m, 3H), 3.92 (s, 3H), 3.85 (t, 1H), 3.32 (m, 2H), 3.15 (m, 1H), 2.98 (s, 3H), 2.45 (m, 1H), 2.20 (m, 2H), 1.94 (s, 2H), 1.43 (m, 2H), 1.23 (t, 1H), 0.99 (q, 1H).

Example 51

(rac)-7-[3-(2,3-dihydro-1H-inden-4-yloxy)propyl]-3-ethyl-4-fluoro-2,14-dimethyl-10,11,12,13,14,15-hexahydro-2H-pyrazolo[3',4':8,9][1,6]diazacycloundecino[10,11,1-hi]indole-8-carboxylic acid

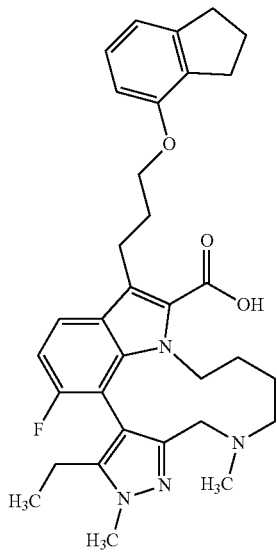 [SMILES: CCc1c2c(nn1C)CN(C)CCCCn1c(C(=O)O)c(CCCOc3cccc4c3CCC4)c3ccc(F)c-2c31]

To a stirred solution of (rac)-ethyl 7-[3-(2,3-dihydro-1H-inden-4-yloxy)propyl]-3-ethyl-4-fluoro-2,14-dimethyl-10,11,12,13,14,15-hexahydro-2H-pyrazolo[3',4':8,9][1,6]diazacycloundecino[10,11,1-hi]indole-8-carboxylate (see Intermediate 74, 58.0 mg, 98.8 μmol, 1.00 eq.) in absolute ethanol (395 μL, 0.25 M) was added a 2.0 M aqueous solution of sodium hydroxide (123 μL, 247 μmol, 2.50 eq.). The resulting suspension was heated at 70° C. for 24 hours and then cooled to room temperature. The mixture was neutralised with 1.0 M aqueous hydrochloric acid (~0.25 mL) and then purified directly by reverse phase flash column chromatography (10-100% acetonitrile/water with 0.1% formic acid gradient) to give the title compound as a white solid (47.0 mg).

LC-MS (Method 4): Rt=3.24 min; MS (ESIpos): m/z=559 [M+H]$^+$.

1H NMR (300 MHz, DMSO-d6) δ 12.99 (s, 1H), 7.66 (dd, J=8.7, 5.5 Hz, 1H), 7.08-6.92 (m, 2H), 6.79 (d, J=7.3 Hz, 1H), 6.62 (d, J=8.0 Hz, 1H), 4.35-4.20 (m, 1H), 3.99 (t, J=6.5 Hz, 2H), 3.82 (s, 4H), 3.49 (d, J=12.5 Hz, 1H), 3.44-3.03 (m, 4H), 2.82 (dt, J=14.0, 7.4 Hz, 4H), 2.41-2.11 (m, 3H), 2.12-1.79 (m, 8H), 1.36-0.93 (m, 4H), 0.83 (t, J=7.5 Hz, 3H).

Example 52

(rac)-3-ethyl-4-fluoro-2,14-dimethyl-7-[3-(5,6,7,8-tetrahydronaphthalen-1-yloxy)propyl]-10,11,12,13,14,15-hexahydro-2H-pyrazolo[3',4':8,9][1,6]diazacycloundecino[10,11,1-hi]indole-8-carboxylic acid

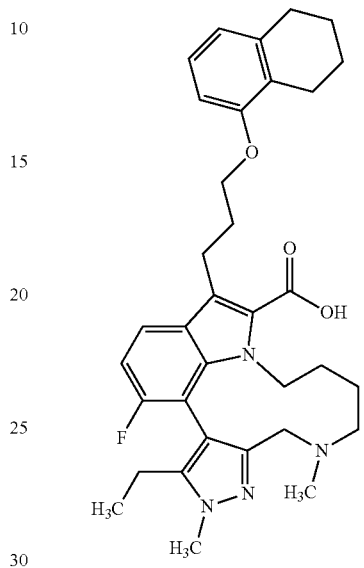

To a stirred solution of (rac)-ethyl 3-ethyl-4-fluoro-2,14-dimethyl-7-[3-(5,6,7,8-tetrahydronaphthalen-1-yloxy)propyl]-10,11,12,13,14,15-hexahydro-2H-pyrazolo[3',4':8,9][1,6]diazacycloundecino[10,11,1-hi]indole-8-carboxylate (see Intermediate 75, 47.2 mg, 78.6 μmol, 1.00 eq.) in absolute ethanol (314 μL, 0.25 M) was added a 2.0 M aqueous solution of sodium hydroxide (98.2 μL, 196 μmol, 2.50 eq.). The resulting suspension was heated at 70° C. for 24 hours and then cooled to room temperature. The mixture was neutralised with 1.0 M aqueous hydrochloric acid (~0.20 mL) and then dry loaded onto Celite. The residue was purified by flash reverse phase column chromatography (10-100% acetonitrile/water gradient buffered with 0.1% formic acid) to give the title compound as a white solid (38.3 mg).

LC-MS (Method 4): Rt=3.70 min; MS (ESIpos): m/z=573 [M+H]$^+$.

1H NMR (300 MHz, DMSO-d6) δ 12.97 (s, 1H), 7.66 (dd, J=8.7, 5.5 Hz, 1H), 7.04-6.91 (m, 2H), 6.66-6.55 (m, 2H), 4.36-4.18 (m, 1H), 3.89 (d, J=43.9 Hz, 5H), 3.57-3.04 (m, 4H), 2.78-2.56 (m, 4H), 2.43-2.11 (m, 2H), 2.05 (m, J=4.6 Hz, 5H), 1.95-1.80 (m, 1H), 1.80-1.56 (m, 4H), 1.38-0.88 (m, 6H), 0.83 (t, J=7.5 Hz, 3H).

Example 53

(rac)-3-ethyl-4-fluoro-7-{3-[(6-fluoro-1-naphthyhoxy]propyl}-2,14-dimethyl-10,11,12,13,14,15-hexahydro-2H-pyrazolo[3',4':8,9][1,6]diazacycloundecino[10,11,1-hi]indole-8-carboxylic acid

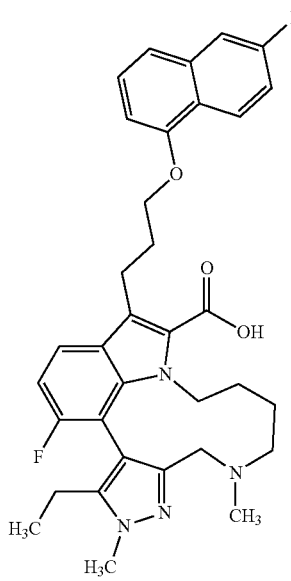

To a stirred solution of (rac)-ethyl 3-ethyl-4-fluoro-7-{3-[(6-fluoro-1-naphthyhoxy]propyl}-2,14-dimethyl-10,11,12,13,14,15-hexahydro-2H-pyrazolo[3',4':8,9][1,6]diazacycloundecino[10,11,1-hi]indole-8-carboxylate (see Intermediate 76, 110 mg, 0.18 mmol, 1.00 eq.) in absolute ethanol (715 µL, 0.25 M) was added a 2.0 M aqueous solution of sodium hydroxide (223 µL, 0.45 mmol, 2.50 eq.). The resulting suspension was heated at 70° C. for 22 hours and then cooled to room temperature. The mixture was neutralised with 1.0 M aqueous hydrochloric acid (0.45 mL) and then purified directly by reverse phase column chromatograhpy (10-100% acetonitrile/water with 0.1% formic acid gradient) to give the title compound as a white solid (53.2 mg).

LC-MS (Method 4): Rt=3.14 min; MS (ESIpos): m/z=587 [M+H]$^+$.

1H NMR (300 MHz, DMSO-d6) δ 8.30 (dd, J=9.3, 5.9 Hz, 1H), 7.76-7.61 (m, 2H), 7.50-7.29 (m, 3H), 6.96 (t, J=9.1 Hz, 1H), 6.85 (dd, J=6.1, 2.7 Hz, 1H), 4.38-4.23 (m, 1H), 4.19 (t, J=6.2 Hz, 2H), 3.97-3.82 (m, 1H), 3.82 (s, 3H), 3.63-3.08 (m, 6H), 2.40-2.10 (m, 5H), 2.05 (s, 3H), 1.89 (d, J=12.6 Hz, 1H), 1.37-0.94 (m, 4H), 0.82 (t, J=7.5 Hz, 3H).

Example 54

(rac)-3-ethyl-4-fluoro-2,14-dimethyl-7-[3-(1-naphthyloxy)propyl]-10,11,12,13,14,15-hexahydro-2H-pyrazolo[3',4':8,9][1,6]diazacycloundecino[10,11,1-hi]indole-8-carboxylic acid

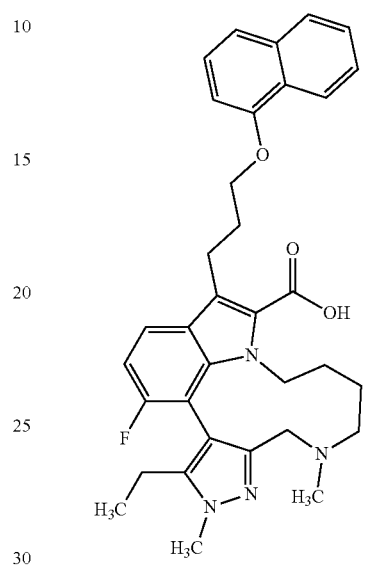

To a stirred solution of (rac)-ethyl 3-ethyl-4-fluoro-2,14-dimethyl-7-[3-(1-naphthyloxy)propyl]-10,11,12,13,14,15-hexahydro-2H-pyrazolo[3',4':8,9][1,6]diazacycloundecino[10,11,1-hi]indole-8-carboxylate (see Intermediate 77, 100 mg, 168 µmol, 1.00 eq.) in ethanol (0.67 mL, 0.25 M) was added a 2.0 M solution of sodium hydroxide in water (209 µL, 419 µmol, 2.50 eq.). The resulting yellow solution was heated at 70° C. for 16 hours, neutralised with 1.0 M hydrochloric acid (~0.42 mL) and then dry loaded onto Celite. The residue was purified by reverse phase column chromatography (30 g HP C18, 10-100% acetonitrile/water with 0.1% formic acid gradient) to give the title compound as a white solid (64.1 mg).

LC-MS (Method 4): Rt=3.17 min; MS (ESIpos): m/z=569 [M+H]$^+$.

1H NMR (300 MHz, DMSO-d6) δ 13.08 (s, 1H), 8.29-8.20 (m, 1H), 7.91-7.80 (m, 1H), 7.71 (dd, J=8.7, 5.5 Hz, 1H), 7.58-7.42 (m, 3H), 7.43-7.30 (m, 1H), 7.03-6.88 (m, 1H), 6.86 (d, J=1.1 Hz, OH), 4.37-4.23 (m, 1H), 4.19 (t, J=6.2 Hz, 2H), 3.82 (s, 4H), 3.50 (d, J=12.5 Hz, 1H), 3.42-3.18 (m, 4H), 2.42-2.10 (m, 5H), 2.06 (s, 3H), 1.97-1.83 (m, 1H), 1.39-0.95 (m, 4H), 0.83 (t, J=7.5 Hz, 3H).

EXPERIMENTAL SECTION

Biological Assays

Examples were tested in selected biological assays one or more times. When tested more than once, data are reported as either average values, median values or as geometric mean values, wherein the average value, also referred to as the arithmetic mean value, represents the sum of the values obtained divided by the number of times tested, the median value represents the middle number of the group of values when ranked in ascending or descending order. If the number of values in the data set is odd, the median is the middle value. If the number of values in the data set is even, the median is the arithmetic mean of the two middle values, and the geometric mean value represents the nth root of the product of n numbers.

Examples were synthesized one or more times. When synthesized more than once, data from biological assays represent average values or median values calculated utilizing data sets obtained from testing of one or more synthetic batch.

An empty field in any of the following tables means that the respective compound has not been tested in that Assay.

The in vitro activity of the compounds of the present invention can be demonstrated in the following assays.

Assay 1
Protein-Protein Interaction Assay: MCL-1/Noxa BH3 Peptide (MCL-1 Assay)

The dose-dependent inhibition by the compounds described in this invention of the interaction between MCL-1 and the BH3 domain of Noxa (both human) was determined using a steady state binding competition assay with time-resolved fluorescence energy transfer (TR-FRET) readout. For that purpose MCL-1 (amino acids 173-321, N-terminal fused to Maltose Binding Protein (MBP) SEQ ID 1)) and a synthetic Noxa BH3-derived peptide of sequence Biotin-PEG2-PEG2-PAELEVE-Nva-ATQLRRFGDKLNFRQKLL-amide (SEQ ID 2) served as protein receptor and tracer ligand respectively. The MBP-MCL-1 was purchased from Beryllium (Bedford, Mass., USA). The expression and purification of this protein construct has been described elsewhere (DOI:10.1371/journal.pone.0125010). The Noxa BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µl of a 2,5-fold concentrated MBP-MCL-1 solution (usually for a 1 nM end concentration in 5 µl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between MBP-MCL-1 and the compounds. After that, 3 µl of a 1.67-fold concentrated solution (in assay buffer) consisting of Noxa BH3-derived peptide (1 nM end concentration) and TR-FRET detection reagents [1.67 nM anti-MBP-Eu cryptate and 1.67 nM streptavidin-XL665 (both from Cisbio Bioassays, Codolet, France)], were added.

The mixture was incubated in the dark for one hour at 22° C. and then overnight at 4° C. The formation of MCL-1/Noxa complexes was determined by measuring the resonance energy transfer of the anti-MBP-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of MCL-1/NOXA complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except MCL-1 were included. $IC_{50}$ values were determined by regression analysis based on a 4 parameter equation (minimum, maximum, $IC_{50}$, Hill; $Y=Max+(Min-Max)/(1+(X/IC_{50})^{Hill})$ using the Screener Software (Genedata).

```
SEQ ID 1:
GKIEEGKLVIWINGDKGYNGLAEVGKKFEKDT

GIKVTVEHPDKLEEKFPQVAATGDGPDIIFWA

HDRFGGYAQSGLLAEITPDKAFQDKLYPFTWD

AVRYNGKLIAYPIAVEALSLIYNKDLLPNPPK

TWEEIPALDKELKAKGKSALMFNLQEPYFTWP

LIAADGGYAFKYENGKYDIKDVGVDNAGAKAG

LTFLVDLIKNKHMNADTDYSIAEAAFNKGETA

MTINGPWAWSNIDTSKVNYGVTVLPTFKGQPS

KPFVGVLSAGINAASPNKELAKEFLENYLLTD

EGLEAVNKDKPLGAVALKSYEEELAKDPRIAA

TMENAQKGEIMPNIPQMSAFWYAVRTAVINAA

SGRQTVDEALKDAQTGSSELYRQSLEIISRYL

REQATGAADTAPMGASGATSRKALETLRRVGD

GVQRNHETAFQGMLRKLDIKNEDDVKSLSRVM

IHVFSDGVTNWGRIVTLISFGAFVAKHLKTIN

QESCIEPLAESITDVLVRTKRDWLVKQRGWDG

FVEFFHV

SEQ ID 2
Biotin-PEG2-PEG2-PAELEVE-Nva-

ATQLRRFGDKLNFRQKLL-amide
```

Assay 2
Protein-Protein Interaction Assay: BCL-XL/Bad BH3 Peptide (BCL-XL Assay)

The dose-dependent inhibition by the compounds described in this invention of the interaction between BCL-XL and the BH3 domain of Bad (both human) was determined using a steady state binding competition assay with time-resolved fluorescence energy transfer (TR-FRET) readout. For that purpose BCL-XL (amino acids 1-212, C-terminal fused to a hexahistidine (6x His) tag (SEQ ID 3) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-XL protein (expressed in Ecol) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µl of a 2,5-fold concentrated His-BCL-XL solution (usually for a 1 nM end concentration in 5 µl reaction volume) in aqueous assay buffer [50 mM Tris/HCl pH 7, 100 mM sodium chloride (NaCl), 50 µM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-XL and the compounds. After that, 3 µl of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-XL/Bad complexes was determined by measuring the resonance energy transfer of the anti-His-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-XL/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-XL were included. $IC_{50}$ values were determined by regression analysis based on a 4 parameter equation (minimum, maximum, $IC_{50}$, Hill; $Y=Max+(Min-Max)/(1+(X/IC_{50})^{Hill})$ using the Screener Software (Genedata).

```
SEQ ID 3
MSQSNRELVV DFLSYKLSQK GYSWSQFSDV

EENRTEAPEG TESEMETPSA INGNPSWHLA

DSPAVNGATG HSSSLDAREV IPMAAVKQAL

REAGDEFELR YRRAFSDLTS QLHITPGTAY

QSFEQVVNEL FRDGVNWGRI VAFFSFGGAL

CVESVDKEMQ VLVSRIAAWM ATYLNDHLEP

WIQENGGWDT FVELYGNNAA AESRKGQERF

NR

SEQ ID 4:
Biotin-PEG2-PEG2-NLWAAQRYGRELRR-

Nle-SDEFVDSFKK-amide
```

Assay 3
Protein-Protein Interaction assay: BCL-2/Bad BH3 Peptide (BCL-2 Assay)

The dose-dependent inhibition by the compounds described in this invention of the interaction between BCL-2 and the BH3 domain of Bad (both human) was determined using a steady state binding competition assay with time-resolved fluorescence energy transfer (TR-FRET) readout. For that purpose BCL-2 (amino acids 1-211, C-terminal fused to a hexahistidine (6× His) tag (SEQ ID 5) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-2 protein (expressed in E. coli) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µl of a 2,5-fold concentrated His-BCL-2 solution (usually for a 1 nM end concentration in 5 µl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-2 and the compounds. After that, 3 µl of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-2/Bad complexes was determined by measuring the resonance energy transfer of the anti-His-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-2/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-2 were included. $IC_{50}$ values were determined by regression analysis based on a 4 parameter equation (minimum, maximum, $IC_{50}$, Hill; $Y=Max+(Min-Max)/(1+(X/IC_{50})^{Hill})$ using the Screener Software (Genedata).

```
SEQ ID 5:
MAHAGRTGYD NREIVMKYIH YKLSQRGYEW

DAGDVGAAPP GAAPAPGIFS SQPGHTPHPA

ASRDPVARTS PLQTPAAPGA AAGPALSPVP

PVVHLTLRQA GDDFSRRYRR DFAEMSSQLH
```

```
LTPFTARGRF ATVVEELFRD GVNWGRIVAF

FEFGGVMCVE SVNREMSPLV DNIALWMTEY

LNRHLHTWIQ DNGGWDAFVE LYGPSMRPLF

D
```

TABLE 2

IC$_{50}$ values of selected examples in biochemical MCL-1 assay (Assay 1), biochemical BCL-2 assay (Assay 3) and BCL-XL assay (Assay 2)

| Example | MCL-1 Assay [M] (median) | BCL-2 Assay [M] (median) | BCL-XL Assay [M] (median) |
|---|---|---|---|
| 1 | 1.8E−9 | >2.00E−05 | >2.00E−05 |
| 2 | 1.2E−9 | | |
| 3 | 1.3E−9 | >2.00E−05 | >2.00E−05 |
| 4 | 6.5E−8 | | |
| 5 | 2.3E−9 | >2.00E−05 | >2.00E−05 |
| 6 | 1.1E−9 | | |
| 7 | 9.7E−10 | >2.00E−05 | >2.00E−05 |
| 8 | 2.6E−8 | | |
| 9 | 2.4E−9 | >2.00E−05 | >2.00E−05 |
| 10 | 1.1E−9 | >2.00E−05 | >2.00E−05 |
| 11 | 2.2E−9 | >2.00E−05 | >2.00E−05 |
| 12 | 8.5E−10 | | |
| 13 | 9.8E−10 | >2.00E−05 | >2.00E−05 |
| 14 | 1.7E−8 | | |
| 15 | 1.3E−9 | >2.00E−05 | >2.00E−05 |
| 16 | 1.9E−9 | >2.00E−05 | >2.00E−05 |
| 17 | 6.0E−8 | | |
| 18 | 1.6E−9 | >2.00E−05 | >2.00E−05 |
| 19 | 1.5E−9 | >2.00E−05 | >2.00E−05 |
| 20 | 1.5E−9 | >2.00E−05 | >2.00E−05 |
| 21 | 8.6E−10 | | |
| 22 | 4.5E−10 | >2.00E−05 | >2.00E−05 |
| 23 | 9.6E−9 | | |
| 24 | 5.8E−10 | >2.00E−05 | >2.00E−05 |
| 25 | 1.3E−8 | | |
| 26 | 1.4E−9 | | |
| 27 | 1.5E−9 | >2.00E−05 | >2.00E−05 |
| 28 | 6.5E−8 | | |
| 29 | 1.5E−9 | >2.00E−05 | >2.00E−05 |
| 30 | 1.3E−9 | >2.00E−05 | >2.00E−05 |
| 31 | 1.8E−9 | >2.00E−05 | >2.00E−05 |
| 32 | 1.1E−9 | >2.00E−05 | >2.00E−05 |
| 33 | 1.7E−9 | >2.00E−05 | >2.00E−05 |
| 34 | 1.3E−9 | >2.00E−05 | >2.00E−05 |
| 35 | 1.3E−9 | >2.00E−05 | >2.00E−05 |
| 36 | 2.1E−9 | >2.00E−05 | >2.00E−05 |
| 37 | 1.2E−9 | >2.00E−05 | >2.00E−05 |
| 38 | 1.1E−9 | | |
| 39 | 8.0E−10 | >2.00E−05 | >2.00E−05 |
| 40 | 4.0E−8 | | |
| 41 | 2.0E−9 | | |
| 42 | 1.7E−9 | >2.00E−05 | >2.00E−05 |
| 43 | 1.1E−7 | | |
| 44 | 1.7E−9 | >2.00E−05 | >2.00E−05 |
| 45 | 1.4E−9 | >2.00E−05 | >2.00E−05 |
| 46 | 2.0E−9 | >2.00E−05 | >2.00E−05 |
| 47 | 8.2E−10 | | |
| 43 | 1.1E−9 | >2.00E−05 | >2.00E−05 |
| 49 | 4.0E−8 | | |
| 50 | 8.4E−10 | >2.00E−05 | >2.00E−05 |
| 51 | 9.1E−10 | >2.00E−5 | >2.00E−5 |
| 52 | 1.7E−9 | >2.00E−5 | >2.00E−5 |
| 53 | 9.1E−10 | >2.00E−5 | >2.00E−5 |
| 54 | 7.2E−10 | >2.00E−5 | >2.00E−5 |

In one embodiment the invention covers compounds of general formula (I) showing an IC$_{50}$ of 1,1xE-9 or less.

Cellular Assays

Assay 4

Induction of Caspase-3/7 Activity upon Treatment of Cells with Selected Compounds The BH3-domain of MCL-1 sequesters pro-apoptotic proteins, thereby inhibiting apoptosis. In contrast, MCL-1 inhibitors are expected to antagonize this effect leading to an increase in apoptosis, which can be determined by measuring the activity of caspase-3/7.

The activity of caspase-3/7 was determined in DLBCL (Diffuse large B-cell lymphoma) cell lines (SUDHL5 and SUDHL10) upon treatment with different compounds, using the Caspase-Glo® 3/7 reagent from Promega (G8092).

The different cell lines were plated in culture medium (RPMI 1640 [GIBCO #22400-089] supplemented with 10% Fetal Bovine Serum) at a density of 3,300 cells in 30 µl/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight.

On the next day, the cells were treated with compounds (stock solution, 10 mM in DMSO) using the HP D300 Digital Dispenser in a concentration range of 3.3×10e-5 M (33 µM) to 5×10e-9 M (5 nM) in a single-dot curve with at least 16 dilutions and a DMSO concentration of 0.33%. Rim wells were excluded. The cells were incubated for 3 h hours in a humidified incubator at 37° C. After this incubation, 30 µl of Caspase-Glo® 3/7 reagent (Promega G8092) was added to each well using the Multidrop Combi Reagent Dispenser, followed by 1 h incubation at 37° C. Finally, luminescence was read at 0.1 ms, with a gain of 3000 using the PHERAstar FS microplate reader (BMG Labtech).

For the evaluation of the results, the background measured with "medium-only" was subtracted from all other values. Then, the values were normalized to DMSO-only treated cells (every value was divided by the mean of the DMSO control). The Bella DRC Master Sheet was used to calculate EC$_{50}$s, with fixed C0=1 and C1=plateau/max induction for the reference compound.

TABLE 3

EC$_{50}$ values of selected examples in cellular caspase induction assay (Assay 4)

| Example | Caspase SUDHL5 [M] (median) | Caspase SUDHL10 [M] (median) |
|---|---|---|
| 1 | 1.4E−6 | 2.5E−6 |
| 2 | 6.0E−7 | 1.3E−6 |
| 3 | 6.5E−7 | 1.3E−6 |
| 4 | >3.3E−5 | nd |
| 5 | 1.0E−6 | 3.5E−6 |
| 6 | 4.0E−7 | 1.1E−6 |
| 7 | 3.7E−7 | 1.0E−6 |
| 8 | 3.0E−5 | >3.3E−5 |
| 9 | 2.7E−6 | 1.8E−5 |
| 10 | 1.7E−6 | 7.8E−6 |
| 11 | 2.1E−6 | 6.5E−6 |
| 12 | 4.8E−7 | 8.0E−7 |
| 13 | 3.4E−7 | 6.8E−7 |
| 14 | 5.4E−6 | 1.4E−5 |
| 15 | 9.7E−7 | 5.8E−6 |
| 16 | 7.2E−7 | 4.1E−6 |
| 17 | >3.3E−5 | >3.3E−5 |
| 18 | 8.4E−7 | 2.3E−6 |
| 19 | 9.6E−7 | 3.8E−6 |
| 20 | 1.4E−6 | 4.0E−6 |
| 21 | 3.5E−7 | 9.0E−7 |

TABLE 3-continued

EC$_{50}$ values of selected examples in cellular caspase induction assay (Assay 4)

| Example | Caspase SUDHL5 [M] (median) | Caspase SUDHL10 [M] (median) |
|---|---|---|
| 22 | 2.1E−7 | 3.8E−7 |
| 23 | 2.7E−6 | 1.1E−5 |
| 24 | nd | 5.4E−7 |
| 25 | nd | >3.3E−5 |
| 26 | 1.5E−6 | 3.3E−6 |
| 27 | 6.6E−7 | 1.6E−6 |
| 28 | >3.3E−5 | >3.3E−5 |
| 29 | 1.2E−6 | 1.7E−6 |
| 30 | 8.7E−7 | 1.7E−6 |
| 31 | 2.5E−6 | 4.5E−6 |
| 32 | 8.0E−7 | 2.6E−6 |
| 33 | 2.9E−6 | 9.1E−6 |
| 34 | 1.8E−6 | 5.9E−6 |
| 35 | 6.2E−6 | 2.0E−5 |
| 36 | 3.5E−6 | 1.2E−5 |
| 37 | 1.7E−6 | 7.2E−6 |
| 38 | 8.7E−7 | 2.0E−6 |
| 39 | 5.6E−7 | 9.4E−7 |
| 40 | 2.1E−5 | >3.3E−5 |
| 41 | 2.2E−6 | 1.4E−5 |
| 42 | 1.8E−6 | 6.3E−6 |
| 43 | >3.3E−5 | >3.3E−5 |
| 44 | 1.6E−6 | 4.5E−6 |
| 45 | 1.4E−6 | 6.4E−6 |
| 46 | 2.5E−6 | 7.7E−6 |
| 47 | 1.4E−6 | 5.0E−6 |
| 48 | 1.2E−6 | 2.1E−6 |
| 49 | >3.3E−5 | >3.3E−5 |
| 50 | 2.0E−5 | >3.3E−5 |
| 51 | 2.3E−7 | 4.4E−7 |
| 52 | 2.8E−7 | 2.1E−7 |
| 53 | 3.8E−7 | 4.9E−7 |
| 54 | 2.3E−7 | 6.8E−7 |

Assay 5
PIxEL: Protein-Protein Interaction in Permeabilized Cells by ELISA

Most MCL1 protein molecules are localized at the mitochondria outer membrane and sequester pro-apoptotic proteins through binding of their BCL2 homology domain 3 (BH3 domain). MEB buffer (150 mM mannitol, 10 mM HEPES pH 7.5, 50 mM KCl, 20 µM EDTA, 20 µM EGTA, 5 mM potassium succinate, 0.1% protease-free BSA (SIGMA) with low dose digitonin (0.002%) permeabilizes plasma membrane while leaves live mitochondria, where MCL1 maintains its native localization and conformation. Unlike biophysical assays (e.g. TR-FRET) that use truncated recombinant MCL1 protein, this assay uses full length endogenous MCL1 protein at mitochondria outer membrane. It measures the interaction between MCL1 protein and biotinylated BIM BH3 peptide. Compounds can compete with BIM BH3 peptide to bind to MCL1 protein. This serum free assay measures the affinity between MCL1 protein and compound in permeabilized cells, therefore it is not affected by serum binding and cell permeability, and can measure the intrinsic compound affinity.

On day 1, RKO colon cancer cell line cells were plated at 0.8 million cells/ml, 100 µl/well in 96-well flat bottom TC plates (Corning). MCL1 antibody (Santa Cruz sc-12756) were diluted at 200 fold (final concentration 1 µg/ml) in carbonate buffer (Thermo Fisher Scientific, pH 9.6), and 50 µl of diluted antibody was added to each well of high bind ELISA plates (SARSTEDT). Each plate was tapped to make sure liquid covering entire bottom of wells and incubate at 37° C. overnight.

On the second day, MCL1 antibody was washed from ELISA plate. 250 µl Odyssey® Blocking Buffer (PBS) (Li-Cor) was added to each well, incubated at room temperature for at least 1 hour, then washed once with 250 µl 1×PBST. Plates with RKO cells were gently washed once with 100 µl/well PBS, once with 100 µl/well MEB buffer without digitonin, then 100 µl of MEB buffer with 0.002% digitonin was gently added to each well. Compounds were added with HP Tecan compound dispenser in 3-fold dilution series, highest dose 30 µM, 10-dose per compound in quadruplicates. Biotin-BIM peptide (synthesized by 21st Century) was added with HP Tecan compound dispenser at 0.2 µM immediately after the addition of compounds. Plates were rocked for 1 hour at room temperature. Then MEB buffer was aspirated and 50 µl of CHAPS buffer (50 mM Tris-Cl, pH 7.4, 150 mM NaCl, 1% CHAPS, 1 mM EDTA, 1 mM EGTA, complete protease inhibitors (Roche), PhosSTOP (Roche)) was added to each well. Plates were rocked for 1 hour at 4° C., then 45 µl cell lysate from each well were transferred to ELISA plates coated with MCL1 antibody. Plates were incubated overnight in the cold room with rocking.

On the third day, ELISA plates were washed once with 250 µl 1×PBST. Streptavidin-poly-HRP (Thermo Fisher Scientific) was diluted to 20 ng/ml in Odyssey blocking buffer plus 0.05% Triton-100, and 100 µl was added to each well of the ELISA plate. Plates were incubated at room temperature for 1 hour with rocking, then washed with 100 µL 1×PBST for 3 times. Each SuperSignal ELISA Femto Maximum Sensitivity substrate was added to a 50-ml tube and mixed, then 100 µl of mixed substrate was added to each well. Plates were shaken for 1 minute then luminescence was measured by Envision plate reader (HP). Signal of each well were normalized by no-compound control and no-cell control. IC$_{50}$ was calculated using Graphic Pad PRISM software.

Table 4 shows the results of the protein-protein interaction in permeabilized cells by ELISA assay (Assay 5).

TABLE 4

IC$_{50}$ values of selected examples in the protein-protein interaction in permeabilized cells by ELISA (Assay 5)

| Example | PIxEL [M] (median) |
|---|---|
| 1 | |
| 2 | |
| 3 | 1.40E−06 |
| 4 | |
| 5 | |
| 6 | |
| 7 | 2.06E−06 |
| 8 | |
| 9 | |
| 10 | |
| 11 | |
| 12 | |
| 13 | 8.72E−07 |
| 14 | |
| 15 | 4.16E−06 |
| 16 | 3.23E−05 |
| 17 | |
| 18 | |
| 19 | |
| 20 | |
| 21 | |

TABLE 4-continued

IC$_{50}$ values of selected examples in the protein-protein interaction in permeabilized cells by ELISA (Assay 5)

| Example | PIxEL [M] (median) |
|---|---|
| 22 | 1.34E−06 |
| 23 | 1.51E−05 |
| 24 | 4.24E−07 |
| 25 | |
| 26 | |
| 27 | 2.43E−06 |
| 28 | |
| 29 | |
| 30 | |
| 31 | |
| 32 | |
| 33 | |
| 34 | |
| 35 | |
| 36 | |
| 37 | 7.35E−06 |
| 38 | |
| 39 | 2.38E−06 |
| 40 | |
| 41 | |
| 42 | 8.91E−06 |
| 43 | |
| 44 | |
| 45 | |
| 46 | |
| 47 | |
| 48 | |
| 49 | |
| 50 | |
| 51 | |
| 52 | |
| 53 | |
| 54 | |

Assay 6

Induction of Cytotoxicity upon Treatment of Cells with Selected Compounds

In principle, compounds that induce apoptosis will concomitantly induce cell cytotoxicity. Therefore, cytotoxicity assays were run in parallel in SUDHL5 and SUDHL10 cells.

The different cell lines were plated in culture medium (RPMI 1640 [GIBCO #22400-089] supplemented with 10% Fetal Bovine Serum) at a density of 3,300 cells in 30 μl/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight. On the next day, the cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 5 h hours in a humidified incubator at 37° C. After this incubation, 30 μl of CellTiter-Glo® Luminescent Cell Viability reagent (Promega, G7573) was added to each well using the Multidrop Combi Reagent Dispenser, followed by 15 min incubation on a shaker at room temperature. Finally, luminescence was read at 0.1 ms, with a gain of 3000 using the PHERAstar FS microplate reader (BMG Labtech).

For the evaluation of the results, each value was normalized to DMSO-only treated cells (every value was divided by the mean of the DMSO control). The Bella DRC Master Sheet was used to calculate IC$_{50}$s, with fixed CI=0 and C0=1.

Assay 7

Assessment of the Anti-Proliferative Effect of Compounds in Different Cell Lines The impact of compounds on the proliferation of different cell lines was assessed using the CellTiter-Glo® Luminescent Cell Viability reagent from Promega (G7573). The cell lines used for the proliferation assays are examples of tumor indications and listed in the table below.

TABLE 5 cell lines, sources and indications

| Cell line | Source | Indication |
|---|---|---|
| SUDHL5 | DSMZ | B-cell lymphoma (GC-DLBCL) |
| SUDHL10 | DSMZ | B-cell lymphoma (GC-DLBCL) |
| MV-4-11 | ATCC | Acute monocytic leukemia |
| HMC-1-8 | JCRB | Triple-negative Breast Cancer |
| SKBR-3 | ATCC | Her2-positive Breast Cancer |
| AMO-1 | DSMZ | Multiple Myeloma |
| A2058 | ATCC | Melanoma |
| NCI-H23 | ATCC | Lung Cancer |
| BxPC-3 | ATCC | Pancreas cancer |
| A2780 | ECACC | Ovarian carcinoma |

The different cell lines were plated in culture medium (RPMI 1640 [Biochrom; #FG 1215] supplemented with 10% Fetal Calf Serum [Biochrom; #S 0415]) at a density of 3,300 cells (for suspension cells) or 800 cells (for adherent cells) in 30 μl/well in a sterile, solid black, flat bottom, polystyrene, TC-treated 384-well microplate (Corning #3571) using Multidrop Combi Reagent Dispenser. In parallel, cells were plated in a reference (day 0) plate for time zero determination. Cells were incubated in a humidified incubator at 37° C. overnight.

On the next day, cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 72 h hours in a humidified incubator at 37° C. The day 0 plate was measured by adding 30 μL/well of CTG solution (CellTiter-Glo® Luminescent Cell Viability reagent, Promega G7573) to time zero wells in the reference plate followed by a 10 minutes incubation and luminescence reading at 0.1 ms. using the PHERAstar FS microplate reader (BMG Labtech).

After 72 h incubation, the treated plates were measured in the same way as the day 0 plate mentioned above. The Bella DRC Master Sheet was used to calculate IC$_{50}$s, with CI=day 0 values and C0=DMSO control values.

Table 6 shows the results of the SUDHL5 and SUDHL10 cytotoxicity and antiproliferation assays.

TABLE 6

IC$_{50}$ values of selected examples in cellular cytotoxicity induction assay (Assay 6) and antiproliferation assay (Assay 7)

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 1 | 1.2E−6 | 3.8E−6 | 9.0E−7 | |
| 2 | 1.0E−6 | 1.6E−6 | 1.4E−6 | |
| 3 | 7.7E−7 | 1.1E−6 | 6.4E−7 | |
| 4 | >3.3E−5 | | >3.3E−5 | |
| 5 | 1.5E−6 | 3.2E−6 | 1.7E−6 | |

TABLE 6-continued

IC$_{50}$ values of selected examples in cellular cytotoxicity induction assay (Assay 6) and antiproliferation assay (Assay 7)

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 6 | 6.4E−7 | 1.3E−6 | 9.8E−7 | |
| 7 | 4.6E−7 | 1.3E−6 | 7.5E−7 | |
| 8 | 2.7E−5 | >3.3E−5 | 1.5E−5 | |
| 9 | 2.9E−6 | 1.5E−5 | 3.7E−6 | |
| 10 | 1.8E−6 | 3.6E−6 | 1.8E−6 | |
| 11 | 2.3E−6 | 7.2E−6 | 2.8E−6 | |
| 12 | 6.0E−7 | 8.2E−7 | 6.5E−7 | 7.2E−7 |
| 13 | 3.9E−7 | 8.0E−7 | 2.9E−7 | |
| 14 | 6.0E−6 | 1.2E−5 | 4.0E−6 | |
| 15 | 1.1E−6 | 3.0E−6 | 5.3E−7 | |
| 16 | 1.4E−6 | 4.3E−6 | 9.3E−7 | |
| 17 | >3.3E−5 | >3.3E−5 | 1.1E−5 | |
| 18 | 8.8E−7 | 1.7E−6 | 1.2E−6 | 1.5E−6 |
| 19 | 1.4E−6 | 2.1E−6 | 1.0E−6 | 1.5E−6 |
| 20 | 1.8E−6 | 2.6E−6 | 1.1E−6 | |
| 21 | 5.1E−7 | 8.5E−7 | 7.3E−7 | 6.3E−7 |
| 22 | 3.3E−7 | 5.5E−7 | 2.7E−7 | |
| 23 | 3.2E−6 | 9.0E−6 | 1.4E−6 | |
| 24 | 3.9E−7 | 6.8E−7 | 3.2E−7 | |
| 25 | 1.2E−5 | 2.2E−5 | 8.1E−6 | |
| 26 | 1.8E−6 | 3.7E−6 | 2.2E−6 | |
| 27 | 1.0E−6 | 1.8E−6 | 6.2E−7 | |
| 28 | 1.8E−5 | >3.3E−5 | 1.2E−5 | |
| 29 | 1.2E−6 | 1.8E−6 | 1.4E−6 | |
| 30 | 1.1E−6 | 1.3E−6 | 1.5E−6 | |
| 31 | 2.9E−6 | 3.6E−6 | 3.0E−6 | |
| 32 | 1.1E−6 | 2.0E−6 | 8.5E−7 | 1.5E−6 |
| 33 | 3.5E−6 | 8.4E−6 | 3.0E−6 | |
| 34 | 2.6E−6 | 4.2E−6 | 1.7E−6 | |
| 35 | 7.1E−6 | 1.5E−5 | 6.0E−6 | |
| 36 | 4.3E−6 | 9.0E−6 | 3.2E−6 | |
| 37 | 2.1E−6 | 4.8E−6 | 1.6E−6 | |
| 38 | 1.0E−6 | 1.4E−6 | 9.3E−7 | 1.0E−6 |
| 39 | 6.2E−7 | 1.0E−6 | 6.8E−7 | |
| 40 | 2.3E−5 | >2.5E−5 | 1.4E−5 | |
| 41 | 3.0E−6 | 7.1E−6 | 2.0E−6 | |
| 42 | 2.0E−6 | 9.6E−6 | 2.1E−6 | |
| 43 | >3.3E−5 | >3.3E−5 | 1.5E−5 | |
| 44 | 1.9E−6 | 4.2E−6 | 5.5E−7 | |
| 45 | 1.9E−6 | 3.4E−6 | 1.9E−6 | |
| 46 | 3.1E−6 | 5.7E−6 | 2.9E−6 | |
| 47 | 2.2E−6 | 5.6E−6 | 2.1E−6 | |
| 48 | 1.3E−6 | 1.9E−6 | 1.4E−6 | |
| 49 | >2.7E−5 | >3.3E−5 | 1.0E−5 | |
| 50 | 1.6E−5 | >3.3E−5 | 6.1E−6 | |
| 51 | 3.6E−7 | 3.6E−7 | 2.6E−7 | |
| 52 | 4.3E−7 | 3.1E−7 | 2.3E−7 | |
| 53 | 3.3E−7 | 6.9E−7 | 3.7E−7 | |
| 54 | 4.5E−7 | 1.4E−6 | 4.4E−7 | |

In one embodiment the invention covers compounds of formula (I) which show an IC50 of 5×E-7 or <5×E-7 in the Antiproliferation Assay SUDHL5.

Table 7 shows the results of the MV-4-11, AMO-1, HMC-1-8 and SKBR-3 antiproliferation assays (Assay 7).

TABLE 7

IC$_{50}$ values of selected examples in antiproliferation assay

| Example | Antiproli MV-4-11 [M] | Antiproli AMO-1 [M] | Antiproli HMC-1-8 [M] | Antiproli SK-BR-3 [M] |
|---|---|---|---|---|
| 01 | 1.13E−5 | | | |
|  | 1.42E−5 | | | |
| 02 | 1.79E−6 | 1.91E−6 | 7.58E−6 | 6.85E−6 |
|  | 3.74E−6 | 2.46E−6 | 1.00E−5 | 7.07E−6 |
|  | 5.58E−6 | | | |
|  | 2.13E−6 | | | |
|  | 7.32E−6 | | | |
| 03 | 1.69E−6 | 2.00E−6 | 6.11E−6 | 9.50E−6 |
|  | 3.49E−6 | | | |
|  | 4.42E−6 | | | |
|  | 6.73E−6 | | | |
| 04 | >3.30E−5 | | | |
| 05 | 9.75E−6 | | | |
|  | 4.71E−6 | | | |
|  | 8.11E−6 | | | |
|  | 6.33E−6 | | | |
| 06 | 3.83E−6 | 2.63E−6 | | 7.29E−6 |
|  | 2.82E−6 | | | |
|  | 2.76E−6 | | | |
|  | 2.35E−6 | | | |
| 07 | 2.37E−6 | 1.91E−6 | | |
|  | 1.94E−6 | | | |
| 08 | 2.13E−5 | | | |
| 09 | 7.50E−6 | | | |
|  | 6.04E−6 | | | |
| 10 | 6.53E−6 | | | |
|  | 4.39E−6 | | | |
| 11 | 7.67E−6 | | | |
|  | 1.28E−5 | | | |
| 12 | 6.01E−7 | 1.51E−6 | | |
|  | 1.30E−6 | 8.69E−7 | | |
|  | 3.09E−6 | | | |
| 13 | 6.79E−7 | 7.47E−7 | | |
|  | 4.12E−7 | 5.64E−7 | | |
| 14 | 2.05E−5 | 7.54E−6 | | |
|  | 8.91E−6 | 1.16E−5 | | |
| 15 | 3.99E−6 | 6.28E−6 | | |
|  | 9.35E−6 | 2.20E−6 | | |
| 16 | 3.55E−6 | 6.95E−6 | | |
| 17 | 2.08E−5 | >3.30E−5 | | |
| 18 | 3.53E−6 | 3.98E−6 | | |
|  | 2.89E−6 | 2.16E−6 | | |
|  | 5.61E−6 | 3.19E−6 | | |
| 19 | 4.30E−6 | 2.62E−6 | | |
|  | 2.90E−6 | 4.06E−6 | | |
|  | 4.90E−6 | | | |
| 20 | 8.18E−6 | 5.98E−6 | | |
|  | 5.54E−6 | 2.49E−6 | | |
| 21 | 3.49E−7 | 1.22E−6 | | |
|  | 1.37E−6 | 9.42E−7 | | |
|  | 1.44E−6 | 1.12E−6 | | |
|  | 1.07E−6 | | | |
| 22 | 1.97E−6 | 1.45E−6 | 2.44E−6 | |
|  | 1.04E−6 | 8.40E−7 | 3.53E−6 | |
|  | 2.52E−7 | 9.16E−7 | | |
|  | | 4.78E−7 | | |
| 23 | 1.55E−5 | 1.63E−5 | | |
|  | | 5.54E−6 | | |
| 24 | | 8.78E−7 | 2.50E−6 | |
| 25 | | 3.28E−5 | 2.09E−5 | |
| 26 | 1.06E−6 | 4.31E−6 | | |
|  | 6.02E−6 | | | |
| 27 | 1.22E−6 | 1.33E−6 | | |
|  | 2.53E−6 | 2.53E−6 | | |
| 28 | 1.38E−5 | >3.30E−5 | | |
| 29 | 2.04E−6 | 2.44E−6 | | |
|  | 2.55E−6 | | | |
| 30 | 1.77E−6 | 1.69E−6 | | |
|  | 3.04E−6 | | | |
| 31 | 6.07E−6 | >3.30E−5 | | |
|  | 8.25E−6 | | | |
| 32 | 4.85E−6 | 3.98E−6 | | |
|  | 4.80E−6 | 4.27E−6 | | |
|  | 4.75E−6 | | | |
| 33 | 1.12E−5 | | | |
| 34 | 1.16E−5 | 6.92E−6 | | |
|  | 1.23E−5 | | | |
| 35 | 1.24E−5 | | | |

TABLE 7-continued

IC$_{50}$ values of selected examples in antiproliferation assay

| Example | Antiproli MV-4-11 [M] | Antiproli AMO-1 [M] | Antiproli HMC-1-8 [M] | Antiproli SK-BR-3 [M] |
|---|---|---|---|---|
| 36 | 1.64E-5 | | | |
| 37 | 8.40E-6 | | | |
|    | 6.80E-6 | | | |
|    | 7.54E-6 | | | |
| 38 | 2.67E-6 | 2.35E-6 | | |
|    | 6.07E-6 | 2.46E-6 | | |
|    | 1.98E-6 | 1.61E-6 | | |
| 39 | 7.99E-7 | 1.72E-6 | 3.17E-6 | |
|    | 3.08E-6 | | | |
| 40 | 1.43E-5 | >3.30E-5 | | |
|    | 1.16E-5 | | | |
| 41 | 1.10E-5 | 1.52E-5 | | |
|    | 1.50E-5 | 1.28E-5 | | |
| 42 | 5.79E-6 | 6.96E-6 | | |
| 43 | 1.25E-5 | >3.30E-5 | | |
| 44 | 9.83E-6 | 7.41E-6 | | |
| 45 | 6.20E-6 | 6.45E-6 | | |
|    | 6.56E-6 | | | |
| 46 | 2.10E-5 | 8.17E-6 | | |
|    | 1.14E-5 | 9.10E-6 | | |
| 47 | 1.02E-6 | | | |
|    | 1.32E-6 | | | |
| 48 | 6.20E-7 | 2.86E-6 | | |
|    | 1.64E-6 | | | |
| 49 | 1.89E-5 | >3.30E-5 | | |
|    | 2.33E-5 | | | |
| 50 | 1.34E-5 | | | |
| 51 | | | | |
| 52 | | | | |
| 53 | | | | |
| 54 | | | | |

In one embodiment the invention covers compounds of formula (I) which show an IC$_{50}$ of 1×E-6 or <1×E-6 in the Antiproliferation Assay AMO-1.

In one embodiment the invention covers compounds of formula (I) which show an IC$_{50}$ of 3×E-6 or <3×E-6 in the Antiproliferation Assay HMC-1-8.

In one embodiment the invention covers compounds of formula (I) which show an IC$_{50}$ of 1×E-6 or <1×E-6 in the Antiproliferation Assay AMO-1 and/or an IC$_{50}$ of 3×E-6 or <3×E-6 in the Antiproliferation Assay HMC-1-8.

In one embodiment the invention covers compounds of formula (I) which show an IC$_{50}$ of 1×E-6 or <1×E-6 in the Antiproliferation Assay AMO-1 and an IC$_{50}$ of 3×E-6 or <3×E-6 in the Antiproliferation Assay HMC-1-8.

In one embodiment the invention covers compounds of formula (I) which show an IC$_{50}$ of 1×E-6 or <1×E-6 in the Antiproliferation Assay AMO-1 or an IC$_{50}$ of 3×E-6 or <3×E-6 in the Antiproliferation Assay HMC-1-8.

Table 8 shows the results of the A2780, NCI-H23, A2058 and BxPC-3 antiproliferation assays.

TABLE 8

IC$_{50}$ values of selected examples in antiproliferation assay (Assay 7)

| Example | Antiproli A2780 [M] | Antiproli NCI-H23 [M] | Antiproli A2058 [M] | Antiproli BxPC-3 [M] |
|---|---|---|---|---|
| 01 | >3.30E-5 | | | |
|    | 2.11E-5 | | | |
| 02 | 1.30E-5 | 7.56E-6 | >3.30E-5 | |
|    | 1.22E-5 | 9.56E-6 | >3.30E-5 | |
|    | 1.45E-5 | | | |
| 03 | 2.38E-5 | 6.94E-6 | >3.30E-5 | |
|    | 1.76E-5 | | | |
|    | 1.53E-5 | | | |
| 04 | >3.30E-5 | | | |
| 05 | 2.54E-5 | | | |
|    | 2.81E-5 | | | |
|    | 2.08E-5 | | | |
|    | 2.77E-5 | | | |
| 06 | 1.45E-5 | | | |
|    | 1.06E-5 | | | |
|    | 1.31E-5 | | | |
| 07 | 8.84E-6 | | | |
|    | 1.32E-5 | | | |
| 08 | 2.00E-5 | | | |
| 09 | 2.31E-5 | | | |
|    | 2.07E-5 | | | |
| 10 | >3.30E-5 | | | |
|    | >3.30E-5 | | | |
| 11 | 1.53E-5 | | | |
|    | 2.35E-5 | | | |
| 12 | 4.68E-6 | | | |
| 13 | 4.11E-6 | | | |
| 14 | 1.98E-5 | | | |
| 15 | | | | |
| 16 | | | | |
| 17 | | | | |
| 18 | | | | |
| 19 | 1.65E-5 | | | |
| 20 | | | | |
| 21 | 3.47E-6 | | | |
| 22 | 3.88E-6 | | | 2.35E-5 |
| 23 | | | | |
| 24 | | | | |
| 25 | | | | |
| 26 | 1.02E-5 | | | |
| 27 | | | | |
| 28 | | | | |
| 29 | 9.17E-6 | | | |
| 30 | 1.12E-5 | | | |
| 31 | 1.21E-5 | | | |
| 32 | 1.52E-5 | | | |
| 33 | 2.33E-5 | | | |
| 34 | 2.09E-5 | | | |
| 35 | 1.50E-5 | | | |
| 36 | 2.95E-5 | | | |
| 37 | >3.30E-5 | | | |
|    | >3.30E-5 | | | |
|    | >3.30E-5 | | | |
| 38 | | | | |
| 39 | 4.84E-6 | | | |
| 40 | 2.96E-5 | | | |
| 41 | | | | |
| 42 | | | | |
| 43 | | | | |
| 44 | | | | |
| 45 | 2.82E-5 | | | |
| 46 | | | | |
| 47 | 2.09E-5 | | | |
|    | 1.89E-5 | | | |
| 48 | 7.17E-6 | | | |
| 49 | 1.51E-5 | | | |
| 50 | >3.30E-5 | | | |
| 51 | | | | |
| 52 | | | | |
| 53 | | | | |
| 54 | | | | |

Assay 8
Protein-Compound Interaction Assay (SPR Assay)

The ability of the compounds described in this invention to bind to MCL-1 may be determined using surface plasmon resonance (SPR). This allows for the quantification of binding in terms of the equilibrium dissociation constant (KD [M]), as well as association and dissociation rate constants (kon [1/M 1/s] and koff [1/s], respectively). The measurements may be performed using Biacore® T200 or Biacore® S200 instruments (GE Healthcare).

For SPR measurements, recombinant MCL-1 (amino acids 173-321, N-terminal fused to Maltose Binding Protein (MBP) (SEQ ID 1) purchased from Beryllium (Bedford, Mass., USA)) was immobilized using standard amine coupling (Johnsson B et al, Anal Biochem. 1991 Nov. 1; 198(2):268-77). Briefly, carboxymethylated dextran biosensor chips (Series S Sensor Chip CMS, GE Healthcare) were activated with 1-ethyl-3-(3-dimethylaminopropyl)-carbodiimide hydrochloride (EDC) and N-hydroxysuccinimide (NHS) according to the supplier's instructions. MBP-MCL-1 was diluted in 1×PBS-P+ (GE Healthcare) and injected on the activated chip surface. Subsequently, a solution of 1 M ethanolamine-HCl (GE Healthcare) was injected to block unreacted groups, resulting in approximately 400-2500 response units (RU) of immobilized protein. A reference surface was generated by treatment with NHS-EDC and ethanolamine-HCl. Compounds were dissolved in 100% dimethylsulfoxide (DMSO) to a concentration of 10 mM and subsequently diluted in running buffer (1×PBS-P+ (GE Healthcare) [generated from PBS-P+ Buffer 10× (GE Healthcare): 0.2 M phosphate buffer with 27 mM KCl, 1.37 M NaCl and 0.5% Surfactant P20 (Tween 20).], 1% v/v DMSO). For SPR binding-measurements, serial dilutions of compound (eight dilution steps, typically ranging from 0.2 nM up to 1 µM) were injected over immobilized protein. Binding affinity and kinetics were measured at 25° C. with a flow rate of 100 µl/min in running buffer. Compounds were injected for 60 s followed by a dissociation time of up to 1000 s.

The double-referenced sensorgrams were fit to a simple reversible Langmuir 1:1 reaction mechanism as implemented in the Biacore® T200 and S200 evaluation software (T200 evaluation software version 2.0 and S200 evaluation software version 1.0, GE Healthcare).

TABLE 9

$K_D$, $k_{on}$ and $k_{off}$ values (geometric mean values) of MCL-1 compound interactions of selected examples as determined in SPR assay

| Example | kon [1/M 1/s] | koff [1/s] | KD [M] |
|---|---|---|---|
| 1 | | | |
| 2 | 2.3E5 | 1.0E-2 | 4.3E-8 |
| 3 | 4.6E6 | 1.9E-2 | 4.2E-9 |
| 4 | | | |
| 5 | | | |
| 6 | | | |
| 7 | 6.0E6 | 1.4E-2 | 2.3E-9 |
| 8 | | | |
| 9 | | | |
| 10 | | | |
| 11 | | | |
| 12 | | | |
| 13 | 1.1E7 | 7.7E-3 | 6.9E-10 |
| 14 | | | |
| 15 | | | |
| 16 | | | |
| 17 | | | |
| 18 | | | |
| 19 | | | |
| 20 | | | |
| 21 | | | |
| 22 | 4.4E6 | 7.2E-3 | 1.6E-9 |
| 23 | 9.7E4 | 2.6E-3 | 2.7E-8 |
| 24 | 3.3E6 | 9.7E-3 | 2.9E-9 |

TABLE 9-continued $K_D$, $k_{on}$ and $k_{off}$ values (geometric mean values) of MCL-1 compound interactions of selected examples as determined in SPR assay

| Example | kon [1/M 1/s] | koff [1/s] | KD [M] |
|---|---|---|---|
| 25 | | | |
| 26 | | | |
| 27 | | | |
| 28 | | | |
| 29 | | | |
| 30 | | | |
| 31 | | | |
| 32 | | | |
| 33 | | | |
| 34 | | | |
| 35 | | | |
| 36 | | | |
| 37 | | | |
| 38 | | | |
| 39 | 1.4E7 | 2.1E-2 | 1.5E-9 |
| 40 | | | |
| 41 | | | |
| 42 | | | |
| 43 | | | |
| 44 | | | |
| 45 | | | |
| 46 | | | |
| 47 | | | |
| 48 | | | |
| 49 | | | |
| 50 | | | |
| 51 | | | |
| 52 | | | |
| 53 | | | |
| 54 | | | |

Assay 9

Equilibrium Shake Flask Solubility Assay

Thermodynamic solubility can be determined by an equilibrium shake flask method [Edward H. Kerns and Li Di (2008) Solubility Methods in: Drug-like Properties: Concepts, Structure Design and Methods, p 276-286. Burlington, Mass.: Academic Press].

A saturated solution of the drug is prepared and the solution is mixed for 24 h to ensure that equilibrium has been reached. The solution is centrifuged to remove the insoluble fraction and the concentration of the compound in solution is determined using a standard calibration curve.

To prepare the sample, 2 mg solid compound are weighed in a 4 mL glass vial. 1 mL phosphate buffer pH 6.5 respectively borate Buffer pH 8 is added. The suspension is put on a stirrer and mixed for 24 hrs at room temperature. The solution is centrifuged afterwards. To prepare the sample for the standard calibration, 1-2 mg (accurate weight) solid sample is dissolved in acetonitrile/water 50:50 and diluted to 20 mL. Sample and standards can be quantified by HPLC with UV-detection. For each sample two injection volumes (5 and 50 µL) in triplicates are made. Three injection volumes (5 µL, 10 µL and 20 µL) are made for the standard.

Chromatographic conditions are as follows:
HPLC column: Xterra MS C18 2.5 µm 4.6×30 mm
Injection volume: Sample: 3×5 µl and 3×50 µl
    Standard: 5 µl, 10 µl, 20 µl
Flow: 1.5 mL/min
Mobile phase: acidic gradient:
    A: Water/0.01% trifluoroacidic acid
    B: Acetonitrile/0.01% trifluoroacidic acid
    0 min→95% A 5% B
    0-3 min→35% A 65% B, linear gradient 3-5 min→35% A 65% B, isocratic
5-6 min→95% A 5% B, isocratic
UV detector: wavelength near the absorption maximum (between 200 and 400 nm)

The areas of sample- and standard injections as well as the calculation of the solubility value (in mg/L) can be determined by using HPLC software (Waters Empower 2 FR).

Assay 10
Caco-2 Permeation Assay

Caco-2 cells (purchased from DSMZ Braunschweig, Germany) were seeded at a density of $4.5 \times 10^4$ cell per well on 24 well insert plates, 0.4 µm pore size, and grown for 15 days in DMEM medium supplemented with 10% fetal bovine serum, 1% GlutaMAX (100×, GIBCO), 100 U/mL penicillin, 100 µg/mL streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by an FCS-free hepes-carbonate transport puffer (pH 7.2). For assessment of monolayer integrity the transepithelial electrical resistance (TEER) was measured. Test compounds were predissolved in DMSO and added either to the apical or basolateral compartment in final concentration of 2 µM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$P_{app}=(V_r/P_o)(1/S)(P2/t)$$

Where $V_r$ is the volume of medium in the receiver chamber, $P_o$ is the measured peak area of the test drug in the donor chamber at t=o, S the surface area of the monolayer, $P_2$ is the measured peak area of the test drug in the acceptor chamber after 2 h of incubation, and t is the incubation time. The efflux ratio basolateral (B) to apical (A) was calculated by dividing the $P_{app}$ B-A by the $P_{app}$ A-B. In addition the compound recovery was calculated. As assay control reference compounds were analyzed in parallel.

Assay 11
CYP Inhibition Assay

The inhibitory potency of the test compounds towards cytochrome P450 dependent metabolic pathways was determined in human liver microsomes applying individual CYP isoform-selective standard probes (phenacetin, coumarin, bupropion, amodiaquine, diclofenac, S-mephenytoin, dextromethorphan, chlorzoxazone, midazolam, testosterone). Reference inhibitors were included as positive controls. Incubation conditions (protein and substrate concentration, incubation time) were optimized with regard to linearity of metabolite formation. The assay was processed by using Genesis Workstation (Tecan, Crailsheim, FRG) in 96-well plates at 37° C. After protein precipitation the metabolite formation was quantified by LC-MS/MS analysis followed by inhibition evaluation and $IC_{50}$ calculation.

The potential of an investigational drug to inhibit CYP enzymes, given by determined $IC_{50}$ values of test compounds in vitro, is a basic requirement in order to assess potential drug-drug interactions (DDI) with comedicated drugs which are relevant substrates of studied CYP isoforms. Such investigations are recommended by pertinent guidelines (i.e. EMA and FDA) for the evaluation of DDIs.

Assay 12
CYP Induction Assay

To evaluate the CYP induction potential in vitro, cultured human hepatocytes from three separate livers are treated once daily for three consecutive days with vehicle control, one of eight concentrations of test compound and known human CYP inducers (e.g. omeprazole, phenobarbital, and rifampin). After treatment, the cells are incubated in situ with the appropriate marker substrates for the analysis of CYP3A4, CYP2B6 and CYP1A2 activity by LC-MS/MS. Following the in situ incubation, the same hepatocytes from the same treatment groups are harvested for RNA isolation and analyzed by qRT-PCR to assess the effect of test compound on CYP1A2, CYP2B6 and CYP3A4 mRNA expression levels.

Assay 13
Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 mL falcon tubes and centrifuged at 50×g for 3 min at room temperature. The cell pellet was resuspended in 30 mL WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0 \times 10^6$ vital cells/mL. The test compound was added to a final concentration of 1 µM. During incubation, the hepatocyte suspensions were continuously shaken and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated using the following formulae: CL'intrinsic [ml/(min*kg)]=kel [1/min]/((cellno/volume of incubation [ml])*fu,inc)* (cellno/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH. The following parameter values were used: Liver blood flow—4.2 L/h/kg rat; specific liver weight—32 g/kg rat body weight; liver cells in vivo—$1.1 \times 10^8$ cells/g liver, liver cells in vitro—$1.0 \times 10^6$/ml; fu,inc and fu,blood is taken as 1.

Assay 14
Investigation of In Vitro Metabolic Stability in Rat Hepatocytes in Liver Microsomes (Including Calculation of Hepatic In Vivo Blood Clearance (CL) and of Maximal Oral Bioavailability (Fmax))

The in vitro metabolic stability of test compounds was determined by incubating them at 1 µM in a suspension liver microsomes in 100 mM phosphate buffer, pH7.4 (sodium dihydrogen phosphate monohydrate+disodium hydrogen phosphate dihydrate) and at a protein concentration of 0.5 mg/mL at 37° C. The microsomes were activated by adding a co-factor mix containing 8 mM Glukose-6-Phosphat, 4 mM magnesium chloride; 0.5 mM NADP and 1 IU/ml G-6-P-Dehydrogenase in phosphate buffer, pH 7.4. The metabolic assay was started shortly afterwards by adding the test compound to the incubation at a final volume of 1 mL. Organic solvent in the incubations was limited to 0.01% dimethylsulfoxide (DMSO) and ≤1% acetonitrile. During incubation, the microsomal suspensions were continuously shaken at 580 rpm and aliquots were taken at 2, 8, 16, 30, 45 and 60 min, to which equal volumes of cold methanol were immediately added. Samples were frozen at −20° C. over night, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, specific liver weight and microsomal protein content the hepatic in vivo blood clearance (CL) and the maximal oral bioavailability ($F_{max}$) were calculated for the different species. The hepatic in vivo blood clearance (CLblood) and the maximal oral bioavailability ($F_{max}$) was calculated using the following formulae: CL'intrinsic [ml/(min*kg)]=kel [1/min]/((mg protein/volume of incubation [ml])*fu,inc)*(mg protein/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH and using the following parameter values: Liver blood flow—1.32 L/h/kg (human), 2.1 L/h/kg (dog), 4.2 L/h/kg (rat); specific liver weight—21 g/kg (human), 39 g/kg (dog), 32 g/kg (rat); microsomal protein content—40 mg/g.; fu,inc and fu,blood is taken as 1.

Assay 15
In Vivo Pharmacokinetics in Rats

For in vivo pharmacokinetic experiments test compounds were administered to male Wistar rats intravenously at doses of 0.3 to 1 mg/kg and intragastral at doses of 0.5 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g., 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g., 48 h, 72 h). Blood was collected into Lithium-Heparintubes (Monovetten®, Sarstedt) and centrifuged for 15 min at 3000 rpm. An aliquot of 100 μL from the supernatant (plasma) was taken and precipitated by addition of 400 μL cold acetonitrile and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters are calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax:

Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t½: terminal half-life (in h); F: oral bioavailability: AUCnorm after intragastral administration divided by AUCnorm after intravenous administration (in %).

Assay 16
In Vivo Pharmacokinetics in Mouse

For in vivo pharmacokinetic experiments test compounds are administered to female CD1 mouse intravenously at doses of 0.3 to 1 mg/kg formulated as solutions using solubilizers such as PEG400 in well-tolerated amounts.

For pharmacokinetics after intravenous administration test compounds are given as i.v. bolus and blood samples are taken at 2 min, 5 min, 15 min, 30 min, 1 h, 2 h, 4 h, 7 h, and 24 h after dosing. Blood is collected via a vena jugularis catheter into Lithium-Heparin coated tubes (Eppendorf) and centrifuged for 15 min at 3000 rpm. An aliquot from the supernatant (plasma) is taken and precipitated by addition of 1:10 (v/v) ice cold methanol and frozen at −20° C. over night. Samples are subsequently thawed and centrifuged at 3000 rpm, 4° C. for 20 minutes. Aliquots of the supernatants are taken for analytical testing using an Agilent 1200 HPLC-system with LCMS/MS detection. PK parameters are calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations can be measured divided by the administered dose (in kg*h/L); t½: terminal half-life (in h); MRT iv (h): mean residence time.

Assay 17
In Vivo Pharmacokinetics in Dog

For in vivo pharmacokinetic experiments test compounds are administered to Beagle dogs intravenously at doses of 0.3 to 1 mg/kg formulated as solutions using solubilizers such as PEG400 in well-tolerated amounts.

For pharmacokinetics after intravenous administration test compounds are given in in dogs as short term infusion (10 min). Blood samples are taken e.g. at 5 min, 10 min (end of short term infusion), 15 min, 30 min, 1 h, 2 h, 4 h, 6 h, 8 h and 24 h after dosing from the vena saphena. Blood is collected into K-EDTA (Monovetten®, Sarstedt) and centrifuged for 15 min at 3000 rpm. An aliquot of 100 μL from the supernatant (plasma) is taken and precipitated by addition of 400 μL cold acetonitrile and frozen at −20° C. over night. Samples are subsequently thawed and centrifuged at 3000 rpm, 4° C. for 20 minutes. Aliquots of the supernatants are taken for analytical testing using an Agilent HPLC-system with LCMS/MS detection. PK parameters are calculated by non-compartmental analysis using a PK calculation software (e.g. Phoenix WinNonlin®, Certara USA, Inc.).

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations can be measured divided by the administered dose (in kg*h/L); t½: terminal half-life (in h); MRT iv (h): mean residence time.

Assay 18

Assessment of the Anti-Proliferation Effect of Compounds in Tumor Xenografts

The suitability of the compounds of the present invention for the treatment of hyperproliferative disorders can be demonstrated in animal models of the following cancer types: breast cancer; esophageal cancer; liver cancer; lung cancer; lymphoma including non-Hodgkin-lymphoma type, diffuse large B-cell lymphoma subtype including GC-DLBCL* and ABC-DLBCL** subtypes, and mantle cell lymphoma; acute leukemia, acute myeloid leukemia type, acute monocytic leukemia; melanoma; multiple myeloma; melanoma; ovarian cancer; pancreas cancer For this purpose, human tumor cells of the respective cancer type are injected subcutaneously into immunocompromised mice. Once the primary tumor growth is established the animals will be then randomized to receive treatment with either compound at maximum tolerated dose or vehicle control for a certain period of time. The difference between those groups in terms of the tumor growth will be used to access the treatment efficacy. The principles of such xenograft studies are summarized in Richmond, A.; Su, Y. (2008). "Mouse xenograft models vs GEM models for human cancer therapeutics". Disease Models and Mechanisms 1 (2-3): 78-82. doi:10.1242/dmm.000976.

The invention claimed is:

1. A compound of formula (I):

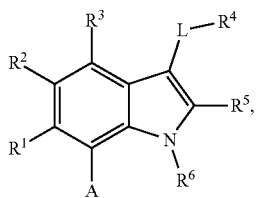 (I)

wherein
A is

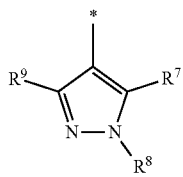 (A1)

or

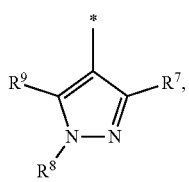 (A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;

or
A is

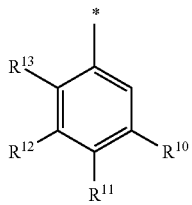 (A3)

wherein optionally one or two of the groups selected from $CR^{11}$, $CR^{12}$ and $CR^{13}$ are replaced by a nitrogen atom,
  wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ is a fluorine atom,
$R^2$ and $R^3$ are each a hydrogen atom;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group, and a $C_3$-$C_5$-cycloalkyl group;
L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;
E is a bond, an oxygen atom, a sulfur atom, a —S(O)— group, a —S(O)$_2$— group or a —NR$^{14}$— group and constitutes the connecting element to $R^4$;
m is 2, 3, or 4;
$R^5$ is selected from a COOH group, a

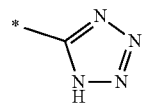

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group, and a —C(O)—NHS(O)$_2$(CH$_2$)$_s$NHCO(aryl) group;
—$R^6$-$R^7$— is selected from $^\#$—(CH$_2$)$_n$—(B)$_t$—(CH$_2$)$_p$—X—$^{\#\#}$, $^\#$(C$_2$-C$_6$-alkenylene)-(B)$_t$—(CH$_2$)$_p$—X—$^{\#\#}$, $^\#$—(CH$_2$)$_n$—(B)$_t$—(C$_2$-C$_5$-alkenylene)—X—$^{\#\#}$, and $^\#$—(CH$_2$)$_q$—(B)—(CH$_2$)$_r$—(B)—(CH$_2$)$_v$—X—$^{\#\#}$,
  wherein $^\#$ is the point of attachment with the indole nitrogen atom and $^{\#\#}$ is the point of attachment with the pyrazole carbon atom bearing the $R^7$ substituent; and
  wherein one or more —CH$_2$— groups may be unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and
  where a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group; and
  where X is an unsubstituted —CH$_2$— group;
—$R^6$-$R^{10}$— is selected from $^\#$—(CH$_2$)$_n$—(B)$_t$—(CH$_2$)$_p$—X—$^{\#\#}$, $^\#$(C$_2$-C$_6$-alkenylene)-(B)$_t$—(CH$_2$)$_p$—X—$^{\#\#}$, $^\#$—(CH$_2$)$_n$—(B)$_t$—(C$_2$-C$_5$-alkenylene)-X—$^{\#\#}$, and $^\#$—(CH$_2$)$_q$—(B)—(CH$_2$)$_r$—(B)—(CH$_2$)$_v$—X—$^{\#\#}$,
  wherein $^\#$ is the point of attachment with the indole nitrogen atom and $^{\#\#}$ is the point of attachment with the carbon atom of the phenyl moiety bearing the $R^{10}$ substituent, one or more —CH$_2$— groups may be unsubstituted or substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, where a —CH=CH— group in any alkenylene can be replaced by a 1,2-(C$_1$-C$_6$)cycloalkylene group which is unsubstituted or substituted one or two times with a halogen atom or a C$_1$-C$_2$-alkyl group, and where X is an unsubstituted —CH$_2$— group;

n is 2, 3, 4, 5, 6, 7, 8, or 9;

t is 0 or 1;

p is 0, 1, 2, 3, 4, or 5;

q is 2, 3, 4, 5, or 6;

r is 2, 3, 4, 5, or 6;

v is 0 or 1;

s is 0, 1, 2, or 3;

where the integers selected for variables n, t, p, q, r, and v result in forming a 9- to 16-membered ring independently from the selection of variable A1, A2 or A3;

B is independently selected from a —C(O)NR$^{15}$— group, a —NR $^{15}$C(O)— group, a —N(R$^{15}$)— group, a —[N(CH$_3$)$_2$]$^+$— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

R$^8$ is selected from a hydrogen atom,
a C$_1$-C$_6$-alkyl group, which is unsubstituted or substituted with one or more substituents independently selected from
a halogen atom, a hydroxyl group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group; and
a C$_3$-C$_6$-cycloalkyl group, R$^9$ is selected from a hydrogen atom,
a C$_1$-C$_4$-alkyl group,
a C$_1$-C$_3$-hydroxyalkyl group,
a C$_1$-C$_4$-haloalkyl group,
a C$_1$-C$_4$-haloalkyl-NH—C(O)—O—(C$_1$-C$_3$-alkylene)- group,
a C$_2$-C$_6$-haloalkenyl group,
a C$_1$-C$_6$-alkyl-O— group,
a C$_1$-C$_4$-haloalkoxy group,
a C$_1$-C$_6$-alkyl-O—(C$_1$-C$_3$-alkylene)- group,
a (C$_3$-C$_7$)-cycloalkyl group,
a (C$_3$-C$_7$)-cycloalkyl-O—(C$_1$-C$_3$-alkylene)- group,
a phenyl-O—(C$_1$-C$_3$-alkylene)- group,
a phenyl-(C$_1$-C$_3$-alkylene)-O—(C$_1$-C$_3$-alkylene)- group,
a R$^{18}$-(phenylene)-(C$_1$-C$_3$-alkylene)-O—(C$_1$-C$_3$-alkylene)- group,
a R$^{18}$-(phenylene)-O—(C$_1$-C$_3$-alkylene)- group,
a R$^{18}$-(phenylene)-(heteroarylene)-O—(C$_1$-C$_3$-alkylene) group,
a (R$^{18}$)-(heterocycloalkylene)-(C$_1$-C$_3$-alkylene)- group,
a (R$^{18}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{18}$)-(heteroarylene)-(C$_1$-C$_3$-alkylene)-O—(C$_1$-C$_3$-alkylene)- group,
a (R$^{18}$)-(heteroarylene)-(phenylene)-O—(C$_1$-C$_3$-alkylene)- group,
a (R$^{19}$)—S(O)$_2$-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—N(C$_1$-C$_6$-alkyl)-(phenylene)-O—(C$_1$-C$_3$-alkylene)- group,
a (R$^{19}$)—S(O)$_2$-(heterocycloalkylene)-(phenylene)-O—(C$_1$-C$_3$-alkylene)- group,
a (R$^{18}$)-(heterocycloalkylene)-(heteroarylene)-O—(C$_1$-C$_3$-alkylene)- group,
a (R$^{19}$)-(heteroarylene)-O—(C$_1$-C$_3$-alkylene)- group,
a (R$^{18}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a (R$^{19}$)—S(O)$_2$-(heterocycloalkylene)-(heteroarylene)-O—(C$_1$-C$_3$-alkylene)- group,
a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{15}$—(C$_1$-C$_3$-alkylene)- group,
a

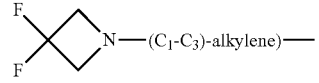

group, and a

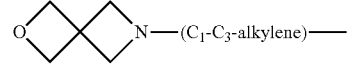

group, where the phenyl ring is unsubstituted or substituted with a halogen atom, a hydroxyl group, or a C$_1$-C$_3$-alkoxy group and the heterocycloalkyl group is unsubstituted or substituted with an oxo (=O) group or is unsubstituted or substituted with one or more substituents independently selected from a halogen atom, a hydroxyl group, a C$_1$-C$_3$-alkyl group, and a C$_1$-C$_3$-alkoxy group, or R$^8$ and R$^9$ together form a 5- or 6-membered ring optionally comprising one or two heteroatoms selected from —O— and —NR$^{14}$—;

R$^{11}$ and R$^{13}$ are each independently selected from a hydrogen atom, a halogen atom, a C$_1$-C$_3$-alkyl group, and a C$_1$-C$_3$-alkoxy group;

R$^{12}$ is selected from a hydrogen atom, a C$_1$-C$_3$-alkoxy group, a C$_1$-C$_3$-alkyl group, a C$_1$-C$_3$-haloalkyl group, a C$_1$-C$_3$-haloalkoxy group, and a NR$^{16}$R$^{17}$ group;

R$^{14}$ is a hydrogen atom or a C$_1$-C$_3$-alkyl group;

R$^{15}$ is independently selected from a hydrogen atom,
a C$_1$-C$_6$-alkyl group
which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;

a phenyl group, a group

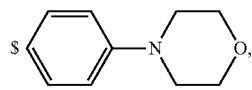

a group

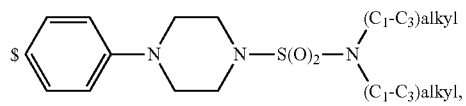

and a group

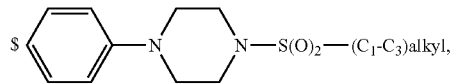

where $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;

$R^{18}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}$R$^{21}$ group; and $R^{20}$ and $R^{21}$ are each independently selected from a hydrogen atom and a $C_1$-$C_6$-alkyl group;

or a tautomer, an N-oxide, or a pharmaceutically acceptable salt thereof, or a pharmaceutically acceptable salt of a tautomer, or a pharmaceutically acceptable salt of an N-oxide, or a mixture of same.

2. The compound of (I) according to claim 1, wherein A is

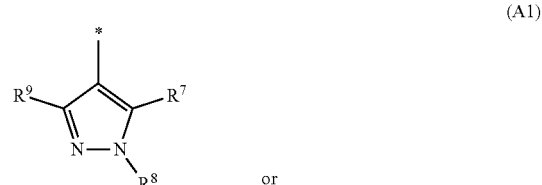

(A1)

or

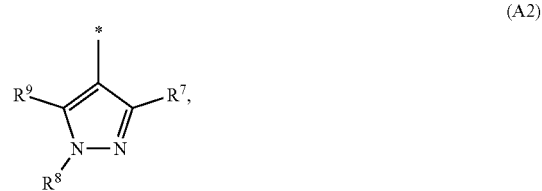

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ is a fluorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to R$^4$;

$R^5$ is selected from a COOH group, a

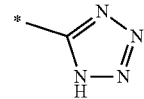

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH2)$_s$NHCO($C_3$-$C_6$-cycloalkyl) group and a —C(O)—NHS(O)$_2$(CH$_2$)$_s$NHCO(aryl) group;

—R$^6$-R$^7$— is selected from #—(CH$_2$)$_n$—(B)$_r$—(CH$_2$)$_p$—X—##, #(C$_2$-C$_6$-alkenylene)-(B)$_r$—(CH$_2$)$_p$—X—##,

—(CH₂)ₙ—(B)ₜ—(C₂-C₅-alkenylene)-X—##, and
—(CH₂)_q—(B)—(CH₂)ᵣ—(B)—(CH₂)ᵥX—##,
wherein # is the point of attachment with the indole nitrogen atom and ## is the point of attachment with the pyrazole carbon atom bearing the R⁷ substituent; and wherein one or more —CH₂— groups may be unsubstituted or substituted with one or more substituents independently selected from a halogen atom, a hydroxyl group, a NR¹⁶R¹⁷ group, a C₁-C₃-alkyl group, a C₁-C₃-haloalkyl group, a C₁-C₃-alkoxy group, and a C₁-C₃-haloalkoxy group, and where a —CH=CH— group in any alkenylene can be replaced by a 1,2-(C₃-C₅)cycloalkylene group which is unsubstituted or substituted one or two times with a halogen atom or a C₁-C₂-alkyl group, and where X is an unsubstituted —CH₂— group;
n is 2, 3, 4, 5, 6, 7, 8, or 9;
p is 0, 1, 2, 3, 4, or 5;
t is 0 or 1;
s is 0, 1, 2, or 3;
where the integers selected for variables n, t, and p result in forming a 9- to 16-membered ring independently from the selection of variable A1 or A2;
B is independently selected from a —C(O)NR¹⁵— group, a —NR¹⁵C(O)— group, a —N(R¹⁵)— group, a —[N(CH₃)₂]⁺— group, a —N(R¹⁵)—C(=O)—N(R¹⁵)— group, a —O—C(=O)—N(R¹⁵)— group, a —N(R¹⁵)—C(=O)—O— group, —O—, —S—, —S(O)—, and —S(O)₂—;
R⁸ is selected from a hydrogen atom,
a C₁-C₆-alkyl group, which is unsubstituted or substituted with one or more substituents independently selected from a halogen atom, a hydroxyl group, a C₁-C₃-alkoxy group, a C₁-C₃-haloalkoxy group, a C₃-C₆-cycloalkyl group, a heterocycloalkyl group and a NR²⁰R²¹ group;
a C₁-C₃-haloalkyl group,
a C₃-C₆-cycloalkyl group, and
a C₁-C₆-alkyl group in which one or two not directly adjacent carbon atoms are independently replaced by a heteroatom selected from —O— and —NH—;
R⁹ is selected from a hydrogen atom,
a C₁-C₄-alkyl group,
a C₁-C₃-hydroxyalkyl group,
a C₁-C₄-haloalkyl group,
a C₁-C₄-haloalkyl-NH—C(O)—O—(C₁-C₃-alkylene)-group,
a C₂-C₆-haloalkenyl group,
a C₁-C₆-alkyl-O— group,
a C₁-C₄-haloalkoxy group,
a C₁-C₆-alkyl-O—(C₁-C₃-alkylene)- group,
a (C₃-C₇)-cycloalkyl group,
a (C₃-C₇-cycloalkyl)-O—(C₁-C₃-alkylene)- group,
a phenyl-O—(C₁-C₃-alkylene)- group,
a phenyl-(C₁-C₃-alkylene)-O—(C₁-C₃-alkylene)- group,
a (R¹⁸)-(phenylene)-O—(C₁-C₃-alkylene)- group,
a (R¹⁸)-(phenylene)-(C₁-C₃-alkylene)-O—(C₁-C₃-alkylene)- group,
a (R¹⁸)-(phenylene)-(heteroarylene)-O—(C₁-C₃-alkylene)- group,
a (R¹⁸)-(heterocycloalkylene)-(C₁-C₆-alkylene)- group,
a (R¹⁸)-(heterocycloalkylene)-(phenylene)-O—(C₁-C₃-alkylene)- group,
a (heterocycloalkenyl)-(phenylene)-O—(C₁-C₃-alkylene)- group,
a (R¹⁸)-(heteroarylene)-(C₁-C₃-alkylene)-O—(C₁-C₃-alkylene)- group,
a (R¹⁸)-(heteroarylene)-(phenylene)-O—(C₁-C₃-alkylene)- group,
a (R¹⁸)-(phenylene)-(C₁-C₃-alkylene)-O—(C₁-C₃-alkylene)- group,
a (R¹⁹)—S(O)₂-(phenylene)-O—(C₁-C₃-alkylene)-group,
a (R¹⁹)—S(O)₂—NH-(phenylene)-O—(C₁-C₃-alkylene)- group,
a (R¹⁹)—S(O)₂—N(C₁-C₆-alkyl)-(phenylene)-O—(C₁-C₃-alkylene)- group,
a (R¹⁹)—S(O)₂-(heterocycloalkylene)-(phenylene)-O—(C₁-C₃-alkylene)- group,
a (R¹⁸)-(heterocycloalkylene)-(heteroarylene)-O—(C₁-C₃-alkylene)- group,
a (R¹⁹)-(heteroarylene)-O—(C₁-C₃-alkylene)- group,
a (R¹⁹)—S(O)₂-(heteroarylene)-O—(C₁-C₃-alkylene)-group,
a (R¹⁹)—S(O)₂-(heterocycloalkylene)-(heteroarylene)-O—(C₁-C₃-alkylene)- group,
a NR²⁰R²¹—(C₁-C₃-alkylene)- group,
a (C₁-C₃-alkyl)-NH—(C₁-C₃-alkylene)- group,
a (C₁-C₃-haloalkyl)-(C₁-C₃-alkylene)-NH—(C₁-C₃-alkylene)- group,
a (C₁-C₃-haloalkyl)-NH—(C₁-C₃-alkylene)- group,
a (C₁-C₃-alkyl)-NH—C(O)—(C₁-C₃-alkylene)- group
a (C₁-C₃-alkyl)-NR¹⁵—C(O)—(C₁-C₃-alkylene)- group
a (C₁-C₃-alkyl)-C(O)—NH—(C₁-C₃-alkylene)- group
a (C₁-C₃-alkyl)-C(O)—NR¹⁵—(C₁-C₃-alkylene)- group,
a

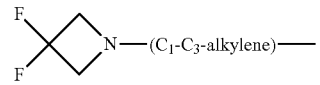

group, and a

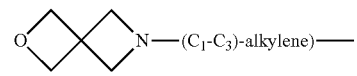

group, where the phenyl ring is optionally substituted with a halogen atom, a hydroxyl group, or a C₁-C₃-alkoxy group and
the heterocycloalkyl group is optionally substituted with an oxo (=O) group or is optionally substituted with one or more substituents independently selected from a halogen atom and a C₁-C₃-alkyl group;
or R⁸ and R⁹ together form a 5- or 6-membered ring optionally comprising one or two heteroatoms selected from of —O—, and —NR¹⁴—;
R¹⁴ is a hydrogen atom or a C₁-C₃-alkyl group;
R¹⁵ is independently selected from a hydrogen atom,
a C₁-C₆-alkyl group, which is optionally substituted with one or more substituents selected from a halogen atom, a C₁-C₃-alkyl group, a C₁-C₃-haloalkyl group, a C₁-C₃-hydroxyalkyl group, a C₁-C₃-alkoxy group, a C₁-C₃-haloalkoxy group, a heterocycloalkyl group, an aryl group, a (R¹⁸)-(heterocycloalkylene)-

(arylene)-O— group, an aryl-O— group, an aryl-($C_1$-$C_3$-alkylene)-O— group, a ($R^{19}$)—S(O)$_2$—arylene-O— group, a ($R^{19}$)S(O)$_2$-heterocycloalkylene-arylene-O— group and an aryl-heteroarylene-O— group;

a phenyl group, a group

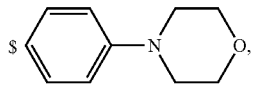

a group

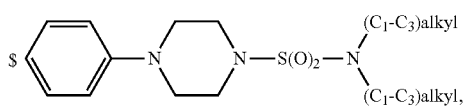

and a group

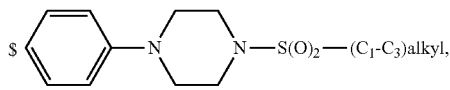

where $ is the point of attachment to the nitrogen atom, to which $R^{15}$ is attached;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)O$R^{21}$ group, a —C(O)NR$^{20}$R$^{21}$ group, a ($C_1$-$C_3$-alkyl)-O—($C_1$-$C_3$-alkylene)-C(O)— group, ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}$R$^{21}$ group; and $R^{20}$ and $R^{21}$ are each independently selected from a hydrogen atom and a $C_1$-$C_6$-alkyl group;

or a tautomer, an N-oxide, or a pharmaceutically acceptable salt thereof, or a pharmaceutically acceptable salt of a tautomer, or a pharmaceutically acceptable salt of an N-oxide, or a mixture of same.

3. The compound of formula (I) according to claim 1, wherein

A is

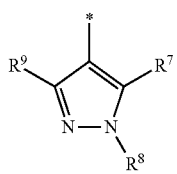 (A1)

or

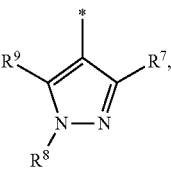 (A2)

wherein $R^6$ and $R^7$, together with two carbon atoms of the pyrazole ring, two carbon atoms of the indole moiety and the nitrogen atom to which $R^6$ is attached, form a 10- to 12-membered ring and * is the point of attachment of these moieties to the indole carbon atom bearing the A substituent;

$R^1$ is a fluorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a $C_1$-$C_3$-alkyl group and a $C_1$-$C_3$-haloalkyl group;

L is a group —(CH$_2$)$_m$-E-;

E is a bond or an oxygen atom and constitutes the connecting element to $R^4$;

m is 2, 3, or 4;

$R^5$ is a COOH group;

—$R^6$-$R^7$— is selected from #—(CH$_2$)$_n$—(B)$_t$—(CH$_2$)$_p$—X—## and #—(C$_2$-C$_6$-alkenylene)-(B)$_t$—(CH$_2$)$_p$—X—##, wherein # is the point of attachment with the indole nitrogen atom and ## is the point of attachment with the pyrazole carbon atom bearing the $R^7$ substituent; and wherein one or more —CH$_2$— groups may be unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, and a $C_1$-$C_3$-alkoxy group, and where a —CH=CH— group in any alkenylene can be replaced by a 1,2-(C$_3$-C$_5$)cycloalkylene group which is unsubstituted or substituted one or two times with a halogen atom or a $C_1$-$C_2$-alkyl group, and where X is an unsubstituted —CH$_2$— group;

n is 3, 4, 5, or 6;

t is 0 or 1;

p is 0;

where the integers selected for variables n, t, and p result in forming a 10- to 12-membered ring independently from the selection of variable A1 or A2;

B is independently selected from a —N(R$^{15}$)— group, a —[N(CH3)$_2$]$^+$— group and —O— group;

$R^8$ is selected from a hydrogen atom and a $C_1$-$C_4$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a NR$^{20}$R$^{21}$ group;

$R^9$ is selected from a hydrogen atom, a $C_1$-$C_4$-alkyl group, a $C_1$-$C_3$-hydroxyalkyl group, a $C_1$-$C_4$-haloalkyl group, a $C_2$-$C_6$-haloalkenyl group, a $C_1$-$C_6$-alkyl-O—($C_1$-$C_3$-alkylene)- group, a ($C_3$-$C_7$-cycloalkyl)- group, a phenyl-O—(C$_1$-C$_3$-alkylene)- group, a (R$^{18}$)-(phenylene)-O—(C$_1$-C$_3$-alkylene)- group, a (R$^{18}$)-(heterocycloalkylene)-(C$_1$-C$_3$-alkylene)- group, a (R$^{18}$)-(heteroarylene)-O—(C$_1$-C$_3$-alkylene)- group, a (R$^{19}$)—S(O)$_2$-(heteroarylene)-O—(C$_1$-C$_3$-alkylene)- group, a NR$^{20}$R$^{21}$—(C$_1$-C$_3$-alkylene)- group, and a (C$_1$-C$_3$-alkyl)-NH—(C$_1$-C$_3$-alkylene)- group, where the phenyl group is unsubstituted or substituted with a halogen atom, a hydroxyl group, or a C$_1$-C$_3$-alkoxy group and the heterocycloalkylene group is unsubstituted or substituted with a substituent independently selected from an oxo (=O) group and a C$_1$-C$_3$-alkyl group;

or

R$^8$ and R$^9$ together form 6-membered ring optionally comprising one or two oxygen atoms;

R$^{15}$ is selected from a hydrogen atom, a C$_1$-C$_3$-alkyl group, a C$_1$-C$_3$-haloalkyl group, a phenyl group, a benzyl group, a group

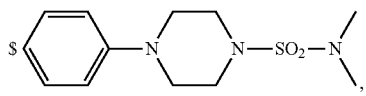

a group

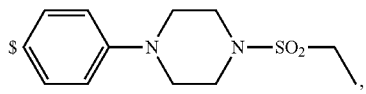

and a group

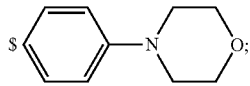

R$^{16}$ and R$^{17}$ are each independently selected from a hydrogen atom, a C$_1$-C$_6$-alkyl group, and a C$_1$-C$_6$-haloalkyl group;

R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a R$^{21}$OC(O)—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, a (C$_1$-C$_3$-alkyl)-C(O)— group, and a C$_3$-C$_6$-cycloalkyl-C(O)— group;

R$^{19}$ is selected from a C$_1$-C$_3$-alkyl group, a C$_3$-C$_6$-cycloalkyl group, and a NR$^{20}$R$^{21}$ group; and R$^{20}$ and R$^{21}$ are each independently selected from a hydrogen atom and a C$_1$-C$_3$-alkyl group;

or a tautomer, an N-oxide, or a pharmaceutically acceptable salt thereof, or a pharmaceutically acceptable salt of a tautomer, or a pharmaceutically acceptable salt of an N-oxide, or a mixture of same.

4. The compound of formula (I) according to claim 1, wherein

A is

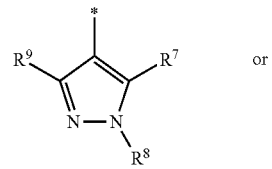

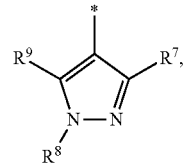

wherein R$^6$ and R$^7$, together with two carbon atoms of the pyrazole ring, two carbon atoms of the indole moiety and the nitrogen atom to which R$^6$ is attached, form a 10- or 11-membered ring and * is the point of attachment of these moieties to the indole carbon atom bearing the A substituent;

R$^1$ is a fluorine atom;

R$^2$ and R$^3$ are each a hydrogen atom;

R$^4$ is an aryl group, which is unsubstituted or substituted with a halogen atom;

L is a group —(CH$_2$)$_m$-E-;

E is an oxygen atom and constitutes the connecting element to R$^4$;

m is 3;

R$^5$ is a COOH group;

—R$^6$-R$^7$— is selected from $^\#$—(CH$_2$)$_n$—(B)$_t$—(CH$_2$)$_p$—X—$^{\#\#}$ and $^\#$—(C$_2$-C$_6$-alkenylene)-(B)$_t$—(CH$_2$)$_p$—X—$^{\#\#}$, wherein $^\#$ is the point of attachment with the indole nitrogen atom and $^{\#\#}$ is the point of attachment with the pyrazole carbon atom bearing the R$^7$ substituent and wherein one or more —CH$_2$— groups may be unsubstituted or substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, and a C$_1$-C$_3$-alkoxy group, and where a —CH=CH— group in any alkenylene can be replaced by a 1,2-(C$_3$-C$_5$)cycloalkylene group and where X is an unsubstituted —CH$_2$— group;

n is 3 or 4;

t is 1;

p is 0 where the integers selected for variables n, t, and p result in forming a 10- to 11-membered ring independently from the selection of variable A1 or A2;

B is independently selected from —O— and —N(R$^{15}$)—;

R$^8$ is selected from a hydrogen atom and, a C$_1$-C$_4$-alkyl group, which is unsubstituted or substituted with one or more substituents independently selected from a halogen atom, a hydroxy group, a C$_3$-C$_6$-cycloalkyl group and a heterocycloalkyl group;

R$^9$ is a C$_1$-C$_4$-alkyl group, a C$_1$-C$_3$-hydroxyalkyl group, a C$_1$-C$_3$-haloalkyl group, a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{18}$-(phenylene)-O—($C_1$-$C_3$-alkylene)- group,
a $NR^{20}R^{21}$—($C_1$-$C_3$-alkylene)- group, and
a ($C_1$-$C_3$-alkyl)-NH—($C_1$-$C_3$-alkylene)- group;

$R^{15}$ is selected from a hydrogen atom, a $C_1$-$C_3$-alkyl group and a $C_1$-$C_3$-haloalkyl group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)OR$^{21}$ group, a —C(O)NR$^{20}$R$^{21}$ group and ($C_1$-$C_6$-alkyl)-C(O)— group; and $R^{20}$ and $R^{21}$ are each independently selected from a hydrogen atom and a $C_1$-$C_3$-alkyl group;

or a tautomer, or a pharmaceutically acceptable salt thereof, or a pharmaceutically acceptable salt of a tautomer, or a mixture of same.

5. The compound of formula (I) according to claim 1, wherein A

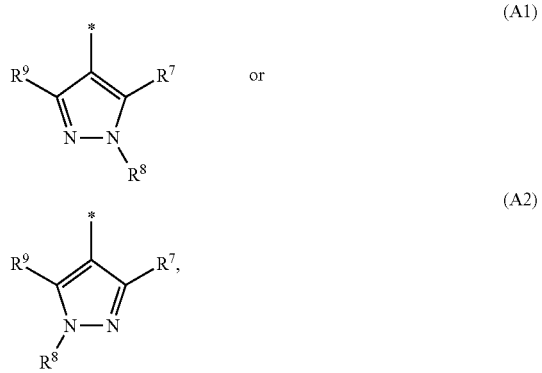

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent $R^1$ is a fluorine atom;
$R^2$ and $R^3$ are each a hydrogen atom;
$R^4$ is a naphthyl group, which is unsubstituted or substituted with a halogen atom;
L is a group —(CH$_2$)$_3$—O—;
$R^5$ is a COOH group;
—$R^6$-$R^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, and wherein # is the point of attachment with the indole nitrogen atom and $^{\#\#}$ is the point of attachment with the pyrazole carbon atom bearing the $R^7$ substituent and
wherein one or more —CH$_2$— groups may be unsubstituted or substituted with one or more halogen atoms,
and where a —CH=CH— group in any alkenylene can be replaced by a

group or a

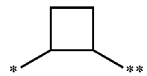

group where * is the point of attachment of the ring to the adjacent —CH$_2$— group or to the indole nitrogen atom and ** is the point of attachment to the adjacent —CH$_2$— group or to —(B)$_t$— and
where X is an unsubstituted —CH$_2$— group;
n is 4;
t is 1;
p is 0;
where the integers selected for variables n, t, and p result in forming a 11-membered ring independently from the selection of variable A1 or A2;
B is independently selected from —O— and —N(R$^{15}$)—;
$R^8$ is a $C_1$-$C_3$-alkyl group;
$R^9$ is a $C_1$-$C_3$-alkyl group; and
$R^{15}$ is selected from a hydrogen atom, a $C_1$-$C_3$-alkyl group, and a $C_1$-$C_3$-haloalkyl group;
or a tautomer, or a pharmaceutically acceptable salt thereof, or a pharmaceutically acceptable salt of a tautomer, or a mixture of same.

6. The compound according to claim 1, which is selected from
(rac)-(11Z)-4-fluoro-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid,
(rac)-4-fluoro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid,
4-fluoro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1),
4-fluoro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, —N-ethylethanamine salt (enantiomer 2),
(rac)-(11Z)-3-ethyl-4-fluoro-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid,
(rac)-3-ethyl-4-fluoro-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid,
3-ethyl-4-fluoro-2-methyl-7-{3-[(naphthalen-1-yl)oxy]propyl}-2,10,11,12,13,15-hexahydro-pyrazolo[4',3':9,10][1,6]oxazacycloundecino[8,7,6-hi]indole-8-carboxylic acid-N-ethylethanamine salt (enantiomer 1),
3-ethyl-4-fluoro-2-methyl-7-{3-[(naphthalen-1-yl)oxy]propyl}-2,10,11,12,13,15-hexahydro-pyrazolo[4',3':9,10][1,6]oxazacycloundecino[8,7,6-hi]indole-8-carboxylic acid-N-ethylethanamine salt (enantiomer 2),
(rac)-(Z)-13-fluoro-10,12-dimethyl-1-(3-(naphthalen-1-yloxy)propyl)-4,7,9,10-tetrahydropyrazolo[4',3':9,10][1]oxa[6]azacycloundecino[8,7,6-hi]indole-2-carboxylic acid, (rac)-13-fluoro-10,12-dimethyl-1-(3-(naphthalen-1-yloxy)propyl)-4,5,6,7,9,10-hexahydropyrazolo[4',3':9,10][1]oxa[6]azacycloundecino[8,7,6-hi]indole-2-carboxylic acid, (rac)-(Z)-12-ethyl-13-fluoro-10-methyl-1-(3-(naphthalen-1-yloxy)propyl)-4,7,9,10-tetrahydropyrazolo[4',3':9,10][1]oxa[6]azacycloundecino[8,7,6-hi]indole-2-carboxylic acid, (rac)-13-fluoro-1-(3-((6-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylic acid, 4-fluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 4-fluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-13-fluoro-1-(3-((4-fluoronaphthalen-1-yl)oxy)propyl)-11,12-dimethyl-4,5,6,7,9,11-hexahydropyrazolo[4',3':9,10][1]oxa[6]azacycloundecino[8,7,6-hi]indole-2-carboxylic acid, 4-fluoro-7-{3-[(4-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 1), 4-fluoro-7-{3-[(4-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 2), (rac)-13-fluoro-11,12-dimethyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylic acid, (rac)-1-(3-((2,3-dihydro-1H-inden-4-yl)oxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-13-fluoro-11,12-dimethyl-4,5,6,7,9,11-hexahydropyrazolo[4',3':9,10][1]oxa[6]azacycloundecino[8,7,6-hi]indole-2-carboxylic acid, (rac)-12-ethyl-13-fluoro-1-(3-((6-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylic acid, 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), 3-ethyl-4-fluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 2)

(rac)-12-ethyl-13-fluoro-1-(3-((4-fluoronaphthalen-1-yl)oxy)propyl)-11-methyl-4,5,6,7,9,11-hexahydropyrazolo[4',3':9,10][1]oxa[6]azacycloundecino[8,7,6-hi]indole-2-carboxylic acid, 3-ethyl-4-fluoro-7-{3-[(4-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 3-ethyl-4-fluoro-7-{3-[(4-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-12-ethyl-13-fluoro-11-methyl-1-(3-((5,6,7,8-tetrahydronaphthalen-1-yl)oxy)propyl)-4,5,6,7,9,11-hexahydropyrazolo[4',3':9,10][1]oxa[6]azacycloundecino[8,7,6-hi]indole-2-carboxylic acid, (rac)-1-(3-((2,3-dihydro-1H-inden-4-yl)oxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-12-ethyl-13-fluoro-11-methyl-4,5,6,7,9,11-hexahydropyrazolo[4',3':9,10][1]oxa[6]azacycloundecino[8,7,6-hi]indole-2-carboxylic acid, (rac)-13-fluoro-1-(3-((6-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylic acid, (rac)-13-fluoro-1-(3-((4-fluoronaphthalen-1-yl)oxy)propyl)-10,12-dimethyl-4,5,6,7,9,10-hexahydropyrazolo[4',3':9,10][1]oxa[6]azacycloundecino[8,7,6-hi]indole-2-carboxylic acid, (rac)-13-fluoro-10,12-dimethyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid, (rac)-1-(3-((2,3-dihydro-1H-inden-4-yl)oxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-13-fluoro-10,12-dimethyl-4,5,6,7,9,10-hexahydropyrazolo[4',3':9,10][1]oxa[6]azacycloundecino[8,7,6-hi]indole-2-carboxylic acid, (rac)-12-ethyl-13-fluoro-10-methyl-1-(3-(naphthalen-1-yloxy)propyl)-4,5,6,7,9,10-hexahydropyrazolo[4',3':9,10][1]oxa[6]azacycloundecino[8,7,6-hi]indole-2-carboxylic acid, (rac)-12-ethyl-13-fluoro-1-(3-((6-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylic acid, 3-ethyl-4-fluoro-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid-N-ethylethanamine salt (enantiomer 1), 3-ethyl-4-fluoro-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-12-ethyl-13-fluoro-1-(3-((4-fluoronaphthalen-1-yl)oxy)propyl)-10-methyl-4,5,6,7,9,10-hexahydropyrazolo[4',3':9,10][1]oxa[6]azacycloundecino[8,7,6-hi]indole-2-carboxylic acid, 3-ethyl-4-fluoro-7-{3-[(4-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 1), 3-ethyl-4-fluoro-7-{3-[(4-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 2), (rac)-12-ethyl-13-fluoro-10-methyl-1-(3-((5,6,7,8-tetrahydronaphthalen-1-yl)oxy)propyl)-4,5,6,7,9,10-hexahydropyrazolo[4',3':9,10][1]oxa[6]azacycloundecino[8,7,6-hi]indole-2-carboxylic acid, (rac)-1-(3-((2,3-dihydro-1H-inden-4-yl)oxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylic acid, (rac)-1-(3-(4-chloro-3,5-dimethylphenoxy)propyl)-12-ethyl-13-fluoro-10-methyl-4,5,6,7,9,10-hexahydropyrazolo[4',3':9,10][1]oxa[6]azacycloundecino[8,7,6-hi]indole-2-carboxylic acid, (rac)-4-fluoro-2,3-dimethyl-7-[3-(i-naphthyloxy)propyl]-10,11,12,13,14,15-hexahydro-2H-pyrazolo[3',4':8,9][1,6]diazacycloundecino[10,11,1-hi]indole-8-carboxylic acid-trifluoroacetic acid salt, 4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid (enantiomer 1), 4-fluoro-2,3-dimethyl-7-{3-[(naphthalen-1-yl)oxy]propyl}-10,11,12,13,14,15-hexahydro-2H-pyrazolo[3',4':8,9][1,6]diazacycloundecino[10,11,1-hi]indole-8-carboxylic acid (enantiomer 2), 8-carboxy-4-fluoro-2,3,14,14-tetramethyl-7-[3-(1-naphthyloxy)propyl]-10,11,12,13,14,15-hexahydro-2H-pyrazolo[3',4':8,9][1,6]diazacycloundecino[10,11,1-hi]indol-14-ium trifluoroacetate, (rac)-7-[3-(2,3-dihydro-1H-inden-4-yloxy)propyl]-3-ethyl-4-fluoro-2,14-dimethyl-10,11,12,13,14,15-hexahydro-2H-pyrazolo[3',4':8,9][1,6]diazacycloundecino[10,11,1-hi]indole-8-carboxylic acid, (rac)-3-ethyl-4-fluoro-2,14-dimethyl-7-[3-(5,6,7,8-tetrahydronaphthalen-1-yloxy)propyl]-10,11,12,13,14,15-hexahydro-2H-pyrazolo[3',4':8,9][1,6]diazacycloundecino[10,11,1-hi]indole-8-carboxylic acid, (rac)-3-ethyl-4-fluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid; and (rac)-3-ethyl-4-fluoro-2,14-dimethyl-7-[3-(1-naphthyloxy)propyl]-10,11,12,13,14,15-hexahydro-2H-pyrazolo[3',4':8,9][1,6]diazacycloundecino[10,11,1-hi]indole-8-carboxylic acid;

or a tautomer, an N-oxide, or a pharmaceutically acceptable salt thereof, or a pharmaceutically acceptable salt of a tautomer, or a pharmaceutically acceptable salt of an N-oxide, or a mixture of same.

7. A method of preparing a compound of formula (I) according to claim 1, said method comprising the step of reacting an intermediate compound of formula (II):

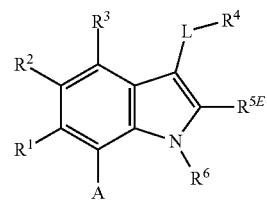

(II)

wherein $R^{5E}$ represents a carboxylic ester group or a benzyl ester group, with an alkali hydroxide in a mixture of water and THF and/or an aliphatic alcohol of formula $C_1$-$C_3$-alkyl-OH, at a temperature from 0° C. to 100° C., to transform the group $R^{5E}$ into a group $R^5$ as defined for the compounds of formula (I), and subsequently optionally to convert the free acid group $R^5$ into a pharmaceutically acceptable salt thereof to obtain a compound of formula (I)

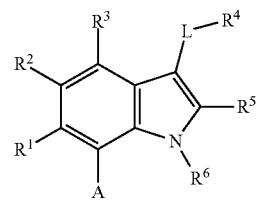

(I)

or a stereoisomer, a tautomer, an N-oxide, or a salt thereof, or a mixture of same and optionally separating enantiomers by means of preparative HPLC on a chiral stationary phase.

8. A pharmaceutical combination comprising:
one or more compounds of formula (I) according to claim 1, and
one or more further anti-cancer agents.

9. An intermediate compound of formula (II):

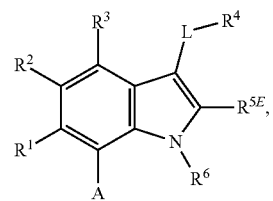

(II)

wherein
A is

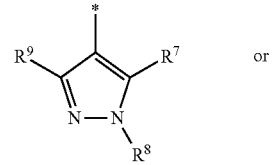

(A1)

or

-continued (A2)

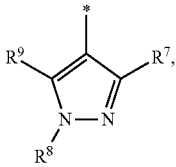

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent:

or

A is (A3)

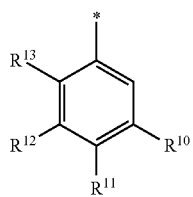

wherein optionally one or two of the groups selected from $CR^{11}$, $CR^{12}$ and $CR^{13}$ are replaced by a nitrogen atom, wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;

$R^1$ is a fluorine atom, $R^2$ and $R^3$ are each a hydrogen atom:

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group, and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —$NR^{14}$— group;

E is a bond, an oxygen atom, a sulfur atom, a —S(O)— group, a —S(O)$_2$— group or a —$NR^{14}$— group and constitutes the connecting element to $R^4$;

m is 2, 3, or 4;

$R^{5E}$ represents a carboxylic ester group;

—$R^6$-$R^7$— is selected from $^\#$—$(CH_2)_n$—(B)$_t$—$(CH_2)_p$—X—$^{\#\#}$, $^\#(C_2$-$C_6$-alkenylene)-(B)$_t$—$(CH_2)$—X—$^{\#\#}$, $^\#$—$(CH_2)_n$—(B)$_t$—$(C_2$-$C_5$-alkenylene)-X—$^{\#\#}$, and $^\#$—$(CH_2)_q$—(B)—$(CH_2)_r$—(B)—$(CH_2)_v$—X—$^{\#\#}$, wherein $^\#$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and where a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group; and where X is an unsubstituted —$CH_2$— group:

—$R^6$-$R^{10}$— is selected from $^\#$—$(CH_2)_n$—(B)$_t$—$(CH_2)_p$—X—$^{\#\#}$, $^\#(C_2$-$C_6$-alkenylene)-(B)$_t$—$(CH_2)_v$—X—$^{\#\#}$, $^\#$—$(CH_2)_n$—(B)$_t$—$(C_2$-$C_5$-alkenylene)-X—$^{\#\#}$, and $^\#$—$(CH_2)_q$—(B)—$(CH_2)_r$—(B)—$(CH_2)_v$—X—$^{\#\#}$, wherein # is the point of attachment with the indole nitrogen atom and $^{\#\#}$ is the point of attachment with the carbon atom of the phenyl moiety bearing the $R^{10}$ substituent, one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, where a —CH=CH— group in any alkenylene can be replaced by a 1,2-($C_1$-$C_6$)cycloalkylene group which is unsubstituted or substituted one or two times with a halogen atom or a $C_1$-$C_2$-alkyl group, and where X is an unsubstituted —$CH_2$— group:

n is 2, 3, 4, 5, 6, 7, 8, or 9;

t is 0 or 1;

p is 0, 1, 2, 3, 4, or 5;

q is 2, 3, 4, 5, or 6;

r is 2, 3, 4, 5, or 6;

v is 0 or 1;

s is 0, 1, 2, or 3;

where the integers selected for variables n, t, p, q, r, and v result in forming a 9- to 16-membered ring independently from the selection of variable A1, A2 or A3;

B is independently selected from a —C(O)$NR^{15}$— group, a —$NR^{15}$C(O)— group, a —$N(R^{15})$— group, a —[N(CH$_3$)$_2$]$^+$— group, a —$N(R^{15})$—C(=O)—$N(R^{15})$— group, a —O—C($R^{15}$)—$N(R^{15})$— group, a —$N(R^{15})$—C(=O)—O— group, —O—, —S—, —S(O)—, and —S(O)$_2$—;

$R^8$ is selected from a hydrogen atom, a $C_1$-$C_6$-alkyl group, which is unsubstituted or substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group; and a $C_3$-$C_6$-cycloalkyl group, $R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{18}$-(phenylene)-($C_1$-$C_3$-alkylene)-O—($C_1$-$C_3$-alkylene)- group,
a $R^{18}$-(phenylene)-O—($C_1$-$C_3$-alkylene)- group,
a $R^{18}$-(phenylene)-(heteroarylene)-O—($C_1$-$C_3$-alkylene) group,
a ($R^{18}$)-(heterocycloalkylene)-($C_1$-$C_3$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

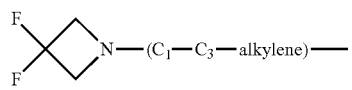

group, and a

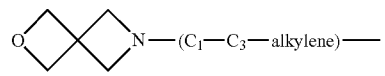

group, where the phenyl ring is unsubstituted or substituted with a halogen atom, a hydroxyl group, or a $C_1$-$C_3$-alkoxy group and
the heterocycloalkyl group is unsubstituted or substituted with an oxo (═O) group or is unsubstituted or substituted with one or more substituents independently selected from a halogen atom, a hydroxyl group, a $C_1$-$C_3$-alkyl group, and a $C_1$-$C_3$-alkoxy group,
or $R^8$ and $R^9$ together form a 5- or 6-membered ring optionally comprising one or two heteroatoms selected from —O— and —$NR^{14}$—;
$R^{11}$ and $R^{13}$ are each independently selected from a hydrogen atom, a halogen atom, a $C_1$-$C_3$-alkyl group, and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;
$R^{14}$ is a hydrogen atom or a $C_1$-$C_3$-alkyl group;
$R^{15}$ is independently selected from a hydrogen atom,
a $C_1$-$C_6$-alkyl group
which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;
a phenyl group,
a group

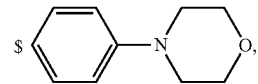

a group

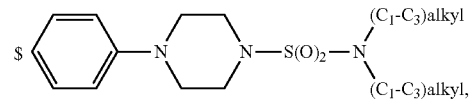

and
a group

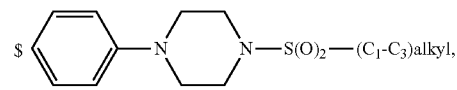

where $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;

$R^{18}$ is selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}$R$^{21}$ group; and $R^{20}$ and $R^{21}$ are each independently selected from a hydrogen atom and a $C_1$-$C_6$-alkyl group;

or a tautomer, an N-oxide, or a salt thereof, or a salt of a tautomer, or a salt of an N-oxide, or a mixture of same.

\* \* \* \* \*

UNITED STATES PATENT AND TRADEMARK OFFICE
CERTIFICATE OF CORRECTION

PATENT NO. : 11,286,263 B2
APPLICATION NO. : 16/764563
DATED : March 29, 2022
INVENTOR(S) : Steven James Ferrara et al.

It is certified that error appears in the above-identified patent and that said Letters Patent is hereby corrected as shown below:

In the Claims

Column 272, Claim number 1, Line number 40, should read:
--X-$^{\#\#}$, $^{\#}$-(C$_2$-C$_6$-alkenylene)-(B)$_t$-(CH$_2$)$_p$-X-$^{\#\#}$,--

At Column 272, Claim number 1, Line number 42, should read:
--$^{\#}$-(CH$_2$)$_q$-(B)-(CH$_2$)$_r$-(B)-(CH$_2$)$_v$-X-$^{\#\#}$,--

Column 272, Claim number 1, Line number 61, should read:
--(CH$_2$)$_p$-X-$^{\#\#}$, $^{\#}$-(C$_2$-C$_6$-alkenylene)-(B)$_t$-(CH$_2$)$_p$--

Column 276, Claim number 2, Line number 67, should read:
-- X-$^{\#\#}$, $^{\#}$-(C$_2$-C$_6$-alkenylene)-(B)$_t$-(CH$_2$)$_p$-X-$^{\#\#}$,--

Column 277, Claim number 2, Line number 2, should read:
--X-$^{\#\#}$, and $^{\#}$-(CH$_2$)$_q$-(B)-(CH$_2$)$_r$-(B)-(CH$_2$)$_v$-X-$^{\#\#}$,--

Column 287, Claim number 6, Line number 26, should read:
--(rac)-4-fluoro-2,3-dimethyl-7-[3-(1-naphthyloxy)propyl]- --

Column 290, Claim number 9, Line number 2, should read:
--X-$^{\#\#}$, $^{\#}$-(C$_2$-C$_6$-alkenylene)-(B)$_t$-(CH$_2$)$_p$-X-$^{\#\#}$,--

Column 290, Claim number 9, Line number 24, should read:
--(CH$_2$)$_p$-X-$^{\#\#}$, $^{\#}$-(C$_2$-C$_6$-alkenylene)-(B)$_t$-(CH$_2$)$_p$- --

Column 290, Claim number 9, Line number 56, should read:
--group, a -O-C(=O)-N(R$^{15}$)- group, a--

Signed and Sealed this
Twenty-ninth Day of November, 2022

Katherine Kelly Vidal
*Director of the United States Patent and Trademark Office*